US011426172B2

(12) United States Patent
Melanson et al.

(10) Patent No.: US 11,426,172 B2
(45) Date of Patent: *Aug. 30, 2022

(54) DEVICES AND METHODS FOR EXCLUDING THE LEFT ATRIAL APPENDAGE

(71) Applicant: Conformal Medical, Inc., Merrimack, NH (US)

(72) Inventors: David A. Melanson, Hudson, NH (US); Andy H. Levine, Newton Highlands, MA (US); James H. Loper, Wales, MA (US); Michael T. Radford, Nashua, NH (US); Carol Devellian, Topsfield, MA (US); Aaron V. Kaplan, Norwich, VT (US); Ronald B. Lamport, Pelham, NH (US)

(73) Assignee: Conformal Medical, Inc., Nashua, NH (US)

( * ) Notice: Subject to any disclaimer, the term of this patent is extended or adjusted under 35 U.S.C. 154(b) by 115 days.

This patent is subject to a terminal disclaimer.

(21) Appl. No.: 15/969,654

(22) Filed: May 2, 2018

(65) Prior Publication Data

US 2018/0250014 A1     Sep. 6, 2018

Related U.S. Application Data

(63) Continuation-in-part of application No. 15/795,083, filed on Oct. 26, 2017, now Pat. No. 11,026,695.

(Continued)

(51) Int. Cl.
*A61B 17/12*     (2006.01)
*A61N 1/372*     (2006.01)
(Continued)

(52) U.S. Cl.
CPC .... *A61B 17/12122* (2013.01); *A61B 17/1215* (2013.01); *A61B 17/12031* (2013.01);
(Continued)

(58) Field of Classification Search
CPC ........ A61B 17/12022; A61B 17/12122; A61B 17/12172; A61B 17/12177
See application file for complete search history.

(56) References Cited

U.S. PATENT DOCUMENTS

| 3,063,453 A | 11/1962 | Brecht |
|---|---|---|
| 3,712,305 A | 1/1973 | Wennerblom et al. |

(Continued)

FOREIGN PATENT DOCUMENTS

| CA | 1341519 | 2/2007 |
|---|---|---|
| CN | 102088927 | 6/2011 |

(Continued)

OTHER PUBLICATIONS

Möbius-Winkler, S., Sandri, M., Mangner, N., Lurz, P., Dähnert, I., Schuler, G. The WATCHMAN Left Atrial Appendage Closure Device for Atrial Fibrillation. J. Vis. Exp. (60), e3671, DOI : 10.3791/3671 (Feb. 28, 2012).

(Continued)

*Primary Examiner* — Todd J Scherbel
(74) *Attorney, Agent, or Firm* — Knobbe Martens Olson & Bear, LLP

(57) ABSTRACT

Devices and methods are described for occluding the left atrial appendage (LAA). The device excludes the LAA from blood flow to prevent blood from clotting within the LAA and subsequently embolizing, particularly in patients with atrial fibrillation. The implantable device is delivered via transcatheter delivery into the LAA and secured within the LAA. The implant comprises an expandable and compliant frame and an expandable and conformable tubular foam body. The device may have a thromboresistant cover at a proximal end. The frame may have recapture struts inclining radially outwardly from a central hub. The frame may have axially extending side wall struts, with adjacent pairs of side (Continued)

wall struts joined at one or more apexes. Anchors extend from the frame and into the foam to engage tissue.

37 Claims, 79 Drawing Sheets

Related U.S. Application Data

(60) Provisional application No. 62/459,503, filed on Feb. 15, 2017, provisional application No. 62/413,632, filed on Oct. 27, 2016.

(51) Int. Cl.
*A61N 1/375* (2006.01)
*A61N 1/39* (2006.01)
*A61B 18/14* (2006.01)
*A61B 17/00* (2006.01)
*A61M 29/00* (2006.01)
*A61B 18/00* (2006.01)
*A61B 90/00* (2016.01)

(52) U.S. Cl.
CPC .. *A61B 17/12131* (2013.01); *A61B 17/12145* (2013.01); *A61B 17/12172* (2013.01); *A61B 17/12177* (2013.01); *A61B 17/12181* (2013.01); *A61B 18/1492* (2013.01); *A61N 1/3756* (2013.01); *A61N 1/37205* (2013.01); *A61N 1/3956* (2013.01); *A61B 17/0057* (2013.01); *A61B 17/00491* (2013.01); *A61B 17/1219* (2013.01); *A61B 17/12036* (2013.01); *A61B 2017/00004* (2013.01); *A61B 2017/00022* (2013.01); *A61B 2017/00221* (2013.01); *A61B 2017/00526* (2013.01); *A61B 2017/00853* (2013.01); *A61B 2017/00893* (2013.01); *A61B 2017/00898* (2013.01); *A61B 2017/00951* (2013.01); *A61B 2017/12054* (2013.01); *A61B 2018/0022* (2013.01); *A61B 2018/00577* (2013.01); *A61B 2018/1435* (2013.01); *A61B 2018/1467* (2013.01); *A61B 2018/1495* (2013.01); *A61B 2090/064* (2016.02); *A61B 2090/3925* (2016.02); *A61B 2090/3966* (2016.02); *A61M 29/00* (2013.01)

(56) References Cited

U.S. PATENT DOCUMENTS

| | | | |
|---|---|---|---|
| 3,812,856 A | 5/1974 | Duncan et al. |
| 3,978,855 A | 9/1976 | McRae et al. |
| 4,061,145 A | 12/1977 | DesMarais |
| 4,475,911 A | 10/1984 | Gellert |
| 5,192,301 A | 3/1993 | Kamiya et al. |
| 5,456,693 A | 10/1995 | Conston et al. |
| 5,634,936 A | 6/1997 | Linden et al. |
| 5,670,572 A | 9/1997 | Ott et al. |
| 5,725,568 A | 3/1998 | Hastings |
| 5,792,179 A | 8/1998 | Sideris |
| 5,823,198 A | 10/1998 | Jones et al. |
| 5,847,012 A | 12/1998 | Shalaby et al. |
| 5,848,040 A | 12/1998 | Tanaka |
| 5,861,003 A | 1/1999 | Latson et al. |
| 5,865,791 A | 2/1999 | Whayne et al. |
| 5,969,000 A | 10/1999 | Yang et al. |
| 5,968,091 A | 11/1999 | Pinchuk |
| 6,152,144 A | 11/2000 | Lesh et al. |
| 6,162,168 A | 12/2000 | Schweich et al. |
| 6,231,561 B1 | 5/2001 | Frazier et al. |
| 6,290,674 B1 | 9/2001 | Roue et al. |
| 6,398,758 B1 | 6/2002 | Jacobsen et al. |
| 6,408,981 B1 | 6/2002 | Smith et al. |
| 6,419,669 B1 | 7/2002 | Frazier et al. |
| 6,423,252 B1 | 7/2002 | Chun et al. |
| 6,436,088 B2 | 8/2002 | Frazier et al. |
| 6,447,539 B1 | 9/2002 | Nelson et al. |
| 6,458,100 B2 | 10/2002 | Roue et al. |
| 6,551,303 B1 | 4/2003 | VanTassel et al. |
| 6,623,450 B1 | 9/2003 | Dutta |
| 6,641,557 B1 | 11/2003 | Frazier et al. |
| 6,651,303 B1 | 11/2003 | Toivanen et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | VanTassel et al. |
| 6,712,804 B2 | 3/2004 | Roue et al. |
| 6,712,810 B2 | 3/2004 | Harrington et al. |
| 6,723,108 B1 | 4/2004 | Jones et al. |
| 6,730,108 B2 | 5/2004 | Van Tassel et al. |
| 6,881,875 B2 | 4/2005 | Swenson |
| 6,941,169 B2 | 9/2005 | Pappu |
| 6,949,113 B2 | 9/2005 | Van Tassel et al. |
| 6,977,323 B1 | 12/2005 | Swenson |
| 6,979,344 B2 | 12/2005 | Jones et al. |
| 6,994,092 B2 | 2/2006 | Van Der et al. |
| 7,011,671 B2 | 3/2006 | Welch |
| 7,044,134 B2 | 5/2006 | Khairkhahan et al. |
| 7,056,294 B2 | 6/2006 | Khairkhahan et al. |
| 7,115,110 B2 | 10/2006 | Frazier et al. |
| 7,128,073 B1 | 10/2006 | Van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,226,458 B2 | 6/2007 | Kaplan et al. |
| 7,291,382 B2 | 11/2007 | Krueger et al. |
| 7,293,562 B2 | 11/2007 | Malecki |
| 7,318,829 B2 | 1/2008 | Kaplan et al. |
| 7,344,543 B2 | 3/2008 | Sra |
| 7,358,282 B2 | 4/2008 | Krueger et al. |
| 7,427,279 B2 | 9/2008 | Frazier et al. |
| 7,549,983 B2 | 6/2009 | Roue et al. |
| 7,566,336 B2 | 7/2009 | Corcoran et al. |
| 7,597,704 B2 | 10/2009 | Frazier et al. |
| 7,695,425 B2 | 4/2010 | Schweich et al. |
| 7,713,282 B2 | 5/2010 | Frazier et al. |
| 7,722,641 B2 | 5/2010 | Van Der et al. |
| 7,727,189 B2 | 6/2010 | VanTassel et al. |
| 7,735,493 B2 | 6/2010 | van der Burg et al. |
| 7,747,047 B2 | 6/2010 | Okerlund et al. |
| 7,780,683 B2 | 8/2010 | Roue et al. |
| 7,803,395 B2 | 9/2010 | Datta et al. |
| 7,824,397 B2 | 11/2010 | Mcauley |
| 7,922,716 B2 | 4/2011 | Malecki et al. |
| 7,972,359 B2 | 7/2011 | Kreidler |
| 7,998,138 B2 | 8/2011 | Mcauley |
| 8,043,329 B2 | 10/2011 | Khairkhahan et al. |
| 8,052,715 B2 | 11/2011 | Quinn et al. |
| 8,057,530 B2 | 11/2011 | Kusleika et al. |
| 8,080,032 B2 | 12/2011 | van der Burg et al. |
| 8,097,015 B2 | 1/2012 | Devellian |
| 8,142,470 B2 | 3/2012 | Quinn et al. |
| 8,157,818 B2 | 4/2012 | Gartner et al. |
| 8,197,496 B2 | 6/2012 | Roue et al. |
| 8,197,527 B2 | 6/2012 | Borillo et al. |
| 8,221,445 B2 | 7/2012 | Van Tassel et al. |
| 8,262,694 B2 | 9/2012 | Widomski et al. |
| 8,287,563 B2 | 10/2012 | Khairkhahan et al. |
| 8,313,504 B2 | 11/2012 | Do et al. |
| 8,323,309 B2 | 12/2012 | Khairkhahan et al. |
| 8,337,487 B2 | 12/2012 | Datta et al. |
| 8,361,111 B2 | 1/2013 | Widomski et al. |
| 8,460,282 B2 | 6/2013 | Mcauley |
| 8,480,708 B2 | 7/2013 | Kassab et al. |
| 8,523,897 B2 | 9/2013 | Van Der et al. |
| 8,535,343 B2 | 9/2013 | Van Der et al. |
| 8,540,760 B2 | 9/2013 | Paul, Jr. et al. |
| 8,603,108 B2 | 12/2013 | Roue et al. |
| 8,636,764 B2 | 1/2014 | Miles et al. |
| 8,690,911 B2 | 1/2014 | Miles et al. |
| 8,647,361 B2 | 2/2014 | Borillo et al. |
| 8,647,367 B2 | 2/2014 | Kassab et al. |

(56) References Cited

U.S. PATENT DOCUMENTS

| | | |
|---|---|---|
| 8,663,268 B2 | 3/2014 | Quinn et al. |
| 8,663,273 B2 | 3/2014 | Khairkhahan et al. |
| 8,685,055 B2 | 4/2014 | VanTassel et al. |
| 8,715,302 B2 | 5/2014 | Ibrahim et al. |
| 8,715,318 B2 | 5/2014 | Miles et al. |
| 8,740,934 B2 | 7/2014 | McGuckin, Jr. |
| 8,764,793 B2 | 7/2014 | Lee |
| 8,784,469 B2 | 7/2014 | Kassab |
| 8,795,328 B2 | 8/2014 | Miles et al. |
| 8,801,746 B1 | 8/2014 | Kreidler et al. |
| 8,828,051 B2 | 9/2014 | Javois et al. |
| 8,834,519 B2 | 9/2014 | van der Burg et al. |
| 8,840,641 B2 | 9/2014 | Miles et al. |
| 8,845,711 B2 | 9/2014 | Miles et al. |
| 9,011,551 B2 | 4/2015 | Oral et al. |
| 9,034,006 B2 | 5/2015 | Quinn et al. |
| 9,089,313 B2 | 7/2015 | Roue et al. |
| 9,131,849 B2 | 9/2015 | Khairkhahan et al. |
| 9,132,000 B2 | 9/2015 | VanTassel et al. |
| 9,161,830 B2 | 10/2015 | Borillo et al. |
| 9,168,043 B2 | 10/2015 | Van Der et al. |
| 9,186,152 B2 | 11/2015 | Campbell et al. |
| 9,351,716 B2 | 5/2016 | Miles et al. |
| 9,421,004 B2 | 8/2016 | Roue et al. |
| 9,445,895 B2 | 9/2016 | Kreidler |
| 9,474,516 B2 | 10/2016 | Clark et al. |
| 9,554,804 B2 | 1/2017 | Erzberger et al. |
| 9,592,058 B2 | 3/2017 | Erzberger et al. |
| 9,592,110 B1 | 3/2017 | Dan et al. |
| 9,649,115 B2 | 5/2017 | Edmiston et al. |
| 9,693,780 B2 | 7/2017 | Miles et al. |
| 9,693,781 B2 | 7/2017 | Miles et al. |
| 9,700,323 B2 | 7/2017 | Clark |
| 9,730,701 B2 | 8/2017 | Tischler et al. |
| 9,743,932 B2 | 8/2017 | Amplatz et al. |
| 9,763,666 B2 | 9/2017 | Wu et al. |
| 9,808,253 B2 | 11/2017 | Li et al. |
| 9,839,431 B2 | 12/2017 | Meyer et al. |
| 9,849,011 B2 | 12/2017 | Zimmerman et al. |
| 9,861,370 B2 | 1/2018 | Clark et al. |
| 9,883,864 B2 | 2/2018 | Miles et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 11,026,695 B2 * | 6/2021 | Melanson ........ A61B 17/12122 |
| 2002/0022860 A1 | 2/2002 | Borillo et al. |
| 2002/0049457 A1 | 4/2002 | Kaplan et al. |
| 2002/0095205 A1 | 7/2002 | Edwin et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111647 A1 | 8/2002 | Khairkhahan et al. |
| 2002/0169377 A1 | 11/2002 | Khairkhahan et al. |
| 2003/0023266 A1 | 1/2003 | Borillo et al. |
| 2003/0051735 A1 | 3/2003 | Pavcnik |
| 2003/0120337 A1 | 6/2003 | Van Tassel et al. |
| 2003/0191526 A1 | 10/2003 | Van Tassel et al. |
| 2003/0199923 A1 | 10/2003 | Khairkhahan et al. |
| 2003/0204203 A1 | 10/2003 | Khairkhahan et al. |
| 2003/0220667 A1 | 11/2003 | van der Burg et al. |
| 2004/0049210 A1 | 3/2004 | VanTassel et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0215230 A1 | 10/2004 | Frazier et al. |
| 2004/0220610 A1 | 11/2004 | Kreidler et al. |
| 2004/0225212 A1 | 11/2004 | Okerlund et al. |
| 2004/0230222 A1 | 11/2004 | van der Burg et al. |
| 2005/0004652 A1 | 1/2005 | van der Burg et al. |
| 2005/0033287 A1 | 2/2005 | Sra |
| 2005/0038470 A1 | 2/2005 | van der Burg et al. |
| 2005/0049573 A1 | 3/2005 | VanTassel et al. |
| 2005/0070952 A1 | 3/2005 | Devellian |
| 2005/0113861 A1 | 5/2005 | Corcoran et al. |
| 2005/0149068 A1 | 7/2005 | Williams et al. |
| 2005/0149069 A1 | 7/2005 | Bertolero et al. |
| 2005/0177182 A1 | 8/2005 | van der Burg et al. |
| 2005/0234540 A1 | 10/2005 | Peavey et al. |
| 2005/0234543 A1 | 10/2005 | Glaser et al. |
| 2005/0267528 A1 | 12/2005 | Ginn |
| 2006/0009715 A1 | 1/2006 | Khairkhahan et al. |
| 2006/0116709 A1 | 6/2006 | Sepetka |
| 2007/0005147 A1 | 1/2007 | Levine |
| 2007/0083230 A1 | 4/2007 | Javois |
| 2007/0129753 A1 | 6/2007 | Quinn et al. |
| 2007/0135826 A1 | 6/2007 | Zaver et al. |
| 2007/0149988 A1 | 6/2007 | Michler et al. |
| 2007/0149995 A1 | 6/2007 | Quinn et al. |
| 2007/0179345 A1 | 8/2007 | Santilli |
| 2007/0270891 A1 | 11/2007 | McGuckin, Jr. |
| 2008/0033241 A1 | 2/2008 | Peh et al. |
| 2008/0125795 A1 | 5/2008 | Kaplan et al. |
| 2008/0243183 A1 | 10/2008 | Miller et al. |
| 2008/0294175 A1 | 11/2008 | Bardsley et al. |
| 2008/0312664 A1 | 12/2008 | Bardsley et al. |
| 2009/0005760 A1 * | 1/2009 | Cartledge ................ A61F 2/07 604/534 |
| 2009/0099596 A1 | 4/2009 | McGunkin, Jr. et al. |
| 2009/0112249 A1 | 4/2009 | Miles et al. |
| 2009/0143791 A1 | 6/2009 | Miller et al. |
| 2009/0157118 A1 | 6/2009 | Miller et al. |
| 2009/0264920 A1 | 10/2009 | Berenstein |
| 2009/0287145 A1 | 11/2009 | Cragg et al. |
| 2009/0306685 A1 | 12/2009 | Fill |
| 2009/0326577 A1 | 12/2009 | Johnson et al. |
| 2010/0076463 A1 | 3/2010 | Mavani et al. |
| 2010/0191279 A1 | 7/2010 | Kassab et al. |
| 2010/0228184 A1 | 9/2010 | Mavani et al. |
| 2010/0228279 A1 | 9/2010 | Miles et al. |
| 2010/0228285 A1 | 9/2010 | Miles et al. |
| 2010/0286718 A1 | 11/2010 | Kassab et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0009853 A1 | 1/2011 | Bertolero et al. |
| 2011/0022079 A1 | 1/2011 | Miles et al. |
| 2011/0022168 A1 * | 1/2011 | Cartledge .............. A61B 17/12 623/2.37 |
| 2011/0054515 A1 | 3/2011 | Bridgemann et al. |
| 2011/0082495 A1 | 4/2011 | Ruiz |
| 2011/0087271 A1 | 4/2011 | Sargent et al. |
| 2011/0178539 A1 | 7/2011 | Holmes, Jr. et al. |
| 2011/0208233 A1 | 8/2011 | McGunkin, Jr. et al. |
| 2011/0218389 A1 | 9/2011 | Gobel |
| 2011/0218566 A1 | 9/2011 | van der Burg et al. |
| 2011/0220120 A1 | 9/2011 | Frigstad et al. |
| 2011/0257674 A1 | 10/2011 | Evert et al. |
| 2011/0264119 A1 | 10/2011 | Bayon et al. |
| 2011/0307003 A1 | 12/2011 | Chambers |
| 2012/0010644 A1 | 1/2012 | Sideris et al. |
| 2012/0029553 A1 | 2/2012 | Quinn et al. |
| 2012/0065662 A1 | 3/2012 | van der Burg et al. |
| 2012/0065667 A1 | 3/2012 | Javois et al. |
| 2012/0157916 A1 | 6/2012 | Quinn et al. |
| 2012/0158022 A1 | 6/2012 | Kaplan et al. |
| 2012/0172927 A1 | 7/2012 | Campbell et al. |
| 2012/0221042 A1 | 8/2012 | Schwartz et al. |
| 2012/0239077 A1 | 9/2012 | Zaver et al. |
| 2012/0283585 A1 | 11/2012 | Werneth et al. |
| 2012/0283773 A1 | 11/2012 | VanTassel et al. |
| 2012/0316584 A1 | 12/2012 | Miles et al. |
| 2012/0323262 A1 | 12/2012 | Ibrahim et al. |
| 2012/0323267 A1 | 12/2012 | Ren |
| 2012/0323270 A1 | 12/2012 | Lee |
| 2012/0330342 A1 | 12/2012 | Jones |
| 2013/0006343 A1 | 1/2013 | Kassab |
| 2013/0012982 A1 | 1/2013 | Khairkhahan et al. |
| 2013/0018413 A1 | 1/2013 | Oral et al. |
| 2013/0018414 A1 | 1/2013 | Widomski et al. |
| 2013/0083983 A1 | 4/2013 | Zhong et al. |
| 2013/0110154 A1 | 5/2013 | van der Burg et al. |
| 2013/0116724 A1 | 5/2013 | Clark et al. |
| 2013/0165965 A1 | 6/2013 | Carlson et al. |

(56) References Cited

U.S. PATENT DOCUMENTS

| | | |
|---|---|---|
| 2013/0178889 A1 | 7/2013 | Miles et al. |
| 2013/0237908 A1 | 9/2013 | Clark |
| 2014/0005714 A1* | 1/2014 | Quick ............. A61B 17/12031 606/200 |
| 2014/0046360 A1 | 2/2014 | van der Burg et al. |
| 2014/0074151 A1 | 3/2014 | Tischler et al. |
| 2014/0128903 A1* | 5/2014 | Alferness ......... A61B 17/12022 606/198 |
| 2014/0257320 A1 | 9/2014 | Fitz |
| 2014/0277074 A1 | 9/2014 | Kaplan et al. |
| 2014/0330368 A1 | 11/2014 | Gloss |
| 2014/0336699 A1 | 11/2014 | van der Burg et al. |
| 2014/0371789 A1 | 12/2014 | Hariton et al. |
| 2015/0005810 A1 | 1/2015 | Center et al. |
| 2015/0039021 A1 | 2/2015 | Khairkhahan et al. |
| 2015/0133989 A1 | 5/2015 | Lubeck et al. |
| 2015/0196305 A1 | 7/2015 | Meyer et al. |
| 2016/0058539 A1 | 1/2016 | Vantassel et al. |
| 2016/0089151 A1 | 3/2016 | Siegel et al. |
| 2016/0106437 A1 | 4/2016 | van der Burg et al. |
| 2017/0042549 A1 | 2/2017 | Kaplan et al. |
| 2017/0042550 A1 | 2/2017 | Chakraborty et al. |
| 2017/0095238 A1 | 4/2017 | Rudman et al. |
| 2017/0100112 A1 | 4/2017 | Van Der et al. |
| 2017/0135801 A1 | 5/2017 | Delaney, Jr. et al. |
| 2017/0224354 A1 | 8/2017 | Tischler et al. |
| 2017/0281192 A1 | 10/2017 | Tieu et al. |
| 2017/0290594 A1 | 10/2017 | Chakraborty et al. |
| 2017/0340336 A1 | 11/2017 | Osypka |
| 2018/0185130 A1 | 7/2018 | Janardhan et al. |
| 2018/0206830 A1 | 7/2018 | Khairkhahan et al. |
| 2018/0250014 A1 | 9/2018 | Melanson et al. |
| 2018/0338824 A1 | 11/2018 | VanTassel et al. |
| 2019/0083075 A1 | 3/2019 | Onushko et al. |
| 2019/0125362 A1 | 5/2019 | Tischler |
| 2019/0336137 A1 | 11/2019 | Chakraborty et al. |
| 2020/0269059 A1 | 8/2020 | Kaiser |

FOREIGN PATENT DOCUMENTS

| | | |
|---|---|---|
| DE | 102006056283 | 6/2008 |
| EP | 1223890 B1 | 4/2004 |
| EP | 1227770 B1 | 9/2004 |
| EP | 1225843 B1 | 2/2005 |
| EP | 308531 A1 | 10/2016 |
| EP | 1469790 B1 | 10/2016 |
| EP | 2872051 B1 | 3/2017 |
| JP | 2003-512128 | 4/2003 |
| JP | 2003-529384 | 10/2003 |
| JP | 2012-530551 | 12/2012 |
| WO | WO 00/27292 | 5/2000 |
| WO | WO2009009466 | 1/2009 |
| WO | WO 2010/148246 | 12/2010 |
| WO | WO2014/011865 | 1/2014 |
| WO | WO 2014/078531 | 5/2014 |
| WO | WO 2014/164572 | 10/2014 |
| WO | WO2016/033170 | 3/2016 |
| WO | WO 2017/161283 | 9/2017 |
| WO | WO2018/185255 | 10/2018 |
| WO | WO2018/185256 | 10/2018 |
| WO | WO 2019/033121 | 2/2019 |

OTHER PUBLICATIONS

Extended European Search Report in European Patent Case No. EP 14 77 9640 dated Sep. 30, 2016.

International Search Report and Written Opinion dated Jan. 19, 2017, in International Application No. PCT/US2016/056450.

International Search Report and Written Opinion dated Jul. 3, 2014, in International Application No. PCT/US2014/022865.

International Search Report dated Jul. 10, 2019, in International Application No. PCT/US2019/29364.

International Search Report issued in International Patent Application No. PCT/US2020/016854, dated Jun. 8, 2020.

* cited by examiner

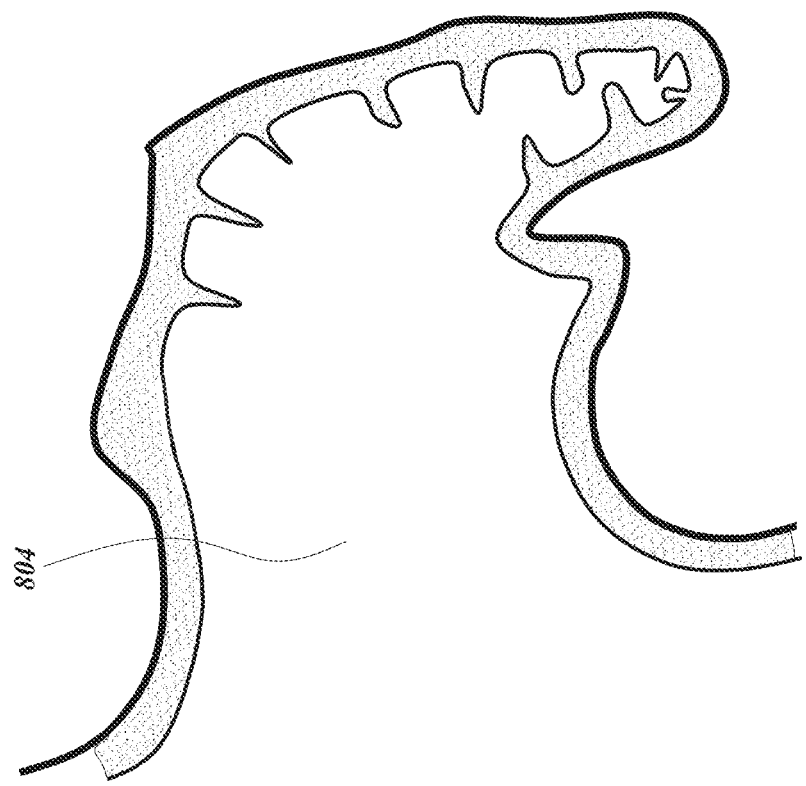
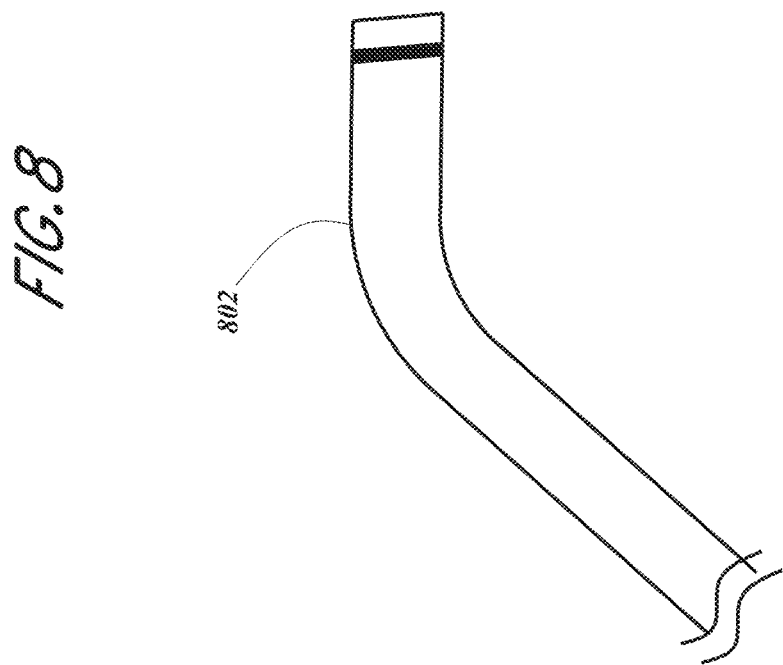
FIG. 8

Plug Deployed

Plug with ILS Loaded

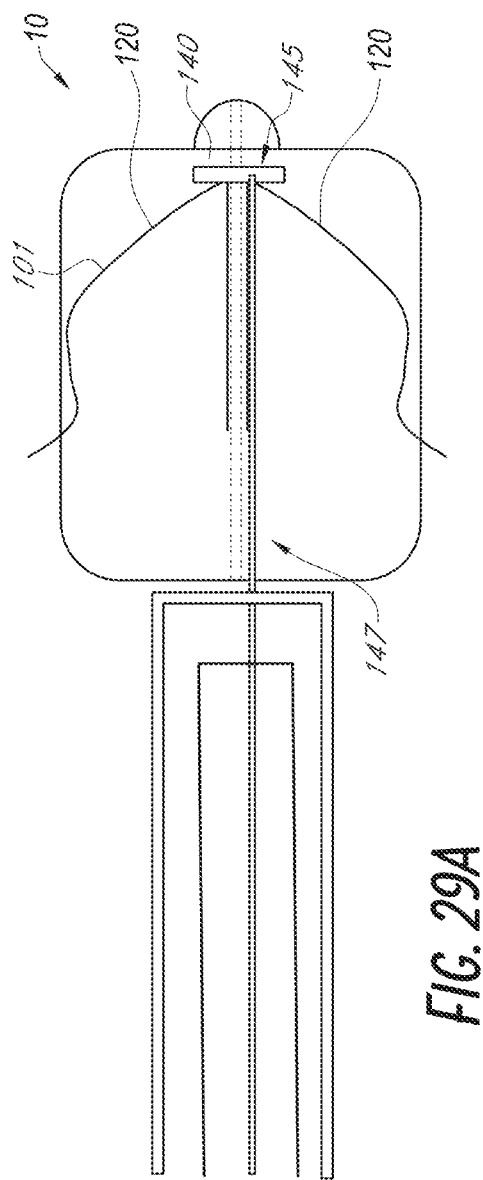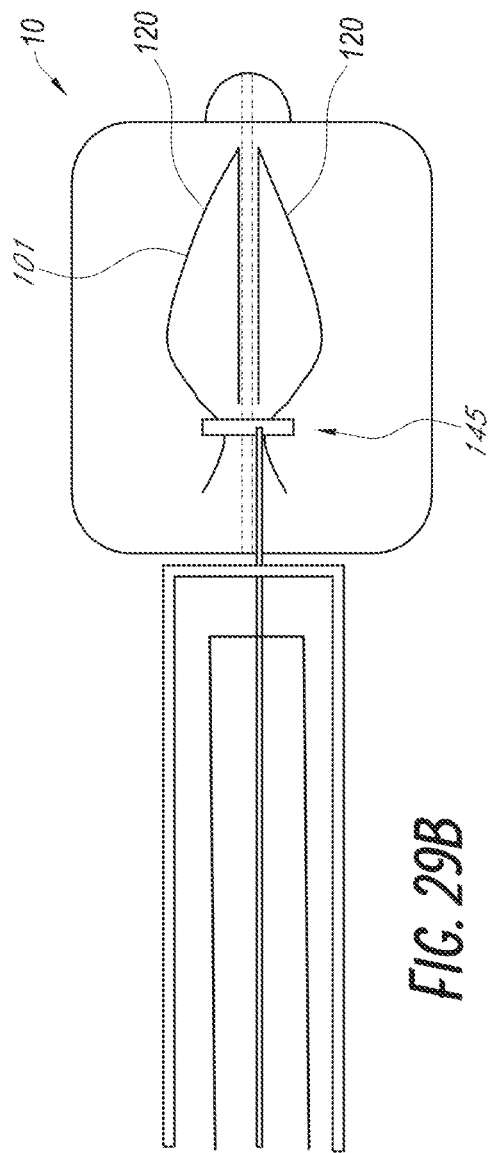
FIG. 29A
FIG. 29B

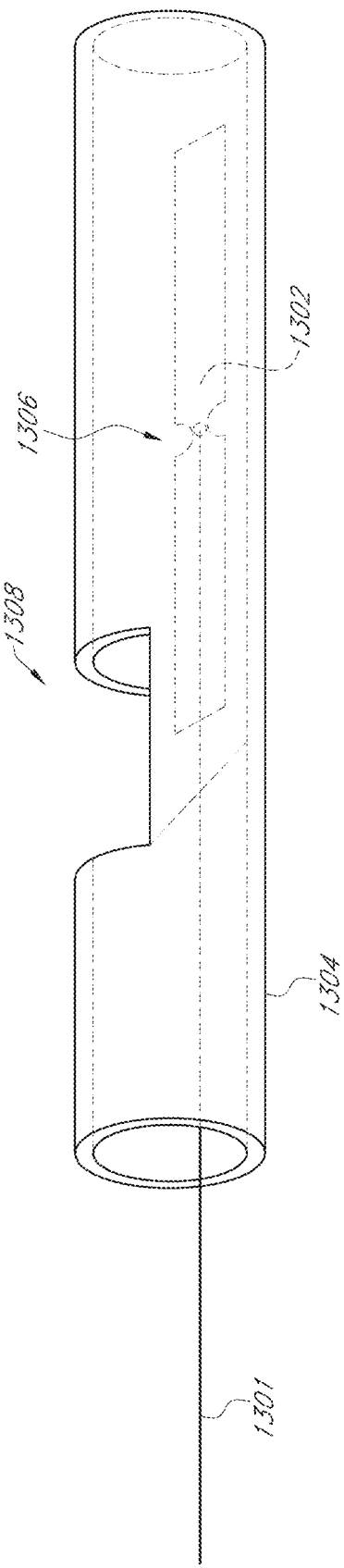
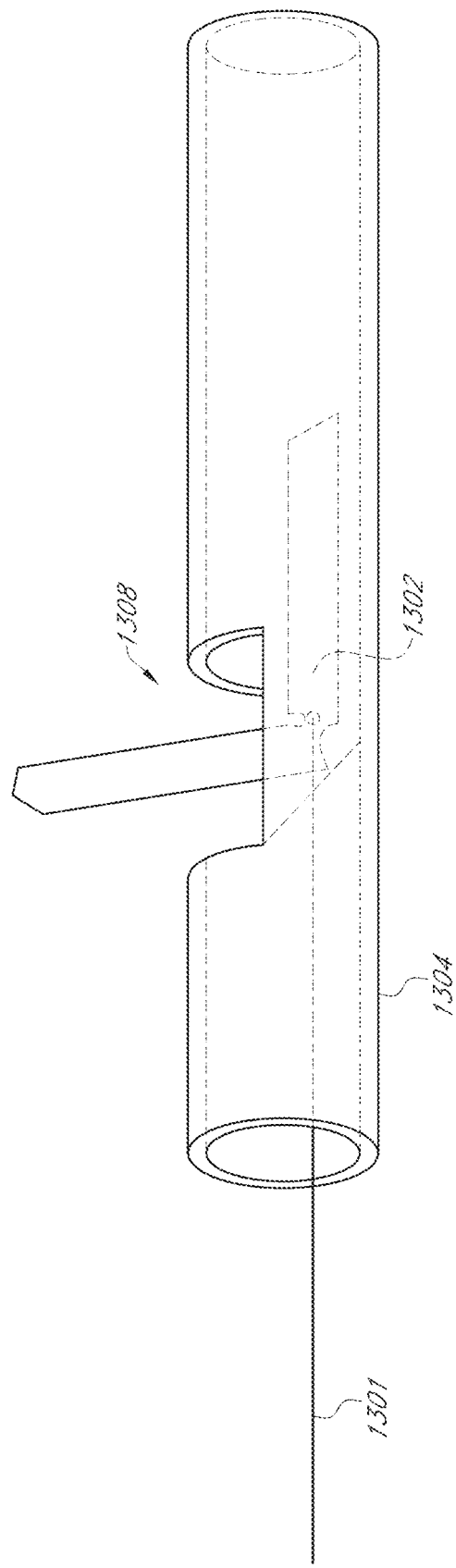
FIG. 39A
FIG. 39B

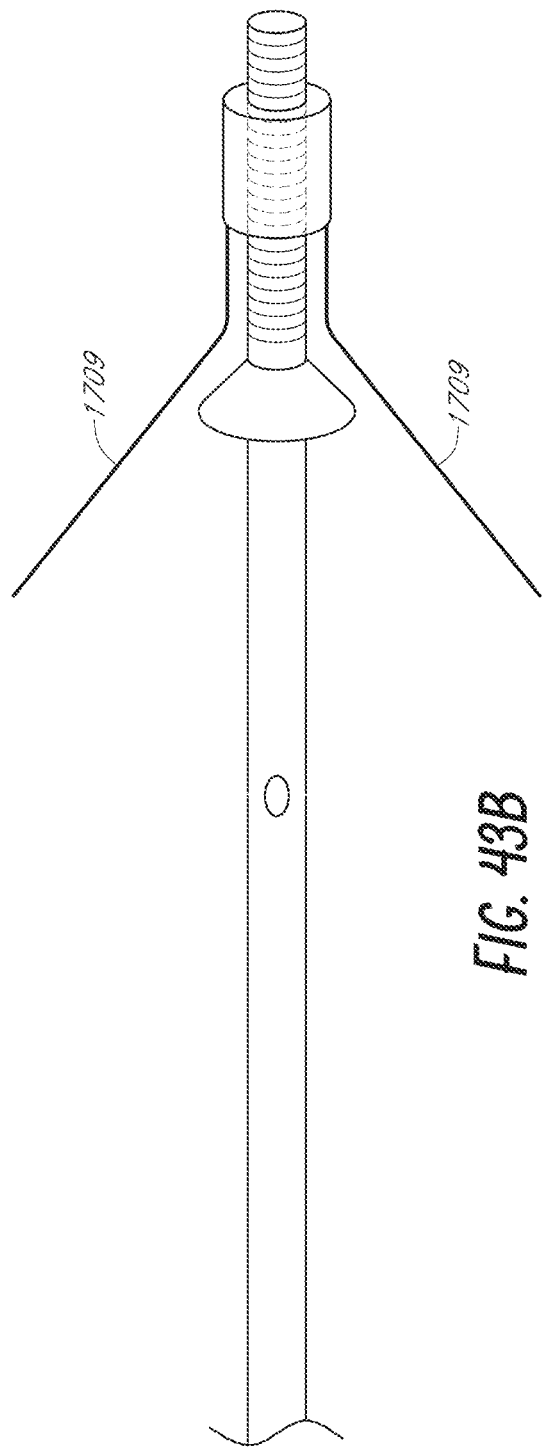

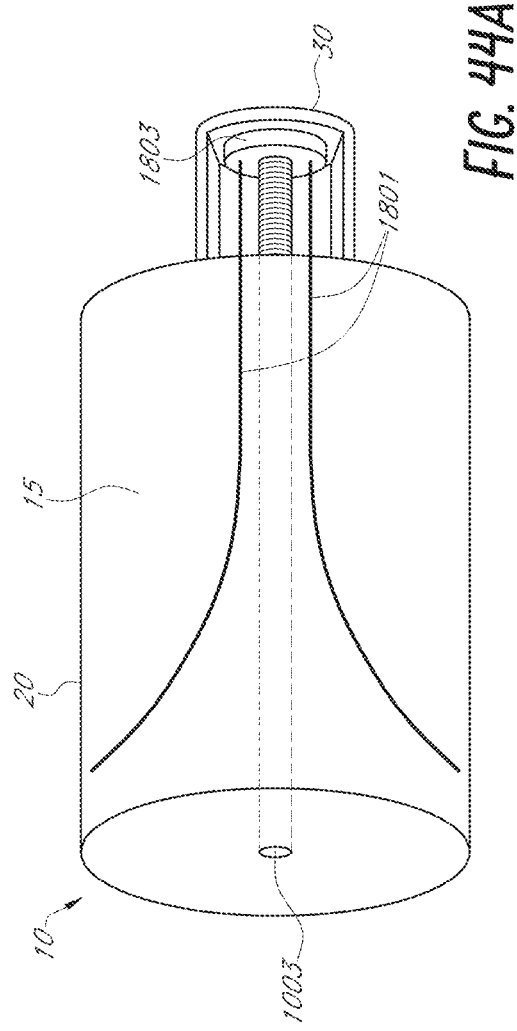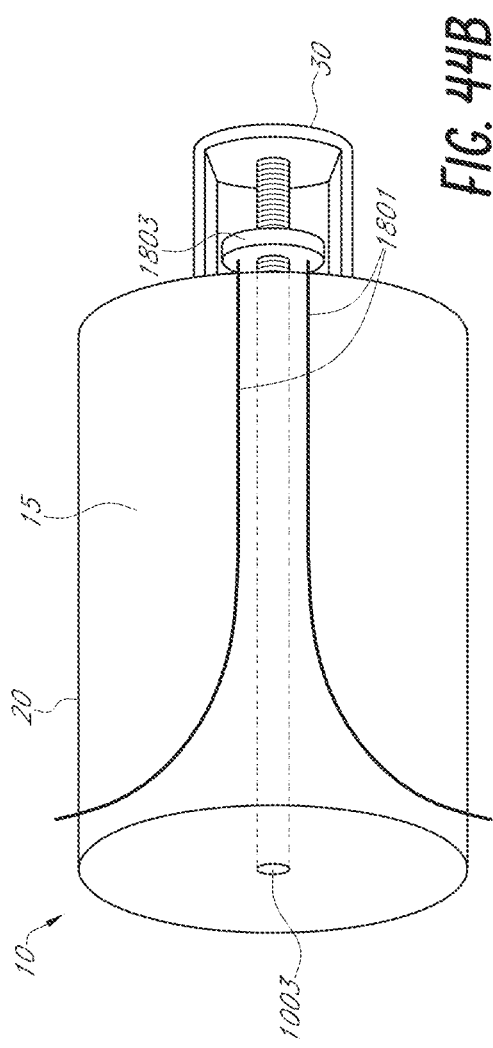

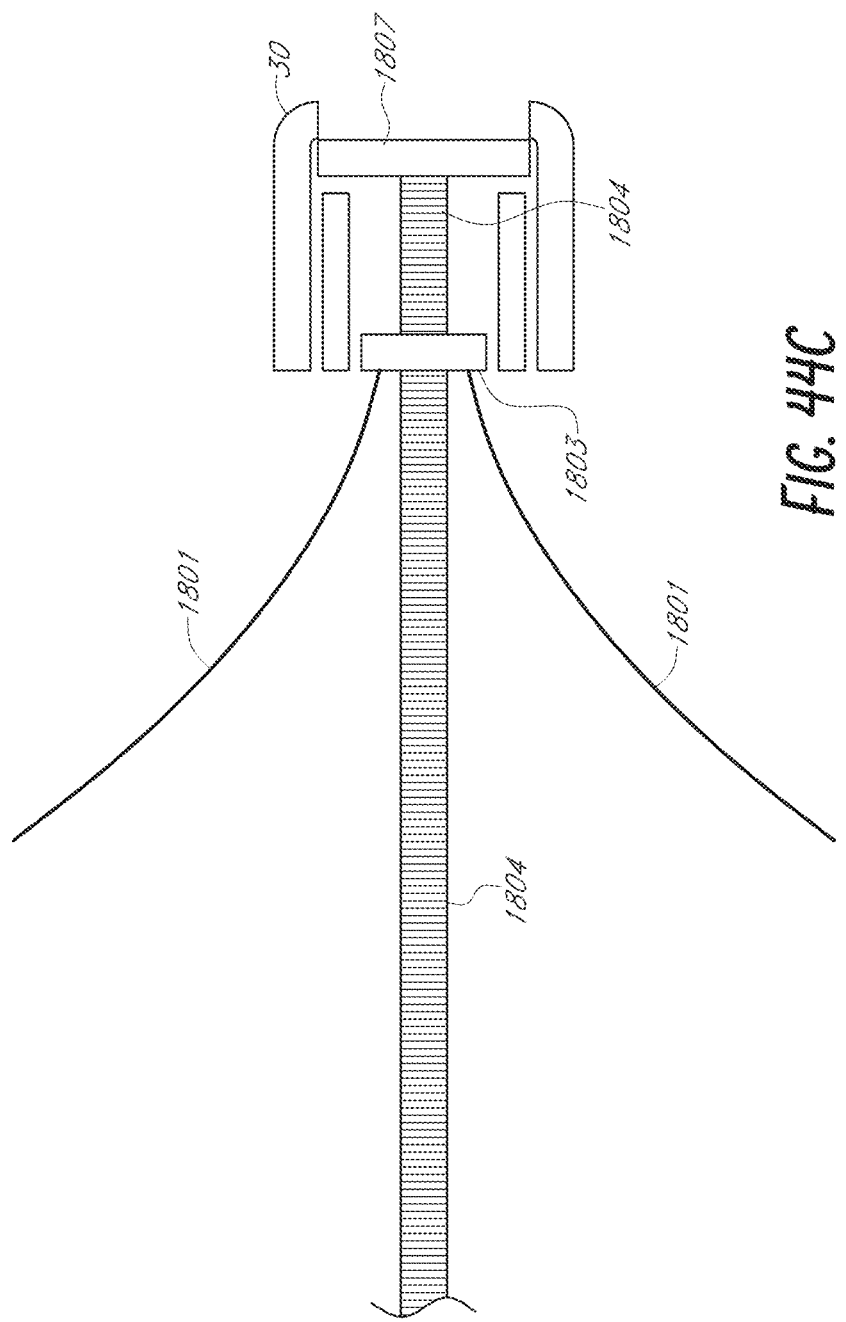

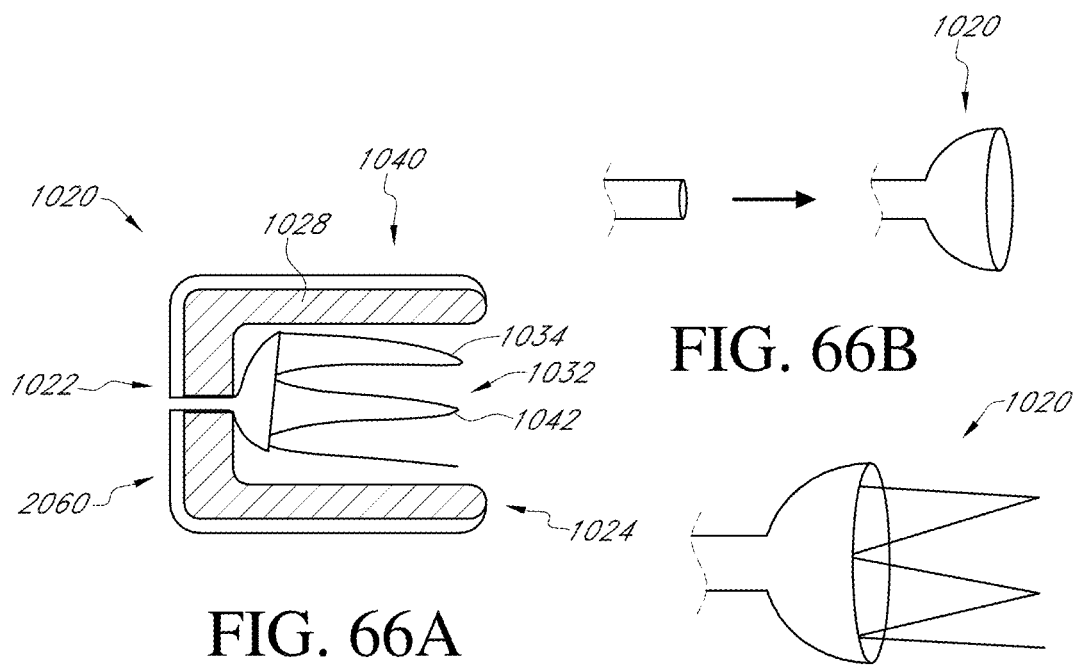
FIG. 66A
FIG. 66B
FIG. 66C
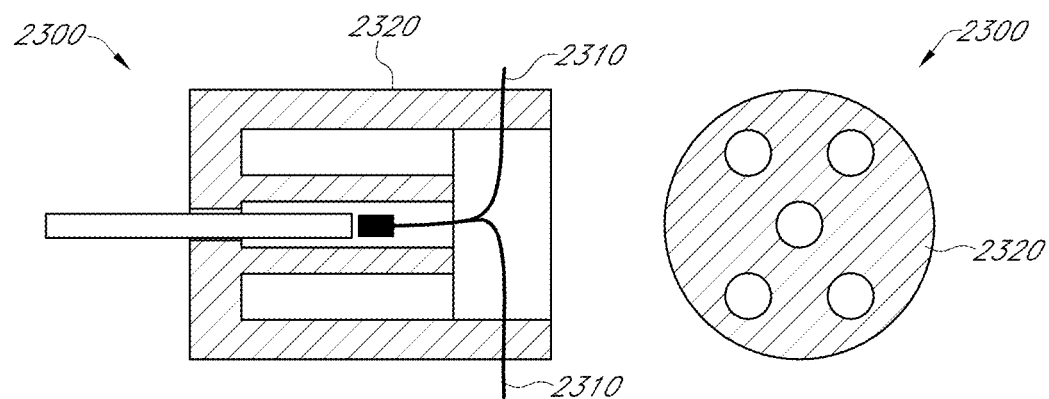
FIG. 67

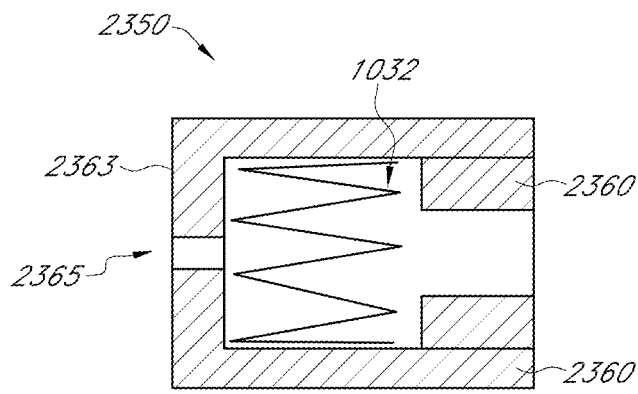 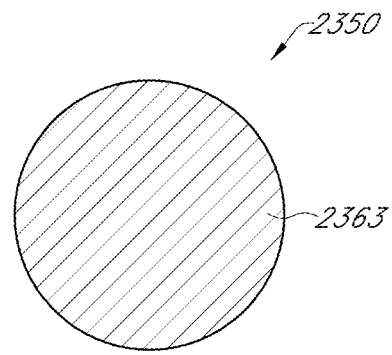
FIG. 68A  FIG. 68B
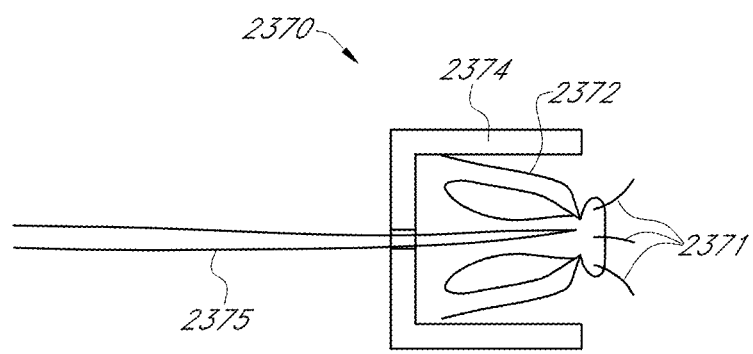
FIG. 69
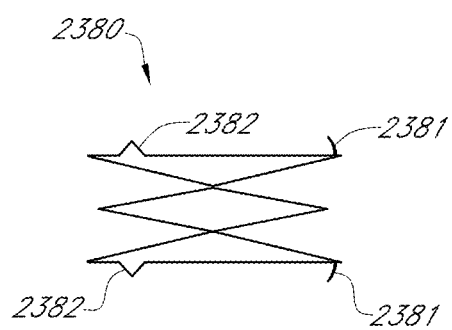 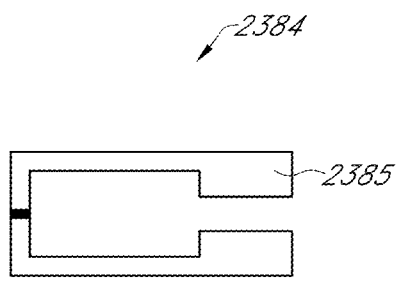
FIG. 70  FIG. 71

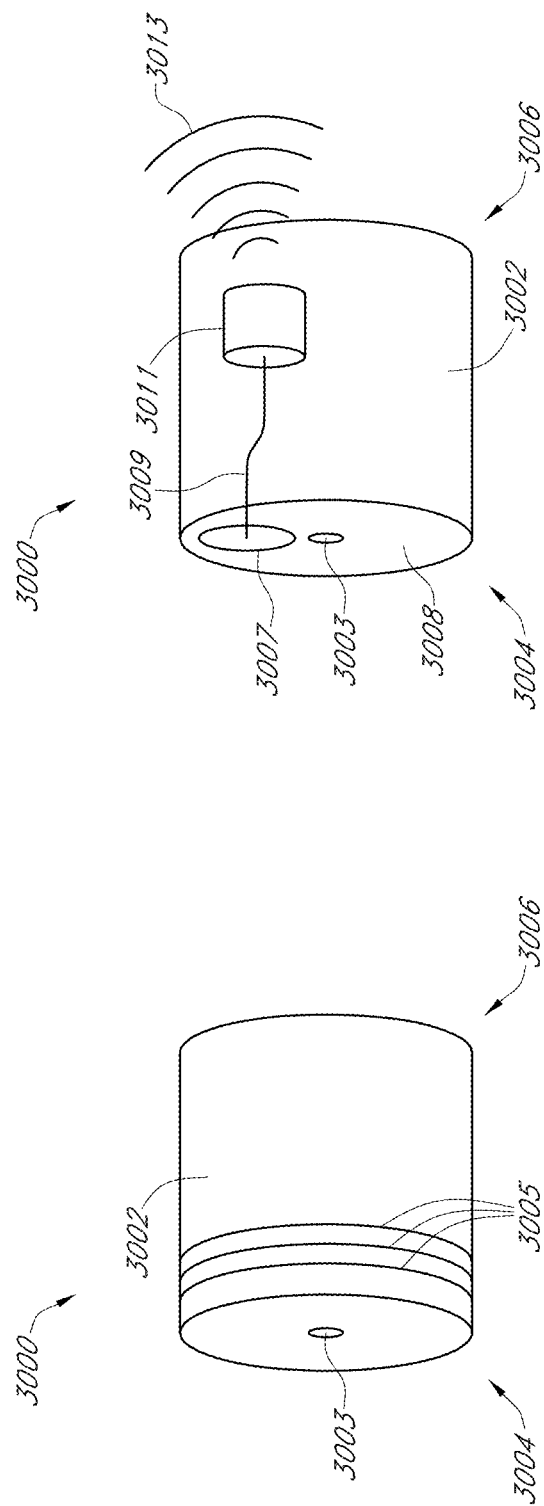

DEVICES AND METHODS FOR EXCLUDING THE LEFT ATRIAL APPENDAGE

INCORPORATION BY REFERENCE TO ANY RELATED APPLICATIONS

Any and all applications for which a foreign or domestic priority claim is identified in the Application Data Sheet as filed with the present application are hereby incorporated by reference under 37 CFR 1.57.

This application is a continuation in part of U.S. application Ser. No. 15/795,083, entitled DEVICES AND METHODS FOR EXCLUDING THE LEFT ATRIAL APPENDAGE and filed Oct. 26, 2017, which claims the benefit of priority to U.S. provisional patent application No. 62/459,503, entitled DEVICES AND METHODS FOR EXCLUDING THE LEFT ATRIAL APPENDAGE and filed Feb. 15, 2017, and to U.S. provisional patent application No. 62/413,632, entitled MULTIFUNCTIONAL LEFT ATRIAL APPENDAGE (LAA) OCCLUDER and filed Oct. 27, 2016, the disclosure of each of which is hereby incorporated by reference herein in its entirety for all purposes and forms a part of this specification.

BACKGROUND

Field

This development relates generally to systems, devices and methods for excluding the left atrial appendage (LAA). In particular, systems, devices and methods for excluding the LAA using an expandable foam implant with a deployable and compliant frame are described herein.

Description of the Related Art

Atrial fibrillation (Afib) is a condition in which the normal beating of the left atrium (LA) is chaotic and ineffective. The left atrial appendage (LAA) is a blind pouch off the LA. In patients with Afib blood stagnates in the LAA facilitating clot formation. These clots (or clot fragments) have a tendency to embolize or leave the LAA and enter the systemic circulation. A stroke occurs when a clot/clot fragment embolizes and occludes one of the arteries perfusing the brain. Anticoagulants, e.g. Coumadin, have been shown to significantly reduce the stroke risk in Afib patients. These drugs reduce clot formation but also increase bleeding complications including hemorrhagic strokes, subdural hematoma, and bleeding in the gastrointestinal tract.

There are about eight million people in the US and EU with Afib. About 4.6 million of these patients are at a high risk for stroke and would benefit from anticoagulation. A large portion of these patients cannot take anticoagulants due to an increased bleeding risk, leaving their stroke risk unaddressed. The prevalence of Afib increases with age.

Existing devices for occluding the LAA have drawbacks. Existing devices are offered in many sizes and must be closely matched to the highly variable LAA anatomy. This is difficult to do using fluoroscopy and often requires adjunctive imaging in the form of transesophageal echocardiography (TEE), cardiac CT and MRI, all with three dimensional reconstructions. If the device is significantly oversized, the LAA ostium may become overstretched leading to tearing, resulting in bleeding into the pericardial space. If the device is too small, it will not adequately seal the ostium and may be prone to embolization. Even if sized correctly, the device forces the oval LAA ostium to take the round shape of the device, often resulting in residual leakage at the edges due to poor sealing.

Existing devices require sufficient spring force or stiffness to seal and anchor to surrounding tissue. If too stiff, these devices may lead to leaking of blood through the tissue into the pericardial space which may lead to cardiac tamponade. Furthermore, the geometry of these devices limits repositioning once the implant is fully expanded. Existing devices also complicate delivery by requiring positioning in the LAA coaxial to the axis of the LAA.

There is therefore a need for an improved LAA occlusion device.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for left atrial appendage (LAA) occlusion.

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure.

Devices and methods are described for occluding the LAA (LAA) to exclude the LAA from blood flow to prevent blood from clotting within the LAA and subsequently embolizing, particularly in patients with atrial fibrillation. An LAA occlusion device is delivered via transcatheter delivery into the LAA and anchored using a compliant frame and foam body. The device conforms to the oval shape of the LAA with superior sealing effect, does not require an excessive number of sizes and thus negates the need for extensive pre-procedure imaging, and can be delivered off-axis thereby allowing for simpler delivery procedure, among other advantages.

A foam body, which can be tubular in shape, and a compliant frame inside or within the foam body, are described that are collapsed for delivery and then expand in place within the LAA. The foam body may have a coating at least partially on the outer surface(s) of the foam body. The coating may be a layer of Polytetrafluoroethylene (PTFE). The device is anchored by structural anchors of the frame and/or by tissue ingrowth from the left atrium (LA) and LAA into the foam. Some embodiments are additionally or alternatively anchored by independent or integrated repositionable anchors, by barbs, and/or by distal anchoring elements. For example, anchors extending from a compliant frame are described which deploy through the compressible foam plug. In some embodiments, repositionable atraumatic anchor system embodiments are also disclosed which can be independent structures or integral to the foam plug and/or skin.

The foam body may be at least partially covered by a proximal end cover. The cover may be an expanded Polytetrafluoroethylene (ePTFE) cover. The cover provides several advantages, such as the following: sufficiently strong to enable handling of the plugs without tearing; allow for repositioning and retrieval of the plugs; provides a thromboresistant surface within the LA which will encourage formation of a neointima; assist in the creation of occlusion zones designed to encourage thromboresistance and endothelialization from the blood and adjacent tissue and anchoring zones designed to promote fast and tenacious tissue ingrowth into the compressible implant from the adjacent non-blood tissue; and can assist in closure at the ostium. The cover, e.g. a layer, jacket or skin, etc., can be independent or can be attached to the foam body, for example with sutures, adhesives, etc. In some embodiments, retrieval finials can be attached at one or more points to aid in retrieval of an embolized device and to increase radiopacity.

Some embodiments are tracked over a guidewire and have a guidewire lumen within the foam that is expandable, to allow for placement of the guidewire, and then is self-closing upon removal of the guidewire. Some embodiments do not require a guidewire lumen. Further, some embodiments may be multi-functional and include features for ablation, pressure-sensing, drug-elution, pacing, electrical isolation, etc.

In one aspect, a left atrial appendage occlusion device comprises a tubular foam body and a cover. The tubular foam body extends axially from a proximal end to a distal end. The cover includes at least a portion that covers the proximal end. The portion that covers the proximal end includes a series of openings therethrough. The foam and cover are configured to allow for a flow rate of water axially through the device of at least four liters per minute, with the water at about sixty-eight degrees Fahrenheit (F) and an upstream pressure of about twenty-five millimeters of Mercury (mmHg).

Various embodiments of the various aspects may be implemented. In some embodiments, the body may include a compressible side wall extending between the proximal end and the distal end and defines a central cavity. The left atrial appendage occlusion device may further comprise an expandable support coupled with the body and configured to compress the side wall against a wall of a left atrial appendage. The foam body may include a proximal face having an area, and the series of openings in the cover may collectively provide an open area that is at least five percent of the area of the proximal face. The open area may be at least ten percent of the area of the proximal face. The open area may be at least fifteen percent of the area of the proximal face. The flow of water may be along a flow axis, and the tubular foam body may extend axially along a device axis. The device axis may be angled with respect to the flow axis by at least thirty degrees. The device may be configured to allow for an off-axis flow rate of water through the device of at least four liters per minute, with the water at about sixty-eight degrees Fahrenheit (F) and an upstream pressure of about twenty-five millimeters of Mercury (mmHg). The off-axis flow may be at least thirty degrees from the axial flow.

In another aspect, a left atrial appendage occlusion device comprises a tubular foam body and a cover. The tubular foam body extends axially from a proximal end to a distal end. The cover includes at least a portion that covers the proximal end. The portion that covers the proximal end includes a series of openings therethrough. The foam body includes a proximal face at the proximal end having an area. The series of openings in the cover collectively provide an open area that is at least five percent of the area of the proximal face.

Various embodiments of the various aspects may be implemented. In some embodiments, the open area may be at least ten percent of the area of the proximal face. The open area may be at least fifteen percent of the area of the proximal face. The foam and cover may be configured to allow for a flow rate of water axially through the device of at least four liters per minute, with the water at about sixty-eight degrees Fahrenheit (F) and an upstream pressure of about twenty-five millimeters of Mercury (mmHg). The body may include a compressible side wall extending between the proximal end and the distal end and define a central cavity. The left atrial appendage occlusion device may further comprise an expandable support coupled with the body and configured to compress the side wall against a wall of a left atrial appendage.

In another aspect, a method of loading a left atrial appendage occlusion device into a delivery catheter is described. The method comprises positioning a proximal end of a loading body adjacent a distal end of the delivery catheter, the loading body having a sidewall defining a channel therethrough with a distal opening at a distal end that is larger than a proximal opening at the proximal end. The method further comprises retracting the left atrial appendage occlusion device proximally through the loading body to thereby radially compress the device, the device comprising a foam body, and receiving the device into the distal end of the delivery catheter.

Various embodiments of the various aspects may be implemented. In some embodiments, the loading body may comprise a frustoconical portion. The loading body may define a central longitudinal axis, and the sidewall may extend at an angle of at least five degrees with respect to the longitudinal axis. The sidewall may extend at an angle of at least ten degrees with respect to the longitudinal axis. The sidewall may extend at an angle at least fifteen degrees with respect to the longitudinal axis The sidewall may define a total angle of at least ten degrees, at least twenty degrees, or at least thirty degrees. The advancing step may comprise pulling a tether proximally through the delivery catheter. The device may be radially compressed within a delivery catheter having an outer diameter of no more than fifteen French. An inner surface of the loading body may be substantially smooth. The method may comprise radially compressing the device to a radial compressed width within the delivery catheter that is no more than twenty percent of a radially uncompressed width of the device. The radial compressed width within the delivery catheter may be no more than fifteen percent of the radially uncompressed width of the device.

In another aspect, a left atrial appendage occlusion device comprises a foam body, an expandable support and at least one anchor. The foam body has a tubular sidewall with a radial uncompressed thickness. The expandable support is coupled with the body. The at least one anchor is coupled with the support and extends through the sidewall when the foam of the sidewall is compressed, and where the at least one anchor has a radial height no greater than the radial uncompressed thickness of the sidewall.

Various embodiments of the various aspects may be implemented. In some embodiments, the device may define a central axis and the at least one anchor may be angled relative to the central axis. The at least one anchor may extend radially outward in a proximal direction at an angle of at least twenty degrees relative to a portion of the central axis that extends proximally to the device. The angle may be at least thirty degrees. The at least one anchor may extend through a radially-compressed portion of the sidewall having a radial thickness less than the radial uncompressed thickness. The left atrial appendage occlusion device may further comprise an attachment that connects the support to the sidewall and radially compresses the sidewall at the radially-compressed portion. The device may further comprise a proximal cover that covers at least a portion of a proximal face of the foam body.

In another aspect, a left atrial appendage occlusion device comprises a foam body, an expandable support and at least one anchor. The foam body has a tubular sidewall comprising at least one first portion having a first radial thickness and at least one second portion having a second radial thickness that is less than the first radial thickness. The expandable support is coupled with the body. The least one anchor is coupled with the support and extends at least partially through the at least one second portion of the sidewall.

Various embodiments of the various aspects may be implemented. In some embodiments, the device may define a central axis and the at least one anchor may be angled relative to the central axis. The at least one anchor may extend radially outward in a proximal direction at an angle of at least twenty degrees relative to the central axis. The angle may be at least thirty degrees. The at least one anchor may extend through the at least one second portion of the sidewall such that a portion of the at least one anchor extends outwardly beyond an outer surface of the at least one second portion of the sidewall. The at least one anchor may have a length equal to the radial uncompressed thickness of the tubular sidewall. The support may comprise a tubular frame portion configured to expand radially outward to compress the sidewall against a wall of a left atrial appendage after implantation of the device. The device may further comprise a proximal cover that covers at least a portion of a proximal face of the foam body.

In another aspect, a left atrial appendage occlusion device comprises a tubular foam body and an expandable support coupled with the body. The device is configured to insert into a non-cylindrical opening of a test body having a non-cylindrical profile, expand radially within the non-cylindrical opening, and conform to the non-cylindrical profile at least at the opening of the test body.

Various embodiments of the various aspects may be implemented. In some embodiments, the device may be configured to conform to the non-cylindrical profile at least at the opening of the test body and leave no radial gaps between the device and the test body opening that are greater than five millimeters. The device may leave no radial gaps that are more than four, three, two and/or one millimeter. The device may be configured to insert into a non-cylindrical opening of a test body having a non-cylindrical profile with a size and shape substantially similar to that of a native left atrial appendage. The device may be configured to insert into a non-cylindrical opening of a test body having a radial stiffness substantially similar to that of a native left atrial appendage and to assume a non-cylindrical profile at least at the opening of the test body after a period of at least thirty days, of at least sixty days, and/or of at least one hundred twenty days. The device may further comprise at least one anchor coupled with the frame and extending at least partially into the tubular foam body.

In some embodiments, the foam body may include a compressible side wall extending between a proximal end and a distal end and define a central cavity. The left atrial appendage occlusion device may further comprise an expandable support coupled with the foam body and configured to compress the side wall against an inner surface of the test body.

In another aspect, a left atrial appendage occlusion device comprises a tubular foam body and an expandable support coupled with the body. The device has a radial uncompressed width. The device is configured to compress radially to a radial compressed width that is no more than fifty percent of the radial uncompressed width.

Various embodiments of the various aspects may be implemented. In some embodiments, the radial compressed width may be no more than forty percent of the radial uncompressed width. The tubular foam body may extend along a longitudinal axis, and the radial uncompressed width may extend along a diameter of the foam body that is perpendicular to the longitudinal axis.

In another aspect, a left atrial appendage occlusion device comprises a tubular foam body and an expandable support coupled with the body. The device extends axially from a proximal end to a distal end, and the proximal end has a radial uncompressed width. The distal end is configured to compress radially to a radial compressed width that is no more than fifty percent of the radial uncompressed width of the proximal end.

Various embodiments of the various aspects may be implemented. In some embodiments, the distal end may be configured to compress radially to a radial compressed width that is no more than forty percent of the radial uncompressed width of the proximal end. The radial compressed width may be no more than thirty percent, no more than twenty percent, no more than ten percent, and/or no more than five percent, of the radial uncompressed width of the proximal end.

In another aspect, a left atrial appendage occlusion device comprises a tubular foam body and an expandable support coupled with the body. The device has an axial uncompressed length. The device is configured to compress axially to an axial compressed length that is no more than fifty percent of the axial uncompressed length.

Various embodiments of the various aspects may be implemented. In some embodiments, the axial compressed length may be no more than forty percent of the axial uncompressed length. The axial uncompressed length may extend from a proximal end of the foam body to a distal end of the foam body.

In another aspect, a left atrial appendage occlusion device is described. The device comprises a conformable, tubular foam body, a compressible side wall and an expandable support. The conformable, tubular foam body has a closed proximal end and a distal end. The compressible side wall extends between the proximal end and the distal end, and defines a central cavity. The expandable support is within the body and configured to compress the side wall against a wall of a left atrial appendage.

In some embodiments, the side wall may have an uncompressed thickness of at least about 0.5 mm. The compressible side wall may have an uncompressed thickness of at least about 1.5 mm. The compressible side wall may have an uncompressed thickness of about 2.5 mm. The compressible side wall may extend in a distal direction beyond a distal end of the support by at least about 2 mm in an unconstrained, expanded state. The compressible side wall may extend in a distal direction beyond a distal end of the support by about 5 mm in an unconstrained, expanded state. The compressible side wall may comprise a foam having a plurality of interconnected reticulations and voids, and further comprising a PTFE coating on at least some of the interconnected reticulations. The closed proximal end may comprise a foam end wall. The foam end wall may further comprise a cover. The cover may comprise ePTFE. The expandable support may be self-expandable. The expandable support may be in the central cavity. The tubular foam body may be substantially cylindrical in an unconstrained, expanded state.

In another aspect, a self-expandable, atraumatic occlusion device is described. The device is configured to conform to the side wall of a left atrial appendage. The device comprises a compressible open cell foam body, a self-expandable support and a proximal end wall. The compressible open cell foam body has a tubular foam side wall and a central cavity. The expandable support is within the cavity. The proximal end wall is on the foam body. The proximal end wall is positioned proximally of the proximal end of the support, and the foam side wall extends distally beyond the distal end of the support to form a distal, atraumatic bumper for preventing contact between the support and a wall of the left atrial appendage in an implantation in which a central longitudinal axis of the occlusion device is non-parallel to a primary longitudinal axis of the left atrial appendage.

In another aspect, a left atrial appendage occlusion device is described. The device comprises an expandable tubular foam cup and an expandable frame. The expandable tubular foam cup has a proximal end, a distal end, a tubular side wall and a proximal end wall. The side wall has a thickness of at least about 1.0 mm and a porosity of at least about 85% open void content. The expandable frame is configured to press the side wall into conforming contact with a wall of the left atrial appendage.

In some embodiments, the tubular side wall may have a thickness of at least about 2 mm. The tubular side wall may have a void content of at least about 90%. The tubular side wall may have an average pore size of at least about 100 microns. The tubular side wall may have an average pore size of at least about 200 microns. The tubular side wall may be provided with a thromboresistant coating. The thromboresistant coating may comprise PTFE. The proximal end wall may be provided with a thromboresistant cover. The frame may further comprise at least three recapture struts inclining radially inwardly in the proximal direction to a hub. The frame may comprise a plurality of axially extending side wall struts, with adjacent pairs of side wall struts joined at an apex. The frame may comprise at least six proximally facing apexes and at least six distally facing apexes. Each recapture strut may be joined to a unique proximally facing apex on the frame. The recapture struts may be integrally formed with the frame. The device may further comprise a lumen through the hub. The device may further comprise anchors to secure the device to tissue. The anchors may be flexible anchors configured to extend through the foam side wall at an inclined angle.

In another aspect, a conformable LAA occlusion device is described. The device comprises a compressible tubular foam wall. The wall comprises a reticulated, cross linked matrix having at least about 90% void content, an average cell size within the range of from about 250-500 microns, a wall thickness of at least about 2 mm and a compressive strength of at least about 1 psi. In some embodiments, the compressive strength is within a range of from about 1 psi to about 2 psi. In some embodiments, the device may have an expandable support configured to compress the side wall against a wall of a left atrial appendage.

In another aspect, a LAA occlusion device is described. The device includes an open cell foam body and an internal locking system. The body has a proximal end, a distal end and an outer skin. The proximal end is configured to face a left atrium and the distal end is configured to face the LAA following implantation in the LAA. The body can be compressed for delivery within a delivery catheter and can self-expand when removed from the delivery catheter. The internal locking system is coupled with the body and comprises at least one deployable tissue anchor. The deployable anchor is configured to deploy from a constrained configuration within the body to a deployed configuration where a tissue engaging segment of the anchor extends outside the body to secure the body within the LAA. The deployable anchor is configured to deploy to the deployed configuration after the body expands within the LAA. The deployable anchor may be retractable from the deployed configuration to a retracted configuration within the body.

In some embodiments, the internal locking system further comprises a plurality of the deployable anchors rotatably coupled with the body, wherein the plurality of anchors are configured to rotate to the deployed and retracted configurations. The internal locking system may comprise four of the deployable anchors. In some embodiments, the body further comprises a plurality of axially extending slots corresponding to the plurality of anchors, wherein each of the plurality of anchors is configured to deploy and retract through the corresponding axial slot.

In some embodiments, the internal locking system further comprises a restraint that restrains the anchor in the constrained configuration, and the anchor is deployed from the constrained configuration to the deployed configuration by removing the restraint from the anchor. The restraint may be a sheath that restrains the anchor in the constrained configuration by covering the anchor, wherein the anchor is deployed from the constrained configuration to the deployed configuration by removing the sheath from covering the anchor. The restraint may be a lasso that restrains the anchor in the constrained configuration by surrounding the anchor, and the anchor is deployed from the constrained configuration to the deployed configuration by removing the lasso from surrounding the anchor.

In some embodiments, the internal locking system further comprises a moveable mount coupled with an end of the anchor, and the anchor is deployed from the constrained configuration to the deployed configuration by axially moving the mount.

In some embodiments, the internal locking system further comprises a constraint configured to move over the anchor to cause the anchor to retract. The constraint may be a ring configured to slide over the anchor to cause the anchor to retract.

In some embodiments, the skin comprises ePTFE.

In some embodiments, the device further comprises at least one tissue ingrowth surface on a sidewall of the body.

In some embodiments, the device further comprises a plurality of openings in the skin to permit tissue ingrowth into the open cell foam body. The plurality of openings of the skin may be located in an anchoring region of the device located at least between the proximal and distal ends of the device, and the device may further comprise an occlusion region located at the proximal end of the device and configured to encourage thromboresistance and endothelialization from the blood and adjacent tissue.

In another aspect, a LAA closure system is described. The system comprises a delivery catheter and a LAA occlusion device. The delivery catheter comprises an elongate flexible tubular body, having a proximal end and a distal end and at least one lumen extending therethrough. The LAA occlusion device is configured to be compressed within the delivery catheter and to self-expand upon deployment from the delivery catheter. The device comprises a self-expandable open cell foam body coupled with an internal locking system. The internal locking system comprises a deployable anchor configured to deploy from a constrained configuration to a deployed configuration after the body expands within the LAA and is configured to retract from the deployed configuration to a retracted position within the body.

In some embodiments, the system further comprises an axially movable deployment control extending through a lumen of the body, for deploying the deployable anchor. The system may further comprise an axially movable deployment control extending through a lumen of the body, for deploying the foam body from the distal end of the closure system. The internal locking system may further comprise a restraint that restrains the anchor in the constrained configuration, and the anchor is actively deployed from the constrained configuration to the deployed configuration by removing the restraint from the anchor using an axially movable deployment control extending through a lumen of the body. The internal locking system may further comprise a moveable mount coupled with an end of the anchor, and the anchor is actively deployed from the constrained configuration to the deployed configuration by axially moving the mount using an axially movable deployment control extending through a lumen of the body.

In another aspect, a method of excluding a LAA is described. The method comprises advancing a guidewire into the LAA, advancing a distal end of a delivery catheter over the guidewire and into the LAA, and deploying a LAA occlusion device from the distal end of the delivery catheter. The device comprises an expandable foam body coupled with an internal locking system having a deployable anchor, and the body expands within the LAA upon deploying from the distal end of the delivery catheter. The method further comprises actively deploying the deployable anchor after the body expands within the LAA. The deployable anchor is configured to retract from the deployed configuration to a retracted position within the body. In some embodiments, the method further comprises retracting the deployable anchor from the deployed configuration to the retracted position.

In another aspect, a LAA occlusion device is described. The device comprises an expandable foam body and an internal locking system. The body can be compressed for delivery within a delivery catheter and can self-expand when removed from the delivery catheter. The internal locking system is coupled with the body and comprises a deployable anchor configured to deploy from a constrained configuration within the body to a deployed configuration where the anchor extends outside the body to secure the body within the LAA. The body is configured to expand upon removal from the delivery catheter, and the deployable anchor is configured to deploy to the deployed configuration after the body expands.

In another aspect, a LAA occlusion device is described. The device comprises an expandable foam body and an internal locking system. The body can be compressed for delivery within a delivery catheter and can self-expand when removed from the delivery catheter. The internal locking system is coupled with the body and comprises a deployable anchor configured to deploy from a constrained configuration within the body to a deployed configuration where the anchor extends outside the body to secure the body within the LAA. The deployable anchor is configured to retract from the deployed configuration to a retracted configuration within the body such that the body can be repositioned within the LAA.

In another aspect, a LAA occlusion device is described. The device comprises an expandable tubular frame, an expandable tubular foam layer and a tissue scaffold. The expandable tubular frame has a proximal end, a distal end and a central lumen. The expandable tubular foam layer is carried by the frame and has a thickness of at least about 0.5 mm. The emboli retention layer is carried by the frame and encloses the lumen at the proximal end.

In some embodiments, the foam layer may have a thickness of at least about 1 mm. The foam layer may have a thickness of at least about 2.5 mm. The foam layer may have a void content of at least about 80%. The foam layer may have a void content of at least about 90%. The foam layer may have an average pore size of at least about 100 microns. The foam layer may have an average pore size of at least about 200 microns. The foam layer may extend across the proximal end of the frame to form the tissue scaffold. The tissue scaffold may be provided with a thromboresistant coating. The tissue scaffold may be provided with a thromboresistant layer. The thromboresistant coating or layer may comprise PTFE. The thromboresistant coating or layer may comprise ePTFE. The frame may further comprise at least three recapture struts inclining radially inwardly in the proximal direction to a hub.

In some embodiments, the foam layer extends across the proximal end of the frame to form the tissue scaffold, and the frame may comprise a plurality of axially extending side wall struts, with adjacent pairs of side wall struts joined at an apex. The device may comprise at least six proximally facing apexes and at least six distally facing apexes. The device may comprise at least three recapture struts joined at a proximal hub, where each recapture strut has a distal end joined to the frame. Each recapture strut may be joined to a unique proximally facing apex on the frame. The recapture struts may be integrally formed with the frame. The device may further comprise a lumen through the hub.

In some embodiments, the device may comprise anchors to secure the device to tissue. The anchors may be static anchors that are configured to deploy upon deployment of the device from a delivery catheter. The anchors may be constrained anchors that are configured to be controllably released into a deployed configuration after expansion of the foam. The anchors may be dynamic anchors that are configured to be deployed from a contracted configuration to a deployed configuration and are further configured to be retracted from the deployed configuration back to a retracted configuration. The anchors may be further configured to be retracted from the deployed configuration back to the contracted configuration.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIGS. 7-15 are sequential schematic cross section views of an embodiment of an LAA and delivery system showing delivery and anchoring techniques that may be used with the various LAA occlusion devices described herein, including but not limited to the devices of FIGS. 85A-90D.

FIGS. 29A-29B are sequential side views of an unlocking mechanism that may be used with the device of FIGS. 27A-27G.

FIGS. 39A-39B are perspective views of an embodiment of a deployable anchor that may be used with the various LAA occlusion devices described herein, including but not limited to the devices of FIGS. 85A-90D.

FIGS. 43A-43C are sequential side views of an embodiment of a deployment constraint that may be used with the various LAA occlusion devices described herein, including but not limited to the devices of FIGS. 85A-90D.

FIGS. 44A-44C are side views of an embodiment of an adjustable two stage anchor system that may be used with the various LAA occlusion devices described herein, including but not limited to the devices of FIGS. 85A-90D.

FIGS. 66A-66C are side views of the implant of FIG. 45A having a proximal cover.

FIG. 67 shows side and end views of an embodiment of an implant having grappling hook anchors.

FIGS. 68A-68B are side and end views respectively of an embodiment of an implant having a thicker distal bumper.

FIG. 69 is a side view of an embodiment of an implant having a constrained anchor deployed in a secondary step.

FIGS. 70-72 depict embodiments of an implant having distal anchors and proximal speed bumps.

FIG. 78 is a side view of an embodiment of an LAA occlusion device having ablative features that may be incorporated with the various LAA occlusion devices described herein.

FIG. 79 is a side view of an embodiment of an LAA occlusion device having pressure-sensing features that may be incorporated with the various LAA occlusion devices described herein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

The devices and related methods are described herein in connection use in occluding, i.e. excluding, a LAA (LAA). The various figures show various embodiments of LAA occlusion devices, systems and methods for delivery of the LAA occlusion devices, and/or methods of using the device to occlude a LAA. The various systems, devices and methods described herein may include the same or similar features and/or functionalities as other LAA occlusion systems, devices and methods as described, for example, in U.S. application Ser. No. 14/203,187 entitled "DEVICES AND METHODS FOR EXCLUDING THE LAA" and filed on Mar. 10, 2014, and/or as described in U.S. Provisional Application No. 62/240,124 entitled "DEVICES AND METHODS FOR EXCLUDING THE LAA" and filed on Oct. 12, 2015, the entire disclosure of each of which is incorporated herein by reference for all purposes and forms a part of this specification.

Some embodiments of an LAA occlusion device 3000 include a foam body 3002, a deployable and compliant frame 3040, and a proximal cover 3100, as primarily shown and described for example with respect to FIGS. 85A-90D. Other features and functionalities that the device 3000 may include and employ are shown and described with respect to FIGS. 1-84 and 91-93B.

Figure 1:
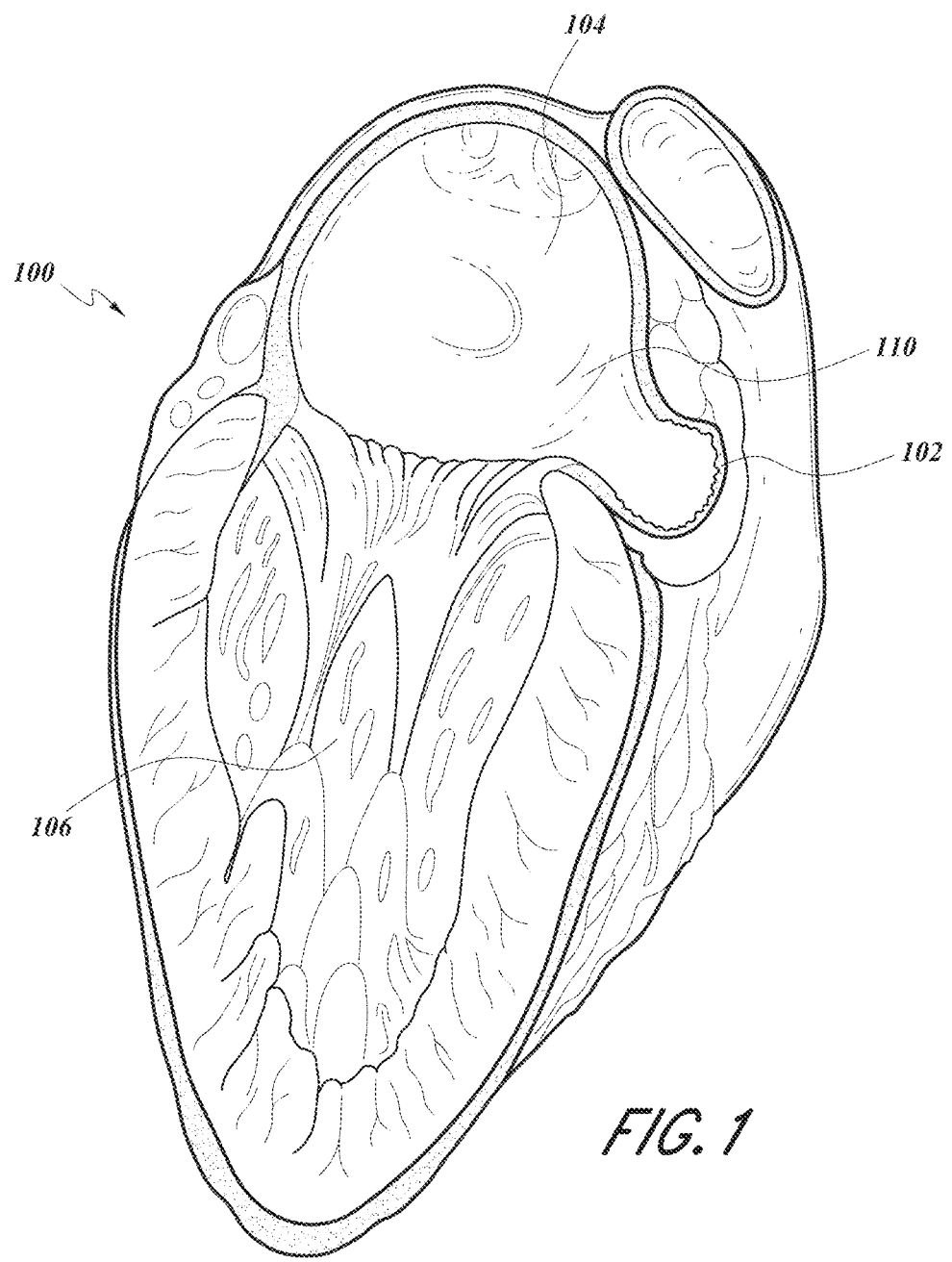
FIG. 1 shows the anatomy of the left atrium (LA) and left atrial appendage (LAA).

The heart 100 is shown in FIG. 1 with the left atrial appendage (LAA) 102, which is a cavity emanating from the left atrium (LA) 104. The LAA 102 is quite variable in shape in all dimensions. If the heart is not beating normally, a condition called atrial fibrillation, blood within the LAA becomes stagnant which promotes clot formation. If blood clots within the LAA, the clots may pass from the LAA 102 to the LA 104, to the left ventricle 106 and out of the heart 100 into the aorta. Vessels that bring blood to the brain branch off the aorta. If the clot passes to the brain via these vessels, it may get stuck and occlude a small vessel in the brain which then causes an ischemic stroke. Strokes have severe morbidities associated with them. The opening of the LAA 102 to the LA 104 is called an ostium 110. The ostium 110 is oval, highly variable and dependent on loading conditions, i.e., left atrial pressure. An object of the LAA occlusion devices described herein is to occlude the ostium 110 thereby sealing off the LA 104 from the LAA 102.

Figure 2:
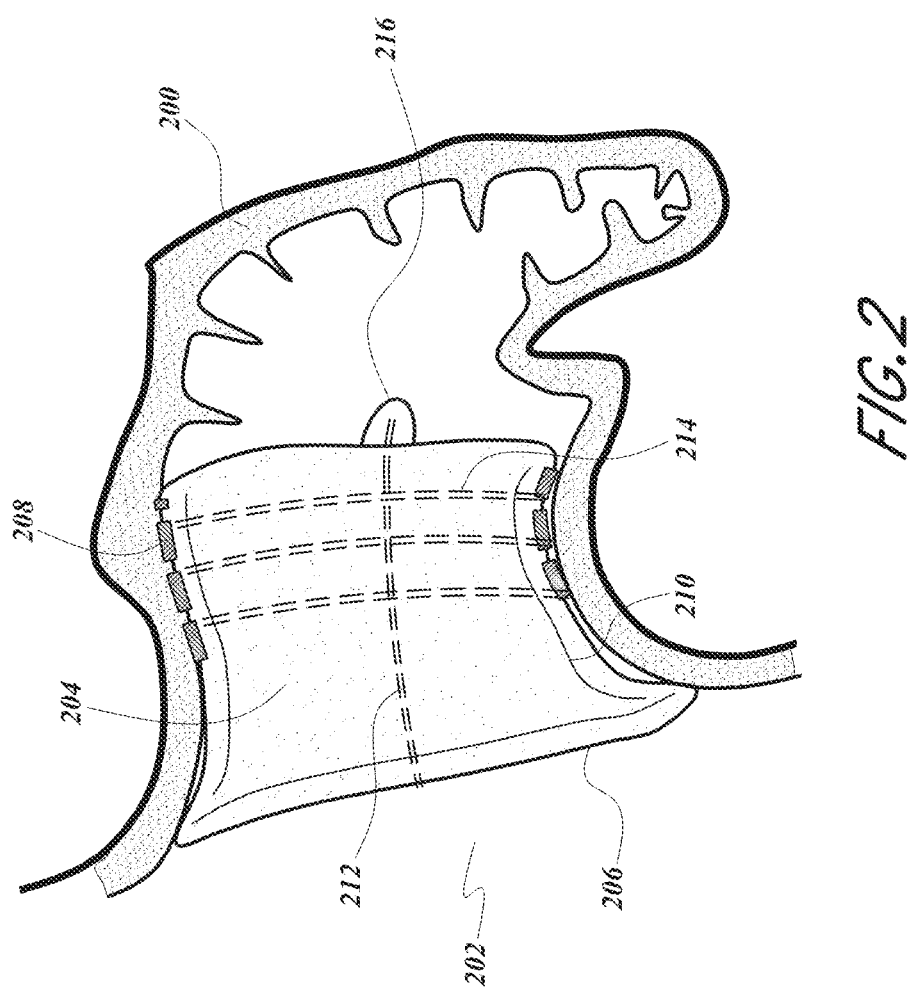
FIG. 2 shows an LAA with an embodiment of an LAA occlusion device implanted in the LAA and that uses adhesive.

One embodiment of an LAA occlusion device is shown in FIG. 2. The occlusion device or plug 204 is placed within the LAA 200 at its opening to the LA 202. It is understood that the "plugs" described herein, such as the plug 204, may have the same or similar features as other implantable "devices" or "implants" described herein, such as the device 10, device 1020, device 3000, foam body 3002, etc., and vice versa. The plug 204 comprises an expandable media such as an open cell foam which enables collapse and expansion of the plug 204 and also to enhance ingrowth of tissue into the foam. The foam plug 204 is at least partially encapsulated within a thin strong layer 206 such as ePTFE (expanded polytetrafluoroethylene), polyolefin or polyester. The layer 206 may be referred to herein as a "skin" or "cover" and the like. Alternatively, bioabsorbable materials could be utilized such as PLA, PGA, PCL, PHA, or collagen. This thin encapsulating layer 206 can be oriented or otherwise modified to be elastomeric in at least one direction, such as radially. The layer 206 may have the same or similar features and/or functionalities as the cover 3100, and vice versa.

The plug 204 may be made of polyurethane, polyolefin, PVA, collagen foams or blends thereof. One suitable material is a polycarbonate-polyurethane urea foam with a pore size of 100 µm-250 µm or 250 µm-500 µm and 90-95% void content. The foam could be non-degradable or use a degradable material such as PLA, PGA, PCL, PHA, and/or collagen. If degradable, the tissue from the LAA will grow into the foam plug and replace the foam over time. The plug 204 may be cylindrical in shape in an unconstrained expansion, but it may also be conical for example with its distal end smaller than the proximal end or reversed. It could also be oval in cross section to better match the opening of the LAA.

The foam plug 204 is oversized radially in an unconstrained expansion to fit snuggly into the LAA and may be 5-50 mm in diameter depending on the diameter of the target LAA. In a free, unconstrained state, the axial length "L" of the plug is less than its outer diameter "D" such that the L/D ratio is less than 1.0. In some embodiments, this ratio may be greater than 1.0. The compliance of the foam material is designed such that it pushes on the walls of the LAA with sufficient force to maintain the plug 204 in place but without overly stretching the LAA wall. The foam and/or skin also conforms to the irregular surfaces of the LAA as it expands, to provide a complementary surface structure to the native LAA wall to further enhance anchoring and promote sealing. Thus, the expandable foam implant described herein conforms to the native configuration of the LAA. In one embodiment, the structure of the foam may be fabricated such that squeezing axially on the opposing ends of the foam causes the foam to increase in diameter.

Figure 3:
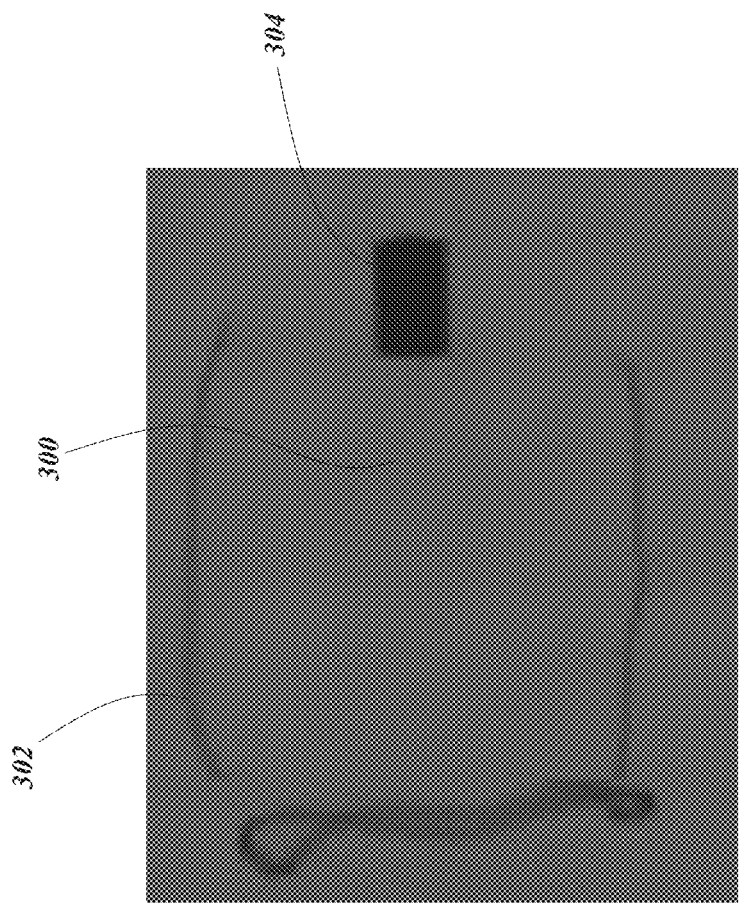
FIG. 3 shows an x-ray image of an embodiment of an LAA occlusion device.

The ePTFE or foam material may be provided with one or two or more radiopaque markers such as radiopaque threads 210 or be filled with or impregnated with a radiopaque filler such as barium sulfate, bismuth subcarbonate, or tungsten which permit the operator to see under x-ray the plug for proper positioning in the anatomy. An x-ray image is shown in FIG. 3 where one cannot see a foam plug 300 but can clearly see threads 302 and a crimp 304 (discussed below). This thread 302 or ribbon may be made from a radiopaque metallic wire or tube such as platinum, platinum-iridium or tungsten or a polymer with a radiopaque filler such as barium, bismuth, tantalum, tungsten, titanium or platinum.

An outer ePTFE layer may be formed from a tube with a diameter about the same diameter of the foam plug and a wall thickness between about 0.0001" and about 0.001" thick and serves to allow one to collapse and pull on the plug 204 without tearing the foam material. The ePTFE material also serves as the blood contacting surface facing the LA 206 and has pores or nodes such that blood components coagulate on the surface and an intimal or neointimal covering of tissue grows across it and anchors tightly to the material. Pore sizes within the range of from about 4µ to about 110µ, ideally 5-35µ are useful for formation and adherence of a neointima.

The outer covering 206 may be constructed of materials other than ePTFE such as woven fabrics, meshes or perforated films made of FEP, polypropylene, polyethylene, polyester or nylon. The covering 206 should have a low compliance (non-elastic), at least longitudinally, be sufficiently strong as to permit removal of the plug, a low coefficient of friction, and be thromboresistant. The outer covering 206 serves as a matrix to permit plug removal as most foams are not sufficiently strong to resist tearing when pulled. The plug 204 can also be coated with or contain materials, such as PTFE. Such materials may enhance the plug's 204 ultrasonic echogenic profile, thromboresistance, and/or lubricity. The plug 204 can also be coated with or contain materials to facilitate echocardiographic visualization, promote cellular ingrowth and coverage.

The outer covering 206 has holes in it to permit contact of the LAA tissue with the foam plug 204 to encourage ingrowth of tissue into the foam plug pores and/or allow blood flow therethrough. These holes may be 1 to 5 mm in diameter or may also be oval with their long axis aligned with the axis of the foam plug, the length of which may be 80% of the length of the foam plug and the width may be 1-5 mm. The holes may be as large as possible such that the outer covering maintains sufficient strength to transmit the tensile forces required for removal. The holes may be preferentially placed along the device. In one embodiment, holes are placed distally to enhance tissue ingrowth from the LAA wall.

Figure 20:
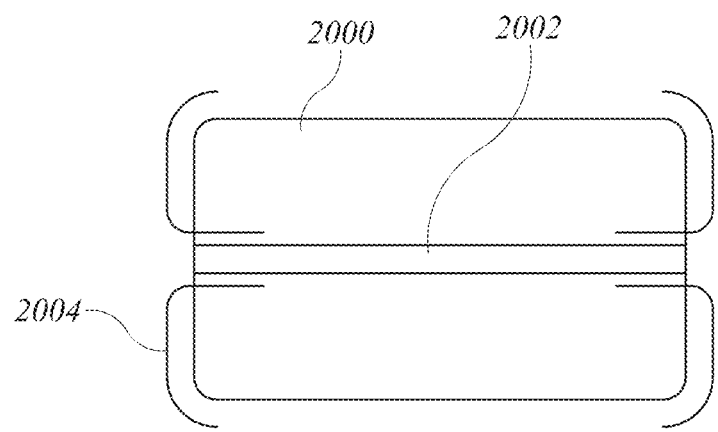
FIG. 20 is a side cross section view of an embodiment of an LAA occlusion device having proximal and distal caps.

In one implementation, the implant is provided with proximal and/or distal end caps of ePTFE, joined together by two or three or four or more axially extending strips of ePTFE. The axially extending strips are spaced apart from each other circumferentially, to provide at least two or three or four or more laterally facing windows through which the open cell foam body will be in direct contact with the tissue wall of the LAA. This outer covering could be a mesh or netting as well. As shown in FIG. 20, the covering 2004 is only on the proximal and distal faces of the plug 2000. They may be glued to the foam plug and then crimped to the center tube 2002.

The implantable plug 204 or devices 10, 1020, 3000 (as described below) may be anchored and secured in place in the LAA by tissue ingrowth and/or with additional anchoring features. In some embodiments, the plug 204 or devices 10, 1020, 3000 may be anchored by tissue ingrowth alone.

Figure 21:
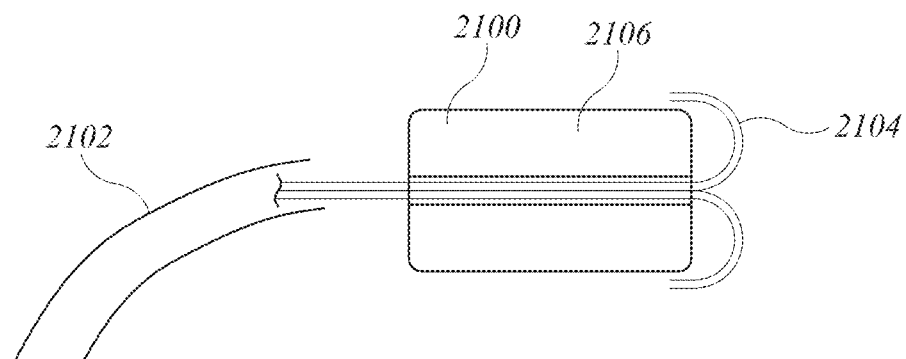
FIG. 21 is a schematic of an embodiment of an implant delivery system that may be used with the various LAA occlusion devices described herein, including but not limited to the devices of FIGS. 85A-90D.

In some embodiments, other anchoring means may be implemented. One means of adhering the foam plug in place within the LAA is to use an adhesive, such as a low viscosity cyanoacrylate (1-200 cps). The adhesive is injected into place along the sidewall near the distal end of the foam plug 208. Holes in the ePTFE covering permit the adhesive to interact between the foam plug 204 and the LAA wall 200. Injection of the adhesive may be accomplished with several means, one of which is to inject through the catheter into the center lumen 212. Passages 214 serve to guide the adhesive to the correct location. The distal end of the foam plug may be restricted at that time to prevent the adhesive from exiting the distal crimp 216. Alternatively, FIG. 21 shows tubes 2104 that are pre-placed through the guide catheter 2102, through the center lumen of the plug 2106 and bend backwards in the LAA to the distal end of the plug 2100. These tubes 2104 pass all the way to the proximal end of the guide catheter 2102 where a fitting is attached to permit injection of the adhesive which then exits the small tubes 2104 at the desired location of the plug. These tubes are made of polyethylene, polypropylene or FEP so that the adhesive will not adhere to the tubes. The tubes 2104 are withdrawn after injection through the guide catheter out of the patient.

Other one part adhesives including aqueous cross linking adhesives, polyurethane, PEG, PGA, PLA, polycaprolactone or a lycine-derived urethane may be used. In addition, these adhesives may be made in two components such that one component is adherent to the foam and the second injected in vivo. Also, these two component adhesives may be injected simultaneously to mix in vivo to prevent fouling of injection tubes.

Figure 4:
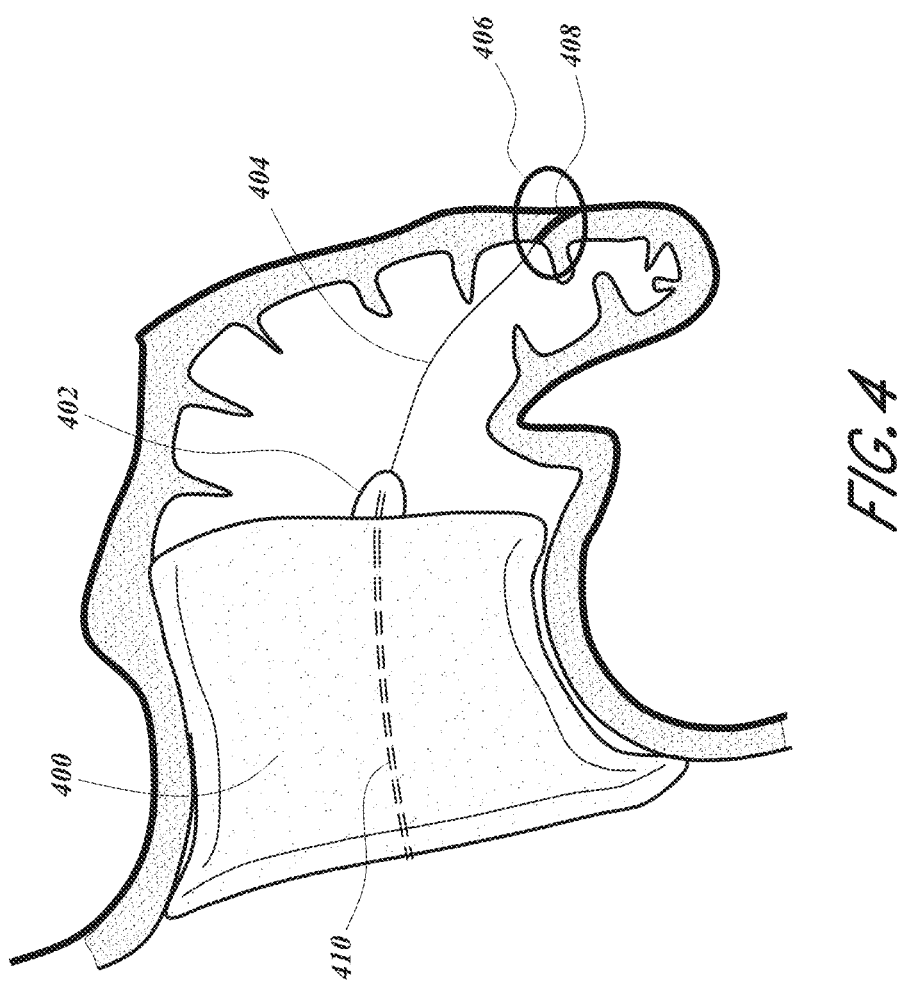
FIG. 4 shows an LAA with an embodiment of an LAA occlusion device and distal anchor implanted in the LA.
Figure 5:
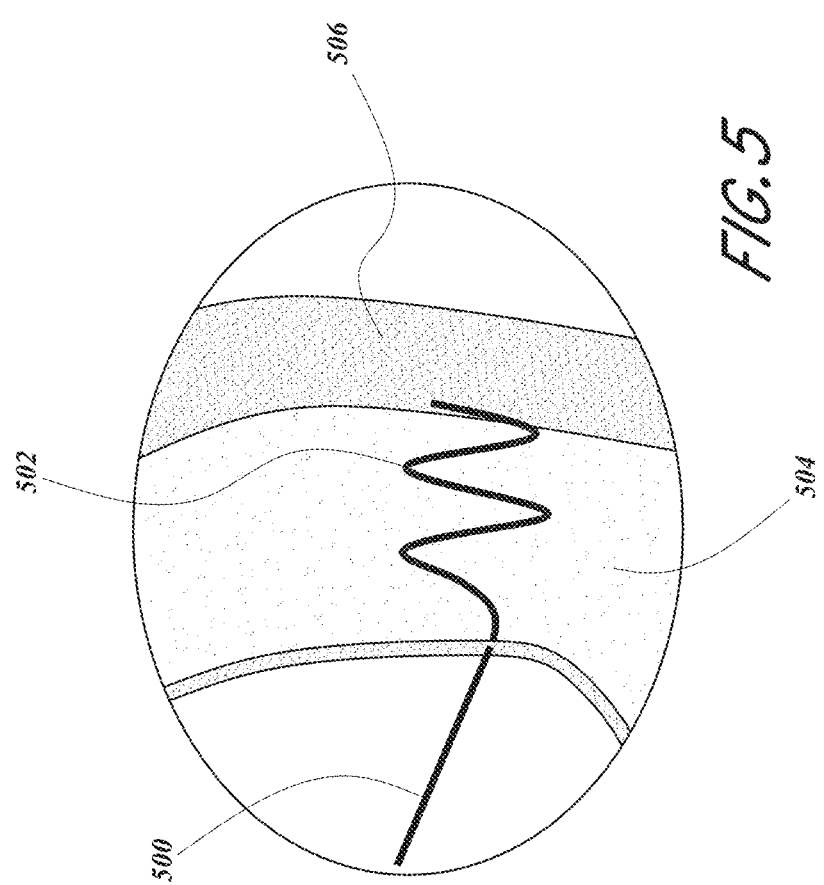
FIG. 5 shows an embodiment of a screw anchor that may be used with the various LAA occlusion devices described herein.

An alternative anchoring means for plug 400 or device 3000, etc. is one or two or more distal anchors as shown in FIG. 4. A wire 404 is passed through a center lumen 410 into the LAA and attached to the distal wall of the LAA. In this case, a screw wire 408 is threaded into the wall of the LAA 406. A closer detail of this is seen in FIG. 5 as screw 502 is shown embedded into the LAA wall 504 but not all the way through the epicardial surface 506.

Additional means of anchoring include the use of a plurality of hooks or barbs or graspers to grab the distal wall and baskets, malecots, distal foam plugs and Nitinol wire birds nests that open within the LAA and push outward on the wall or engage the protrusions of the LAA. It may be desirable to place the plug then engage the anchor as a secondary step. One such embodiment could include a multitude of nitinol wires with a ball or catch welded proximal to the anchor tip. These could be gathered with the delivery catheter then released when the ideal plug position has been confirmed.

Figure 6:
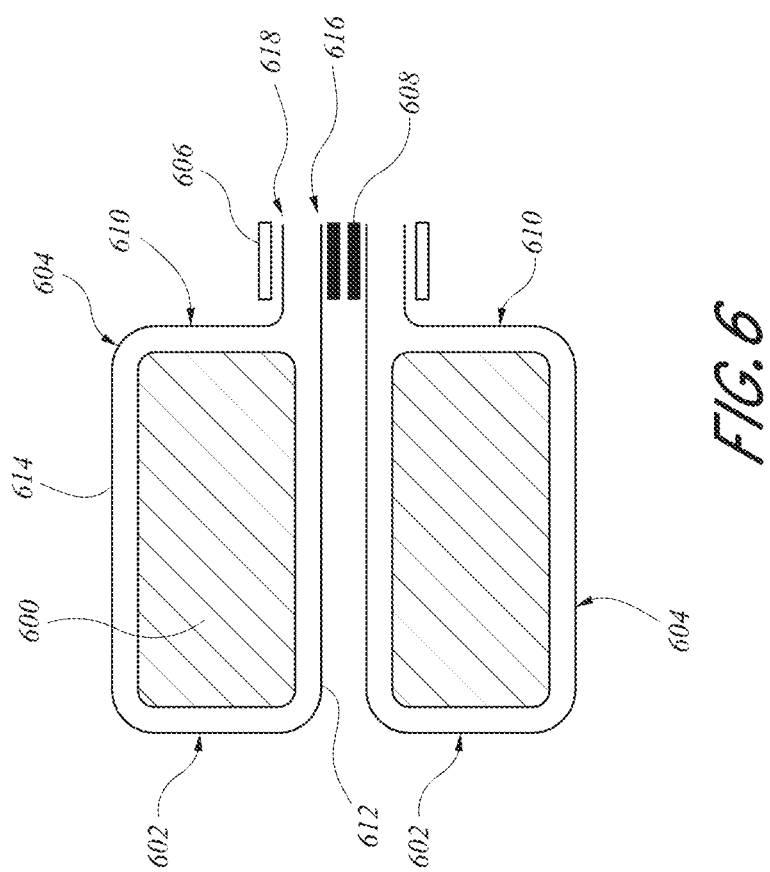
FIG. 6 shows a longitudinal cross section of an embodiment of an LAA occlusion device.
Figure 7:
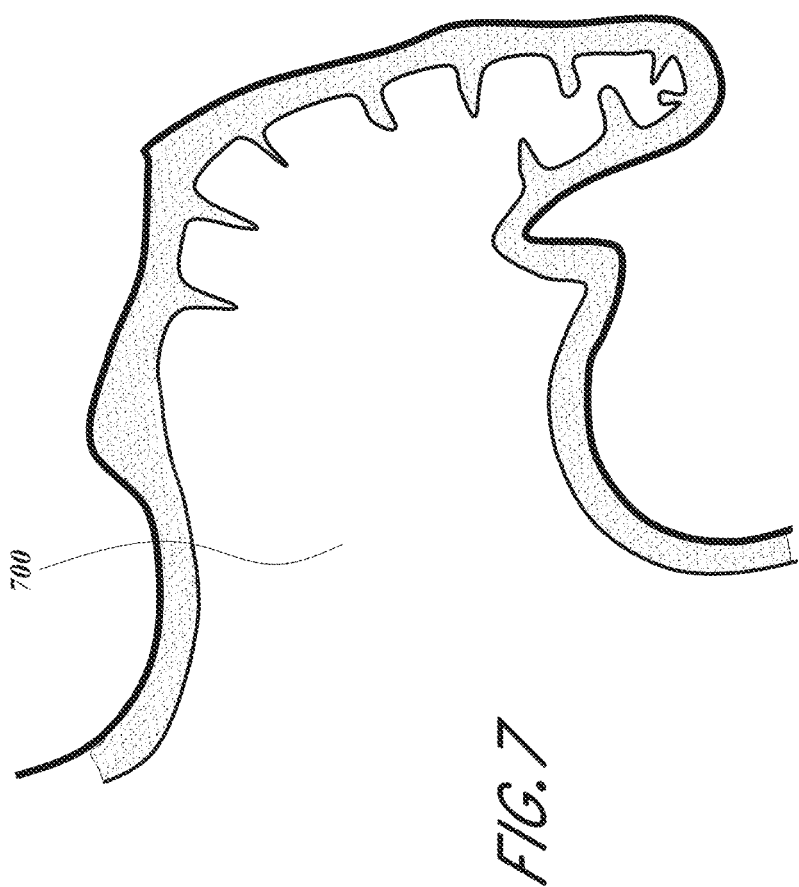
Figure 9:
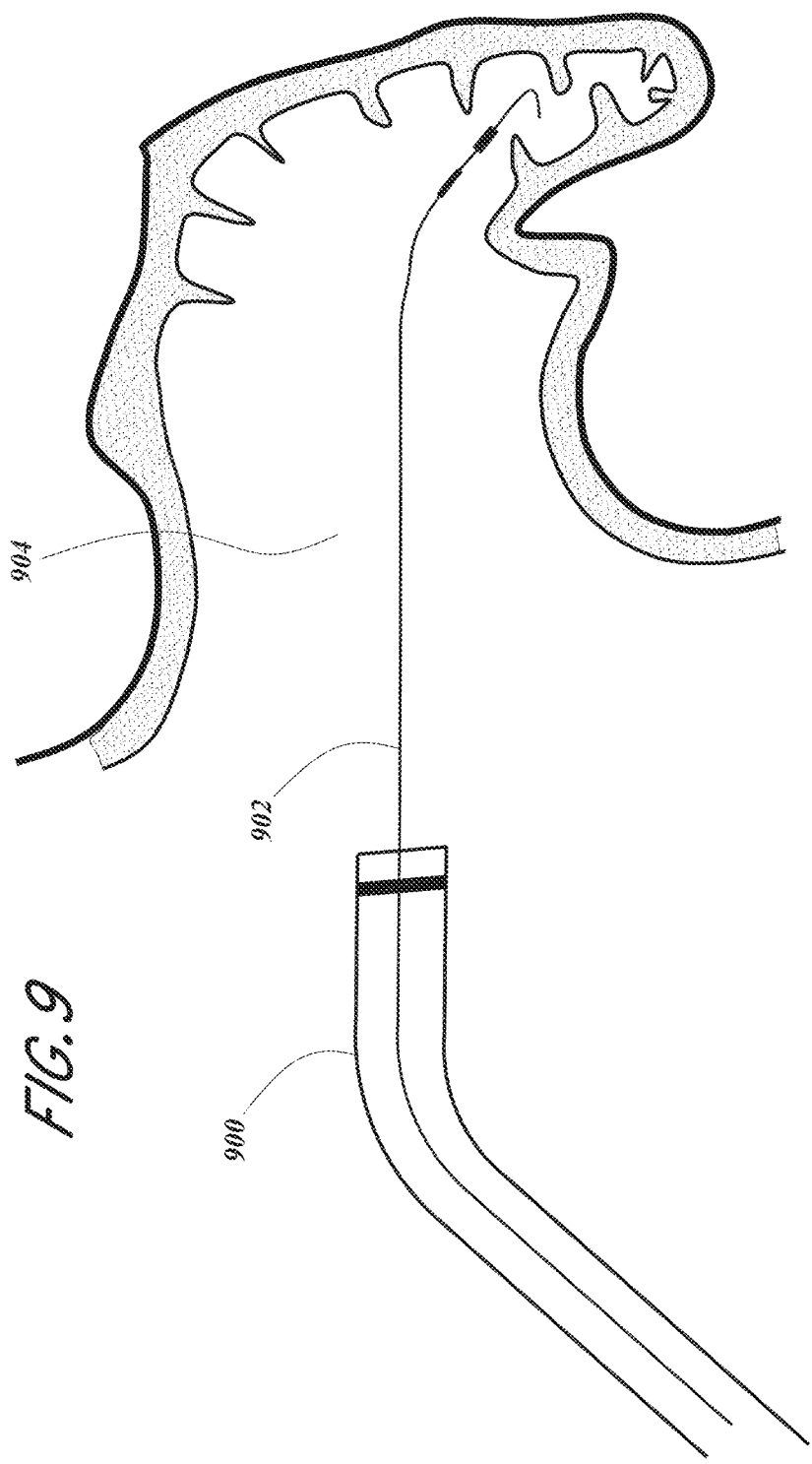
Figure 10:
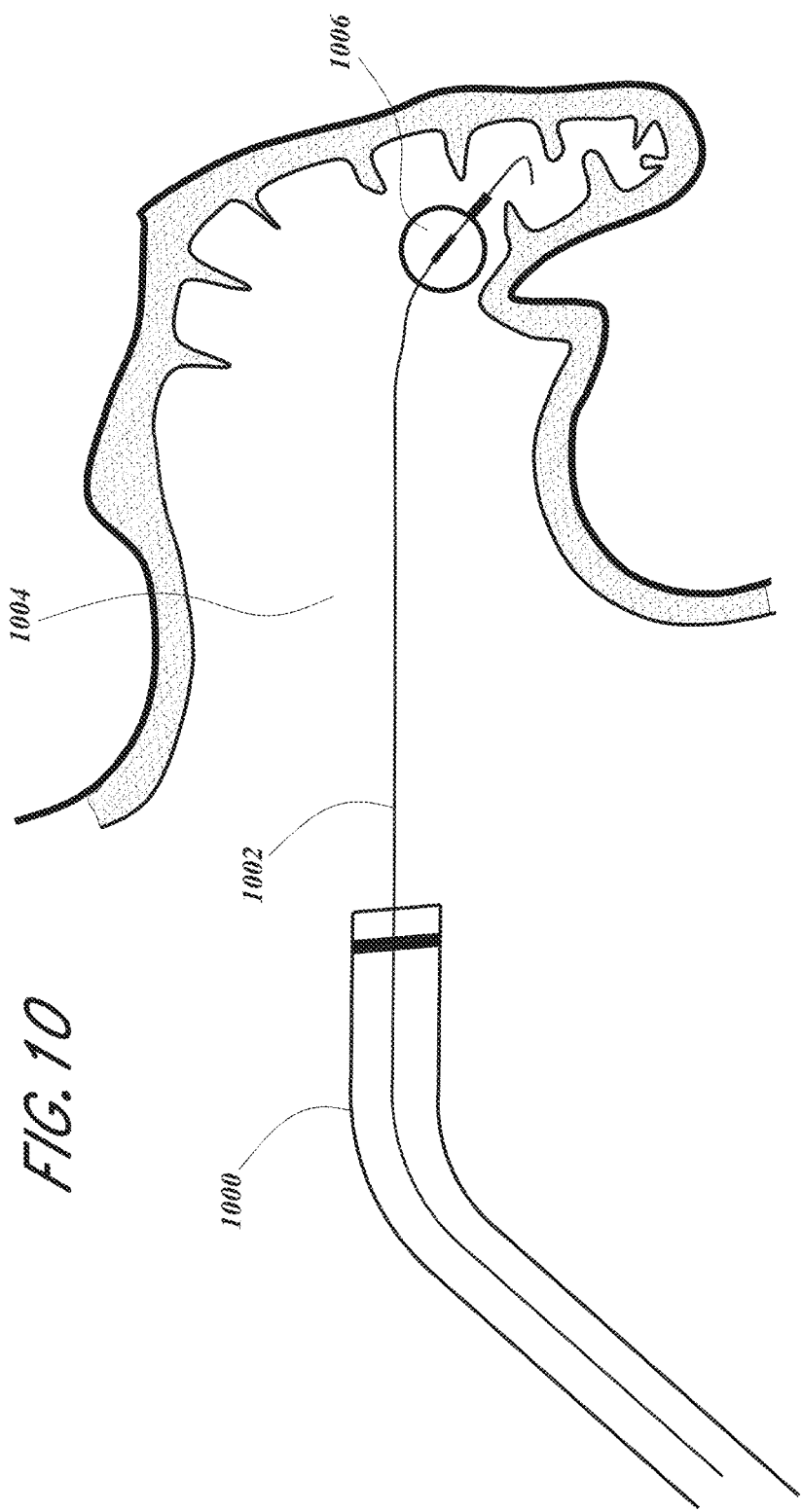
Figure 11:
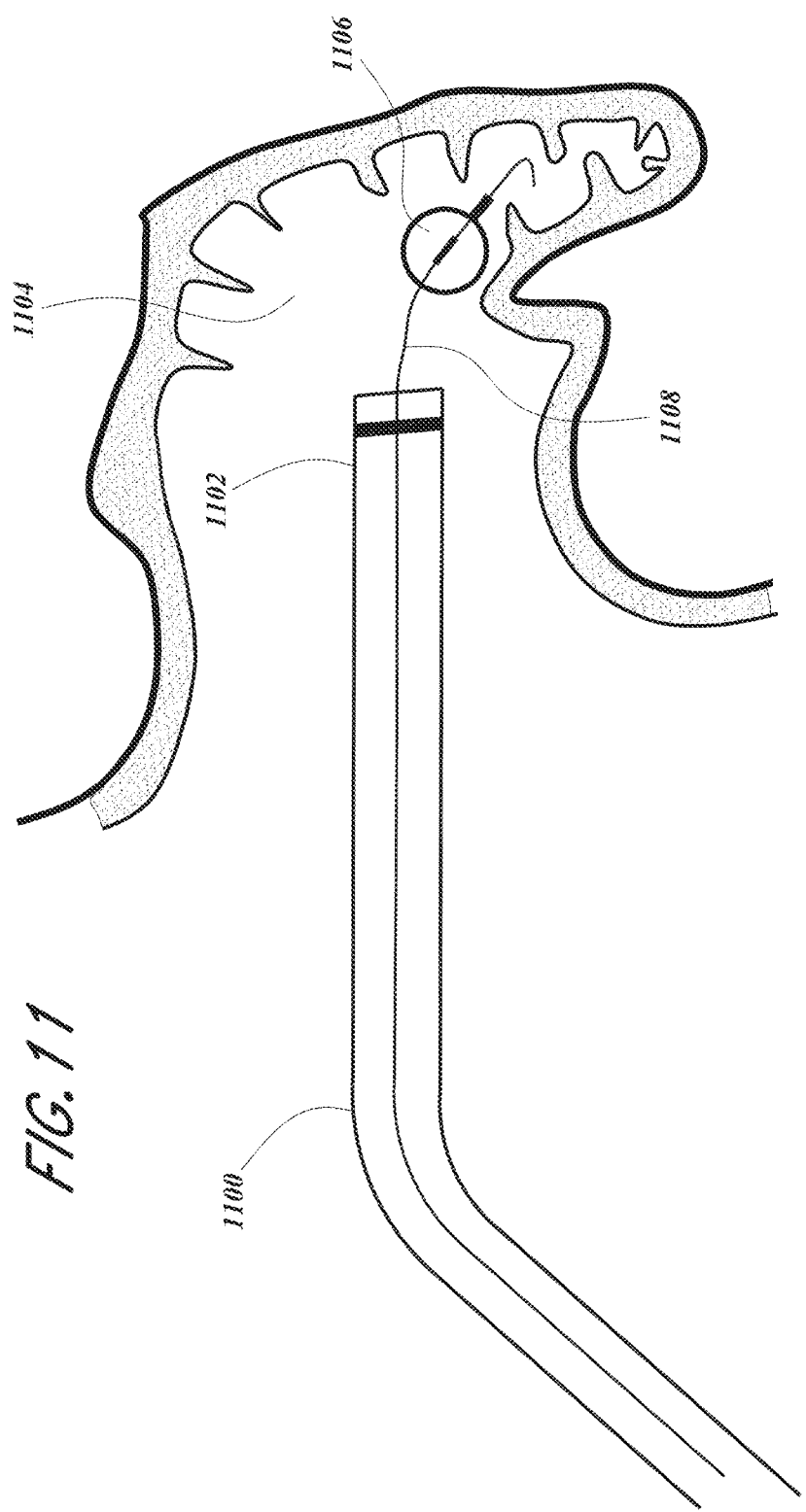

A cross section of one embodiment is shown in FIG. 6 with foam plug 600 and the LA face 602 and the LAA face 610. The ePTFE material 604 encapsulates the foam plug 600 and its open ends are connected with an attachment structure such as a wire, suture or tubular crimp 606 over an inner tube 608. The inner tube 608 may be made of an implant grade stainless steel such as 304 or 316 grades or a cobalt-chromium alloy such as MP35n and the crimp 606 may be made of annealed 304 or 316 stainless steel or a cobalt-chromium alloy such as MP35n. This crimp also serves as an element which can be snared should the device need to be removed.

Referring to FIG. 6, the tubular ePTFE layer 604 extends along an inner layer 612 which lines the guidewire lumen, and everts out around the left atrial face 602 to form outer layer 614. In some embodiments, the layer 604 may cover the entire proximal face and/or part of the sidewall, such as the cover 3100 or the cover over proximal face 1064', as further described herein. As further shown in FIG. 6, a first end 616 of inner layer 612 is disposed concentrically within a second end 618 of outer layer 614. The first end 616 and second end 618 are clamped between inner tube 608 and outer crimp 606. In this manner, the implant can be encapsulated in a manner that presents a seamless left atrial face 602, and preserves the integrity of the guidewire lumen with inner tube 608.

An embodiment of a technique for placement of an LAA occlusion device is shown in FIGS. 7 through 15. To close the LAA, the LA is first accessed from the venous system. One approach is to use a Brockenbrough-style needle to puncture the atrial septum to access the LA from the right atrium (RA). The basic needle-puncture technique is performed obtaining venous access typically via the right femoral vein. A Mullins sheath and dilator are then tracked over a 0.025" or 0.032" guidewire previously placed in the superior vena cava (SVC). Fluoroscopic and echocardiographic imaging, such as transesophageal echo (TEE) or intracardiac echo (ICE), are typically utilized. If echo is not utilized, it is common to also place a pigtail catheter in the aortic root to define the location of the aortic valve, a step not necessary when using echo.

Once the Mullins sheath and dilator are in the SVC, the guidewire is removed and a trans-septal needle is placed through the dilator. The needle contains a stylette to prevent skiving off of polymeric material from the dilator lumen as it traverses to the tip. Once the needle is near the dilator tip, the stylette is removed and the needle is connected to a manifold and flushed. The Mullins sheath/dilator set and the needle (positioned within the dilator tip) are retracted into the SVC toward the RA as a unit. As the system is withdrawn down the wall of the SVC into the RA and positioned in the fossa ovale, the preferred puncture location.

Once proper position in the fossa ovale is observed, the needle is advanced across the fossa ovale into the LA. Successful trans-septal puncture can be confirmed by echo, pressure measurement, $O_2$ saturation and contrast injection. Once the needle position is confirmed to be positioned in the LA, the sheath and dilator can be advanced over it into the LA. In some cases, the user will first pass a guidewire through the needle into the LA and into an upper pulmonary vein (typically the left) prior to crossing. Alternative options include the use of radiofrequency trans-septal needles, which are useful for crossing very thick or hypertrophic septa, or the use of a safety wire placed through the needle and utilized for the initial puncture.

Referring to FIGS. 8 through 15, a guide catheter 802 is placed through the femoral vein into the right atrium of the heart and across the intra-atrial septum into the LA as described above and positioned near the LAA ostium 804. A guidewire 902 usually of 0.035" diameter is placed through guide catheter 900 and into the LAA 904. This guidewire 1002 may have attached to its distal end a balloon 1006 which is inflated in the LAA and serves as a bumper to prevent guide catheter 1100 from perforating the wall of the LAA. The guide catheter 1100 is then advanced over the guidewire 1108 into the LAA 1104. A radiopaque marker 1102 is used to guide catheter placement under fluoroscopy.

Figure 13:
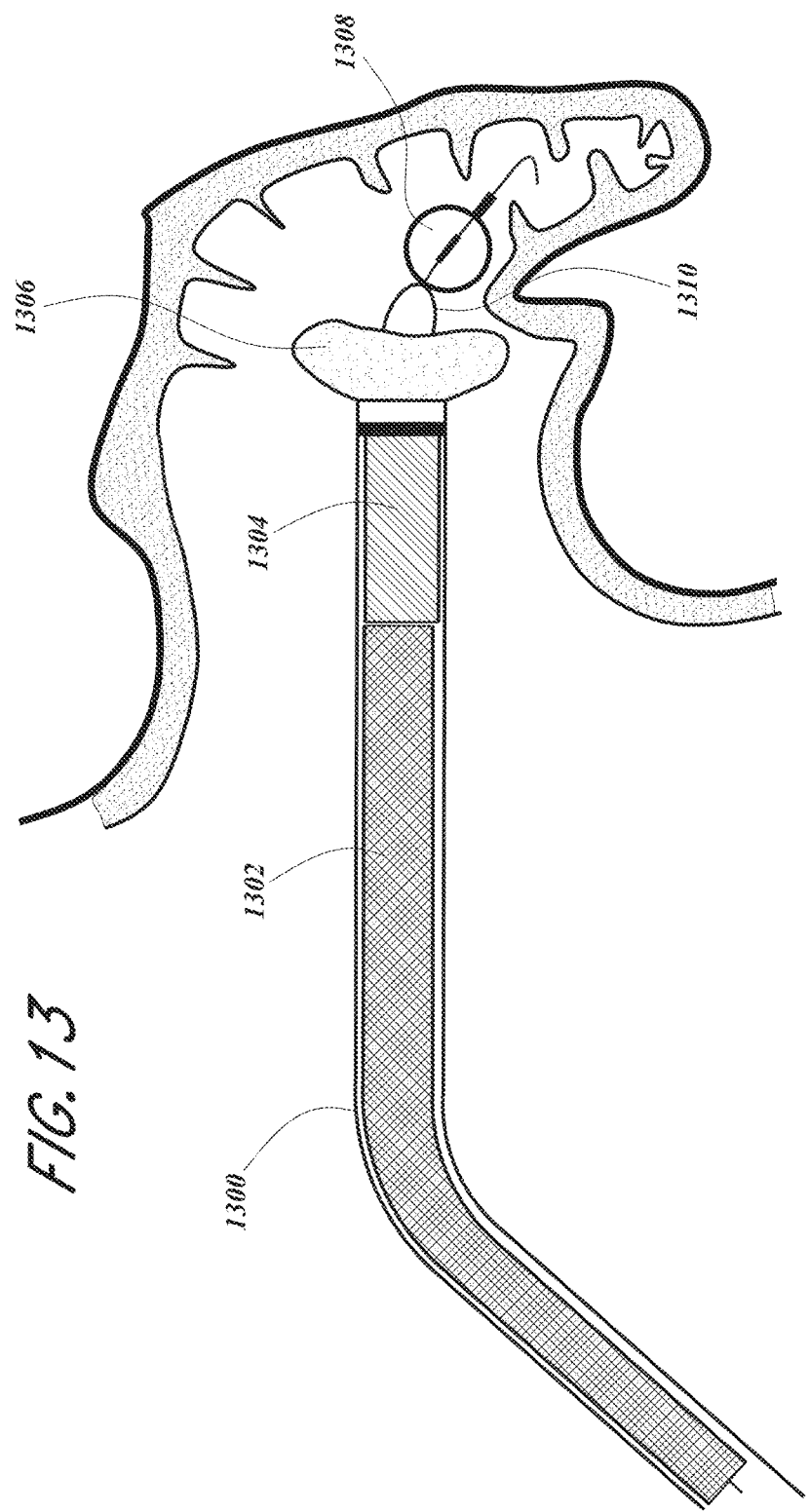
Figure 14:
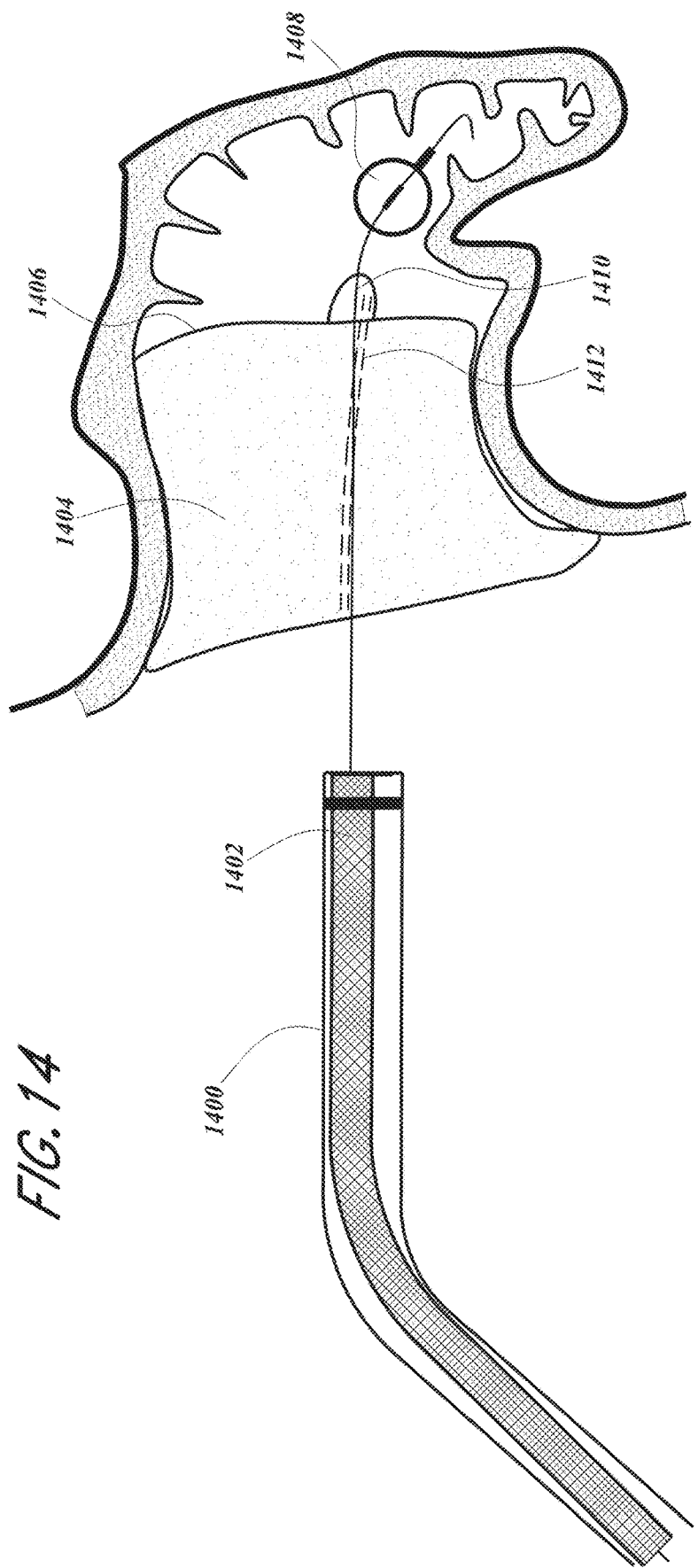
Figure 15:
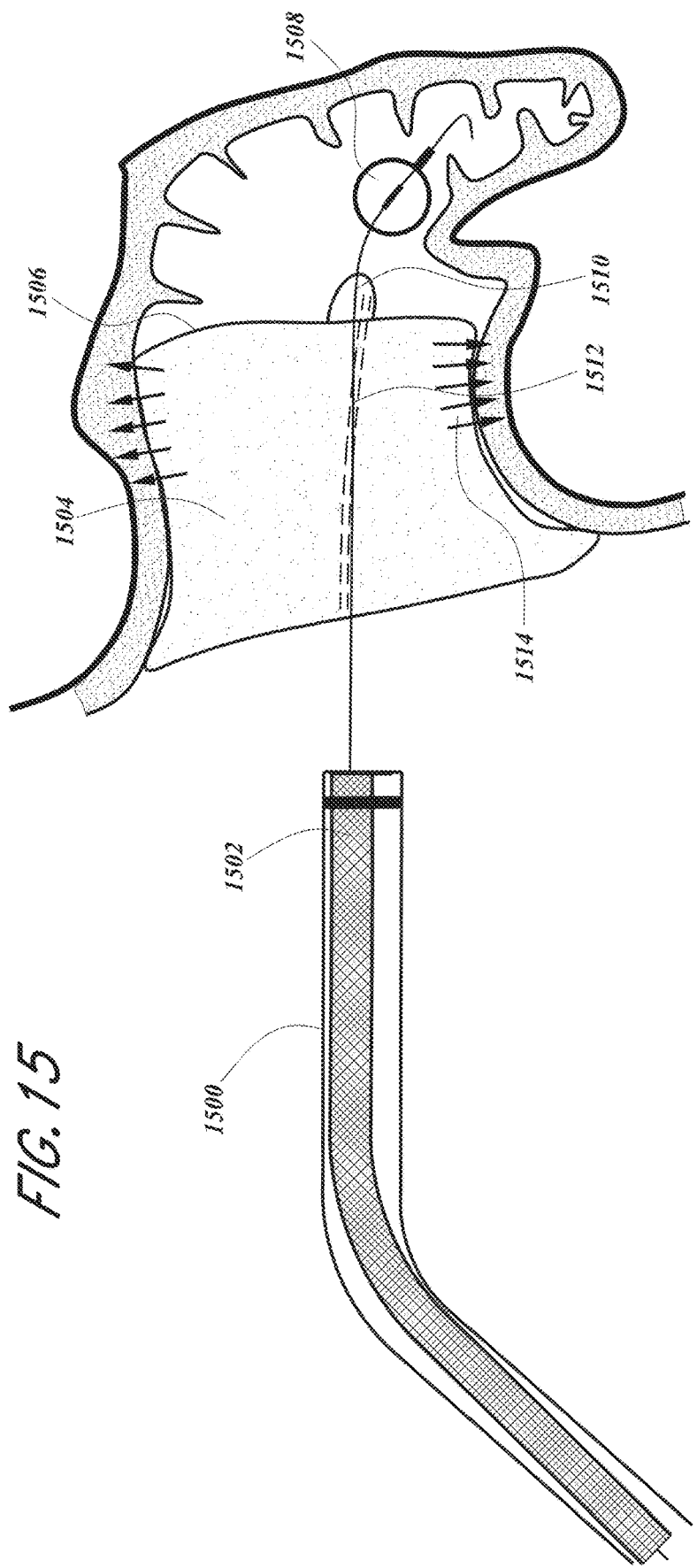

The foam plug 1204 is then pushed through the guide catheter 1200 with pusher 1202 and is shown exiting the guide catheter 1300 slowly in FIG. 13 until it is fully deployed as shown in FIG. 14. The foam plug 1404 position may then be adjusted in place using the distal balloon 1408 and the guide catheter 1400, sliding the foam plug proximally by pulling on the balloon 1408 through shaft 1412 or sliding it distally by pushing guide catheter 1400 distally. The guidewire may also contain a pressure sensor within it such that sealing of the LAA is monitored and confirmation of a sufficient seal is made. Once the placement is satisfactory, the adhesive 1514 may be injected and/or mechanical anchors be deployed anchoring the plug 1404 to the wall. The guidewire balloon 1508 is deflated, after which the guidewire is removed. In an alternative embodiment, a binary adhesive system can be used where one component of the binary system is bonded to the outer surface of the skin covering the foam plug. The second component can be injected at the interface between foam plug and the wall of the LAA such that bonding happens only at the interface minimizing the risk of adhesive embolization. In some embodiments, adhesives and balloons may or may not be used, for example with the device 3000 further described herein.

Figure 12:
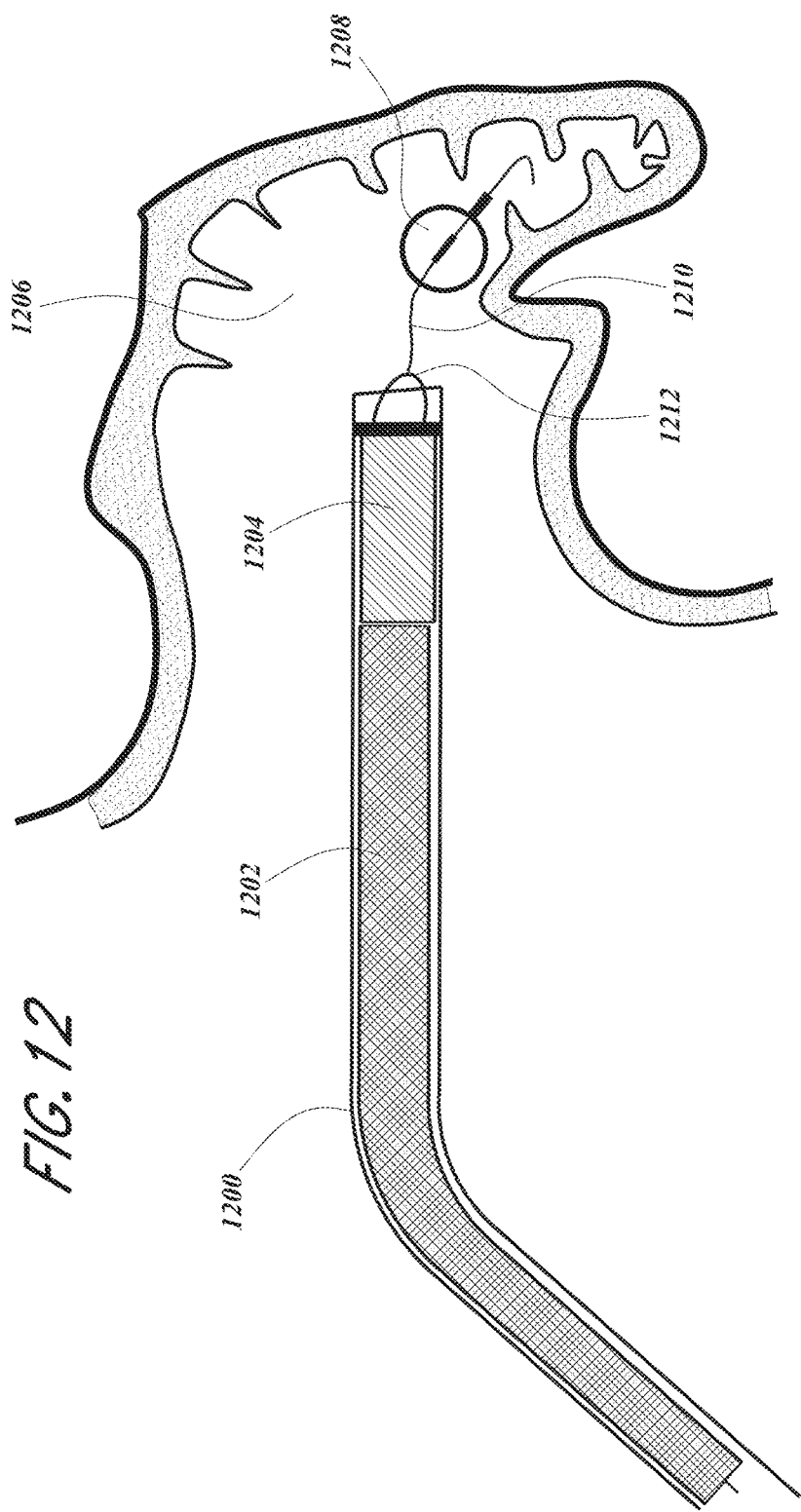

An alternative to pushing the plug through the entire length of the guide catheter is that the plug 1204 may be initially located at the distal end of the guide catheter 1200 as shown in FIG. 12. The guidewire 1210 passes through the center of the plug 1204 and in this mode, the pusher 1202 only needs to push the plug a short ways to deploy it into the LAA.

For alternative anchors, they may be deployed, the shafts disconnected and removed. Disconnection mechanisms may be any of several types, such as threaded, electrolytic detachment, or others known in the art. In some embodiments, a suture attachment may be implemented, for example as described with respect to FIG. 24.

Figure 16:
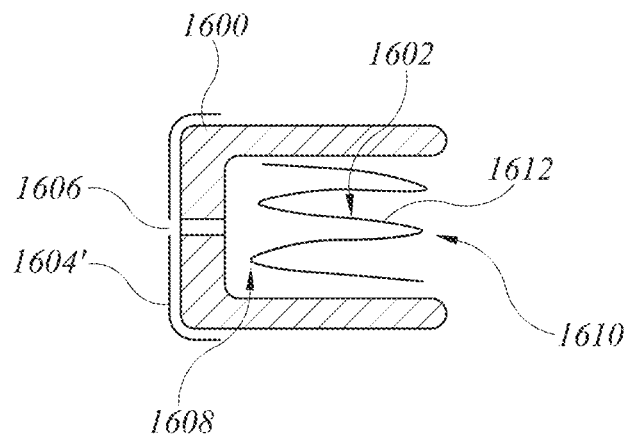
FIG. 16 is a side cross section view of an embodiment of an LAA occlusion device having a foam body, frame and proximal cover.

As shown in FIG. 16, in some embodiments, a foam body 1600 and metal frame such as stent 1602 may be included. The foam body 1600 and stent 1602 may have the same or similar features and/or functionalities as respectively the foam body 3002 and tubular body 3080 (see FIGS. 85A-90D), and vice versa. The foam 1600 is designed to provide ingrowth of tissue and also to provide a cushion of the metal stent 1602 onto the tissue of the LAA. The proximal face 1604' of the plug is covered in ePTFE, polyester or another thromboresistant tissue scaffold material to facilitate sealing with the desired pore size to encourage overgrowth.

The stent 1602 may be made of Nitinol to enable it to pack into a 10, 12, 14, 16, 18 or 20F delivery catheter and expand to its desired diameter. The stent 1602 may be braided, laser cut or wire formed. Any of a variety of stent wall patterns may be utilized, depending upon the desired performance. The stent 1602 may be a balloon expandable stent, or self-expandable stent. In the illustrated embodiment, the self-expandable stent 1602 comprises a plurality of proximal apexes 1608 and distal apexes 1610 connected by a plurality of zig zag struts 1612. A hole 1606 allows passage of the guidewire for delivery. This design may be advantageous in that the expansion force exerted by the plug on the LAA can be controlled separately from the foam characteristics. Also, it may be easier to pack this concept into a smaller geometry. For example, the plug can be packed into a smaller geometry by reducing the amount of foam that must be compressed into the delivery catheter while maintaining sufficient dilation force.

Alternatively, the foam plug may be constructed of two foams. One denser core to provide force, for example radial force, and an outer softer foam to engage the tissue irregularities. The softer foam could also be located on the proximal and/or distal ends to facilitate retrieval.

Figure 17:
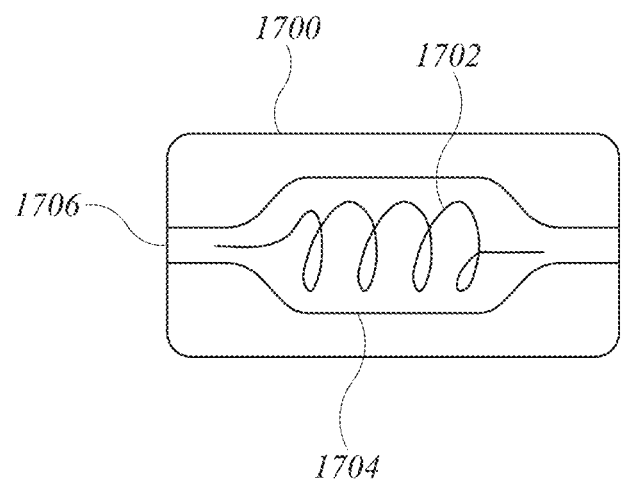
FIG. 17 is a side cross section view of an embodiment of an LAA occlusion device having metal coils and foam.

Another means of adding stiffness to the foam plug is shown in FIG. 17 where a cavity 1704 in the foam plug 1700 is made and a coil of wire 1702 may be advanced from the guide catheter at the proximal end 1706 into the cavity 1704. As the wire enters the cavity, it expands to its predetermined size and exerts force on the foam radially outwards. The type and amount of wire may be determined in vivo using x-ray guidance to examine the radial expansion of the foam into the LAA.

Instead of wires as shown in FIG. 17, a balloon may be passed into the foam and inflated to provide radial force while the outer foam serves to engage the tissue irregularities and tissue ingrowth. Following inflation, the balloon may be detached from a deployment catheter and the deployment catheter withdrawn. The balloon is preferably provided with a valve, to prevent the escape of inflation media. Inflation media may be any of a variety of media which is convertible between a first, flowable state and a second, hardened state such as by cross linking or polymerization in situ.

Figure 18:
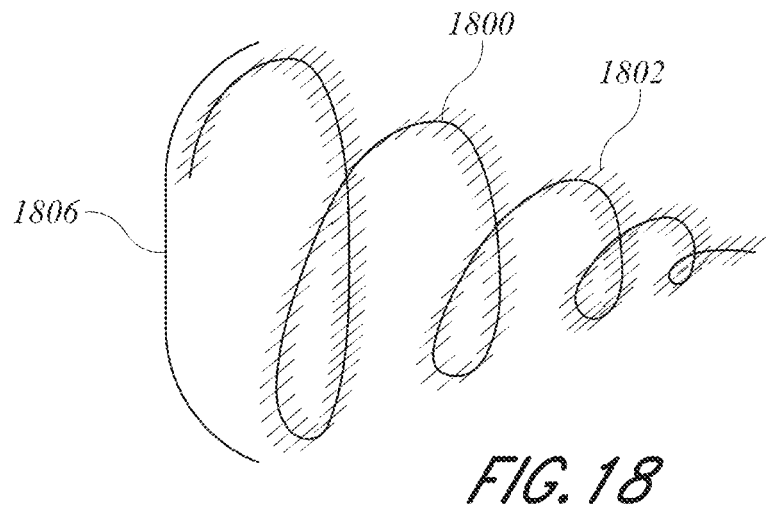
FIG. 18 is a side view of an embodiment of an LAA occlusion device having a single metal coil.

Another LAA plug is shown in FIG. 18 as a spring like implant wire 1800 that is covered with foam 1802 to encourage ingrowth. The proximal face of the implant is covered with a sheet of ePTFE or other tissue scaffolding material. This implant may be stretched out for delivery and released in place.

Rather than using a foam, a low porosity outer bag without perforations could be placed in the LAA and then filled with a substance to provide the radial expansion. This substance may be a hydrogel, cellulose or polyvinylacetate.

Figure 19:
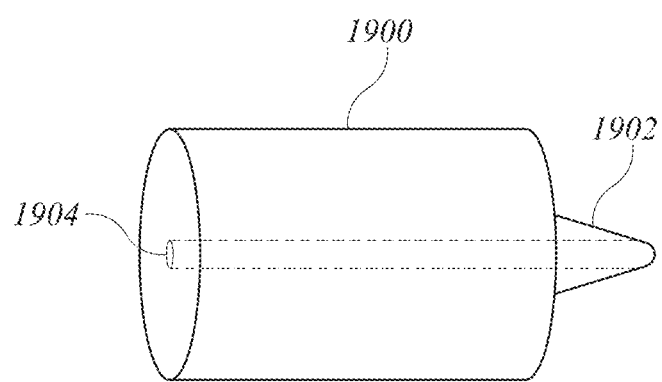
FIG. 19 is a side view of an embodiment of an LAA occlusion device having a dilating distal tip.

Rather than requiring the use of a separate dilation device to cross the septum, the distal crimp element 1902 may be formed in a tapered manner such that it extends from the distal end of the catheter 1200 and serves as a dilating tip to dilate the opening in the septum as the catheter is advanced. See FIG. 19.

Figure 22:
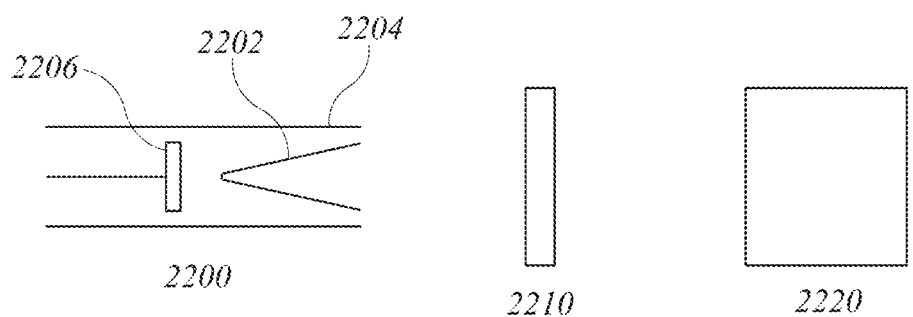
FIG. 22 is a schematic of an embodiment of a delivery of an expanding foam system that may be used with the various LAA occlusion devices described herein, including but not limited to the devices of FIGS. 85A-90D.

An alternative plug design uses a foam such as cellulose sponge material that is compacted and dehydrated such that it can be packed into the guide catheter. This foam material 2202 may be packed into the guide catheter as shown in FIG. 22. The foam plug 2202 is then advanced from the distal end of the guide catheter 2204 with a plunger 2206 into the LAA. The plug exits the guide catheter and opens to a disc shape 2210. As the foam absorbs fluid in the blood, its length expands to form a cylinder 2220 filling the LAA. Expansion ratios for compressed cellulose materials may be as high as 17:1, expanded to compressed length.

Figure 23:
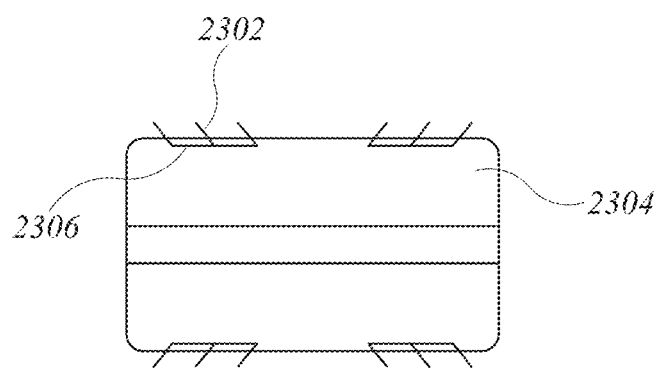
FIG. 23 is a side view of a plug with barbs that may be used with the various LAA occlusion devices described herein, including but not limited to the devices of FIGS. 85A-90D.

It may be advantageous to use small barbs 2302 in FIG. 23 to further engage the plug 2204 into the LAA. Barbs may be unidirectional or bidirectional to resist movement in either the proximal or distal direction. These barbs are embedded into the foam plug and may be 0.1 to 1 mm in height. It may be desirable to place the plug then engage the barbs as a secondary step. One such embodiment could include a multitude of nitinol barb wires with a ball or catch welded proximal to the barb tip. These could be gathered with the delivery catheter within a sleeve or suture then released when the ideal plug position has been confirmed.

Figure 24:
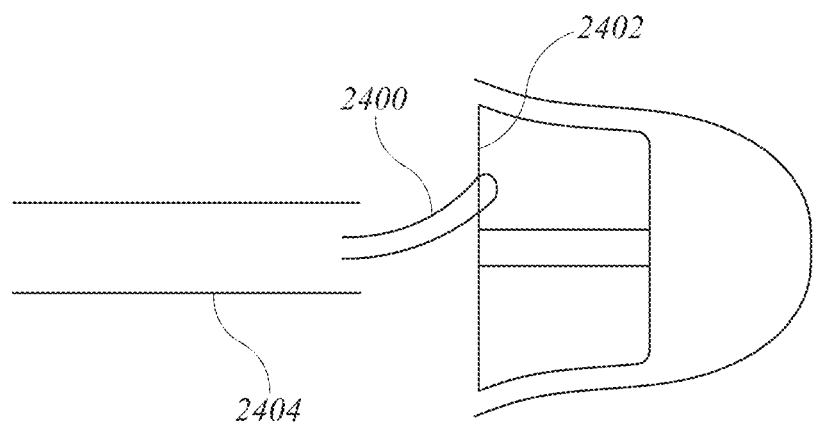
FIG. 24 shows an embodiment of an LAA occlusion device having a retrieval suture attachment that may be used with the various LAA occlusion devices described herein, including but not limited to the devices of FIGS. 85A-90D.

One means of removing a device that is not functioning properly is to releasably attach a retrieval suture 2400 to the implant, such as to the proximal cap 2402 which also passes proximally throughout the entire length of the guide catheter 2404 in FIG. 24. If the device is to be removed, pulling on both ends of the suture 2400 will pull the outer covering into the guide catheter 2404 which can then be removed from the patient. If the device is properly placed, the suture 2400 may be cut and removed leaving the plug in place.

Deployment of the occlusion device has been discussed primarily in the context of a transvascular access. However, the implants may alternatively be deployed via direct surgical access, or various minimally invasive access pathways (e.g. jugular vein). For example, the area overlying the xiphoid and adjacent costal cartilage may be prepared and draped using standard techniques. A local anesthetic may be administered and skin incision may be made, typically about 2 cm in length. The percutaneous penetration passes beneath the costal cartilage, and a sheath may be introduced into the pericardial space. The pericardial space may be irrigated with saline, preferably with a saline-lidocaine solution to provide additional anesthesia and reduce the risk of irritating the heart. The occlusion device may thereafter be introduced through the sheath, and through an access pathway created through the wall of the LAA. Closure of the wall and access pathway may thereafter be accomplished using techniques understood in the art.

Depending upon the desired clinical performance, any of the LAA occlusion devices described herein may be provided with a drug or other bioactive agent, which may be injected via the deployment catheter, or impregnated within the open cell foam or coated on the implant. The bioactive agent may be eluted or otherwise released from the implant into the adjacent tissue over a delivery time period appropriate for the particular agent as is understood in the art.

Useful bioactive agents can include those that modulate thrombosis, those that encourage cellular ingrowth, through-growth, and endothelialization, and potentially those that resist infection. For example, agents that may promote endothelial, smooth muscle, fibroblast, and/or other cellular growth into the implant including collagen (Type I or II), heparin, a combination of collagen and heparin, extracellular matrix (ECM), fibronectin, laminin, vitronectin, peptides or other biological molecules that serve as chemoattractants, molecules MCP-1, VEGF, FGF-2 and TGF-beta, recombinant human growth factors, and/or plasma treatment with various gases.

Anti-thrombotics can typically be separated into anti-coagulants and antiplatelet agents. Anti-Coagulants include inhibitors of factor(s) within the coagulation cascade an include heparin, heparin fragments and fractions as well as inhibitors of thrombin including hirudin, hirudin derivatives, dabigatran, argatroban and bivalrudin and Factor X inhibitors such as low molecular weight heparin, rivaroxaban, apixaban.

Antiplatelet agents include GP 2b/3a inhibitors such as epifibitide, and abciximab, ADP Receptor agonists (P2/Y12) including thienopyridines such as ticlopidine, clopidogrel, prasugrel and tacagrelor and aspirin. Other agents include lytic agents, including urokinase and streptokinase, their homologs, analogs, fragments, derivatives and pharmaceutical salts thereof and prostaglandin inhibitors.

Antibiotic agents can include, but are not limited to penicillins, cephalosportins, vancomycins, aminoglycosides, quinolonges, polymyxins, erythromycins, tetracyclines, chloraphenicols, clindamycins, lincomycins, sulfonamides, their homologs, analogs, derivatives, pharmaceutical salts and combinations thereof.

Biologic agents as outlined above maybe be added to the implant 204 and may be injected through the delivery catheter into the space between the proximal cap 206 and the foam plug 204. This may serve as a reservoir to minimize thrombus formation during the initial implantation and reduce the need for systemic anticoagulation following device implantation.

An electronic pressure sensor may be embedded into the proximal end of the foam plug which may be used to transmit LA pressure to a remote receiver outside the body for the monitoring of LA pressure which is useful to monitor cardiac function. In addition, a cardiac pacer or defibrillator may be embedded into the foam plug and attached electrically to the distal anchor. A drug delivery reservoir may be embedded with connection to the LA for controlled delivery of biologic agents as outlined above.

Figure 25A:
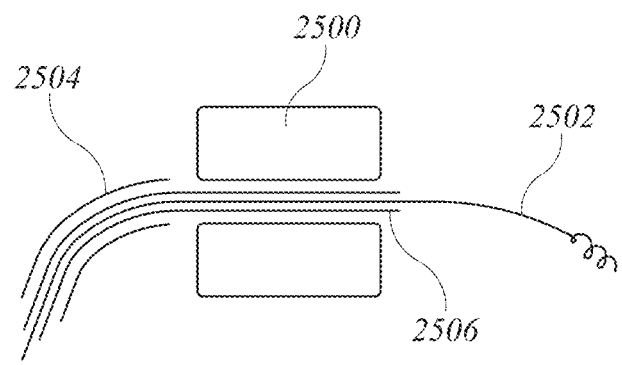
FIGS. 25A-26 show embodiments of distal anchoring systems that may be used with the various LAA occlusion devices described herein, including but not limited to the devices of FIGS. 85A-90D.
Figure 25B:
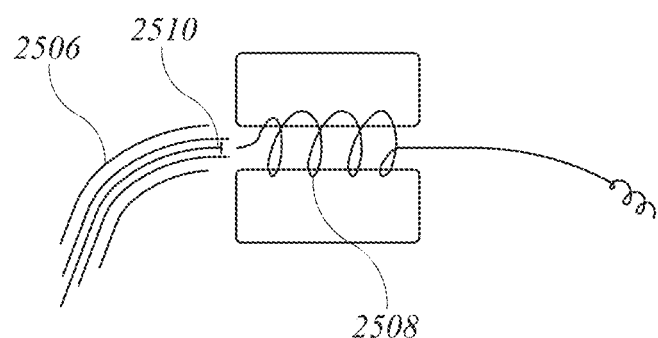

Another means of anchoring is shown in FIG. 25A where the foam plug 2500 is placed in the LAA. The distal screw lead 2502 is advanced and screwed into the LAA wall. Guide 2506 is pulled proximally as shown in FIG. 25B. When this guide 2506 is pulled back, the screw lead wire, made of Nitinol, bunches up into a "birds nest" 2508 or forms a coil inside the foam plug 2500. The screw lead wire 2502 is pushed distally from the guide catheter 2504 with a pusher 2510 and continues to bunch up into the foam. The catheter system 2504, 2506 and 2510 are then removed.

Figure 26:
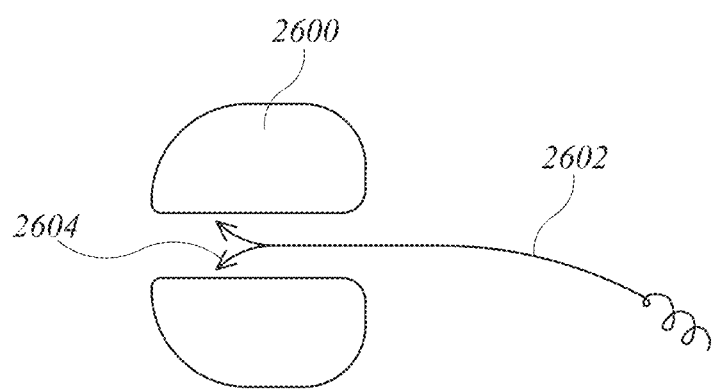

Another means of anchoring the distal anchor element to the foam is shown in FIG. 26. Two barbed leads 2604 are attached to anchor 2602 such that when advanced into place in the foam plug 2600, the barbs 2604 dig into the foam plug.

FIGS. 27A-27G are various views of an embodiment of a device 10 for occlusion of the LAA (LAA). The device 10 may include the same or similar features as other devices for occlusion of the LAA described herein, such as the plug 204, device 1020, device 3000, etc., and vice versa. The device 10 includes an internal locking system 101 for securing the device 10 within the LAA. In some embodiments, the device 10 may not include the internal locking system 101 or other anchoring features, for example the device 10 may be anchored by tissue ingrowth alone. The occlusion device 10 comprises an expandable media such as an open cell foam body 15, for example a plug. The body 15 enables collapse and expansion of the device 10 and also enhances ingrowth of tissue into the foam.

Figure 27A:
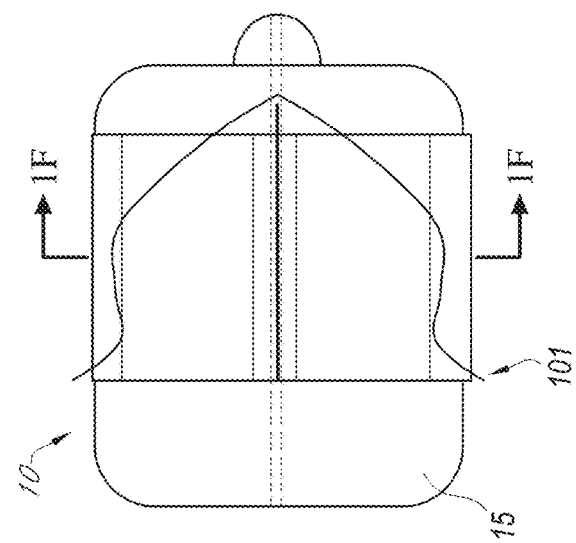
FIGS. 27A-27G are various views of an embodiment of an LAA occlusion device with an internal locking system that may be used with the various LAA occlusion devices described herein, including but not limited to the devices of FIGS. 85A-90D.
Figure 27B:
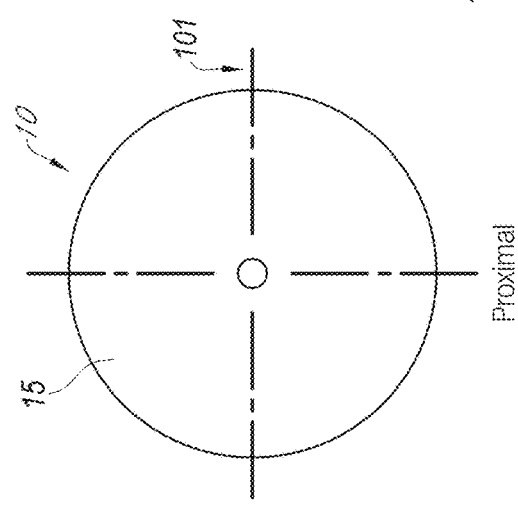
Figure 27C:
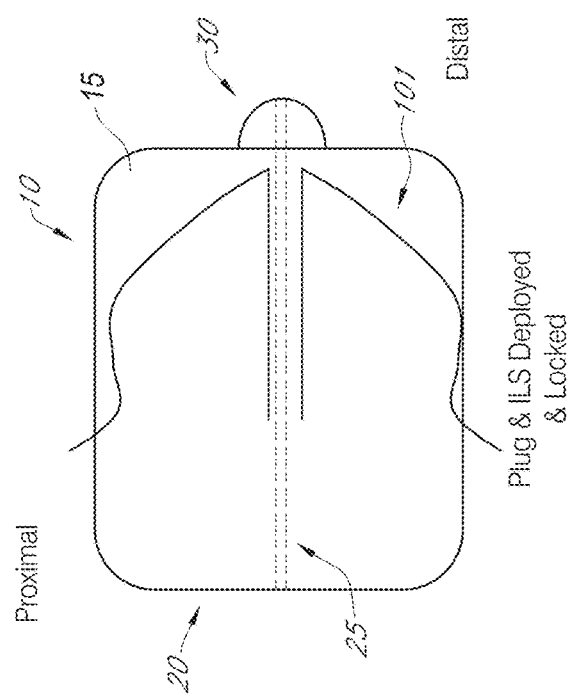
Figure 27F:
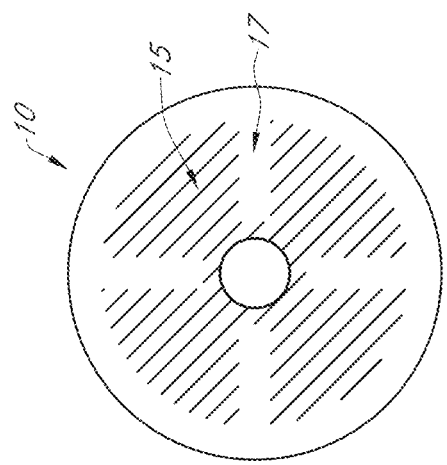
Figure 27E:
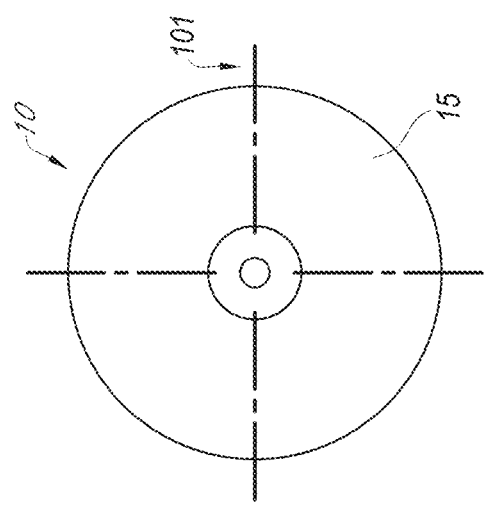
Figure 27D:
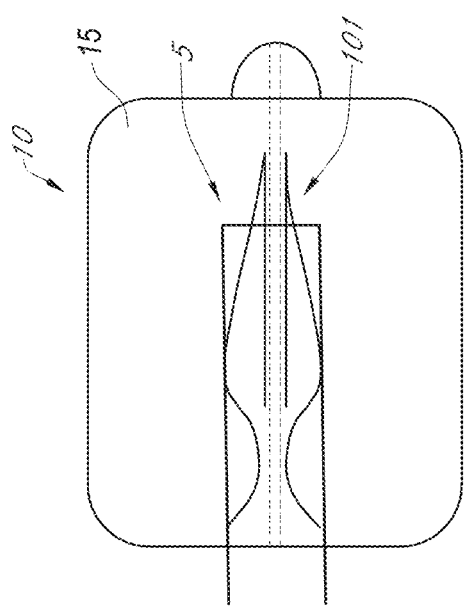
Figure 27G:
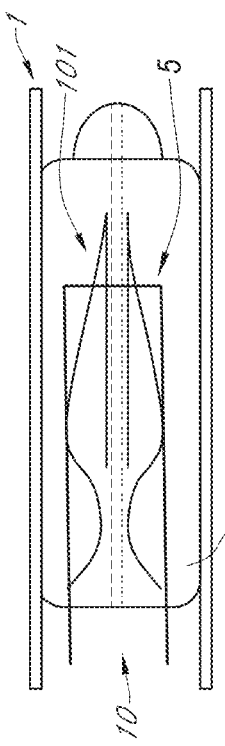

The body 15 of the device 10 shown in FIG. 27A through FIG. 27F is in its expanded configuration. The body 15 is in a compressed configuration in FIG. 27G. The device 10 includes the foam body 15, a skin 20, a central lumen 25, a finial 30, and a dynamic internal locking system 101 which anchors the device 10 within the LAA. FIG. 27A is a side cross-section view of the device 10 showing the body 15 and the internal locking system 101 in a deployed configuration. FIG. 27B is an end view of the proximal end of the device 10 showing the body 15 and the internal locking system 101 in a deployed configuration. FIG. 27C is a side view of the device 10 showing the body 15 and the internal locking system 101 in a deployed configuration. FIG. 27D is a side cross-section view of the device 10 showing the body 15 in a deployed configuration and the internal locking system 101 in a constrained configuration. FIG. 27E is an end view of the distal end of the device 10 showing the body 15 and the internal locking system 101 in a deployed configuration. FIG. 27F is a cross-section view of the device 10 taken along the line 1F-1F as shown in FIG. 27C. FIG. 27G shows the body 15 and internal locking system 101 loaded and compressed within a delivery sheath 1. The device 10 may be delivered via a delivery catheter in the configuration shown in FIG. 27G. The body 15 of the device 10 may then expand with the internal locking system 101 still constrained, as shown in FIG. 27D. The internal locking system 101 may then deploy into the deployed configuration as shown in FIG. 27A.

FIG. 27G shows the body 15 and internal locking system 101 loaded and compressed within an embodiment of a delivery sheath 1. In some embodiments, the delivery sheath 1 may be an outer delivery catheter. The body 15 and internal locking system 101 are loaded and compressed within a delivery catheter 5. The device 10 may be entirely or partially inside the delivery catheter 5. In some embodiments, the delivery catheter 5 may be an inner delivery catheter. The device 10 may be loaded and compressed with the delivery catheter 5 inside of the delivery sheath 1. Removing the delivery sheath 1, for example by retracting the delivery sheath 1 in the proximal direction, may allow the body 15 of the device 10 to expand. The body 15 expands while the internal locking system 101 is still constrained, for example by the delivery catheter 5. FIG. 27D shows the body 15 in its deployed state, with the internal locking system 101 in a constrained configuration within the delivery catheter 5. This demonstrates the first step in the deployment process, specifically placement of the device 10 within the LAA where the body 15 is expanded and the internal locking system 101 is constrained and thus the anchors are not deployed. The second step of the deployment process is shown in FIG. 27A where the internal locking system 101 has been deployed through the body 15. In some embodiments, this second step is reversible to retract the anchors, for example if placement of the device 10 within the LAA is unacceptable. The internal locking system 101, for example an anchoring component or system as further described herein, is deployed from within the body 15 to deploy at least one and in some implementations at least 2 or 4 or 6 or more anchors of the internal locking system 101 outside the body 15 to engage adjacent anatomy of the LAA.

The internal locking system 101 may be controllably deployed a period of time after the body 15 expands. For instance, the location, orientation, etc. of the device 10 may be verified with various imaging techniques such as by fluoroscopy with injection of contrast media via the central lumen before the internal locking system 101 is deployed and the anchors secure the device 10 within the LAA. In some embodiments, even after deployment of the internal locking system 101 and anchors thereof, the anchors may be retracted to a position within the body 15 for repositioning, and/or retrieval of the device 10 from, within the LAA.

FIG. 27F shows an embodiment of the device having slots 17. The slots 17 are formed within the foam body 15. For instance, material of the foam body 15 may be removed to facilitate deployment of the internal locking system 101, such as outward expansion of anchors to engage the tissue.

The device 10 may have any or all of the same or similar features and/or functionalities as the other plugs described herein, for example the plug 204, etc. For example, the device 10 is at least partially encapsulated within the skin 20. In some embodiments, the skin 20 may cover the proximal end of the body 15. The skin 20 may be a thin, strong outer layer. The skin 20 may be a thin, encapsulating layer. The skin 20 may be fabricated from ePTFE (expanded polytetrafluoroethylene), polyolefin, polyester, other suitable materials, or combinations thereof. In some embodiments, the skin 20 may be fabricated from bioabsorbable materials, for example polylactic acid (PLA), Polyglycolic acid (PGA), ploycaprolactone (PCL), PHA, collagen, other suitable bioabsorbable materials, or combinations thereof. The skin 20 can be oriented or otherwise modified to be elastomeric in at least one direction, such as radially.

The body 15 may be made of polyurethane, polyolefin, PVA, collagen foams or blends thereof. One suitable material is a polycarbonate-polyurethane urea foam with a pore size of 100-250 um and 90-95% void content. The body 15 may be non-degradable or use a degradable material such as PLA, PGA, PCL, PHA, and/or collagen. If degradable, the tissue from the LAA will grow into the foam body 15 and replace the foam over time. The body 15 may be cylindrical in shape in an unconstrained expansion, but it may also be conical with its distal end smaller than the proximal end, or vice versa. The body 15 may also be oval in cross section to better match the opening of the LAA.

The device 10 is oversized radially in an unconstrained expansion to fit snuggly into the LAA. The device 10 may be 5-50 millimeters (mm) and generally at least about 10 mm or 15 mm in diameter in its unconstrained configuration, for example depending on the diameter of the target LAA. The length "L" of the device 10 may be less than, similar to or greater than its diameter "D" such that the L/D ratio is less than 1.0, about or greater than about 1.0, greater than about 1.5, or greater than about 2.0. The L/D ratio may be greater than 1.0 to maximize its stability. However, in some embodiments, the L/D ratio may be less than 1.0, for example, from about 0.2 to about 0.9, or from about 0.3 to about 0.8, or from about 0.4 to about 0.6. The compliance of the material of the device 10 is designed such that it pushes on the walls of the LAA with sufficient force to maintain the plug in place but without overly stretching the LAA wall. The foam body 15 and/or skin 20 also conforms to the irregular surfaces of the LAA as it expands, to provide a complementary surface structure to the native LAA wall to further enhance anchoring and promote sealing. Thus, the expandable foam body 15 conforms to the native irregular configuration of the LAA. In some embodiments, the structure of the foam body 15 may be fabricated such that axial compression on the opposing ends of the body 15 such as by proximal retraction of a pull wire or inner concentric tube causes the foam to increase in diameter.

The body 15 and/or skin 20, for example the foam material and/or ePTFE, may be provided with one, two or more radiopaque markers, such as radiopaque threads 210 (see FIG. 2) or filled with or impregnated with a radiopaque filler such as barium sulfate, bismuth subcarbonate, or tungsten, which permit the operator to visualize under x-ray the device 10 for proper positioning in the anatomy. Visualization of the device 10 may be used to verify the position of the device 10 before deployment of anchors to secure the device 10 in place.

The skin 20, such as an outer ePTFE layer, may have a thickness between about 0.0001 inches and about 0.0030 inches. In some embodiments, the thickness of the skin 20 may be between about 0.0003 inches and about 0.0020 inches. In some embodiments, the thickness of the skin 20 may be between about 0.0005 inches and about 0.0015 inches. The thickness of the skin 20 may be uniform, for example the same or approximately the same no matter where the thickness is measured. In some embodiments, the thickness of the skin 20 may be non-uniform, for example the thickness may be different in different portions of the skin 20.

The skin 20, such as an outer ePTFE layer, may also serve as the blood contacting surface on the proximal end of the device 10 facing the LA. The skin 20 may have pores or nodes such that blood components coagulate on the surface and an intimal or neointimal covering of tissue grows across it and anchors tightly to the skin material. Pore sizes may be within the range of from about 4µ to about 110µ. In some embodiments, the pore sizes are within the range of from about 30µ to about 90µ. In some embodiments, the pore sizes are within the range of from about 30µ to about 60µ. Such ranges of pore sizes are useful for formation and adherence of a neointima. In some embodiments, the skin 20, such as an outer ePTFE layer, may be formed from a tube with a diameter about the same diameter of the foam body 15. and allows one to collapse and pull on the body 15 without tearing the foam material.

The skin 20 may be constructed of materials other than ePTFE such as woven fabrics, meshes or perforated films made of FEP, polypropylene, polyethylene, polyester or nylon. The skin 20 may have a low compliance (e.g. non-elastic), for instance a low compliance longitudinally, may be sufficiently strong as to permit removal of the plug, may have a low coefficient of friction, and/or may be thromboresistant. The skin 20 serves as a matrix to permit plug removal as most foams are not sufficiently strong to resist tearing when pulled. The body 15 can also be coated with or contain materials to enhance its ultrasonic echogenic profile, thromboresistance, lubricity, and/or to facilitate echocardiographic visualization, promote cellular ingrowth and coverage.

The skin 20 may include holes to permit contact of the LAA tissue with the foam body 15. Exposure of the foam body 15 to the LAA or other tissue has benefits for example encouraging ingrowth of tissue into the foam plug pores and/or increasing friction to hold the body 15 in place. These holes may be 1 to 5 mm in diameter or may also be oval with their long axis aligned with the axis of the foam plug, the length of which may be 80% of the length of the foam plug and the width may be 1-5 mm. The holes may be as large as possible such that the outer covering maintains sufficient strength to transmit the tensile forces required for removal. The holes may be preferentially placed along the device 10. In some embodiments, the holes are placed distally to enhance tissue ingrowth from the distal LAA wall.

In some embodiments, the device 10 includes an occlusion region and anchoring region. The proximal portion of the device 10 facing the LA after the device is implanted in the LAA may include the occlusion region. The occlusion region may be a blood contacting surface on the proximal end of the device 10 that is thromboresistant while promoting formation of a neointima at the occlusion region. The occlusion zone encourages thromboresistance and endothelialization from the blood and adjacent tissue. The anchoring zone promotes fast and tenacious tissue ingrowth into the device 10 from the adjacent non-blood tissue. The anchoring zone may be lateral surfaces of the device 10 that interface with tissue adjacent and/or within the LAA. The anchoring zone can also include the distal end of the device 10 that faces the distal wall of the LAA after implantation.

Figure 28B:
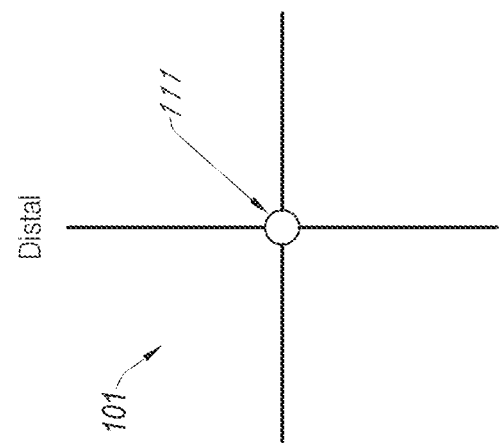
FIGS. 28A-28D are various views of an embodiment of an internal locking system that may be used the device of FIGS. 27A-27G.
Figure 28D:
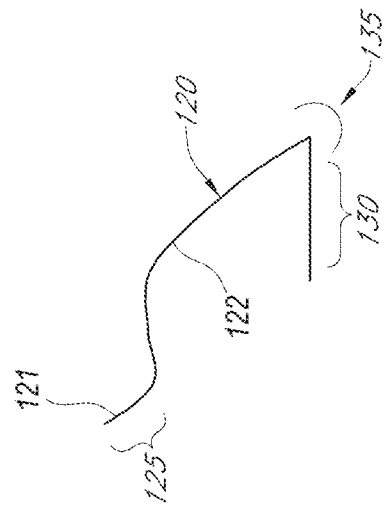
Figure 28A:
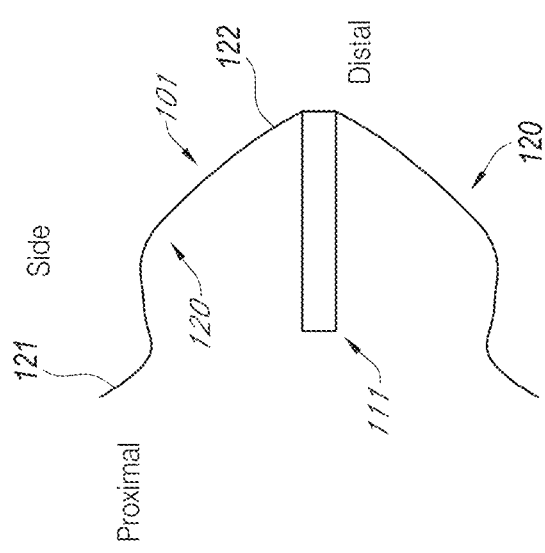
Figure 28C:
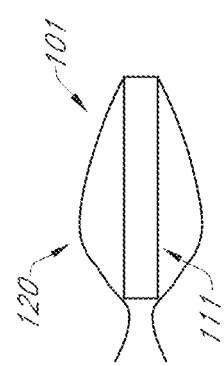

FIGS. 28A-28D are various views of an embodiment of an internal locking system 101 that may be used with the device 10. In some embodiments, multiple internal locking systems 101 may be used with the device 10. FIG. 28A is a side view of the internal locking system shown in a deployed configuration. FIG. 28B is an end view of a distal end of the internal locking system 101 in a deployed configuration. FIG. 28C is a side view of the internal locking system 201101 in a constrained configuration. FIG. 28D is a side view of an embodiment of an anchor 120 of the internal locking system 101.

Any of a variety of structures may be utilized as the dynamic internal locking system 101 with the device 10. In general, at least about two or four or six or more tissue anchors 120 may be actively or passively advanced from the implantable device 10 into adjacent tissue surrounding the implantation site. Following deployment of the device 10 and expansion of the body 15, a tissue engaging segment 121 of the tissue anchor 120 will extend beyond the skin by at least about one, and in some implementations at least about two or four 4 mm or more. The tissue engaging segment 121 is carried by a support segment 122 of the tissue anchor 120 which extends through the foam body 15, and may be attached to a deployment control such as a pull wire, push wire, tubular support or other control structure depending upon the desired configuration.

The locking system 101 discussed primarily herein is a passive deployment construction. Removal of a constraint allows the tissue anchors 120 to laterally self-expand to deploy into adjacent tissue. Self-expansion may be accomplished by constructing the tissue anchor 120 using nitinol, Elgiloy, stainless steel or other shape memory or spring bias materials. The constraint may be removed by proximal retraction or distal advance until the tissue anchors 120 are no longer engaged by the constraint, depending upon the construction of the locking system 101.

Alternatively, tissue anchors 120 may be deployed actively such as by distal advance, proximal retraction or rotation of a control, or inflation of a balloon positioned within the device 10 to actively drive the anchors 120 through the skin 20 or corresponding apertures on the skin 20 and into tissue. For example, a plurality of support segment 122, such as struts, may be joined at a distal end to a central hub 111, and incline radially outwardly in the proximal direction. Proximal retraction of the hub 111 will cause the tissue engaging segment 121 to advance along its axis beyond the skin 20 and into the adjacent tissue. The inclination angle of the support segment 122, for example the struts, may be reversed, in another construction, such that distal advance of the hub 111 will deploy the tissue engaging segments 121 beyond the skin 20. Proximal or distal advance of the hub 111 may be accomplished by proximal or distal advance of a control such as a control wire or inner tube releasably engaged with the hub 111.

Depending upon the desired clinical performance, the tissue anchors 120 may be retractable, such as by axial distal or proximal movement of the control depending upon the inclination angle of the anchors 120. In the embodiment primarily illustrated herein, re-sheathing the anchors 120 may be accomplished by advancing the tubular constraint along the ramped surface of the tissue anchor 120 to move the anchor 120 radially inwardly towards the central longitudinal axis of the device 10. In the case of an anchor 120 which deploys by advance along its own longitudinal axis, the anchor 120 may be retracted by advancing the control in the opposite direction from the direction advanced to deploy the anchors 120.

Referring to FIGS. 28A-28D, the internal locking system 101 includes a central tubular element or hub 111 and anchors 120. The anchors 120 may be arms, segments, or other members extending from the hub 111. Each anchor 120 may comprise a tissue engaging segment 121 and a support segment 122 which extends to the hub 111 or other control. The internal locking system 101 has a single central tubular hub 111 and a multitude of the anchors 120. As shown, there are four anchors 120. There may be two, three, four, five, six, seven, eight, or more anchors 120. The anchor 120 may be rotatably, hingedly, or otherwise moveably coupled with the hub 111. The anchor 120 may thus move relative to the hub 111, for example after being released from a restraint holding the anchor 120 in a constrained configuration to deploy into a deployed configuration. As further example, the anchor 120 may move from the deployed configuration to a retracted position, as further described herein. The anchor 120 may be curvilinear as shown, for example to allow the anchor 120 to take the geometry shown in FIG. 28A when unconstrained.

The illustrated anchor 120 may have a distal region 130, a hinge region 135, and/or a proximal region 125. The distal region 130 interacts with the hub element 111. The hinge region 135 and the curvilinear geometry as shown allow the end of the proximal region 125 to extend beyond the body 15, for example beyond a sidewall of the body 15. The proximal region 125 includes a tissue engaging segment 121 configured to engage adjacent tissue. The tissue engaging segment 121 may be the entire proximal region 125 or a portion thereof, for example the tip, etc. The proximal region 125 may thus include a sharpened tissue engaging segment 121, a shaped tissue engaging segment 121, an angled tissue engaging segment 121, a thickness configured for tissue engagement, and/or other suitable features. In some embodiments, the proximal region 125 may retract back within the body 15, as further described herein. In the embodiment shown, the anchor 120 and central tube 111 are distinct elements which are affixed to one another as shown. In other embodiments, the anchor 120 and tube 111 are a single, integral unit.

The internal locking system 101 is made from biocompatible metallic wire such as Nitinol, implant grade stainless steel such as 304 or 316, or cobalt-chromium based alloys such as MP35N or Elgiloy. In some embodiments, the internal locking system 101 may be cut from a single tubular piece of metal fabricated via machining or laser cutting followed by a secondary forming or annealing step using similar materials.

The internal locking system 101 may be in a constrained configuration as the device 10 is placed in position in the LAA and the body 15 expands therein. Then, in a secondary step, the internal locking system 101 locks or otherwise secures the device 10 in the LAA by engaging the anchors 120. If the position is not considered optimal, or if the device 10 otherwise needs to be repositioned within and/or removed from the LAA, the internal locking system 101 and anchors 120 thereof can be unlocked and the device 10 repositioned and/or removed.

FIGS. 29A-29B are sequential side views of an axially movable loop type unlocking mechanism that may be used with the device 10 to release the tissue anchors. FIG. 29A is a side cross-section view of the device 10 showing the tissue anchors of internal locking system 101 in a deployed configuration. FIG. 29B is a side cross-section view of the device 10 showing the tissue anchors in a retracted configuration. An embodiment of an unlocking system 140 is shown. The unlocking system 140 includes a ring 145. The ring 145 may be moved over the anchors 120 to move the anchors 120 to retracted configurations. The ring 145 may be moved by a pull rod 147. The ring 145 may be releasably attached to the pull rod 147. The pull rod 147 may extend through a catheter to engage the ring 145. The unlocking system 140 may be utilized if, after the internal locking system 101 is deployed, it is desirable to unlock the device 10 from within the LAA in order to reposition and/or remove the device 10.

In the illustrated construction, deployment of the tissue anchors by distal advance of the restraint enables reversible deployment, so that subsequent proximal retraction of the restraint will retract the tissue anchors. Alternatively, proximal retraction of the restraint to release the tissue anchors will irreversibly release the tissue anchors.

Figure 30:
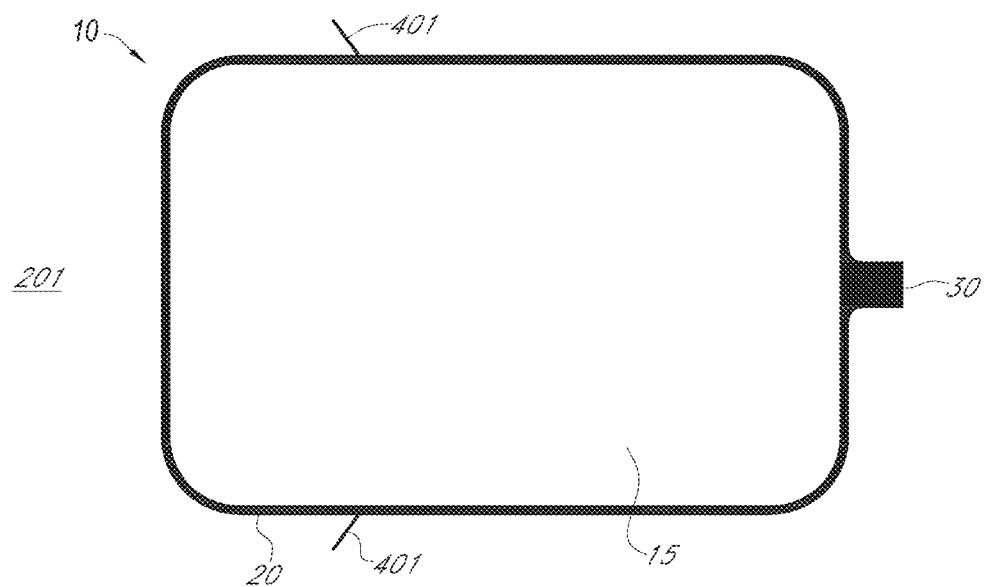
FIG. 30 is a side view of an embodiment of an LAA occlusion device having flexible anchors that may be used with the various LAA occlusion devices described herein, including but not limited to the devices of FIGS. 85A-90D.

FIG. 30 is a side view of an embodiment of the device 10 having flexible anchors 401. The device 10 shown in FIG. 30 may have the same or similar features and/or functionalities as the other devices for excluding the LAA described herein, and vice versa. The device 10 may be in the configuration shown in FIG. 30 adjacent to or within an LA 201. The device 10 in FIG. 30 includes the expandable body 15, such as an open cell foam body, which enables collapse and expansion of the device 10, and at least partially encased within the skin 20, which may be a thin, strong layer fabricated from ePTFE (expanded polytetrafluoroethylene), polyolefin, or polyester which assists with healing, anchoring, and retrieval. The device 10 may also be deployed, and, if desired, repositioned and/or retrieved, or the device 10 may be permanently fixated within the LAA by engaging an anchoring system, such as the internal locking system 101, as described herein. The anchors 401, which may be metallic, may be fabricated from Nitinol. The anchors 401 may be small diameter Nitinol wire approximately 0.001 inches to approximately 0.010 inches in diameter. In some embodiments, the anchors 401 may be approximately 0.0005 inches to approximately 0.020 inches in diameter. The anchors 401 may be deployed upon expansion of the body 15. For example, the anchors 401 may self-deploy upon deployment of the device 10 from a delivery catheter. The anchors 401 may be relatively short and extremely flexible. The anchors 401 may be unable to penetrate the tissue or cause any anchoring immediately after deployment of the device 10.

Figure 31:
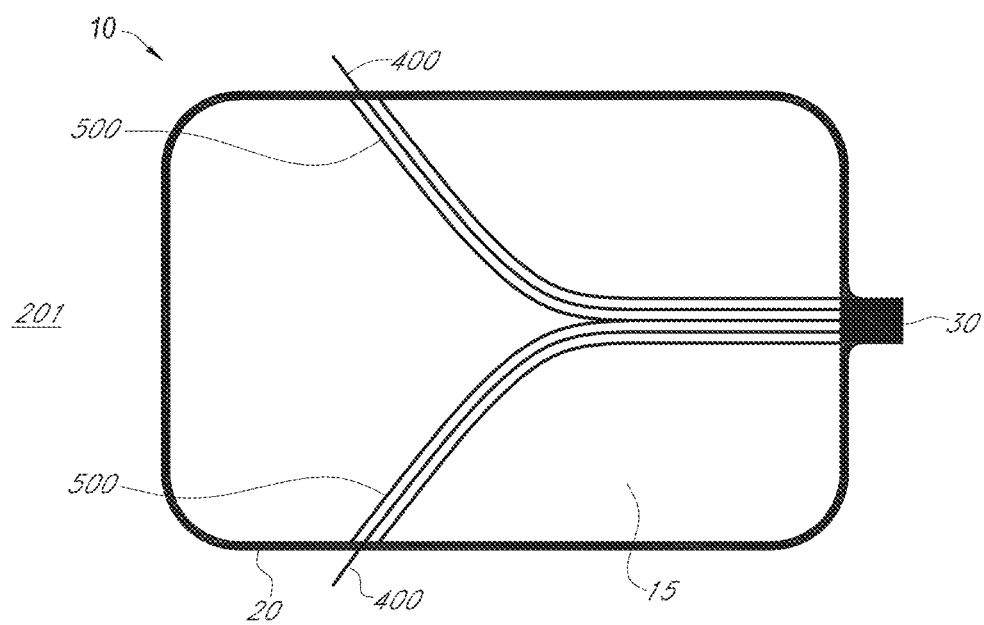
FIGS. 31-32 are side views of an embodiment of an LAA occlusion device having flexible anchors and stiffening tubular members configuration that may be used with the various LAA occlusion devices described herein, including but not limited to the devices of FIGS. 85A-90D.

FIG. 31 is a side view of an embodiment of a device 10 for occlusion of the LAA having anchors 401 with tubes 500. The device 10 may be positioned adjacent to or within the LA 201. The anchors 401 may be flexible anchors, or in some embodiments the anchors 410 may be relatively stiffer, as further described. The tubes 500 may be stationary or moveable tubes, as further described. In some embodiments the tubes 500 are hypotubes. The tubes 500 may be stainless steel, polyamide, or other suitable materials. The tubes 500 may surround a corresponding anchor 401, as further described.

In some embodiments, the anchors 401 may be fixed such that they do not move axially. For example, the anchors 401 may have a portion, such as a tissue engaging segment 121, of a fixed length extending outside the body 15. The portion of the anchors 401 extending outside the body 15 may be bent when compressed within a delivery catheter and/or sheath, and these portions of the anchors 401 may then straighten out to the configuration shown in FIGS. 31 and 32 after deployment of the body 15. The fixed length portion of the anchors 401 extending beyond the body 15 may be from about 1 mm to about 5 mm, or from about 1.5 mm to about 4 mm, or from about 2 mm to about 3 mm. This length of exposed anchor 401 outside the body 15 may be effectively shortened by deployment of a corresponding tube 500, as further described. Deployment of the corresponding tube 500 about the corresponding anchor 400 may shorten the effective length of exposed anchor 401, i.e. the length of the anchor 401 extending beyond the end of the tube 500 after deployment of the tube 500, from about 0.5 mm to about 1 mm. These are merely examples of different lengths of the anchor 401 and other suitable lengths may be implemented.

In some embodiments, the anchors 401 may be moveable axially. For example, the anchors 401 may not deploy or otherwise extend outside the body 15 immediately upon expansion of the body 15. Following acceptable positioning of the device 10 within the LAA, the flexible anchors 401 may then be advanced through a corresponding tube 500. The anchors 401 may move axially in any suitable manner, including those described elsewhere herein. The anchor 401 may be moved through the tube 500 either before or after the tube 500 has been moved and deployed outside the body 15, as described below.

Figure 32:
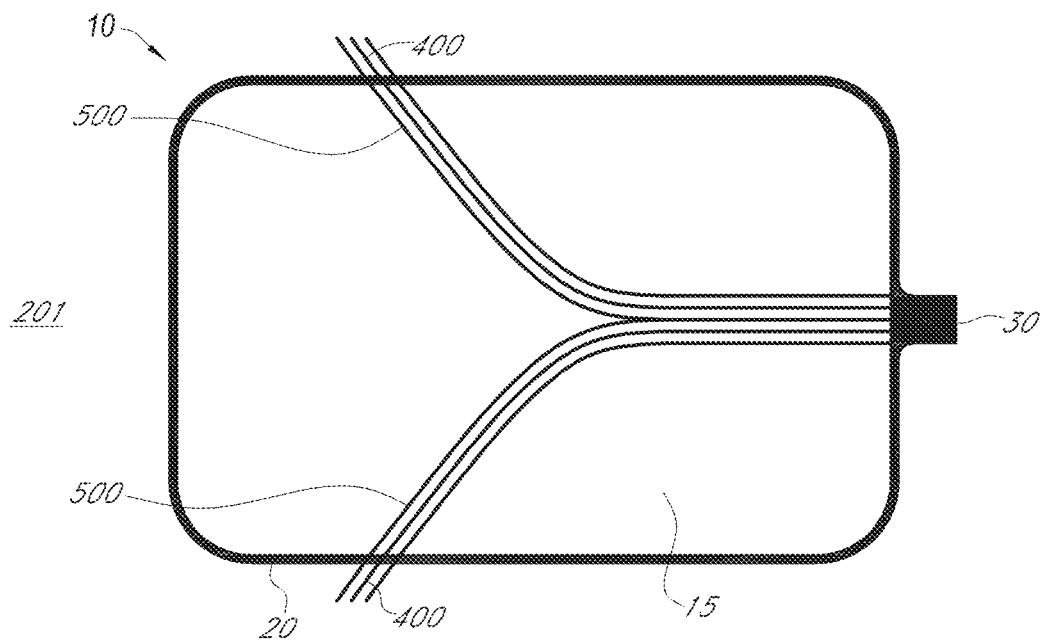

In some embodiments, the tubes 500 are moveable and deploy outside the body 15. The tubes 500 may be moveable in embodiments having either fixed or moveable anchors 401. The tubes 500 may be pre-loaded over corresponding wire anchors 401 as shown in FIG. 31, for example one tube 500 per anchor 401. The tube 500 may then be moved over the corresponding anchor 401 as shown in FIG. 32. The tube 500 may straighten the anchor 401 and add mechanical integrity. The tube 500 may also act as a perforation protector to prevent the anchor 401 from puncturing through the wall of the LAA. Movement of the tube 500 over the corresponding anchor 401 may shorten the exposed length of the anchor 401, as described. This may provide for a stiffer tissue engaging segment of the anchor 401 due to the shortened exposed length.

In some embodiments, the tubes 500 extend from the delivery catheter to or near the outer surface of the body 15 but do not extend outside the body 15. Instead, the tubes 500 just guide the anchor 401, for example around the curve, and support the wire 401 right up to tissue penetration. The tubes 500 may set the launch angle so the anchor 401 does not buckle and hits the tissue at the right angle. In this embodiment, the anchor 401 may have relatively more stiffness than in the embodiments where the anchors 401 are relatively flexible, in order to provide a more secure anchoring of the device 10 to the tissue. It is understood the tube 500 may provide this guiding function to the corresponding anchor in any of the embodiments described herein having moveable anchors, such as the moveable anchors 401, the anchors 120, etc.

The flexible anchors 401 and/or the external stiffening tube 500 may be made from biocompatible metallic materials such as Nitinol, implant grade stainless steel such as 304V or 316LVM, cobalt-chromium based alloys such as MP35N or Elgiloy, other suitable materials, or combinations thereof. The anchor 401 length can vary from 0.1 mm to 5 mm in length with an external stiffening tube 500 that covers from 10% to 90% of the exposed length of the anchor 401.

Figure 33:
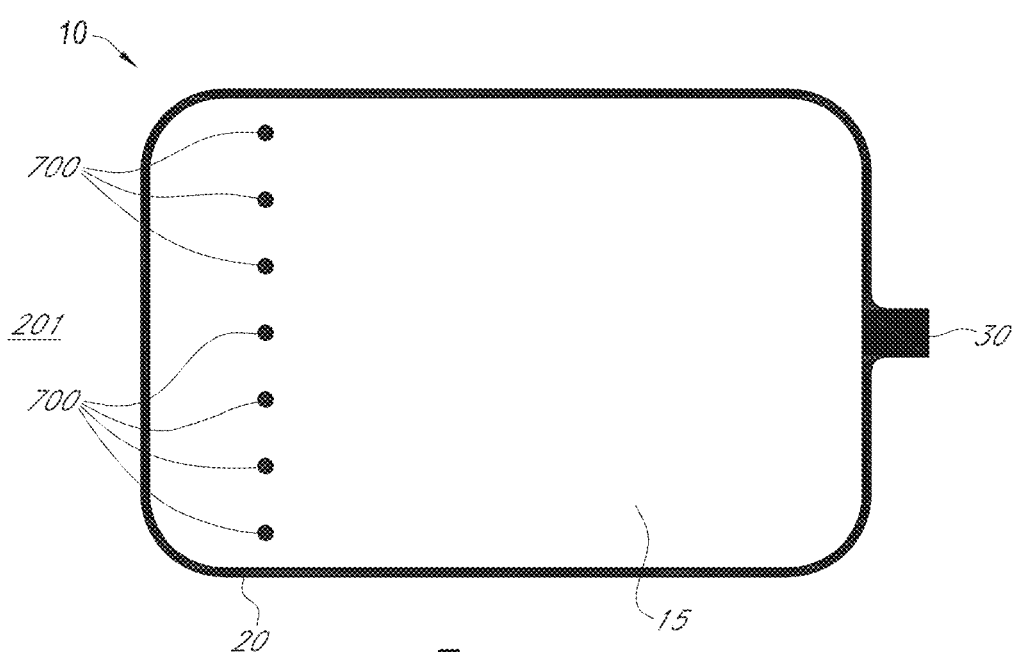
FIG. 33 is a side view of an embodiment of an LAA occlusion device having discrete attachments of an outer skin to an internal foam that may be used with the various LAA occlusion devices described herein, including but not limited to the devices of FIGS. 85A-90D.

The skin 20 at least partially surrounds the body 15 and portions of the skin 20 may or may not be attached to the body 15. The various devices 10 described herein may have the body 15 at least partially encased within the skin 20, which may be fabricated from a material such as ePTFE (expanded polytetrafluoroethylene), polyolefin, or polyester which assists with healing, anchoring, and retrieval. FIG. 33 is a side view of an embodiment of a device 10 for occlusion of the LAA having discrete points of attachment 700 of the skin 20 to the internal foam body 15. For clarity, the points of attachment 700 are shown as dots in the figures. It is understood the points of attachment 700 may not be visible from outside the device 10, for example the skin 20 may be bonded to the body 15 at the points of attachment 700, etc. In some embodiments, in addition or alternatively to bonding, the skin 20 may be secured for example with sutures to the body 15 at the points of attachment 700, and thus some or all of the points of attachment 700 may be visible from outside the device 10. The device 10 may be in the configuration shown in FIG. 33 adjacent to or within the LA 201. The skin 20 may be attached to the body 15 at the various separate points of attachment 700. As shown in FIG. 33, the skin 20 can be partially attached, with portions thereof not attached at all, to the body 15. This may allow, for example, the skin 20 to move during expansion of the body 15 that occurs after deployment of the device 10 from the delivery catheter. The skin 20 may, in some embodiments, be attached at points of attachment 700 located near the proximal side of the device 10, for example to help promote closure of the ostium of the LAA, such as with a rim 800 as described below. The skin 20 may, for example, be tacked in place in one or more points of attachment 700 near the proximal face so that any bunching of the skin 20 that occurs during implantation occurs near the ostium but within the LAA. This can be achieved using sutures, adhesive bonding, heat bonding, other suitable approaches, or combinations thereof.

Figure 34:
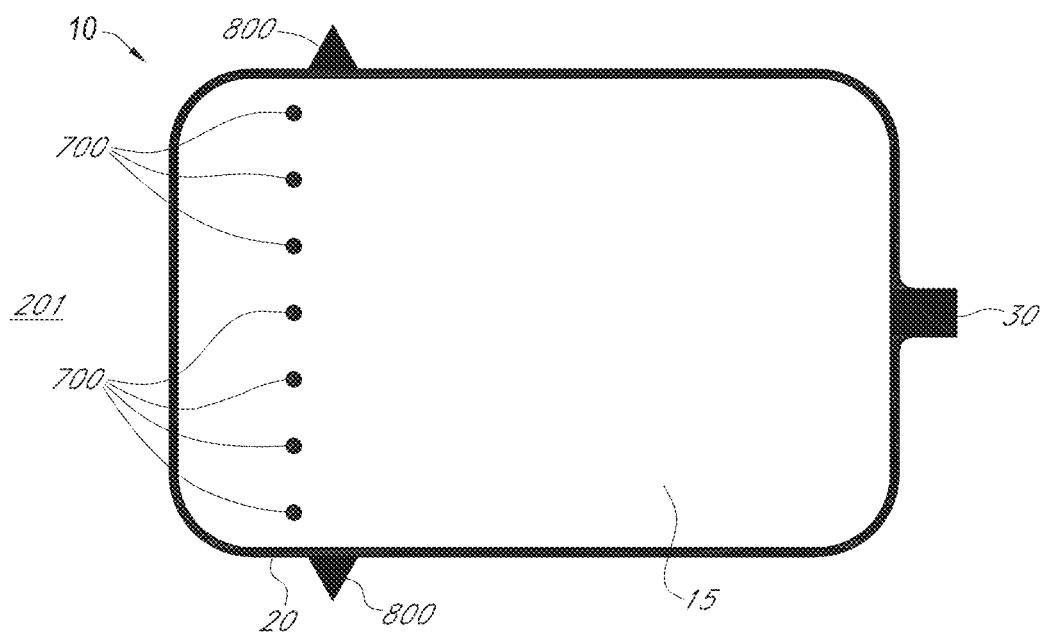
FIG. 34 is a side view of the device of FIG. 34 including an outer rim.

The selective location of the points of attachment 700 may facilitate with formation of a circumferential rim 800 of the skin 20. The rim 800 is shown schematically in FIG. 34 as a triangular rim for clarity. It is understood the rim 800 may be a variety of different shapes depending on the configuration of the device 10, the shape of the LAA, etc. Further, the rim 800 may extend completely or partially around the device 10. The rim 800 may surround the ostium of the LAA. The formation of the rim 800 may help to completely seal the entrance to the LAA around the device 10 and thereby prevent leakage. The attachment points 700 between the skin 20 and the body 15 can prevent irregular bunching of the fabric and instead guide any excess material to form the sealing rim 800 around or near the proximal face of the device 10, as shown in FIG. 34. The rim 800 may form upon expansion of the body 15 after deployment from the delivery catheter, as described herein. Alternatively the attachment points 700 can be designed so as to prevent any bunching at all of the fabric and provide a smooth surface, such as a smooth proximal surface.

Figure 35:
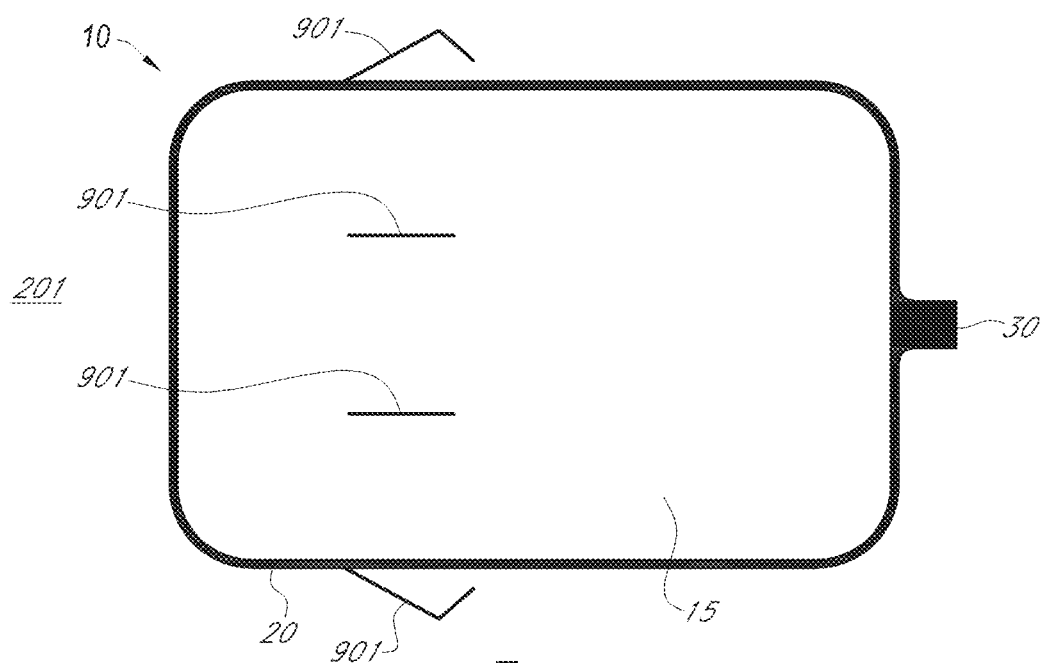
FIG. 35 is a side view of an embodiment an LAA occlusion device having anchors with deployed V-tips that may be used with the various LAA occlusion devices described herein, including but not limited to the devices of FIGS. 85A-90D.
Figure 36:
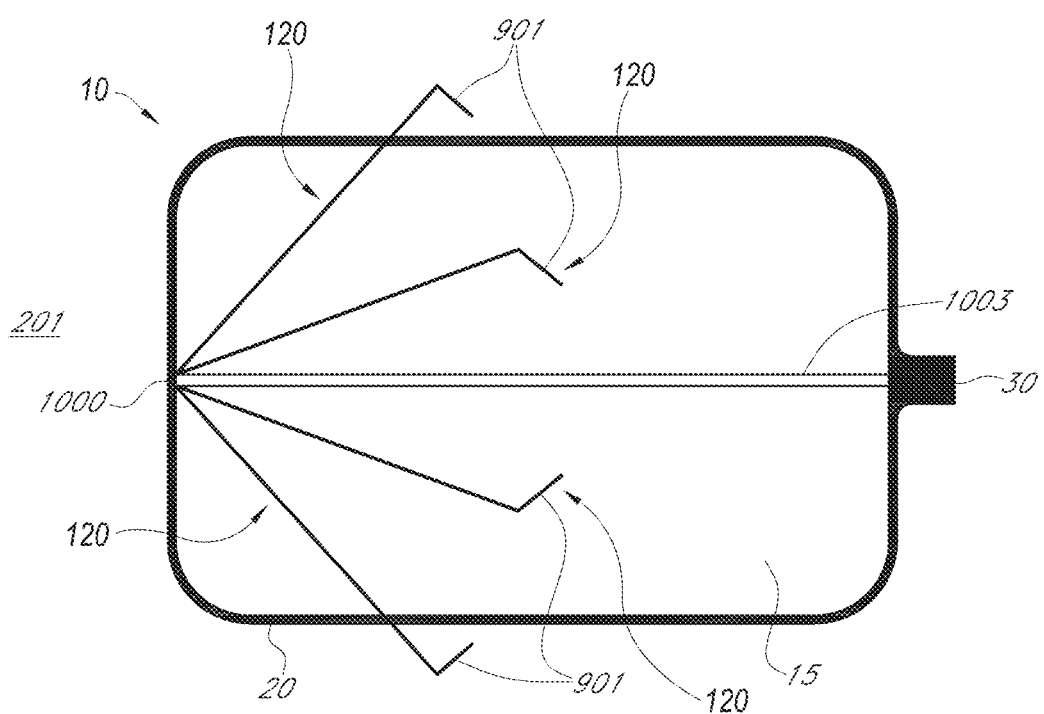
FIG. 36 is a side view of an embodiment an LAA occlusion device having deployed anchors with V-tips that may be used with the various LAA occlusion devices described herein, including but not limited to the devices of FIGS. 85A-90D.

FIGS. 35-36 are side views of embodiments of the device 10 having anchors 120 with V-tips 901 shown in the deployed configuration. The V-tips may be located in the proximal region 125 and/or may form all or part of the tissue engaging segment 121 of the anchor 120, as described herein. The V-tips 901 form a V-shaped point. The V-tips 901 are generally in the shape of a "V" or an otherwise angled, segmented shape. The V-tips 901 may be sharp barbs or hooks. The V-tips 901 may be formed from wire or laser-cut tubing or other suitable methods. As shown in FIG. 35, one or more of the V-tips 901 are attached to the body 15 encased in the skin 20. The V-tips 901 can be attached to the body 15 and/or to the skin 20. In some embodiments, the V-tips 901 are ends of anchors 1000. For example, the V-tips 901 may be part of the anchors 1000 that are within the body 15 and skin 20, as shown in FIG. 36. The distal ends of the V-tips 901 may be free to slide along and collapse or expand. The distal ends of the V-tips 901 may be attached to the body 15, skin 20, and/or the anchors 1000 to allow the V-tips 901 to collapse and retract. During retrieval into a catheter or sheath, the V-tips 901 can flatten out when engaging the inner diameter of the catheter or sheath. The V-tips 901 can be formed from Nitinol, implant grade stainless steel such as 304 or 316, cobalt-chromium based alloys such as MP35N or Elgiloy, other suitable materials, or combinations thereof. The V-tips 901 may then recover their pre-set shape after deployment or re-deployment.

Figure 37A:
FIGS. 37A-37C are side views of various embodiments of anchors that may be used with the various LAA occlusion devices described herein, including but not limited to the devices of FIGS. 85A-90D.
Figure 37B:
Figure 37C:

FIGS. 37A-37C are side views of various embodiments of V-tips that may be used with the anchors described herein. FIG. 37A is a side view of an embodiment of the V-tip 901. The V-tip 901 includes two angled segments. The segments may form the angle in a free state. The angle may be various angular amounts. In some embodiments, the angle formed by the V-tip 901 is no more than about 170°, 160°, 150°, 140°, 130°, 120°, 110°, 100°, 90°, 80°, 70°, 60°, or any smaller, greater or intermediate angular amount. FIG. 37B is a side view of an embodiment of a wave V-tip 1101. The wave V-tip 1101 may include a curved segment and an angled straight segment. FIG. 37C is a side view of an embodiment of a two-wave V-tip 1103. The two-wave V-tip 1103 may include two curved segments. The curved segments may promote engagement of the tip with the inner wall of the LAA. The end of the various V-tips may be smooth and rounded or sharp to promote tissue penetration. In some embodiments, all of the V-tips may have the same shape. In some embodiments, some of the V-tips may have a first shape and other V-tips may have a second shape different from the first shape. In some embodiments, some of the V-tips may be attached to the skin 20 and or body 15. In some embodiments, some of the V-tips may be attached to the anchors 1000.

Figure 38:
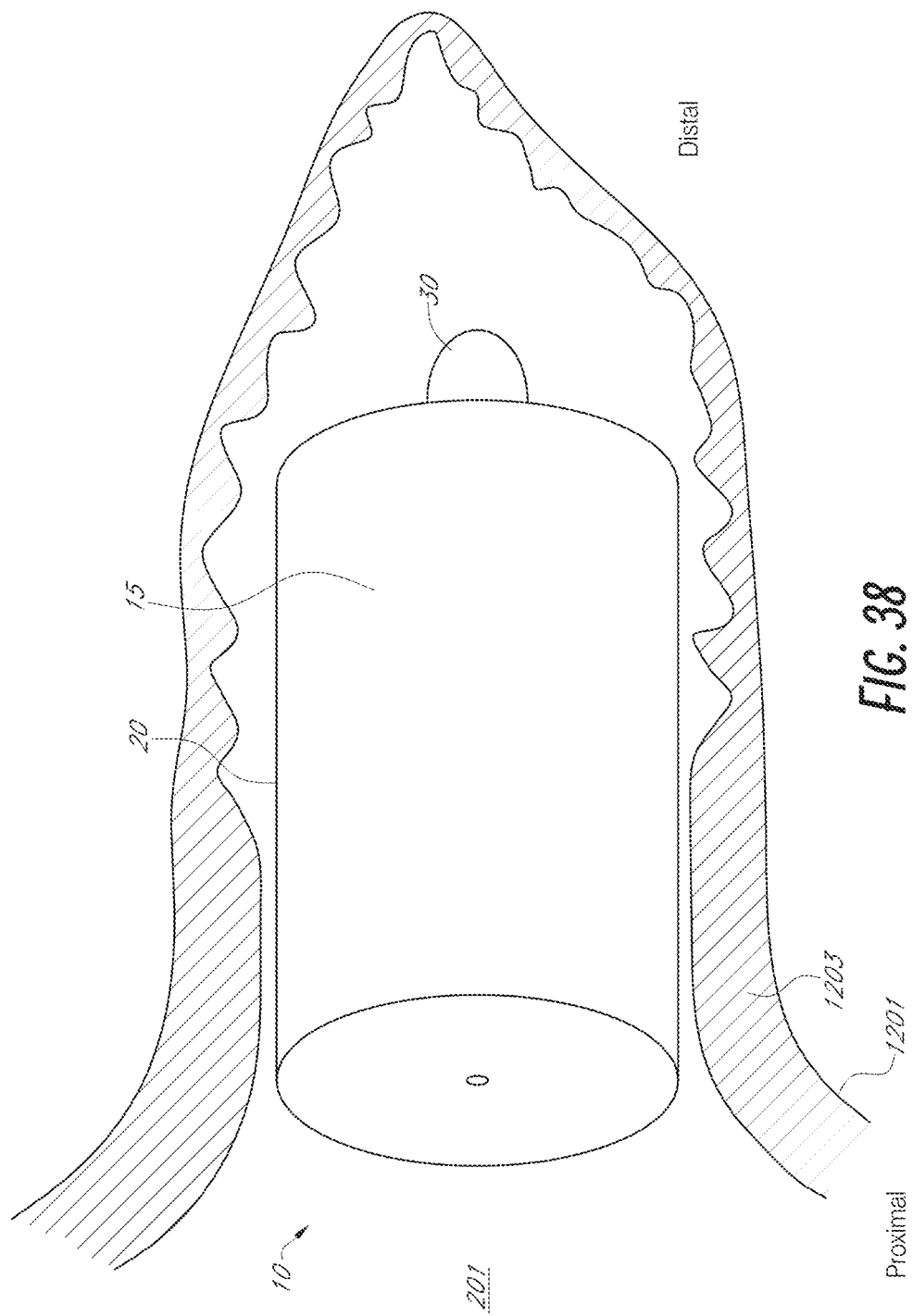
FIG. 38 is a side view of an embodiment of an LAA occlusion device implanted inside an LAA.

FIG. 38 is a side view of another embodiment of the device 10 for occlusion of the LAA implanted inside an LAA 1201. The device 10 includes a body 15 with a skin 20 and finial 30 placed within the LAA 1201. The LAA includes a thicker proximal portion 1203 closer to the ostium. The internal locking system 101, for example anchors thereof, may be configured to engage with the thicker proximal portion 1203 of the LAA. The various anchors, V-tips etc. described herein for the various embodiments of the device 10 may be used to secure the anchors in the thicker proximal portion 1203. In some embodiments, the device 10 may be deployed from the catheter such that the body 15 expands. The location, orientation, etc. of the expanded body 15 within the LAA may be verified, for example by imaging, as described herein. The location, orientation, etc. of the expanded body 15 within the LAA may be verified to ensure engagement of the internal locking system 101, for example anchors thereof, with the thicker proximal portion 1203. Then, the internal locking system 101, for example anchors thereof, may be deployed to engage the thicker proximal portion 1203. If after deployment of the internal locking system 101, for example anchors thereof, it is determined that the anchors did not engage with the thicker proximal portion 1203, the anchors may be retracted, as described herein, in order to reposition and/or retrieve the device 10.

In some embodiments, the internal locking system 101, for example anchors thereof, may be preloaded surface elements releasably constrained or otherwise locked down in a collapsed or constrained position or configuration. The internal locking system 101, for example anchors thereof, may be constrained using a restraint. The restraint may be a dissolvable polymer, a lasso, or wires that can be retracted to release the anchors. The restraint may be similar to a deadbolt. Other anchoring concepts include Velcro integral to the ePTFE, electrically orientable/ratcheting anchoring elements, unidirectional Gecko tape, or wires pre-attached to the finial 30. In some embodiments, the body 15 with skin 20 may be secured within the LAA by texturing the body 15 and exposing the body 15 to the tissue through holes in the skin 20 to increase the friction with the cardiac surface to a high enough level to prevent implant migration.

FIGS. 39A-39B are perspective views of an embodiment of a deployable anchor 1302 activated by a pull wire 1301 and shown, respectively, in the constrained and deployed configuration, that may be used with the various devices 10, 1020, 3000 etc. for occlusion of the LAA described herein. A two-stage anchoring system allows deployment of the anchors 1302 after implantation and expansion of the body 15. This embodiment incorporates one or more hinged anchors 1302. The anchors 1302, which be a barb or other anchoring element, may lie flat during delivery and during deployment of the body 15. Next, when pulled or pushed, the anchors 1302 bend at a hinge 1306 and extend outward from the surface of the body 15 and into the LAA tissue. The anchors 1302 may bend at the hinge 1306 using a hollow constraining element 1304 which can be a thin, metallic, round or rectangular box such as a round or rectangular shaped tube, and the pull wire 1301, for example a sliding element, which can be a wire or suture. The pull wire 1301 is attached to the proximal end of the anchor 1302 and extends back through the delivery catheter or sheath. When the pull wire 1301 is retracted, the anchor 1302 slides back though a slot 1308 in the tube 1304 and bends at the preformed hinge 1306. A portion of the anchor 1302 then extends out through the slot 1308.

Figure 40A:
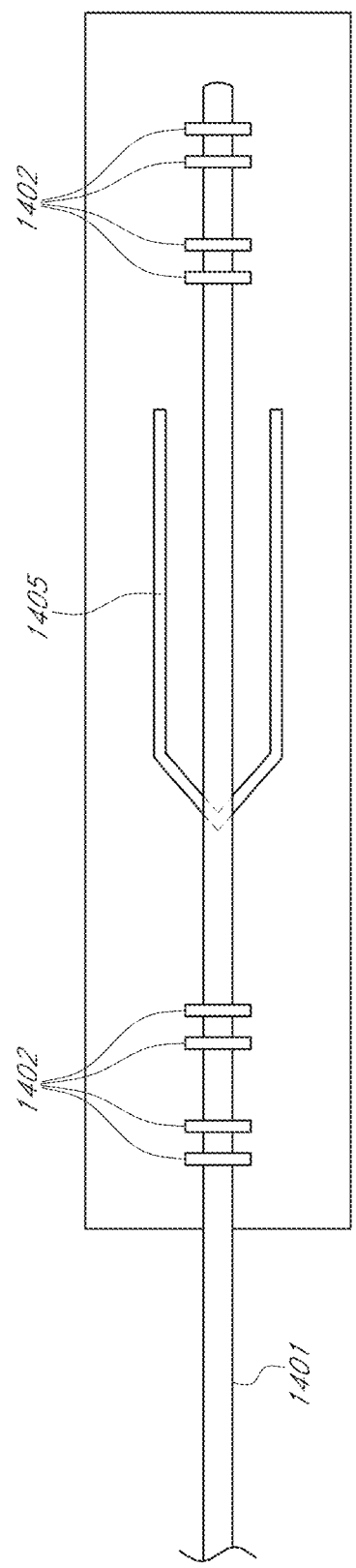
FIGS. 40A-40B are perspective views of an embodiment of a deployable anchor that may be used with the various LAA occlusion devices described herein, including but not limited to the devices of FIGS. 85A-90D.
Figure 40B:
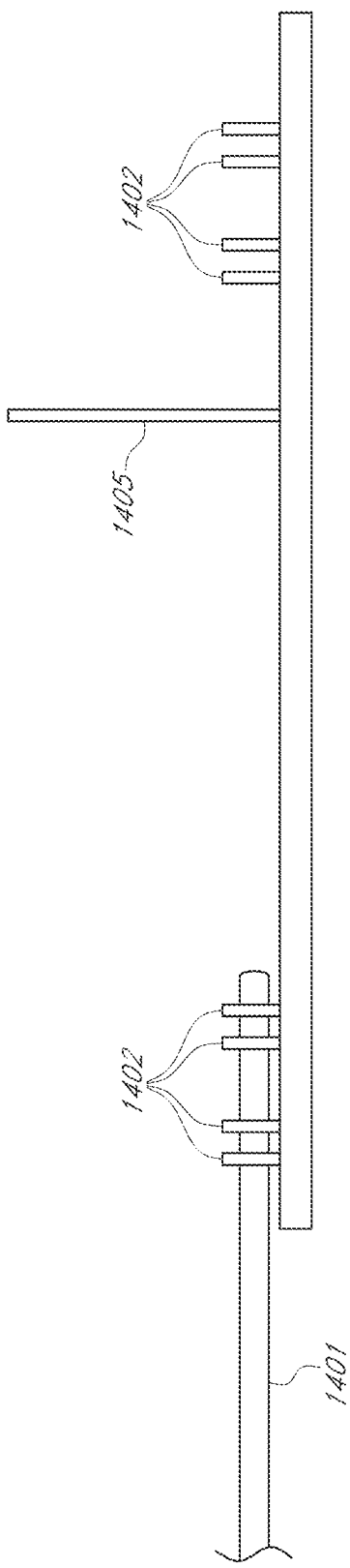

FIGS. 40A-40B are perspective views of an embodiment of a deployable anchor 1405 activated by a lock wire 1401 and shown, respectively, in the constrained and deployed configuration, that may be used with the various devices 10, 1020, 3000 etc. for occlusion of the LAA described herein. The anchor 1405, which be a barb or other anchoring element, may be formed from wire or a flat sheet of Nitinol or other shape memory material and heat set to be in an expanded configuration. One or more of the anchors 1405 can be placed along the skin 20 or otherwise along an external surface of the body 15. One or more corresponding guides 1402, such as loops, may be located along the skin 20 or the body 15. The guides 1402 may be located on both sides of the anchor 1405, as shown. The guides 1402 on a first side of the anchor 1405 may fix the anchors 1405 in place. The guides 1402 on a second, opposite side of the anchor 1405 may act as a guide for the lock wire 1401, which may be a restraining wire, suture, etc. The lock wire 1401 may be used to constrain the anchors 1405 in a constrained configuration, for example in the flat position as shown in FIG. 40A. When the lock wire 1401 is retracted, the anchors 1405 deploy, as shown in FIG. 40B. The anchors 1405 may extend perpendicular to the body 15, or at an angle.

Figure 41A:
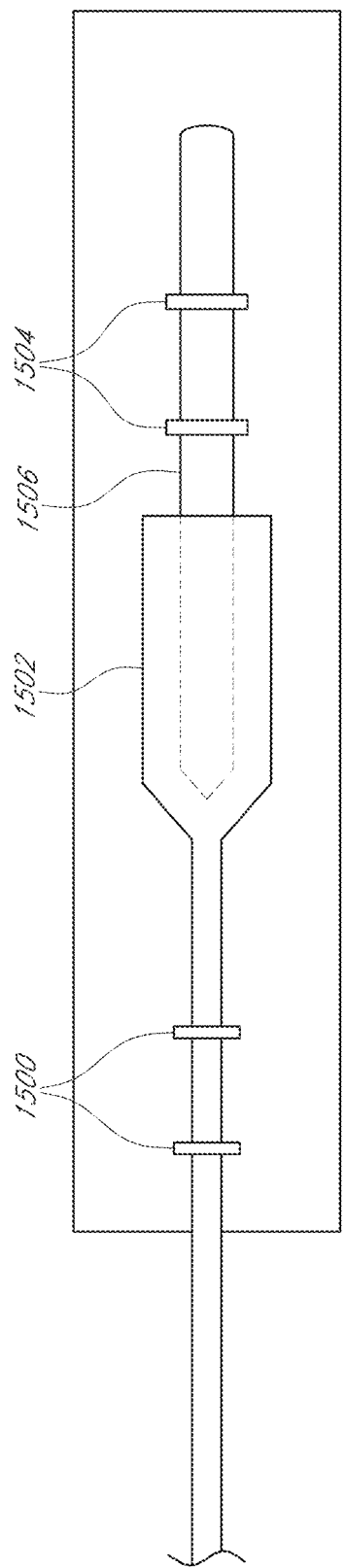
FIGS. 41A-41B are perspective views of an embodiment of a deployable anchor that may be used with the various LAA occlusion devices described herein, including but not limited to the devices of FIGS. 85A-90D.
Figure 41B:
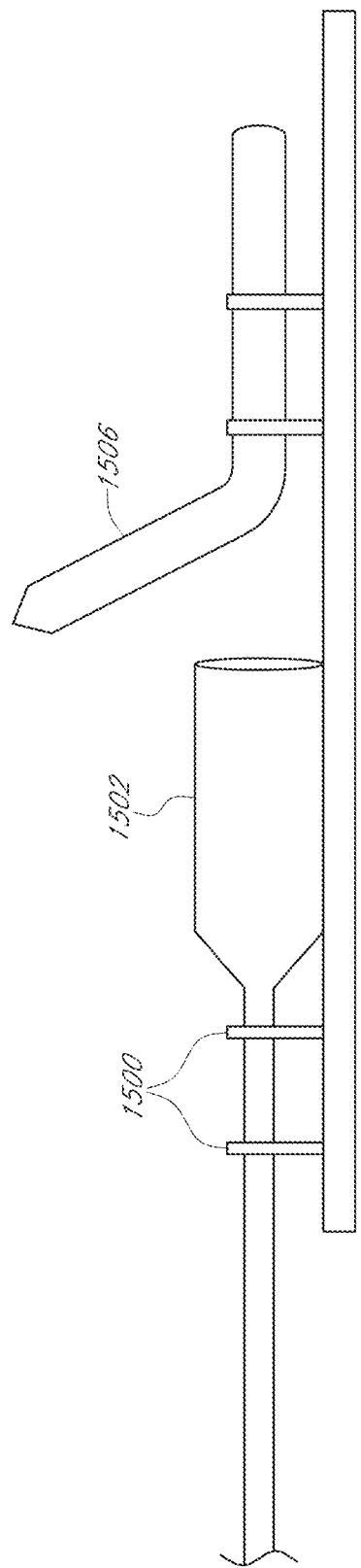

FIGS. 41A-41B are perspective views of an embodiment of a deployable anchor 1506 activated by a sheath 1502 and shown, respectively, in the constrained and deployed configuration, that may be used with the various devices 10, 1020, 3000 etc. for occlusion of the LAA described herein. The anchor 1506, which be a barb or other anchoring element, may be formed from wire or a flat sheet of Nitinol or other shape memory material and heat set to be in an expanded configuration.

One or more of the anchors 1506 may be placed along the skin 20 or otherwise along an external surface of the body 15. One or more corresponding guides 1500 and locking loops 1504 may be located along the skin 20 or the body 15. The guides 1500 may be located on a first side of the anchor 1506 and the locking loops 1504 may be located on a second, opposite side of the anchor 1506, as shown. The anchors 1506 are held in the constrained or restrained configuration or position by a sheath cover 1502. The sheath cover 1502 may be tubular or rectangular in shape. The sheath cover 1502 constrains the anchors 1506. The sheath cover 1502 may constrain the anchors 1506 in a flat position as shown in FIG. 41A. When the sheath cover 1502 is retracted, the anchors 1506 deploy, as shown in FIG. 41B. The anchors 1506 may extend at an angle to the body 15, or perpendicularly.

Figure 42B:
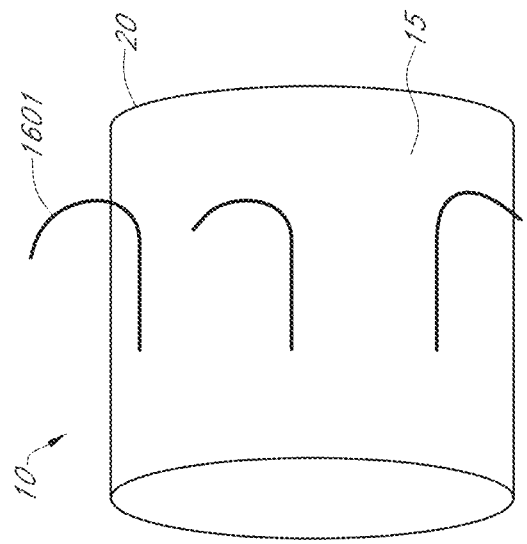
FIGS. 42A-42D are various views of embodiments external deployable anchors that may be used with the various LAA occlusion devices described herein, including but not limited to the devices of FIGS. 85A-90D.
Figure 42A:
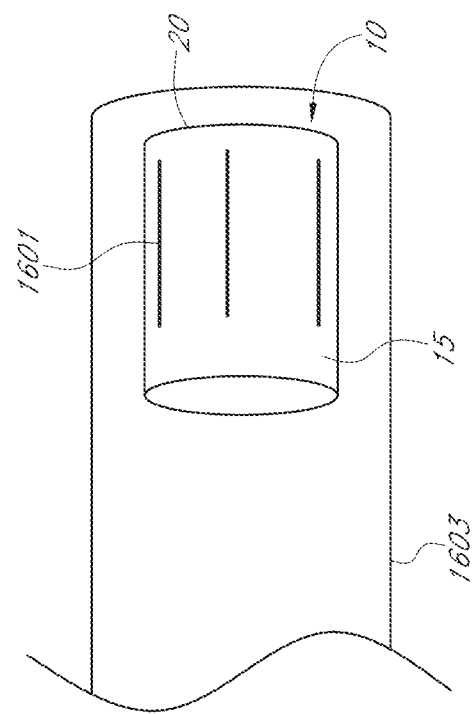
Figure 42D:
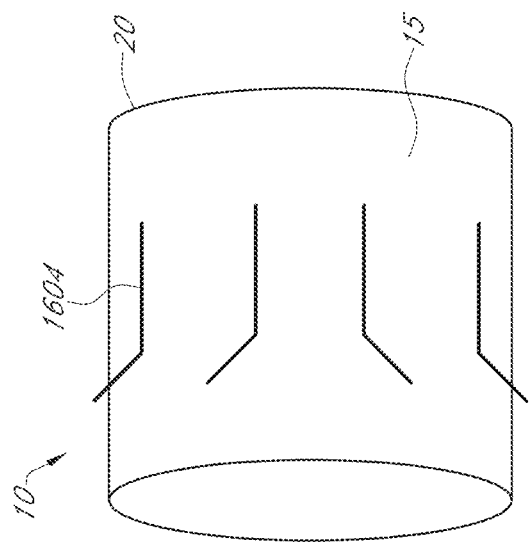
Figure 42C:
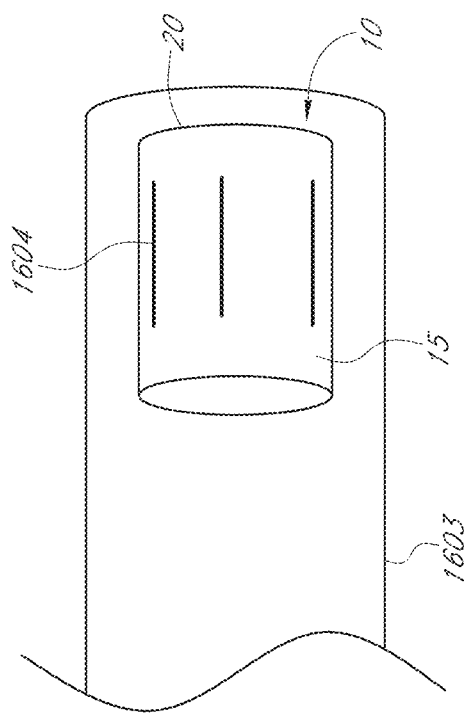

FIGS. 42A-42D are various views of embodiments of the device 10 for occlusion of the LAA having external deployable anchors 1601, 1604 which can be collapsed and expanded by retraction into or out of a sheath or outer catheter. FIG. 42A is a side view of the device 10 having anchors 1601 constrained by a delivery sheath 1603. FIG. 42B is a side view of the device 10 unconstrained by the delivery sheath 1603 with the anchors 1601 deployed. FIG. 42C is a side view of the device 10 having anchors 1604 constrained by the delivery sheath 1603. FIG. 42D is a side view of the device 10 unconstrained by the delivery sheath 1603 with the anchors 1604 deployed. The body 15 with skin 20 can contain the anchors 1601 or 1604 which are fixed to the surface of the skin 20 and are unconstrained and therefore expanded in a free state, as shown in FIGS. 42B and 42D. The delivery sheath 1603, such as a catheter, may be used to constrain the anchors 1601 or 1604. The anchors 1601 or 1604 may then expand when the body 15 is unconstrained by the delivery sheath 1603, for example when the when the body 15 is released from the delivery sheath 1603. The anchors 1601 may deploy into a curved shape as shown in FIG. 42B. The anchors 1604 may deploy into an angled shape as shown in FIG. 42D. The anchors 1603 or 1604 after deployment may point toward either the proximal or distal side of the body 15.

Figure 43A:
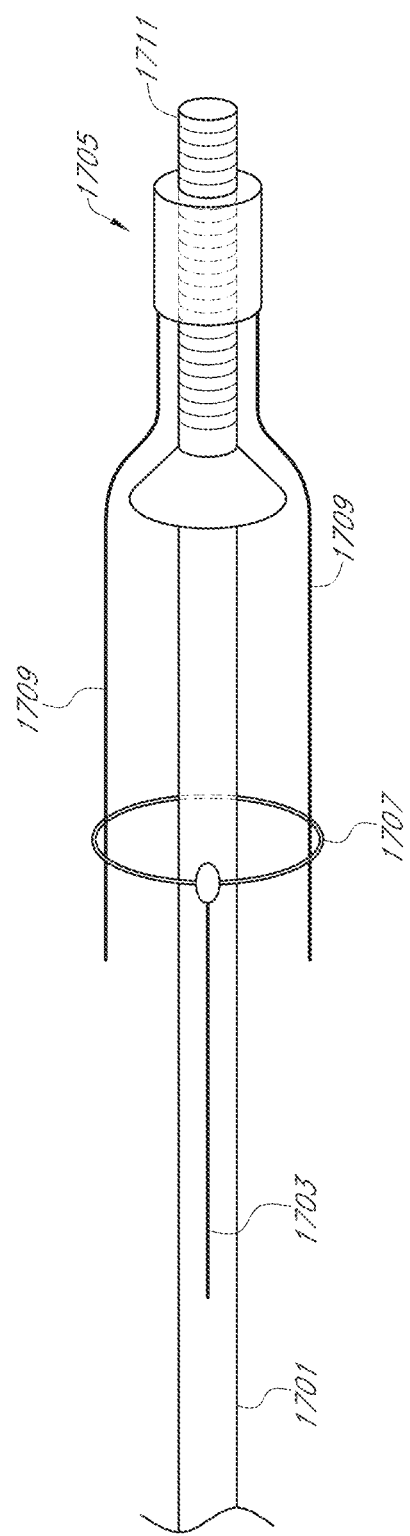
Figure 43C:
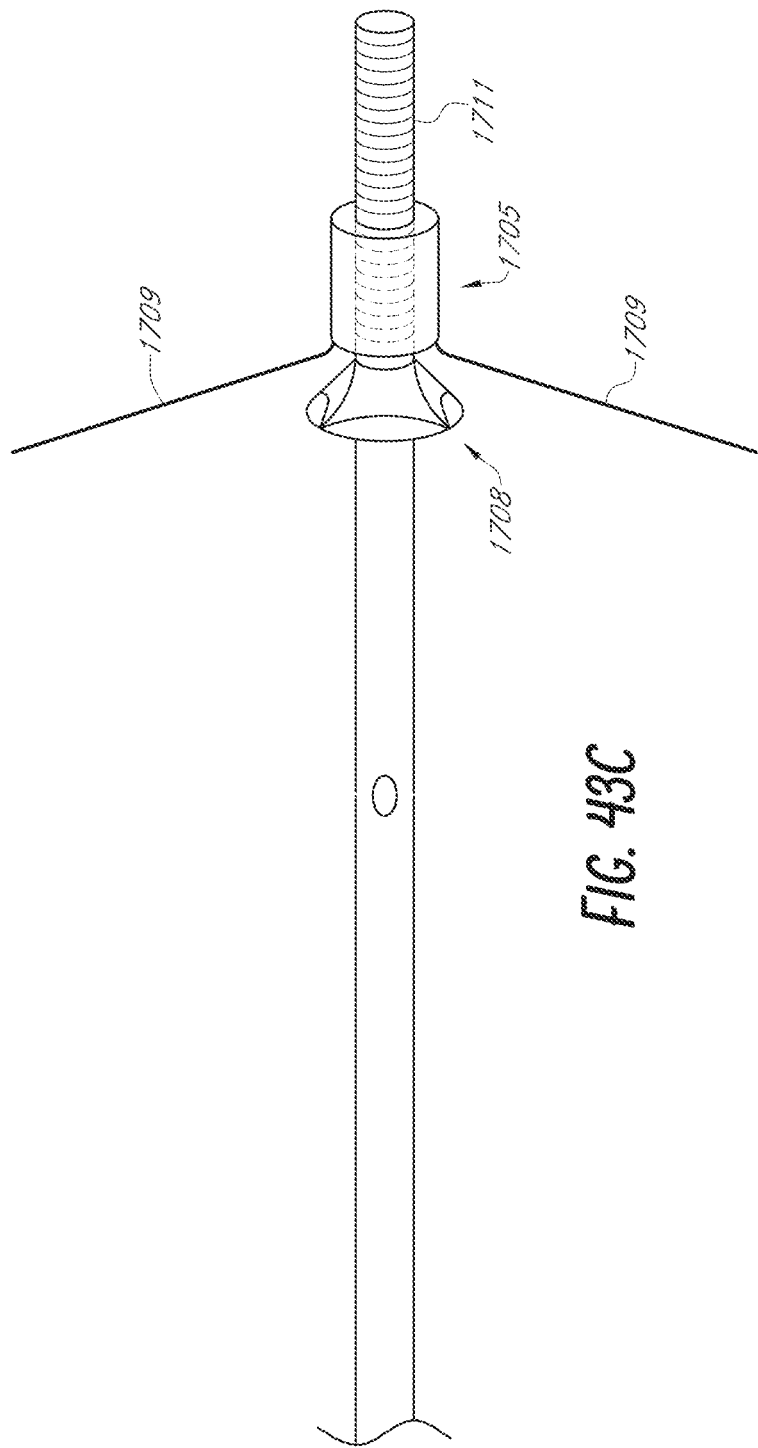

FIGS. 43A-43C are sequential side views of an embodiment of the device 10 for occlusion of the LAA shown, respectively, constrained by a lasso 1707, deployed, and adjusted with a mount 1705. One or more anchors 1709 may be pre-mounted within the body 15 and attached distally to the mount 1705. The mount 1705 may be a ring-like member having an opening extending therethrough. The mount 1705 is positioned over a rod 1701 with end 1711. The mount 1705 can move, for example slide, over the rod 1701 in the proximal direction. In some embodiments, the mount 1705 may be pulled proximally, for example by a pull wire. In some embodiments, the mount 1705 may move when the rod 1701 is rotated. In some embodiments, the mount 1705 and/or end 1711 of the rod 1701 may be threaded. Movement of the mount 1705 causes the anchor 1705 to move. The device may include a tapered cone 1708. The cone 1708 may be attached to the end of the rod 1701. The mount 1705 may be moved toward the cone 1708 to adjust the height of the anchors 1709. Thus, the anchors 1709 are angled more in FIG. 17C relative to FIG. 17B. The anchor 1709 may move through the body 15 and into the tissue. The anchors 1709 may be adjusted to increase or decrease the amount of tissue penetration, for example by moving the mount 1705 as described. For retrieval, this process can be reversed. In some embodiments, the lasso 1707, attached to a wire 1703, may extend, for example thread, through the threaded rod 1701 and be placed around the anchors 1709 to retract the anchors 1709 back into the body 15. In some embodiments, the lasso 1707 may be used to initially constrain the anchors 1709 and then retract to allow the anchors 1709 to deploy.

FIGS. 44A-44C are side views of an embodiment of the device 10 for occlusion of the LAA having an adjustable two stage anchor system with anchors 1801 activated by moving a mount 1803 along a rod 1804. The anchors 1801 may be internal grappling hook type structures placed within the body 15 and skin 20. The anchors 1801 may be introduced through a central lumen 1003 that extends through the body 15, as shown in FIG. 43A. The anchors 1801 may then travel through the body 15 and skin 20 to engage tissue, as shown in FIG. 43B. The anchors 1801 may be adjusted to increase or decrease the amount of tissue penetration. The anchors 1801 are attached at distal ends to the moveable mount 1803. The mount 1803 is prevented from rotating, for example the mount 1803 may be notched to prevent rotation of the mount 1803 within the finial 30, as shown in FIG. 43C. The mount 1803 is threaded onto the threaded rod 1804 that can be rotated clockwise or counter clockwise to change the linear position of the mount 1803. The distal end of the rod 1804 may couple with a cap 1807. The cap 1807 may rotate with the rotation of the rod 1804. The mount 1803 may move proximally causing the anchors 1801 to extend past the surface of the body 15 and skin 20 as shown in FIG. 43B. The mount 1803 may move distally to pull the anchors 1801 back within or under the surface of the skin 20. The depth of penetration of the anchors 1801 may be controlled, for example to account for the non-circular cross-section of the LAA. In some embodiments, the anchors 1801 may be deployed individually. Another option is to deploy the anchors 1801 distal to the body 15 with skin 20 and control the stiffness of the anchors 1801 such that they apply a reasonably uniform penetrating force to the tissue at contact.

Various features for LAA (LAA) occlusion may be included, such as those described, for example, in U.S. patent application Ser. No. 15/290,692, filed Oct. 11, 2016 and titled DEVICES AND METHODS FOR EXCLUDING THE LAA, in U.S. patent application Ser. No. 14/203,187, filed Mar. 10, 2014 and titled DEVICES AND METHODS FOR EXCLUDING THE LAA, in European Patent Application no. EP 14779640.3, filed Aug. 24, 2015 and titled DEVICES AND METHODS FOR EXCLUDING THE LAA, and in PCT Patent Application no. PCT/US2014/022865, filed Mar. 10, 2014 and titled DEVICES AND METHODS FOR EXCLUDING THE LAA, the entire disclosure of each of which is hereby expressly incorporated by reference for all purposes and forms a part of this specification. Further additions and improvements to these and other concepts are described below. The embodiments described in the sections below may include the same or similar features and/or functionalities as the embodiments described above, and vice versa, except as otherwise noted or indicated by context.

A. Basic Plug Design Components and Improvements

Various occlusion devices and associated features are described with respect to FIG. 45A to FIG. 77. The same or similar features and/or functionalities of the various devices as shown and described with respect to FIG. 45A to FIG. 77 may be present in the various devices as shown and described with respect to FIGS. 1-44C and 78-93B, and vice versa.

Figure 45A:
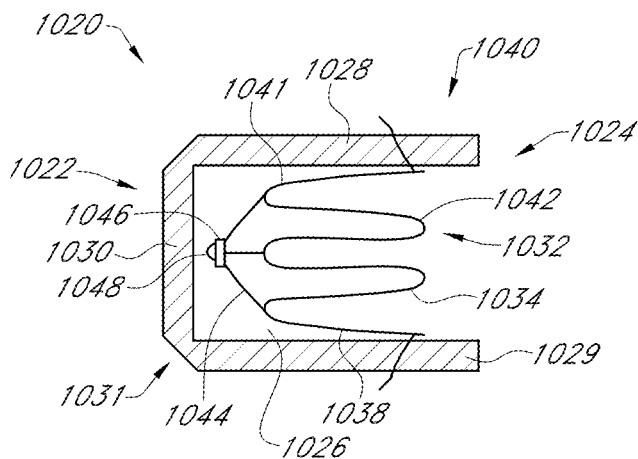
FIG. 45A is a cross-sectional view of an embodiment of an LAA occlusion device shown in an expanded configuration and having a foam cup body, proximal cover, and a deployable frame that includes a hub, recapture struts and a tubular body.
Figure 45B:
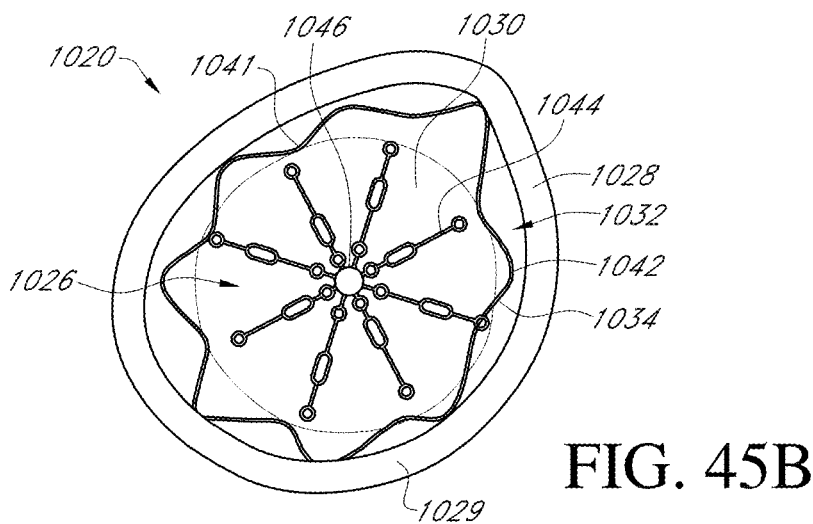
FIGS. 45B and 45C are, respectively, a distal end view and a proximal perspective view of the device of FIG. 45A.
Figure 45C:
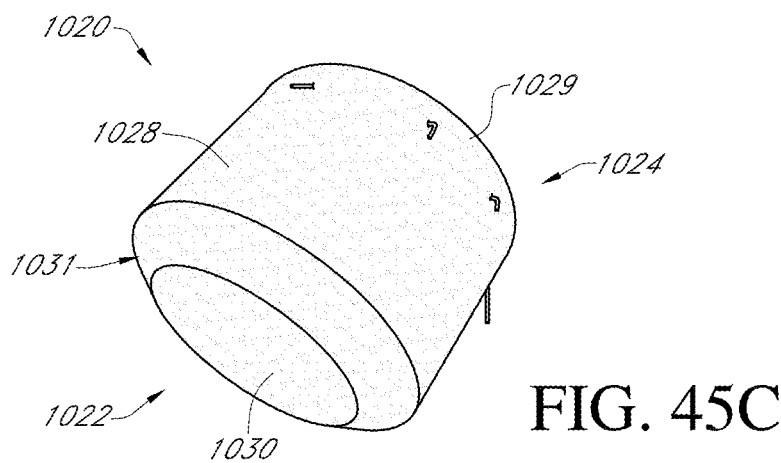

As shown in FIGS. 45A-45C, the device 1020 (sometimes referred to herein as "implant") may utilize a cored-out foam "cup." In some embodiments, this may be similar to the foam 1600 design shown in and described with respect to FIG. 16 and/or the foam body 3002 described with respect to FIGS. 85A-93B. The "cup" design may be contrasted with a solid or generally solid tubular foam plug, such as those described and shown in FIGS. 2 and 6. Regarding the cup design of FIGS. 45A-45C, the approximate thickness of the foam may be about 2.5 mm but can range from about 0.25 mm to about 10 mm. Note that the thickness may be significantly thicker than the typical stent coating or covering as utilized in other applications (e.g. coronary stents, peripheral stents, AAA liners, etc.). In this application, where we are occluding, the thickness of the foam adds some desired structure between the gaps of the internal support structure 1032, such as a stent. In some embodiments, the thickness may be at least about 0.25 mm; in some embodiments at least about 0.50 mm, 0.75 mm, 1.0 mm or 2.0 mm or greater in an unconstrained state, and in one implementation about 2.5 mm, with thickness selected depending upon the desired performance.

FIG. 45A is a cross-sectional view of the preferred embodiment showing the components of the implant 1020 having a proximal (atrial) end 1022, a distal (LAA) end 1024 and an interior cavity 1026 in the expanded configuration. An expandable tubular wall 1028 defines the interior cavity 1026, which may be enclosed at its proximal end 1022 by a tissue scaffold 1030 or other barrier configured to span the ostium and isolate the LAA from the atrium post deployment. The proximal edge of the tubular wall 1028 may be provided with a ramped reentry or recapture surface such as an annular chamfer 1031 extending circumferentially or otherwise around the proximal edge of the implant 1020, preferably continuously, to facilitate proximal retraction of the implant into the deployment sheath to permit repositioning or removal if desired. A distal extension 1029 of the tubular wall 1028 extends distally beyond the internal support (discussed below) to form an atraumatic leading edge.

The tissue scaffold 1030 may be integrally formed with the tubular wall 1028 or may be bonded thereto. The tissue scaffold 1030 and the tubular wall 1028 may have approximately the same thickness and pore characteristics, discussed below. Alternatively the tissue scaffold may comprise a different material such as ePTFE, PTFE, Dacron, or others known in the art, configured to support tissue ingrowth and isolate the LAA, but thinner than the tubular wall 1028.

An expandable, internal support structure 1032 such as a wave stent 1034 or other frame may be provided. The illustrated wave stent 1034 comprises a plurality of struts 1038, adjacent pairs of struts joining to form a plurality of proximal apexes 1041 and distal apexes 1042. The stent 1034 may be laser cut from tube stock as is known in the art. Each of at least three, and preferably at least 4 or 6 or 8 or more of the proximally facing apexes 1040 is provided with a reentry or recapture strut 1044, which incline radially inwardly in the proximal direction to a central hub 1046. Recapture struts may be cut from the same tube stock as the stent. Hub 1046 may be provided with a central lumen, such as for delivery over a guidewire, or for releasable engagement with a deployment device (not illustrated). Alternatively, the hub 1046 may be provided with an attachment such as an eyelet 1048 for receiving a suture loop. A suture or other retention element may extend distally from the deployment catheter, through the tissue scaffold 1028, through the eyelet 1048 and proximally back through the tissue scaffold 1028 and into the deployment catheter. Following satisfactory positioning of the implant 1020, the suture may be removed, releasing the implant 1020 from the deployment catheter leaving a homogeneous tissue scaffold 1030 as resilience of the material closes the suture tracks. In one preferred implementation the implant 1020 is deployed from the delivery catheter without advancing over the wire and the hub lacks a central lumen. In one embodiment, the implant is secured to the delivery system using any of a variety of means known in the art including screw mechanisms or ball in socket attachment mechanism, which can also pivot.

The tubular wall 1028 may be attached to the stent 1034 by adhesives, sutures or other bonding techniques known in the art. In the illustrated embodiment, the tubular wall 1028 is sutured to the stent 1034 and the tissue scaffold 1030 is sutured to the recapture struts 1044, with the support structure 1032 carried within the cavity 1026. Alternatively, at least a portion of the support structure 1032 may be carried on the outside surface of the tubular wall 1028 or tissue scaffold 1030. The wave stent may be embedded within the tubular wall 1028 such as by sandwiching the stent between inner and outer layers of foam which are then bonded together. Similarly the recapture struts may be enclosed between inner and outer polymer layers. The polymeric material can also be foamed around the stent so that a secondary attachment process is not required.

FIG. 45B is a distal end view of an embodiment of the implant 1020 showing the internal metallic structure having a central hub 1046 and eight recapture struts 1044 inclining radially inwardly to the hub 1046. A plurality of suture retainers such as apertures 1050 are attached to or formed in the struts 1044 to receive the sutures used to secure the tissue scaffold 1030. This reduces the tendency of material of the tissue scaffold 1030 to slide distally along the struts 1044 if the implant 1020 is proximally retracted into the deployment catheter.

The frame may be expandable from a contracted delivery configuration to an expanded deployed configuration. The frame may be retractable from an expanded deployed configuration to a contracted delivery configuration. The frame may be generally tubular, e.g. circular, rounded, segmented, polygonal, other shapes, or combinations thereof in the unconstrained, expanded configuration, and preferably presses the foam into conformance with the shape of the inside surface of the LAA. This permits the deployed implant to minimize leaks, the largest of which is no more than about 4 mm or 3 mm or 2 mm or less and in some deployments essentially no leaks as viewed on color Doppler.

FIG. 45C is a proximal end perspective view of the outside of an embodiment of the implant 1020 having a unitary foam shell and showing the proximal chamfer 1028, in an unconstrained expansion. Anchors deployed near the distal end of the frame are discussed in further detail below.

Some advantages of the cored-out foam "cup", as compared to a solid foam plug, are as follows: it still behaves like a full foam plug with respect to conformability and sealing; it allows incorporation of an internal metallic frame which can be optimized to provide the desired amount of expansion for sealing and anchoring by providing an optimal radial force and an attachment point for the anchors, and a front face inside the proximal face to aid in collapse of the foam for retrieval; by sizing the metallic frame so that it is shorter in length than the foam cup, an atraumatic distal bumper is formed which is entirely foam and can be extruded from the sheath tip as the tip is advanced within the LAA; and the reduced overall volume of material aids with the following: it significantly reduces the delivery profile, it is easier to flush to remove air prior to delivery into the vascular system, and it makes the plug more porous to blood so that if embolized within the cardiovascular system, it allows more blood to flow through it.

In an embodiment, the proximally facing edges of the foam plug 1040 are chamfered to aid in loading and retrieval. Also, while there can still be a central location to allow tracking of the implant 1020 over a guidewire-type device, in some embodiments there is no lumen or there is just a slit in the foam plug 1040, as it is not desirable to have a significant residual central hole which may cause thrombus formation or allow leakage. The slit can be a single slit, double cross-shaped slit, or multiple slits. The objective is to still allow tracking over a guidewire but to be sure the hole closes completely once the guidewire is removed. In the case of a solid face, the implant 1020 may not be tracked over a guidewire and may instead, for example, be delivered through a long transseptal sheath.

Please note that the term "guidewire", as utilized above, can mean an actual medical device sold as a guidewire or it can be a catheter, such as a pigtail catheter, which is initially placed in the LAA over which the LAAC (LAA Closure) implant 1020 is tracked.

Diameters: The LAA may vary in diameter from about 15 mm to about 33 mm and as such, the implant 1020 diameter must be able to accommodate this variation in sizes. The more the implant 1020 may accommodate various large ranges of diameters, the fewer predetermined sizes are needed, thereby simplifying the procedure for implantation. The construct of this implant 1020 is such that it may accommodate diameters less than 50% of the fully expanded diameter. The preferred plug 1040 diameters may be about 27 mm, 33 mm, and 35 mm. Ideally, only 1-2 sizes would be needed to close a large range of LAA diameters. This is a key advantage of the foam plug 1040 concept as compared to metal cage type devices with fabric tissue scaffolds.

Depth: The preferred plug 1040 length (the depth of the occluder within the LAA generally along a proximal-distal direction) is 20 mm and is independent of the diameter of the implant 1020. This allows for good implant 1020 stability while still accommodating the majority of anatomies. The distal tip of the foam plug 1040 is very soft, providing an atraumatic tip as it enters the LAA when the distal tip of the implant 1020 is allowed to protrude past the distal dip of the delivery catheter or sheath. The short depth makes placement of the plug 1040 more robust, as there is less need to align delivery catheters with the LAA, as is needed with longer devices.

Foam and Porosity: The average pore size of the foam is 250-500 microns. The foam has a very high void content (90-95%) to promote quick and thorough tissue ingrowth. The open cell foam permits blood to flow through it. If the plug 1040 should embolize, it will be open enough to allow enough blood flow to be safe until it can be retrieved. Additionally, the large void content should be beneficial for proper flushing of the implant 1020 to prevent air introduction into the vascular system. The porosity and cell size may be as described with respect to the foam body 3002 of the device 3000, shown and described for example with respect to FIGS. 85A-90D.

The compliance and thickness of the foam are designed to provide a good seal against the tissue with minimal compression. While other devices require significant oversizing to obtain a seal, this implant 1020 may require only ≤1 mm of oversizing.

LA Facing Surface: ePTFE (expanded Polytetrafluoroethylene) or PTFE as the skin/layer for the implant 1020 such as over or partially over the plug 1040, as described above, may be ideal for supporting neointimal formation without thrombus formation. While embodiments may be described with respect to ePTFE, it is understood that PTFE may also be used. It may, however, reduce safety due to the inability or reduced ability to allow blood flow through the surface of an embolized implant 1020 due to the low porosity of the ePTFE, even though blood flow may be enabled around the outer surfaces of the cup. ePTFE porosity is much lower than that of the open cell foam, so blood flow across the membrane may be negligible. It is, however, hydrophobic which is beneficial for thromboresistance. One option, to maintain the desired open porosity of the foam structure while adding the thromboresistance of ePTFE and/or PTFE, is to add a PTFE coating via vapor deposition to the foam. The thromboresistant coating may contain ePTFE or PTFE. This creates a highly porous surface that simulates the ePTFE morphology. Methods of attachment could include vapor deposition, as mentioned above or elastomeric glue (although this may eliminate porosity at the attachment points). If ePTFE is preferred, that could be attached by encasing the metallic frame in ePTFE then wrapping through the center, around the OD, and attaching via sutures.

It may be desirable to reduce the pore size of the foam to between about 30-200 um, as further described herein.

Barbs/Anchors: There are several options or types of barb designs that may be implemented for anchoring the implant 1020 within the LAA. The following are some examples: 1) Static: always engages tissue when the plug is deployed. This makes re-sheathing and repositioning of the implant 1020 more difficult. 2) Constrained: the implant 1020 can be deployed with barbs constrained. The implant 1020 can then be repositioned, as needed. The barbs are then released when the plug 1040 is in its final position. 3) Dynamic: barbs can be deployed or retracted as desired without dislodging plug. Dynamic barbs may allow for deployment and retraction, for example to reposition and/or remove the implant 1020.

In some embodiments, the implant 1020 may have different features form other implants described herein. In some embodiments, the implant 1020 may include any or all of the following features: does not have a central lumen; has a spoked element against the proximal face inside the cup in addition to the wave stent; has anchors/barbs that can preferably be activated as a secondary step following placement of the plug itself; has a layer on the proximal face, which may be similar to the proximal face 1604' shown in FIG. 16 or the layer 3100 shown in FIG. 85A, although in some embodiments the PTFE may be applied via vapor deposition coating as opposed to expanded PTFE (ePTFE) attached as a secondary material.

B. Endoskeleton System with Proximal Spokes

Figure 46:
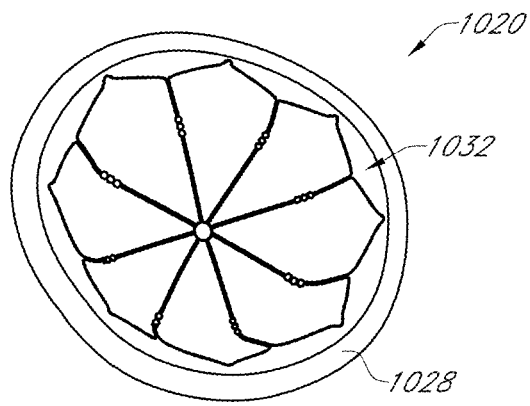
FIG. 46 is a distal end view of the LAA occlusion device of FIG. 45A.

The implant 1020 may include a foam plug 1040 with a central endoskeleton that includes a proximal spoke face 1080 with several radial struts. This configuration improves the ability to retrieve (re-sheath) the foam implant 1020. The stent version depicted in FIG. 45A and FIG. 45B may be laser cut from a superelastic nitinol tube, however, numerous other biocompatible metallic materials can be utilized such as shape memory Nitinol, stainless steel, MP35N, or Elgiloy. While this embodiment is self-expandable, a balloon-expandable design could be utilized. Additionally the frame could be fabricated from drawn wire as opposed to being laser cut from a tube. Loops can be provided along each strut to allow for attachment to the foam via sutures, although other attachment processes could be utilized, such as adhesive bonding. The loops located mid strut can be oval in shape and staggered, to allow easier loading into the delivery catheter and ease of fabrication. Additionally, as shown in FIG. 46, there may be no loops. While the embodiment shown in FIG. 45A has 8 struts, anywhere from 4 to 32 struts may be utilized. In general, it is preferred that the foam be attached to the frame at numerous points including the center. This promotes retrieval without damage to the foam and the suture loops are beneficial for this. In other embodiments, the foam could be formed around the endoskeleton so that it is within the foam, eliminating the need for a secondary attachment step. As shown in FIG. 45A, it is preferable that the proximal foam face have a chamfer at the edges to minimize the bulk of the material in this area to aid in re-sheathing.

Figure 47A:
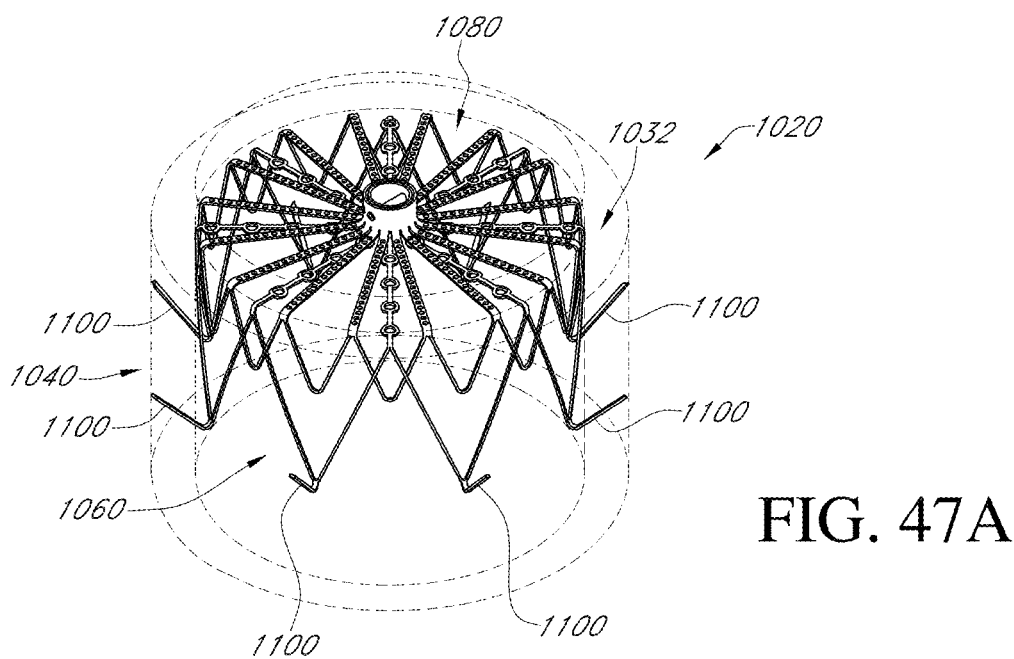
FIGS. 47A-47B are perspective and side views respectively of the LAA occlusion device of FIG. 45A having a single piece internal frame.
Figure 47B:
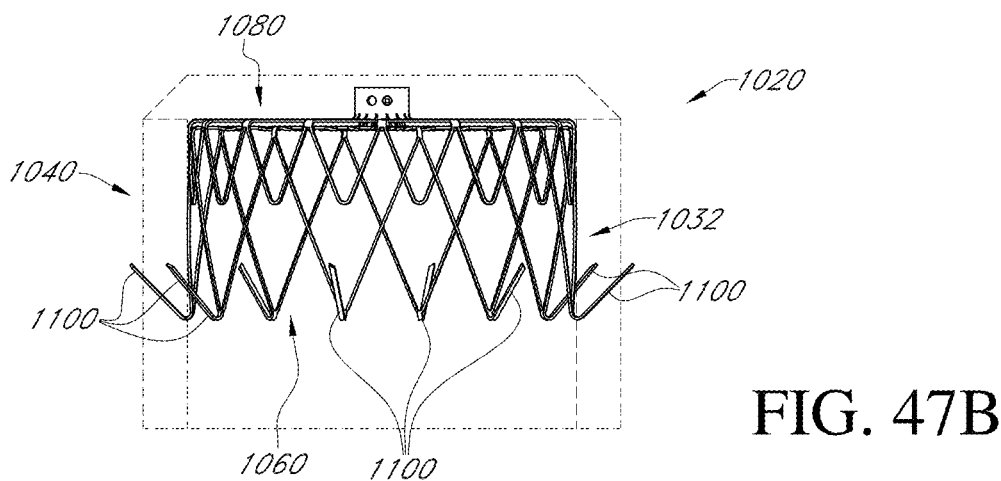
Figure 48:
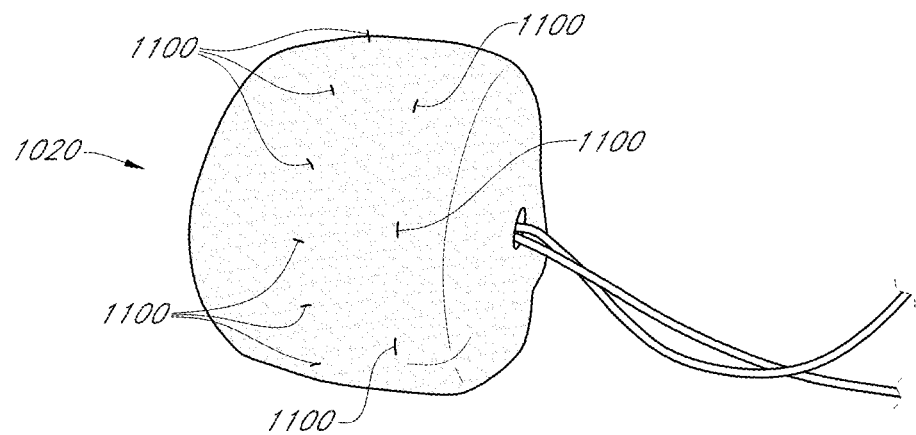
FIG. 48 is a perspective view of the device of FIG. 45A.
Figure 49:
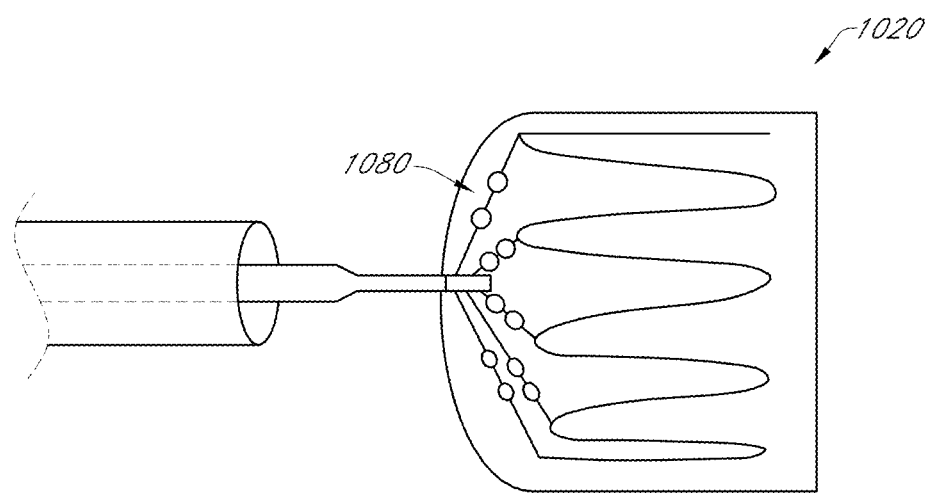
FIGS. 49-50 are side views of the device of FIG. 45A as attached to a delivery catheter shown, respectively, in embodiments of an expanded configuration and a partially collapsed configuration.
Figure 50:
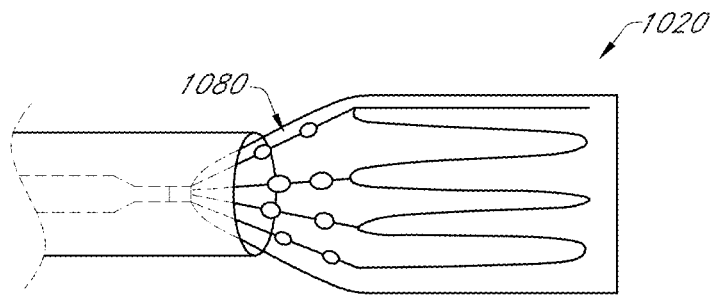

FIGS. 47A-47B are perspective and side views respectively of an embodiment of the LAA occlusion device 1020 having an internal frame 1032, which may be a single piece. While the design shown in FIG. 45B is fabricated from two separate pieces—the proximal spoke face 1080 with eight struts and a wave stent—in some embodiments there may be a single piece unit frame 1032, such as that shown in FIGS. 47A and 47B. In some embodiments the proximal spoke face 1080 may support re-sheathing, the eight crown wave cage stent 1060 supports the foam cylinder plug 1040, and the eight to sixteen, or fewer or more, barbs or anchors 1100 located within the cylinder provide anchoring to resist embolization. The anchors 1100 can be located proximal, distal, and/or centrally along the length of the cylinder. The anchors 1100 can preferably range in size, when fabricated from a Nitinol tube, from about 0.003" to about 0.009" in thickness and from about 0.007" to about 0.015" in width. In some embodiments the anchors 1100 may extend about 1 mm from the surface of the implant 1020 but can range from extending about 0.5 mm to about 2 mm, or less or more, from the surface of the implant 1020. The anchors 1100 may be in a single location along the length of the cylinder or staggered, as shown in FIG. 48. In vitro anchoring dislodgement resistance with these designs may be in the 0.5 lb to 1.5 lb force range. There may be a single row of anchors 1100 as shown. There may be multiple FIG. 49 depicts the implant 1020 with central endoskeleton that includes a proximal spoke face 1080 in its fully expanded configuration as attached to the delivery catheter. FIG. 50 depicts the implant 1020 in an embodiment of its collapsed configuration. Variations include an outer sheath component of the delivery catheter that can be stretchable or slit at the tip, aiding in tapering collapse. A reduced coefficient of friction on the foam face may reduce the forces required to collapse the implant into the catheter. This may be done, for example, by applying a layer of PTFE via vapor deposition or other processes to the foam, or by a layer of expanded PTFE (ePTFE) attached to the proximal face using adhesives or mechanical methods such as suturing. Secure attachment of the foam face to the spoked system may be obtained by suture attachment or other methods including adhesive bonding. which will prevent the foam from bunching up during retrieval which can result in increasing forces and potentially tearing of the foam. If not securely attached with distributed forces, the metallic spoked element may pull through the foam during re-sheathing, destroying the implant.

C. Proximal (Blood-Contacting) Surface of the Foam

The foam implant 1020 may be comprised of porous open cell foam. The foam can be any of a variety of currently available materials including polyurethane-based biomaterials such as polyurethane or polycarbonate-polyurethane, or polyvinyl acetal (PVA) (Ivalon®). The foam can also be reticulated, such as a net. An embodiment utilizes a non-resorbable reticulated polyurethane-based biomaterial. Additionally, resorbable foams could also be utilized including a polyhydroxyalkanoate (PHA) such as poly-4-hydroxybutyrate (P4HB) or cross-linked resorbable polyester urethane-urea scaffolds.

Pore sizes in the material may be from about 50 micron to about 800 micron, preferably from about 250 micron to about 500 micron. Such a high void content (e.g. from about 90% to about 95%) material promotes quick and tenacious tissue ingrowth and effectively mimics the extracellular matrix. While such a high void content material is desirable for tissue ingrowth, it may not be ideal for thromboresistance, which is required for the left atrial (LA) surface. A thromboresistent surface is desired on the face that faces the LA. If modifications are made to the LA facing surface to promote blood compatibility, those modifications may be extended from about 1 mm to about 20 mm, preferably from about 1 mm to about 5 mm, onto the sides of the implant 1020 to assure thromboresistance in the event the implant 1020 is deployed with a portion of the implant's 1020 side surface projecting outside the LAA and into the blood environment. If there is a hole within the proximal face, such as a guidewire lumen, the thromboresistent surface may extend at least partially within that lumen. Additionally, this thromboresistent layer should promote tissue ingrowth and endothelialization.

Various methods may be used to create a thromboresistent proximal face of the implant 1020, including but not limited to the following. For example, an expanded PTFE (ePTFE) skin or layer may be applied to the outside surface of the foam implant as described elsewhere herein. It could be attached by encasing the metallic frame in ePTFE then wrapping through the center, around the OD, and attaching to the frame. This can be done using numerous methods including suturing or adhesive bonding, including the use of elastomeric glue (although this may eliminate porosity at the attachment points). This ePTFE layer can extend into the guidewire lumen, if there is one. In addition to ePTFE, electrospun, melt blown, non-woven, knitted or woven fibers of PTFE, polyester, PGA, PLA, poly-4-hydroxybutyrate (P4HB) or other biocompatible fiber materials can be utilized to create a porous biocompatible surface.

In some embodiments, a coating of a hydrophobic material such as PTFE is applied over the proximal face using any of numerous processes known to one skilled in the art including vapor deposition coating. Ideally this coated layer would also extend partially onto the sides of the implant. While some embodiments may not include a guidewire lumen, if a central lumen is present, the coating would preferably extend at least partially (e.g. about 1 mm) into it. To promote thromboresistance, this coated layer would decrease the porosity of the blood-contacting face to a porosity from about 30 microns to about 200 microns, preferably from about 100 microns to about 150 microns. Materials which could be utilized for this include conformal coatings such as PTFE applied in a thickness of about 50-100 microns, polyurethane spray or dip coatings, albumin, polyethylene glycol (PEG), or poly(ethylene oxide) (PEO), all with or without the incorporation of heparin or nitric oxide. The PEG or PEO would ideally be attached via a grafting process. In the preferred embodiment, the outer layer would also be lubricious to assist in re-sheathing of the implant. This can be achieved with both hydrophobic materials, such as ePTFE and PTFE, and hydrophilic ones, such as PEO and PEG. In order to produce a desirable combination of porosity and blood compatibility, a two-step process may be utilized where the foam is first coated with a base layer, such as a polyurethane-based biomaterial, then in a second step a more thromboresistant and lubricious surface is created utilizing PTFE, PEG, or PEO. Heparin or other anticoagulants may be added to the final blood-contacting surface.

Another option to create smaller pore sizes with an ePTFE-like material would be to attach an electrospun layer of PTFE to the face of the foam using suturing. A very thin layer (<1 mm) can be made and attached via suturing or adhesive bonding.

Another desired property of the foam of the plug 1040 is to provide echogenicity of the implant 1020, which allows for visualization by echocardiography. To promote echogenicity, a porous surface may be adequate; however, in certain cases a hydrophilic surface may be beneficial. To promote blood compatibility and a hydrophilic surface, the preferred embodiment would be a foam implant which has a surface grafted with PEO or PEG.

D. Static Barb (Anchor) Designs

Static barbs engage tissue when the plug 1040 is deployed, e.g. expanded. While this simplifies fabrication, it makes re-sheathing and repositioning of the implant more difficult.

Figure 51:
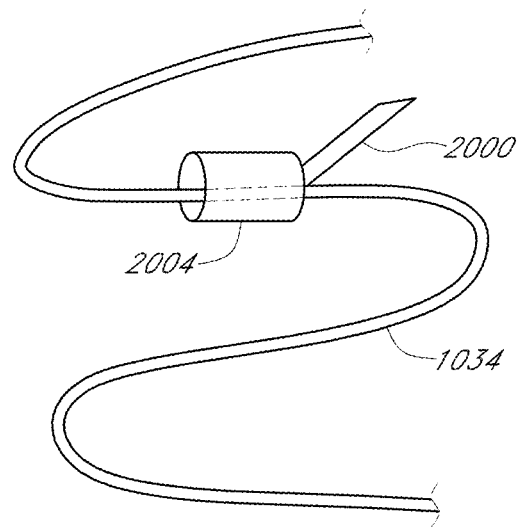
FIGS. 51-55 are schematics showing various embodiments of static barbs that may be used with the various occlusion devices described herein, such as the devices of FIG. 45A or 85A.

In some embodiments, as shown in FIG. 51, a barb 2000 may be fabricated from wire and crimped onto the stent 1034, in this example a wave stent. The barb may be made from Nitinol wire of any diameter, with a preferred range of about 0.005" to about 0.012". The tip can be sharpened for ease of penetration into the tissue. It can be attached to the stent frame using a crimp sleeve made from stainless steel, Nitinol, or titanium tubing. It may require filler wires inside the crimp tube to prevent rotation of the barb. It could also be attached by welding, using a laser or other energy source.

Figure 52:
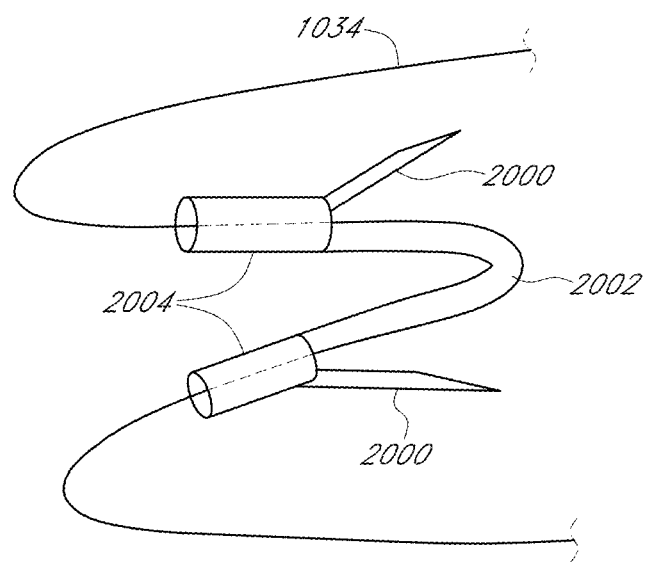
Figure 53:
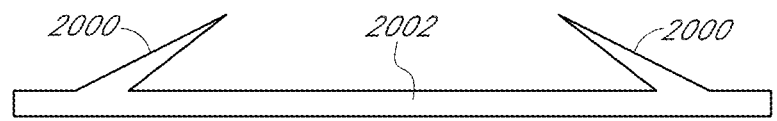

Referring to FIG. 52, in some embodiments a laser cut double barb 2000 system can be utilized. This can be fabricated from a Nitinol tube 2002 cut to allow two crimp ends with one barb 2000 near each crimp 2004 with a continuous Nitinol connection that follows the curvature of the stent 1034, in this example a wave form. An advantage of this embodiment is that it takes less labor to fabricate and shape the barbs, is easier to create sharp tips, and the curvature of the tube wall results in stiffening the barbs. FIG. 53 shows an embodiment of the laser cut part of FIG. 52 prior to forming the crown curvature.

Figure 54:
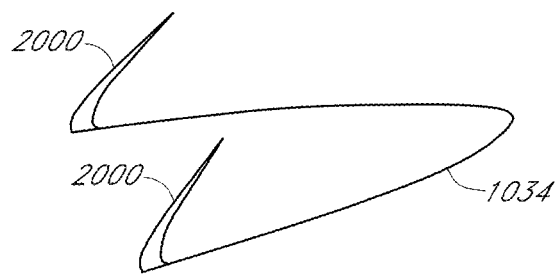

Referring to FIG. 54, in some embodiments the wire form follows the curvature of the wave support cage 1034 (stent), terminating in two barbs 2000. It can be crimped to the wave cage or can be sewn with sutures, welded, or glued in place on the wave cage (stent). The advantage is that crimping is not required to prevent barb rotation.

Figure 55:
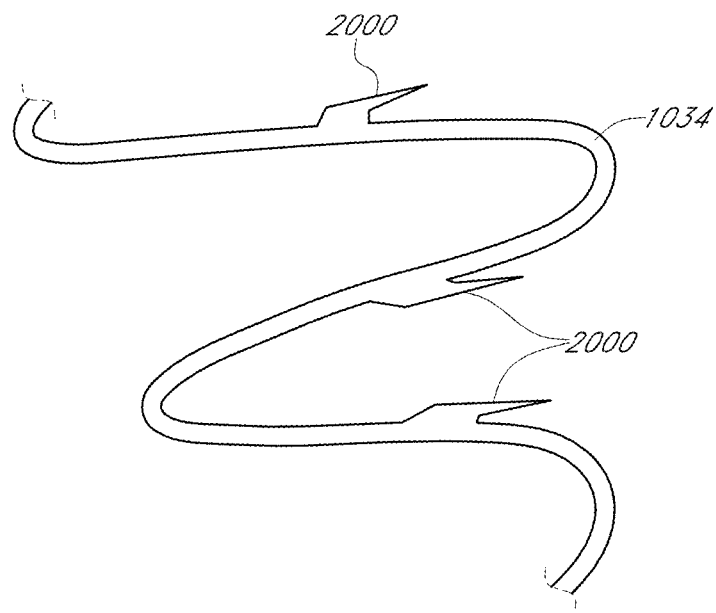

Referring to FIG. 55, in some static barb embodiments, a laser-cut wave support cage (stent) can be fabricated with integrated barbs 2000. The advantage of this concept is that no secondary attachment step is required to attach the barbs to the cage. It may also be easier to add more barbs. A limitation is that it may be difficult to have 8 crowns (waves) with barbs on every strut as there may not be enough material available, therefore 6 crowns may be preferable.

E. Constrained Barb (Anchor) Designs

With constrained barbs 2010, the implant 1020 can be deployed in the LAA with the barbs 2010 constrained and can therefore be repositioned, as needed, prior to barb release. The barbs 2010 are released when the implant 1020 is in its final position.

Figure 56:
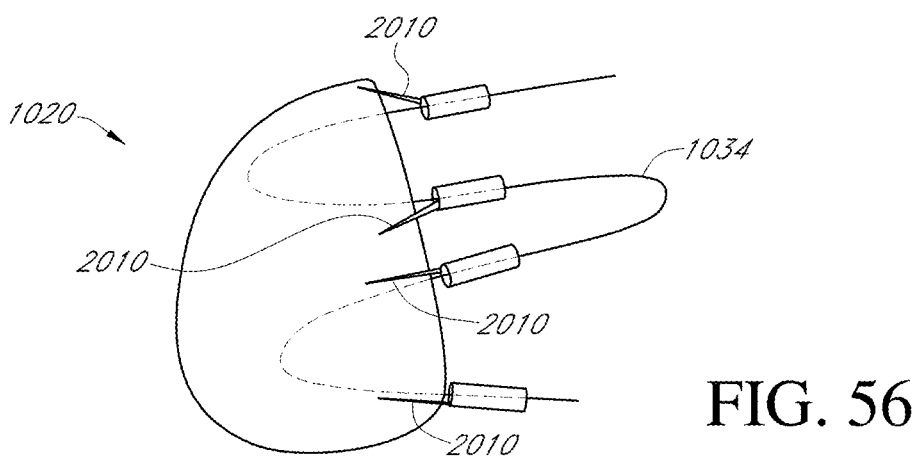
FIGS. 56-58 are schematics showing various embodiments of constrained barbs that may be used with the various occlusion devices described herein, such as the devices of FIG. 45A or 85A.

In one embodiment, as shown in FIG. 56, a lasso-style constraint system can be added to static barbs to create constrained, deployable barbs 2010. A suture material can be tucked between the barbs 2010 and struts to prevent spinning upon deployment. Removal of the lasso can release multiple barbs in a circular array.

Figure 57:
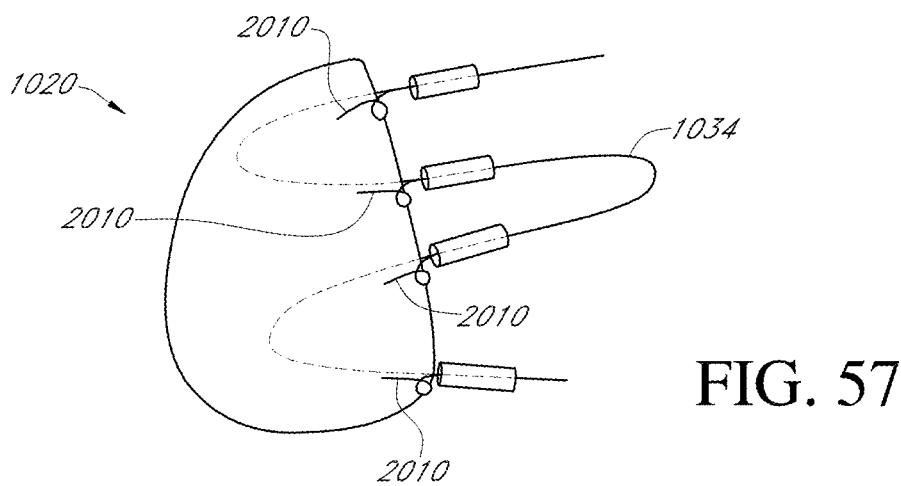

As shown in FIG. 57, barbs can be formed with a loop approximately midway along the barb 2010 which allows suture or thread to be placed through the loop, forming a lasso. This prevents full expansion of the barbs 2010 until the body of the implant is in its final desired position within the LAA.

Figure 58:
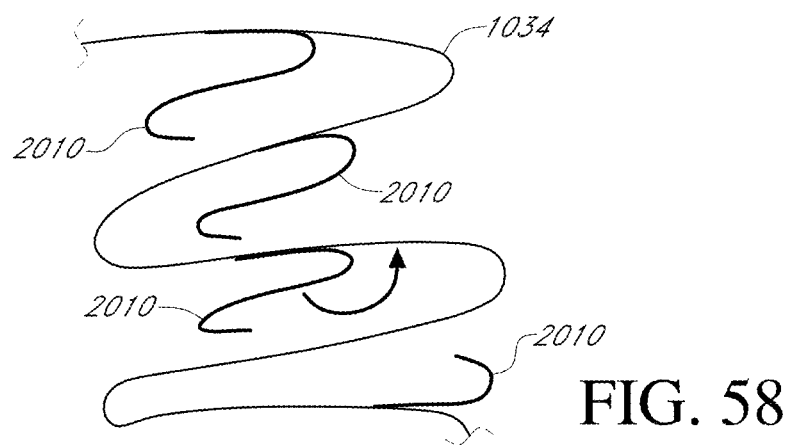

A flipping-barb option is shown in FIG. 58. In this embodiment, barbs 2010 can be elongated designs that are folded back inside a cored-out foam opening prior to loading into the delivery system. This may require drawstrings or other locking elements to hold the barbs in a constrained configuration. Once the implant 1020 is in its final desired location, the constraint is removed and the barbs are no longer constrained and flip into position, engaging the tissue.

F. Dynamic Barb (Anchor) Designs

Dynamic barbs 2020 can be deployed or retracted as desired without dislodging the implant. Dynamic barbs 2020 may be the preferred option for some procedures, for example for recapture of the implant 102 into the delivery catheter and/or sheath.

Figure 59:
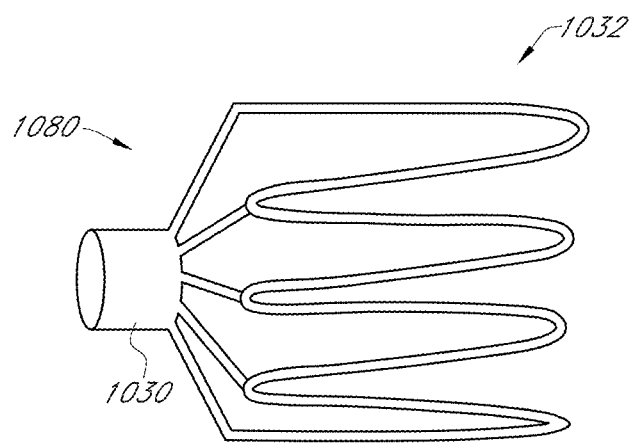
FIGS. 59-65 are schematics showing various embodiments of dynamic barbs that may be used with the various occlusion devices described herein, such as the devices of FIG. 45A or 85A.
Figure 60:
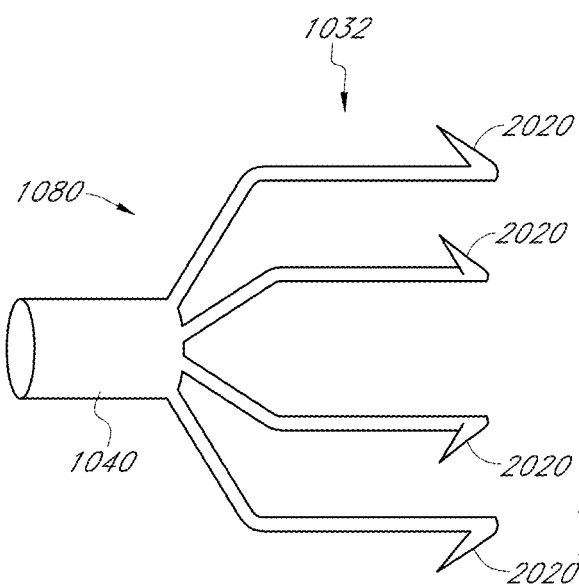

One embodiment is a tube within a tube. In this embodiment, as shown in FIG. 59, a laser cut tube 1030 may be utilized to construct a one-piece front spoked face 1080 and wave stent 1032 from a single piece of preferably superelastic Nitinol tubing. Other materials, including shape memory Nitinol, stainless steel, MP35N, or Elgiloy, could be utilized. A second smaller laser cut tube 1040, as shown in FIG. 60, may be utilized to form an inner spoked barb array.

Figure 61:
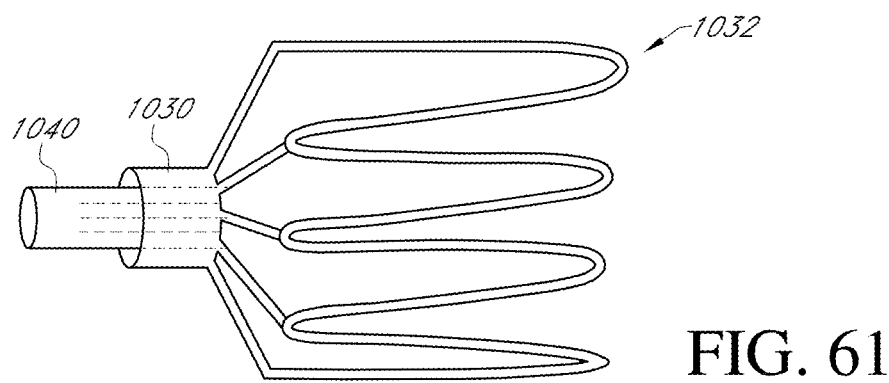
Figure 62:
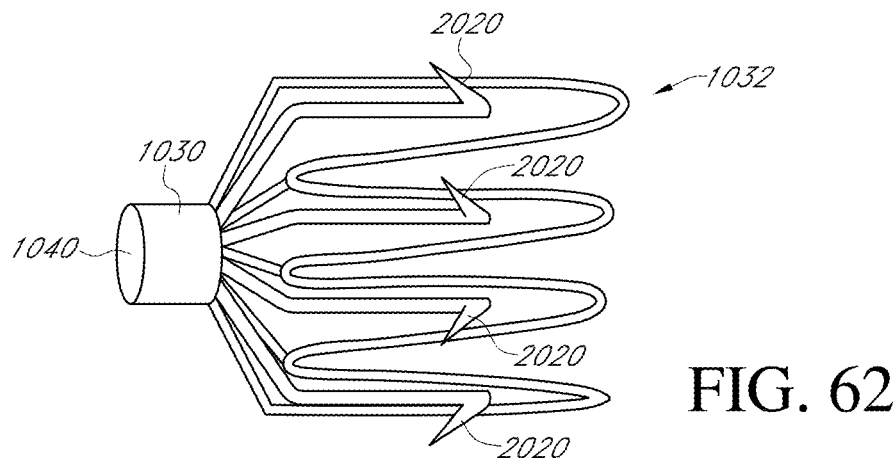

As shown in FIG. 61, during deployment of the foam implant, the front spoked face and wave stent may be deployed while the spoked barb array remains in a constrained position. The implant 1020 can be repositioned, as needed, then distal motion of the inner tube 1040 with respect to the outer tube 1030 allows the barbs 2020 to expand and engage, as shown in FIG. 62. The inner spoked barb array can be re-constrained and re-released repeatedly until disconnected from the delivery catheter transmission lines.

Figure 63:
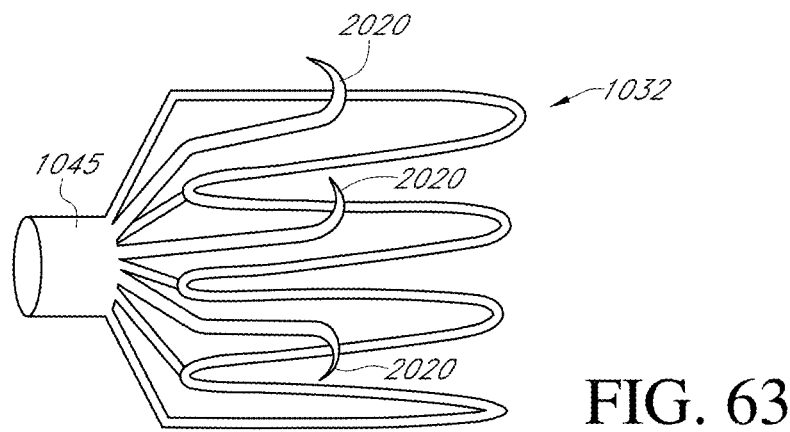

In another embodiment, as shown in FIG. 63, a dynamic barb 2020 design which can preferably be fabricated from a single component is illustrated. This embodiment can be cut from a laser cut tube 1045, preferably superelastic Nitinol, where half of the front spokes connect to wave points of the stent cage 1032 to support re-sheathing while the other half of the spokes are formed into the barbs 2020.

Figure 64:
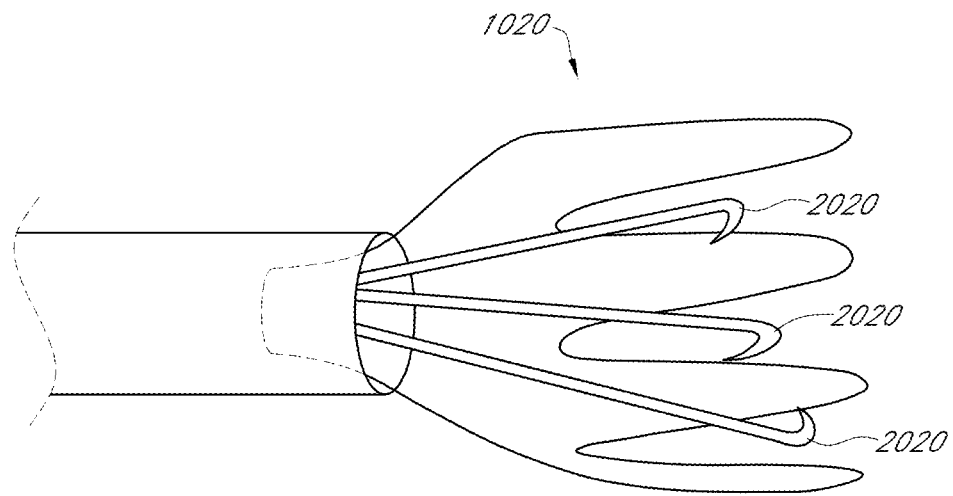

Recapture or re-sheathing of the implant 1020 may initiate the barb retraction by collapsing the front spoke face, as shown in FIG. 64, thereby simultaneously retracting the barbs 2020 from the tissue. This allows for safe repositioning of the implant 1020 with a minimal amount of resheathing required (limiting the length of implant required to be fully retracted into the sheath).

Figure 65:
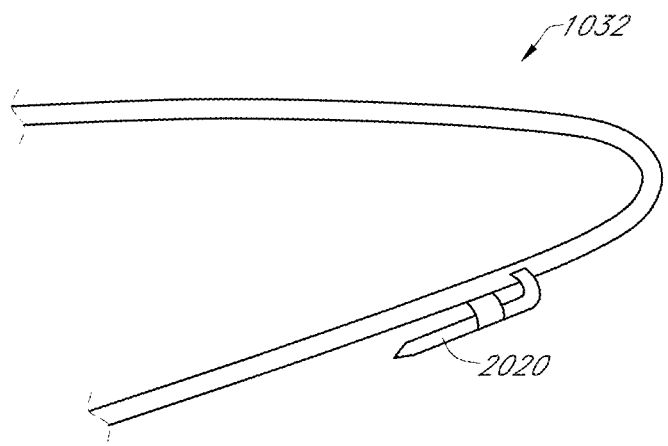

In another embodiment, as shown in FIG. 65, a dynamic hinged barb system is illustrated. This is a laser cut wave form integrated barb 2020 with a living hinge and constraint. When the constrained end is heat-set, it may curl inward to ride over or under the wave strut. When positioned over the wave strut, its sharp barb end may point to the inner diameter of the assembly. When popped into position under the strut, the opposing barb end may see-saw upwards to engage tissue. Activation of the hinged barbs 2020 can be accomplished through the use of a lasso threaded in a circular array between each barb and the corresponding strut. Cinching inward on the lasso can pop the retention constraint from above the strut to below the strut, causing the opposing barb end to be raised above the surface of the strut where it can engage a tissue surface.

G. Embodiments with Foam Cup, Wave Stent, and ePTFE Layer

As shown in FIGS. 66A-66C, the foam cup plug 1040 with internal wave or zig-zag anchor (for example, as shown in and described with respect to FIG. 16) can be modified to be completely covered on the outer surface by an ePTFE layer 2060. This layer 2060 can attach to the distal end 1024 of the foam via suture or adhesive bonding as opposed to just the proximal face 1022. It can wrap over the entire external surface and into the central lumen on the proximal face, attaching to the proximal portion of the wave stent by lamination or adhesive bonding. Other biomaterials or coatings could be utilized including, but not limited to, PTFE or polyurethane.

H. Dynamic and Static Anchor Concepts

The embodiment of an implant 2300 shown in side cross-section view and end view in FIG. 67, respectively, includes anchors 2310 that can be tied, welded, or crimped together at their proximal ends. The anchors 2310 may be made of Nitinol wire to permit loading into the delivery system without taking a set. There could be 8-16 wires formed in the curve. The anchors may act like a "grappling hook". The assembly is loaded into the delivery catheter in a straightened position. As they are pushed out of the delivery catheter, they take the shape shown in FIG. 67 and pierce into the tissue through the foam 2320. The foam 2320 is cored out as shown to reduce the volume of foam needed to compress into the delivery system and yet maintain sufficient radial force to seal the tissue.

The embodiment of the implant 2350 shown in FIGS. 68A and 68B includes a wave stent internal anchor with barbs within a foam plug which has been cored out to be thicker on the distal end to create a larger atraumatic foam tip bumper 2360 when collapsed within but partially deployed from the delivery catheter. The proximal face 2363 can have an internal lumen 2365 as shown in FIG. 68A, but may not include an internal lumen as shown in FIG. 68B.

I. Constrained Anchor Deployed in Secondary Step

The embodiment of an implant 2370 shown in FIG. 69 has barbs/anchors 2371 pre-attached to a wave stent 2372 inside the foam 2374. A suture 2375 is looped around the distal end of the wave stent 2372 to compress the stent 2372 and pull the barbs 2371 inward. The suture 2375 is tied with a slip knot. After delivery of the device 2370 into place, one end of the suture 2375 is pulled and the knot comes free and the suture is removed, allowing the stent 2372 to open radially and the barbs 2371 to engage the tissue. The barbs 2371 can be located distal to the foam 2374 as shown, or pre-engaged with the foam 2374 and penetrating through the foam 2374.

J. Internal Stent with Increased Embolization Resistance

Figure 72:
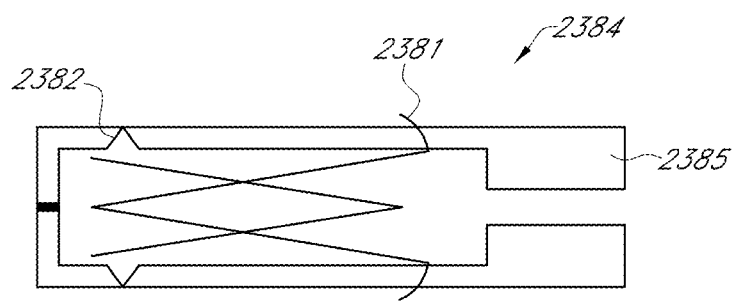

A metallic stent-like frame 2380 with distal static barbs 2381 and a proximal "speed bump" 2382 is disclosed as shown in FIGS. 70-72. It could be a zig-zag stent (as shown) or a wave stent or other similar expandable embodiment. The bumps 2382 placed on the external portion of the metallic stent frame 2380 can be rounded or pointed in design. Their purpose is to provide added resistance and stability for the implant when deployed in the LAA, to prevent embolization. In the preferred embodiment, the foam "cup" 2384 could be shaped as depicted in FIG. 71 to provide added material 2385 on the distal end for an atraumatic bumper when the distal end of the implant is partially deployed from the delivery catheter. It may or may not have an internal lumen for a guidewire.

K. Constrained Atraumatic Anchor

Figure 73:
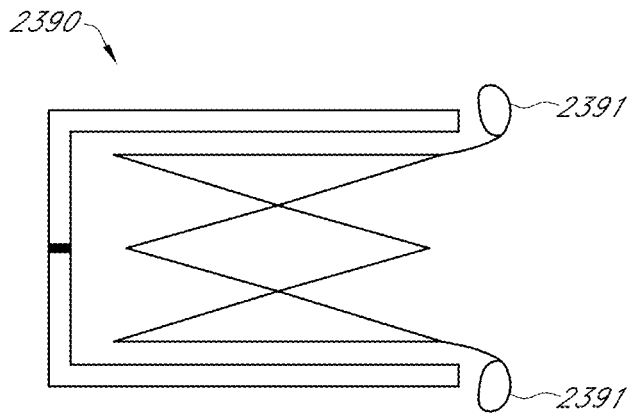
FIGS. 73-75 depict embodiments of an implant having distal loops.
Figure 74:
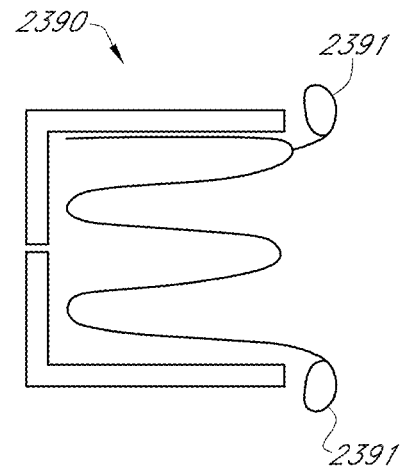

As shown in FIGS. 73 and 74, a wave or zig-zag or other stent 2390 may be fabricated with distally located loops 2391 which engage the tissue in the LAA to anchor the implant in place and prevent dislodgement resistance. Because they are round and not sharp, this limits the risk of perforation, however, if a totally rounded loop does not provide adequate dislodgement resistance, the tips can be modified to incorporate a sharp feature. Loop anchors 2391 can be placed on each stent end or on just a few, so anywhere from 4-16 anchors can be placed.

Figure 75:
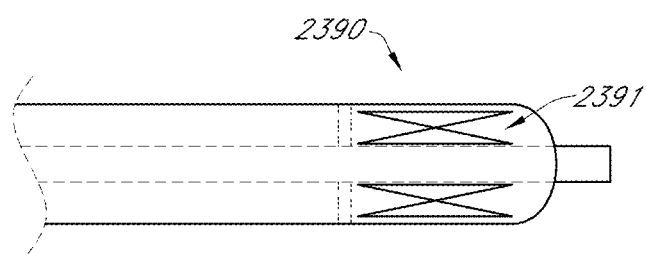

During delivery of the implant through the vascular system and into the heart and LAA, the loops 2391 are folded toward the center of the constrained stent and are lined up next to each other, as shown in FIG. 75. The inner catheter is placed through the loops 2391 to keep them constrained. When the system is in the LAA, the outer catheter/sheath is retracted, deploying the proximal portion of the implant. If positioning appears acceptable, the inner catheter can be removed, allowing the distal portion of the implant to fully expand and the loop anchors to engage the LAA tissue.

L. Perfusion Element & Barb Options

In the event of the implant being dislodged after deployment in the LAA, it is anticipated that the device would travel into the LA, across the mitral valve and into the left ventricle, then out the left ventricular outflow track, across the aortic valve and into the aorta and distal circulation. In this journey, it is possible that the device may get lodged in any of the above structures, interrupting flow and causing distal ischemia and possible hemodynamic collapse. It therefore would be desirable for an implant 2392 to have design features which would allow for distal perfusion, for example as shown in FIGS. 76 and 77.

Figure 76:
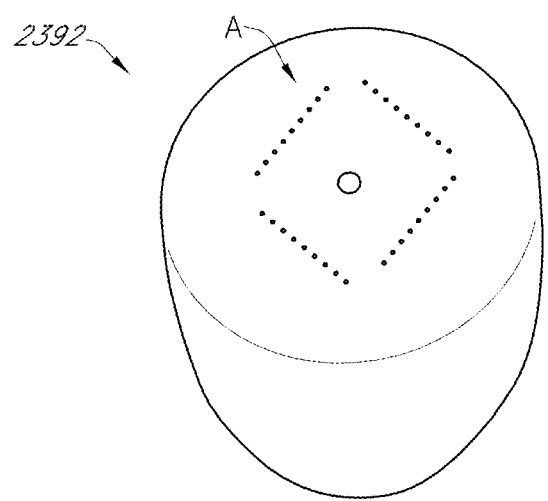
FIGS. 76-77 depict embodiments of an implant having perfusion elements.

FIG. 76 is a top view of an embodiment of the implant showing the left atrial surface. Within the surface is seen a valve, which in the shown embodiment is a simple cut (A) which would open up when sufficient pressure was applied, allowing for flow through the device 2392. This flow could be bi-directional or uni-directional and depending on the specific conditions allowing for flow rates from 10 ml/min to 5 L/min. In the embodiment as shown, this would be accomplished without loss of structural integrity, the loading conditions would result in the device 2392 separating into a multiple sub sections each of which would be retrievable using standard technique. A specific device could have a single valvular element or an array (as shown).

Figure 77:
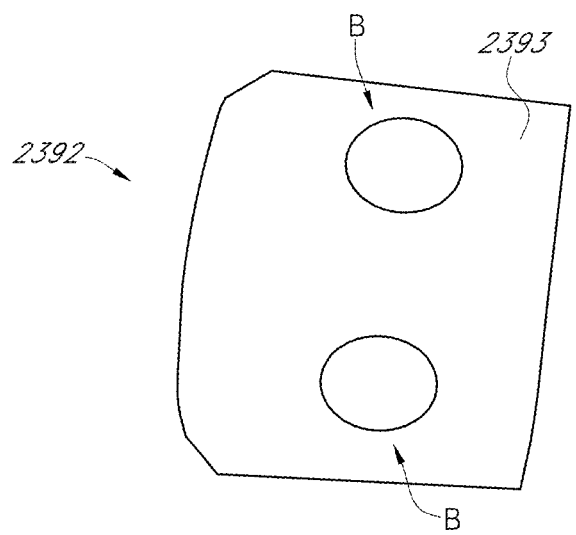

As shown in FIG. 77, in some embodiments, a series of side ports (B) may be cut in the side wall of the foam 2393 of the implant 2392 to allow for blood flow in the case of dislodgement and distal embolization. These can vary in size and number from 1-20 ports of about 0.1 mm to about 5 mm in diameter. They can also vary in shape including but not limited to circular, oval, and rectangular.

Regarding barb designs, such as those described herein, in addition to having an array of barbs deployed at different distances from the LA surface, barbs can be incorporated which penetrate into the tissue to different depths. In one embodiment, the barbs placed most proximal on the implant can be longer so they penetrate deeper into the thicker proximal LAA tissue whereas those placed most distal on the implant are shorter, so they penetrate less deep into the delicate distal tissue, to maximize embolization resistance while minimizing the risk of perforation. In another embodiment the proximal and distal barbs can be the same length but can be fabricated from different diameters of wire or can be cut at different thicknesses from tubing material, so that the barbs that engage the more delicate distal LAA tissue are more flexible, or they are designed to primarily engage the internal trabeculations within the LAA, whereas the proximally located barbs penetrate the tissue. Alternatively, two barbs can be placed at each crown point of the stent, as opposed to one.

M. Multi-Functional Occlusion Devices

FIGS. 78-84 depict various features that may be used, either alone or in combination, with any of the LAA occlusion devices and methods described herein. In some embodiments, the features of FIGS. 78-84 may be incorporated into the device 3000 and associated features and methods shown and described with respect to FIGS. 85A-94B.

FIG. 78 is a side view of an embodiment of the LAA occlusion device 3000 with ablative features. The LAA occlusion device 3000 has an array of ablative elements 3005. The ablative elements 3005 deliver energy to the tissue in and around the LAA ostium to electrically isolate the LAA. In the shown embodiment, the array of ablative elements 3005 is positioned at the proximal end 3004 of the body 3002. The ablative elements 3005 may be electrically connected through a deployment catheter to an energy source. Energy may be provided via radiofrequency, ultrasonic, electrical, or other suitable methods. An inner lumen 3003 extends through the body 3002. In some embodiments, there may not be the lumen 3003.

FIG. 79 is a side view of an embodiment of the LAA occlusion device 3000 with pressure sensing features. The device 3000 has a pressure sensor 3007 on its proximal surface 3008. In some embodiments, the sensor 3007 may be on the proximal surface 3102 of the proximal cover 3100 (see FIG. 85A). In some embodiment, the sensor 3007 does not protrude into the LAA, such as a flat sensor on the proximal surface 3008 or 3102. The sensor 3007 is electrically connected via a wire 3009 to an electronic element 3011. The electronic element 3011 has the capability of transducing and storing the signal generated by the sensor 3007. This information may be transmitted with a signal 3013 remotely. The electronic element 3011 may be powered remotely or by an internal battery.

Figure 80:
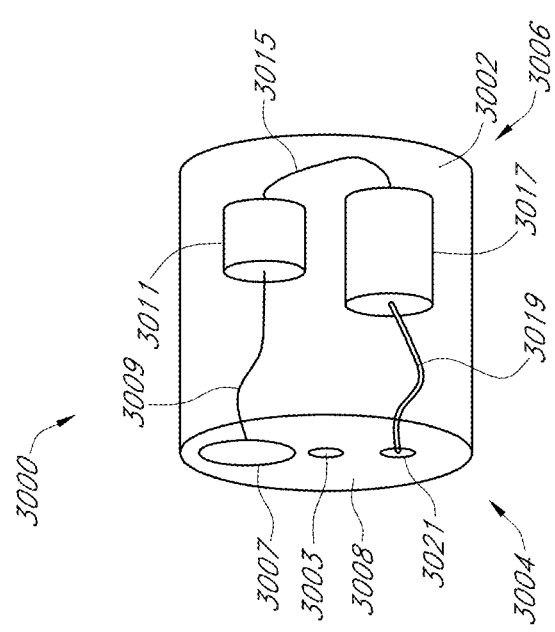
FIG. 80 is a side view of an embodiment of an LAA occlusion device having drug elution features that may be incorporated with the various LAA occlusion devices described herein.

FIG. 80 is a side view of an embodiment of the LAA occlusion device 3000 with drug elution features. The device 3000 has a sensor 3007 on its proximal surface 3008. The sensor 3007 may be on the proximal surface 3102 of the proximal cover 3100 (see FIG. 85A). The sensor 3007 is electrically connected via a first wire 3009 to an electronic element 3011. The electronic element 3011 is electrically connected via a second wire 3015 to a drug reservoir 3017 which is fluidly connected via a conduit 3019 to a drug exit port 3021. This allows for drug to be delivered into the LA, as well as for monitoring concentration of specific chemical(s) and or states and to deliver agents in response, e.g., blood sugar level driving insulin delivery. The sensor 3007 may detect the level of various chemicals and the reservoir 3017 may be controlled, for example by the electronic element 3011, to elute drug via the port 3021 in response.

Figure 81:
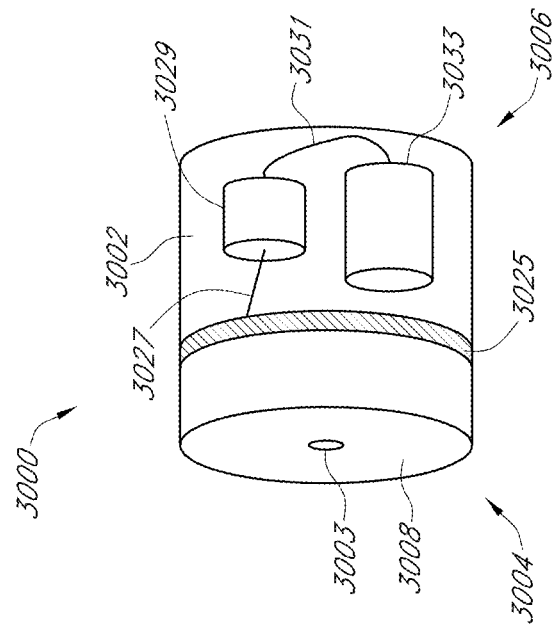
FIG. 81 is a side view of an embodiment of an LAA occlusion device having pacing/defibrillatory features that may be incorporated with the various LAA occlusion devices described herein.

FIG. 81 is a side view of an embodiment of the LAA occlusion device 3000 with pacing/defibrillatory features. The device 3000 has an electrical pacing element 3025, such as an electrode. The pacing element 3025 extends circumferentially about the body 3002. The pacing element 3025 may be in other configurations. The pacing element 3025 is connected by a wire 3027 to a pace generator 3029. The generator 3029 is attached by a wire 3031 to a battery 3033. This pacing system may pace the atrium and defibrillate the atrium when in atrial fibrillation. The generator 3029 and/or battery 3033 may include components for controls, communications, commands, etc.

In some embodiments, the LAA may be electrically isolated. The LAA may be electrically isolated with an occlusion device that incorporates one or more ablative elements, such as those shown and described with respect to FIGS. 78-81, conduct the ablation to electrically isolate the LAA, then disengage the occlusion device 3000 leaving it in place within the heart. In some embodiments, the LAA may first be electrically isolated and then the device 3000 implanted, as described herein, for example with respect to FIGS. 82-84. In some embodiments, conformable circumferential ablation via a foam plug with ablation elements may be incorporated.

Figure 82:
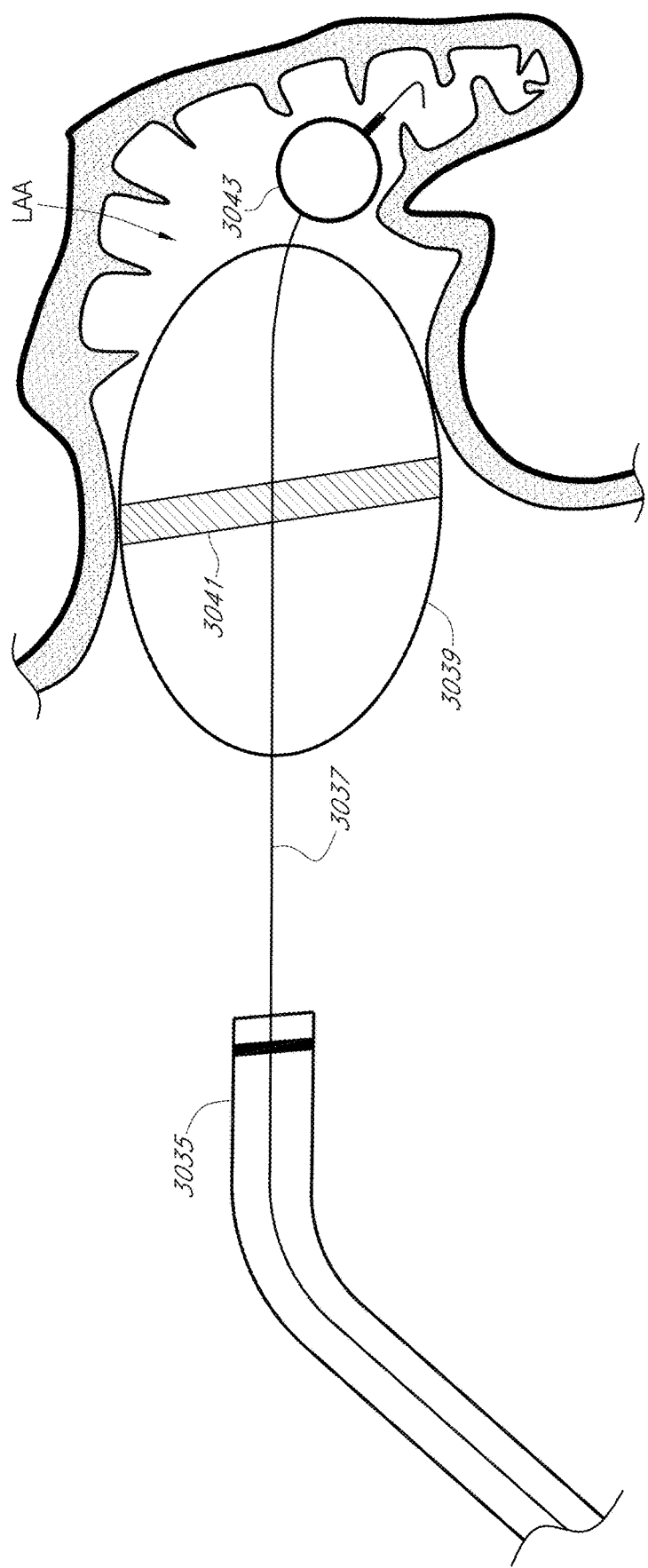
FIGS. 82-84 depict various systems and methods for electrically isolating the LAA that may be used with the various LAA occlusion devices described herein.
Figure 83:
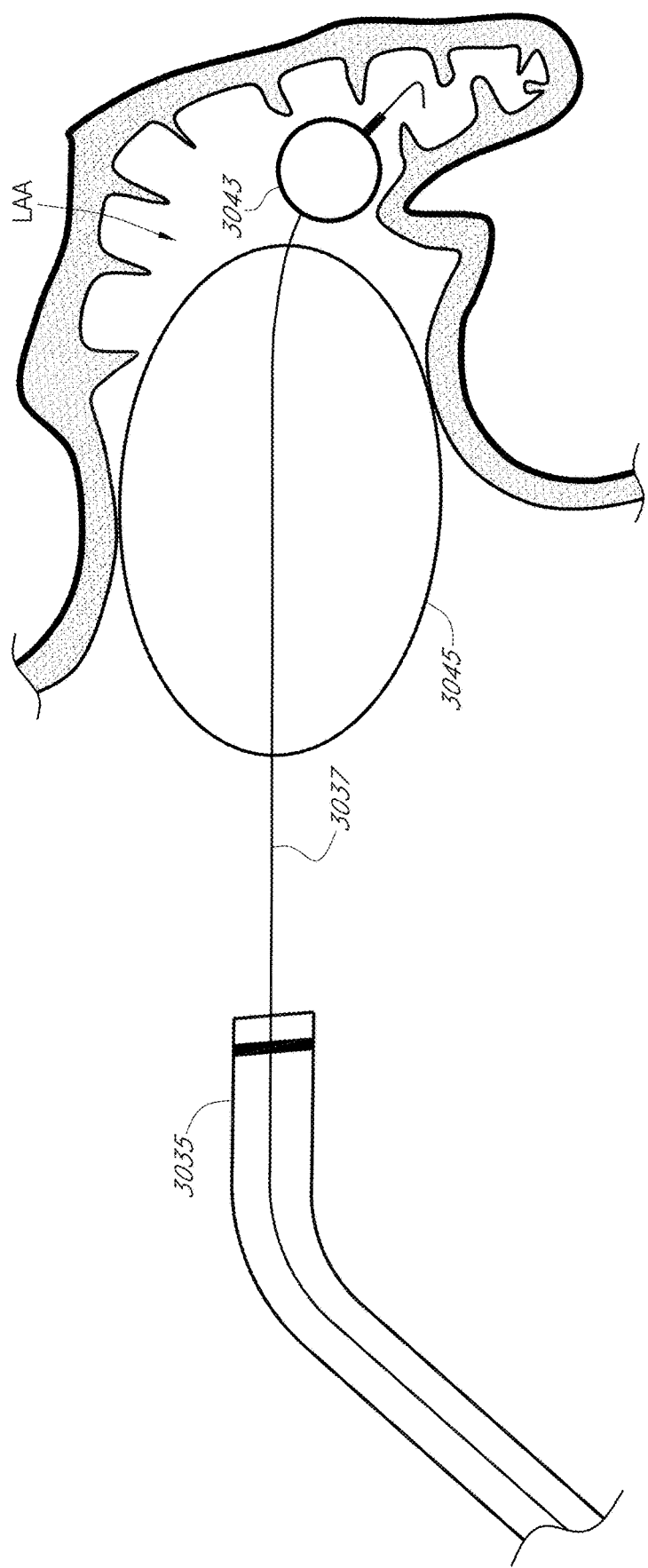
Figure 84:
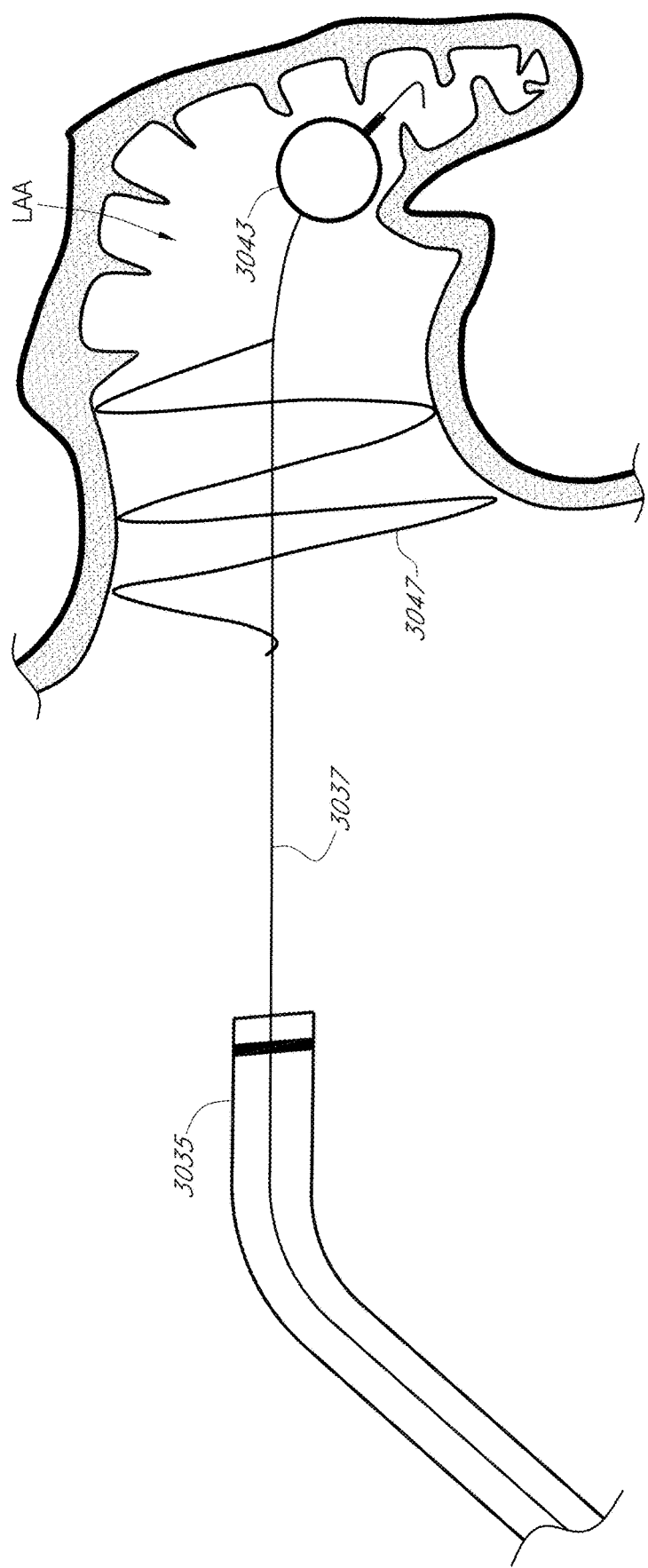

FIGS. 82-84 depict various systems and methods for electrically isolating the LAA that may be used with the device 3000. In some embodiments, the LAA may be electrically isolated followed by LAA closure. For example, the systems and methods shown in FIGS. 82-84 may be used to conduct the isolation, followed by LAA occlusion using the various LAA occlusion devices described herein, such as the device 3000.

FIG. 82 is a side view of an embodiment of over the wire circumferential ablation balloon system. An over-the-wire balloon catheter 3035 is placed over a guidewire 3037 and into the LAA (LAA). The balloon 3039 can have one or more circumferential ablative elements 3041, such as apposed radiofrequency (RF) elements, to electrically isolate the LAA using RF to treat atrial fibrillation. The ablative element 3041 extends circumferentially about the balloon 3039. The ablative element 3041 may be in other configurations. This guidewire 3037 may have attached to its distal end a balloon 3043 which is inflated in the LAA and serves as a bumper to prevent guide catheter 1100 from perforating the wall of the LAA. These features may be similar to those described with respect to FIGS. 8-11.

FIG. 83 is a side view of an embodiment of over the wire circumferential ablation ultrasound balloon system. An over-the-wire balloon catheter 3035 is placed over a guidewire 3037 and into the LAA (LAA). A balloon 3045, such as a circumferential ablation ultrasound balloon, is used to electrically isolate the LAA using ultrasound (US) to treat atrial fibrillation. The guidewire 3037 may have attached to its distal end the balloon 3043, as described with respect to FIG. 82.

FIG. 84 is a side view of an embodiment of an over-the-wire circumferential ablation helical wire system with ablation elements. An over-the-wire circumferential ablation helical wire 3047 with one or more ablation elements is placed into the LAA (LAA). The wire 3047 can be used to electrically isolate the LAA using radiofrequency to treat atrial fibrillation.

N. Embodiments with Compressible Foam Body, Proximal Cover, and Compliant Frame Having Proximal Recapture Struts and Distal Tubular Body FIGS. 85A-93B show another embodiment of an LAA occlusion device 3000. The device 3000 described herein may have the same or similar features and/or functionalities as other LAA occlusion devices described herein, and vice versa. Any of the features of the device 3000 described with respect to FIGS. 85A-93B may therefore apply to features of the devices described with respect to FIGS. 1-84, such as the implant 1020, and vice versa.

Figure 85A:
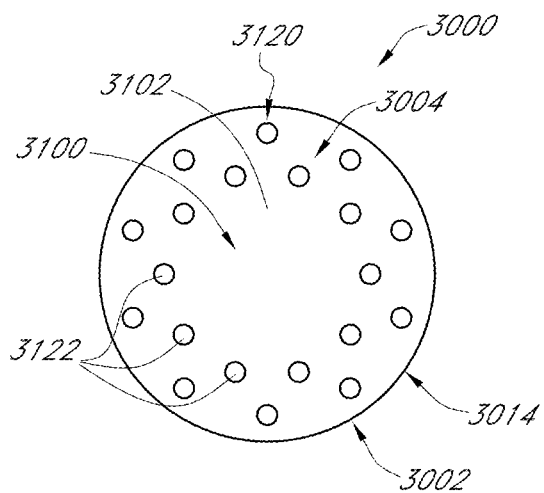
FIGS. 85A-85C are proximal, distal and side views, respectively, of an embodiment of an LAA occlusion device having a compressible foam body, an expandable frame, and a proximal cover.
Figure 85B:
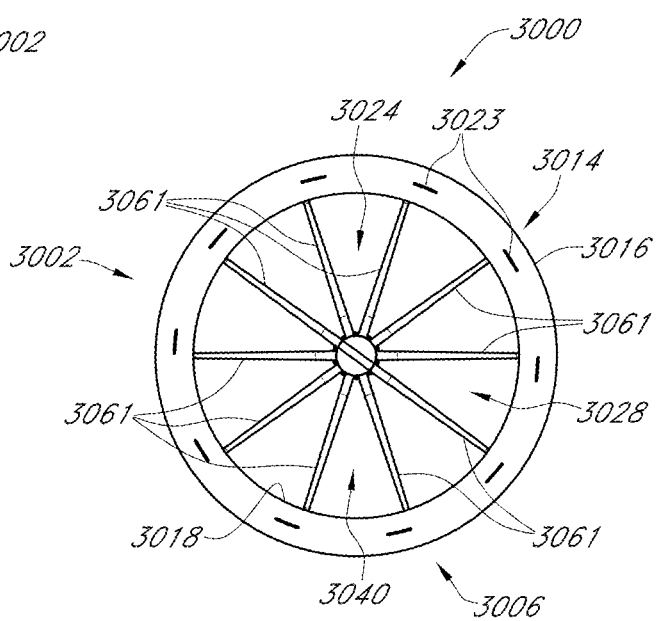
Figure 85C:
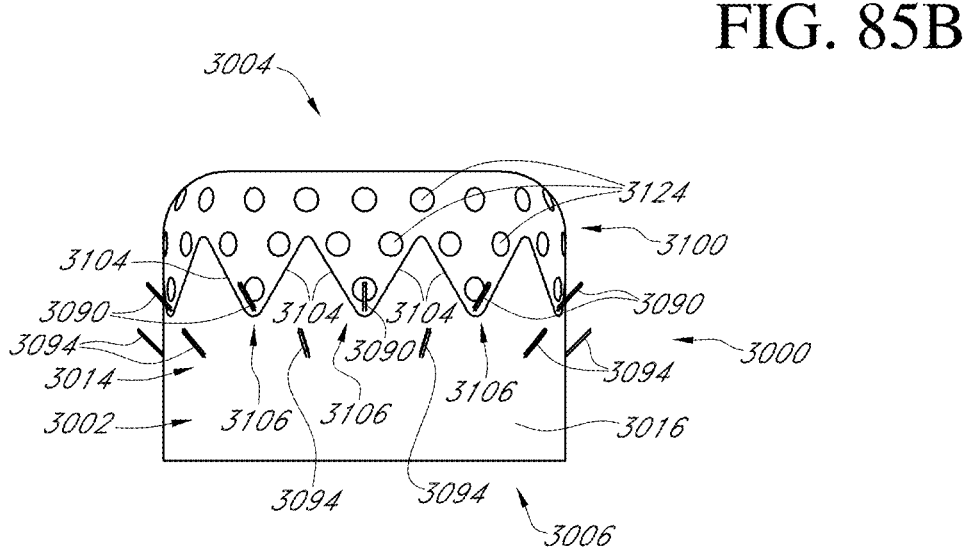
Figure 85D:
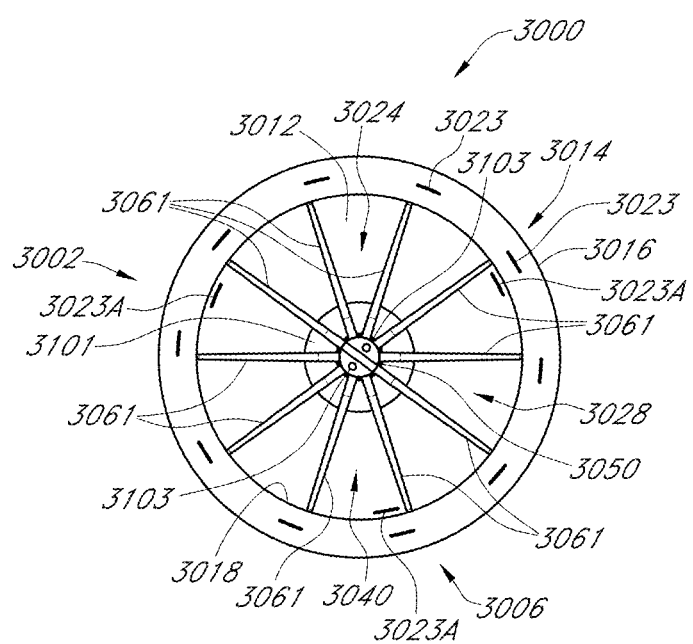
FIG. 85D is a distal view of the embodiment of the LAA occlusion device of FIGS. 85A-85C additionally having an interior cover and proximal markers.
Figure 86A:
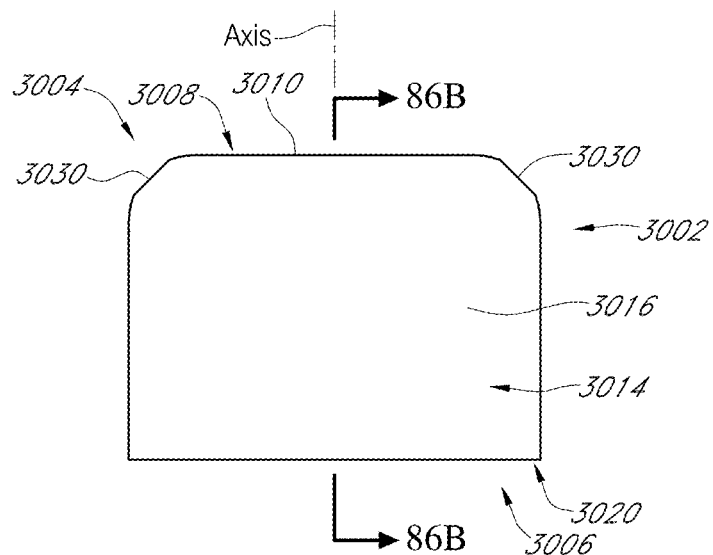
FIGS. 86A-86B are side and cross-section views, respectively, of the compressible foam body of FIGS. 85A-85C.
Figure 86B:
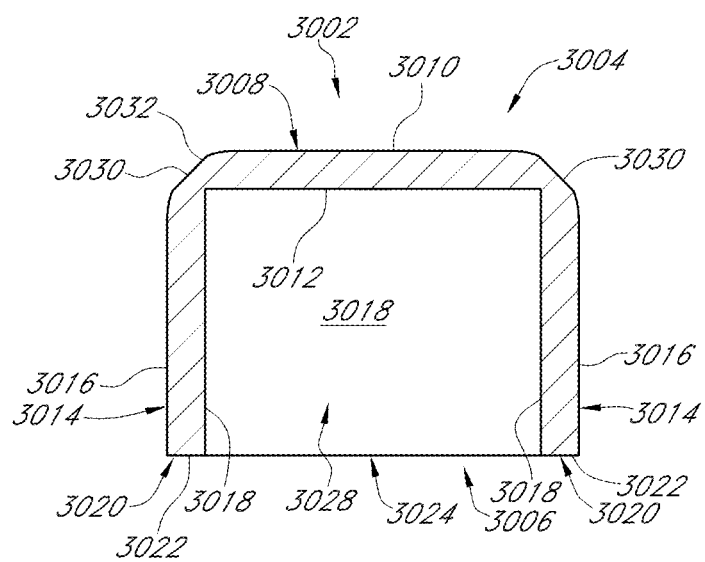
Figure 86C:
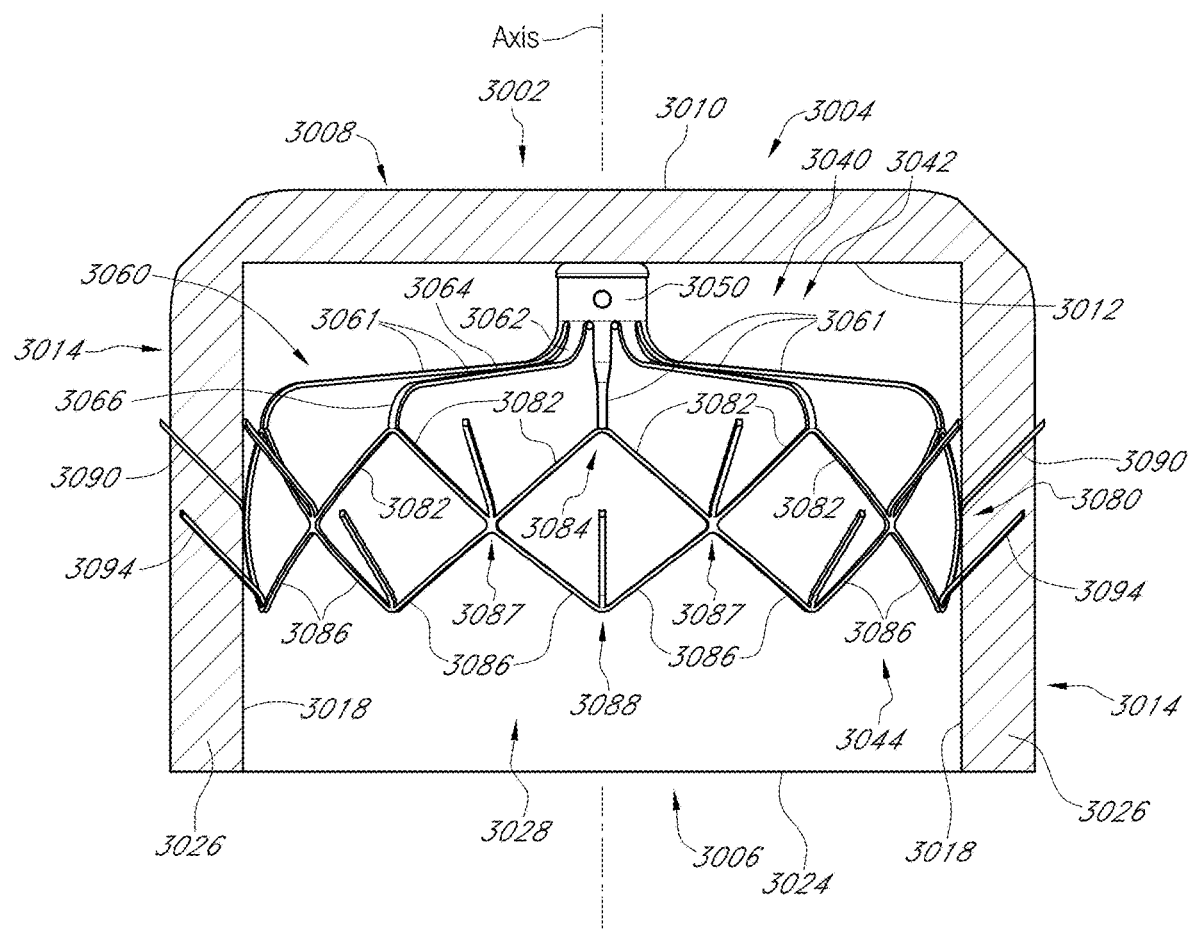
FIG. 86C is a cross-section view of the foam body of FIGS. 85A-85C with the expandable frame.

FIGS. 85A-85C show the LAA occlusion device 3000 having a foam body 3002, an expandable support or frame 3040, and a proximal cover 3100. FIG. 85D shows the LAA occlusion device 3000 additionally having an interior cover 3101 and proximal markers 3023A. FIGS. 86A-86C show the foam body 3002, with the body 3002 shown in cross-section in FIGS. 86B and 86C. FIG. 86C additionally includes the full view (i.e. non-cross section) of the frame 3040. The device 3000 is shown in an expanded configuration in these figures. The device 3000 has a longitudinal axis as shown, which may be defined by the foam body 3002, as further described.

1. Compressible Foam Body

The body 3002 is formed from a compressible material, such as foam. The body 3002 may be a foam formed from reticulated (e.g. net-like) polycarbonate polyurethane-urea. The body 3002 may be cut, formed or assembled into a cup shape, as further described. The body 3002 may have a thickness and compressibility sufficient to engage the surrounding tissue and conform to the anatomic irregularities under radial force applied by the inner frame, as further described. The use of a compressible material such as foam for the body 3002 provides a complete seal of the LAA and superior performance for LAA occlusion over existing devices, as further described. The structure of the foam of the body 3002 comprises a three dimensional network of interconnected reticulations, spaced apart to form a network of interconnected open pores, as further described. The reticulations can carry a coating, such as PTFE, while preserving the open pores, as further described.

The foam material of the body 3002 has a high porosity. "Porosity" as used herein has its usual and customary meaning and refers to open void content between the interconnected reticulations of the foam. The porosity of the body 3002 may be at least about 65%, at least about 70% at least about 75%, at least about 80%, at least about 85%, at least about 90%, at least about 95% or more. The porosity may be within the range of approximately 90-95%. The porosity may be approximately 90%. The porosity may be approximately 95%. The porosity may be 90%, 91%, 92%, 93%, 94%, or 95%. The high porosity promotes quick and tenacious tissue ingrowth, allows it to be compressed into a small catheter, and/or allows blood to pass if the implant embolizes, among other advantages.

The foam body 3002 has pores or cells formed between the interconnected reticulations of the foam material. The foam body 3002 has cells with sizes in the range of from about 250 µm to about 500 µm. The foam may have a cell size from about 125 µm to about 750 µm, from about 175 µm to about 650 µm, from about 200 µm to about 600 µm, from about 225 µm to about 550 µm, from about 275 µm to about 450 µm, less than 125 µm, or greater than 750 µm. These sizes may refer to the size of the cell prior to application of any coating, such as PTFE. The cell size may thus change, e.g. decrease, after application of the coating. The desired porosity and/or cell size may be determined based on allowing the passage of blood while blocking debris of a size capable of potentially causing ischemic stroke. The allowable size of such debris may drive the selection of the particular porosity and/or cell size. For example, the cell size from about 250 µm to about 500 µm may be based on prevention of debris of a particular size from passing through the body 3002.

In an embodiment, the foam body 3002 is made from a non-resorbable, reticulated, cross-linked, polycarbonate polyurethane-urea matrix, structurally designed to support fibrovascular tissue ingrowth, with a fully interconnected, macroporous morphology with over 90-95% void content and cell sizes ranging from 250 to 500 µm.

The body 3002 has a proximal end 3004 and a distal end 3006. In some embodiments, the axial length of the device 3000 from the proximal end to the distal end in a free, unconstrained state is 20 mm. As used herein, the "free, unconstrained" state, and the like, refers to a state of the device 3000 without any external forces applied to the device 3000 other than a normal or reactive force from a surface (e.g. table top) on which the device 3000 is placed. In some embodiments, this axial length may be from about 10 mm to about 30 mm, from about 12 mm to about 28 mm, from about 14 mm to about 26 mm, from about 16 mm to about 24 mm, from about 18 mm to about 22 mm, or about 20 mm. The body 3002 may have any of these lengths regardless of outer diameter of the body 3002.

The proximal end 3004 of the body 3002 has a proximal end wall or face 3008. The proximal face 3008 faces generally toward the LA when the device 3000 is implanted into the LAA. The device 3000 may be implanted off-axis, as further described, in which case the proximal face 3008 may not reside at a perpendicular to a longitudinal axis of the LA. The proximal face 3008 thus provides a closed proximal end 3004 of the body 3002. The closed proximal end 3004 is configured to span the ostium but the porosity, as further described, is sufficient to permit the passage of blood while blocking debris of a size capable of potentially causing ischemic stroke. This membrane may be formed by the body 3002 and/or the cover 3100. In some embodiments, the proximal face 3008 or portions thereof may be open. For example, there may not be a proximal face 3008, there may be a partial proximal face 3008, there may be a proximal face 3008 with portions removed, etc. In some embodiments, the proximal face 3008 or portions thereof is/are not included and any opening or openings is/are covered by the cover 3100. The size of any such openings in the proximal face 3008 may be driven by the desired size of embolic debris to be prevented from escaping the LAA, as further described.

The proximal face 3008 is flat or generally flat and generally perpendicular to the longitudinal axis of the device 3000. The proximal face 3008 has a circular or generally circular shape as viewed from the proximal end 3004 in an unconstrained expansion. In some embodiments, the proximal face 3008 may be flat, rounded, segmented, angled with respect to the longitudinal axis, other shapes, or combinations thereof. The proximal face 3008 may have a non-circular, polygonal, other rounded shape, other shapes, or combinations thereof, as viewed from the proximal end 3004.

The proximal face 3008 has an outer surface 3010 and an opposite inner surface 3012. The outer surface 3010 faces proximally away from the device 3000 and the inner surface 3012 faces distally toward the frame 3040. The surfaces 3010, 3012 may define outer and inner sides of the proximal face 3008. The thickness of the proximal face 3008 may be measured axially between the outer surface 3010 to the inner surface 3012. This thickness in a free, unconstrained state (e.g. uncompressed and expanded) may be from about 0.5 mm to about 5 mm, from about 1 mm to about 4 mm, from about 2 mm to about 3 mm, about 2.5 mm, or 2.5 mm. In some embodiments, the thickness may be less than 0.5 mm or greater than 5 mm. The thickness of the proximal face 3008 may be uniform or non-uniform. Thus the thickness may be greater or smaller in different regions of the proximal face 3008.

The body 3002 includes a sidewall 3014 extending distally from the proximal face 3008. The sidewall 3014 extends circumferentially about a perimeter of the proximal face 3008 to form a closed cross-section (i.e. extends circumferentially 360 degrees about the axis). The sidewall 3014 extends axially to define a tubular body concentric about the longitudinal axis of the device 3000. The longitudinal axis extends through a geometric center of the tubular body defined by sidewall 3014. The sidewall 3014 is tubular or generally tubular, e.g. cylindrical, along the axis. In some embodiments, the sidewall 3014 may be conical or frustoconical, for example where the proximal end is wider than the distal end or vice versa. The sidewall 3014 may have an outer profile at the proximal end thereof, and as viewed from the proximal or distal end, to match that of the outer perimeter of the proximal face 3008.

In some embodiments, the cross-section of the sidewall 3014 may not be closed, for example where there are openings in the sidewall 3014. Thus cross-sections taken at various locations along the longitudinal axis may or may not show a closed section. In some embodiments, the sidewall 3014 may be non-tubular, non-cylindrical, non-circular, polygonal, other rounded shapes, other shapes, or combinations thereof. In some embodiments, as shown, the sidewall 3014 may extend continuously for the entire length from the proximal end 3004 to the distal end 3006. In some embodiments, the sidewall 3014 may not extend continuously for the entire length from the proximal end 3004 to the distal end 3006. For example, the sidewall 3014 may include a plurality of disconnected sections, such as annular portions of the sidewall, located and spaced along the longitudinal axis and connected to the frame 3040.

The sidewall 3014 has an outer surface 3016 and an opposite inner surface 3018. The outer surface 3016 faces radially outward from the axis. The inner surface 3018 faces radially inward toward the axis. The thickness of the sidewall 3014 may be measured radially between the outer surface 3016 to the inner surface 3018. This thickness in a free, unconstrained state (e.g. uncompressed) may be from about 0.5 mm to about 5 mm, from about 1 mm to about 4 mm, from about 2 mm to about 3 mm, about 2.5 mm, or 2.5 mm. In some embodiments, the thickness may be less than 0.5 mm or greater than 5 mm. The thickness of the sidewall 3014 may be uniform or non-uniform. Thus the thickness may be greater or smaller in different regions of the sidewall 3014. The thickness of the sidewall 3014 may be the same or different as the thickness of the proximal face 3008. In some embodiments, the thickness of the proximal face 3008 is 2.5 mm and the thickness of the sidewall 3014 is 2.5 mm. In some embodiments, the thickness of the proximal face 3008 is about 2.5 mm and the thickness of the sidewall 3014 is about 2.5 mm.

The sidewall 3014 has a distal free end 3020 having a distal surface 3022. The distal surface 3022 is flat or generally flat and perpendicular to the longitudinal axis of the device 3000. In some embodiments, the distal surface 3022 is non-flat, angled with respect to the axis of the device 3000, curved, rounded, segmented, other shapes, or combinations thereof.

The body 3002 may have a distal opening 3024. The opening 3024 is formed by the distal free end 3020 of the sidewall 3014. The opening 3024 is at a distal end of an internal central volume or cavity 3028 of the body 3002 that is formed at least partially by the sidewall 3014, the proximal face 3008 and/or the shoulder 3030. The frame 3040 may reside within the cavity 3028, as further described. The distal opening 3024 may be completely open. In some embodiments, the distal opening 3024 may be mostly open, partially open, or closed, for example where the body 3002 has a distal face similar to the proximal face 3008 to enclose or partially enclose the cavity 3028.

The body 3002 has a shoulder 3030, shown as a bevel, that extends between the proximal face 3008 to the sidewall 3014. The shoulder 3030 may be an intersection of a proximal end of the sidewall 3014 and the proximal face 3008. The shoulder 3030 extends circumferentially about the entire perimeter of the intersection. The shoulder 3030 has an outer surface 3032. The outer surface 3032 may be a beveled surface. The outer surface 3032 is flat or generally flat in an axial direction. The outer surface 3032 extends circumferentially about the entire perimeter of the shoulder 3030. In some embodiments the shoulder 3030 and/or outer surface 3032 may be non-flat, rounded, other shapes in an axial direction, or combinations thereof. The shoulder 3030 and/or outer surface 3032 may extend circumferentially less than the entire perimeter of the shoulder 3030. The thickness of the shoulder 3030 may be measured inward perpendicularly to the outer surface 3032. The thickness of the shoulder 3030 may be the same as the thicknesses of the proximal face 3008 and/or the sidewall 3014, as described herein. In some embodiments, the thickness of the shoulder 3030 may be different from the thicknesses of the proximal face 3008 and/or the sidewall 3014. The shoulder 3030 may function as a recapture ramp, to facilitate drawing the implant proximally into the deployment catheter.

The compressibility of the body 3002 contributes to the superior sealing capability of the device 3000. The foam may be compressible to provide a larger radial "footprint" and spread out the radial forces from struts on the frame 3040, as further described. The foam body 3002 may have a compressive strength of at least 1 pound per square inch (psi) or within a range of about 1 psi to about 2 psi, or no more than about 2 psi. The "compressive strength" here refers to the pressure to compress the foam to 50% strain. With some foam materials for the body 3002, the pressure may not change from 50% strain through at least 80% strain, and the relation of pressure versus strain may be flat or generally flat. Thus, even with thicker foams for the body 3002, the body 3002 will not exert much more outward force on the tissue due to the increased thickness by itself. In an embodiment, the foam body 3002 is a reticulated, cross linked matrix having at least about 90% void content, an average cell size within the range of from about 250-500 microns, a wall thickness of at least about 2 mm and a compressive strength of at least about 1 psi. In an embodiment, the body 3002 is formed from a foam material having or substantially having the material properties indicated in Table 1. In some embodiments, the body 3002 is formed from materials described in, for example, U.S. Pat. No. 7,803,395, issued Sep. 28, 2010, and titled "Reticulated elastomeric matrices, their manufacture and use in implantable devices," or U.S. Pat. No. 8,337,487, issued Dec. 25, 2012, and titled "Reticulated elastomeric matrices, their manufacture and use in implantable devices," the entire disclosures of which are incorporated herein by reference.

TABLE 1

Example material properties for an embodiment of foam material that may be used for the foam body 3002.

| Material Property | Value |
| --- | --- |
| Permeability | 311 Darcy |
| Average Cell Size | 377 μm |
| Density | 2.7 lb/ft$^3$ |
| Compressive Strength | 1.1 psi |
| Tensile Strength Parallel | 68 psi |
| Tensile Strength Perpendicular | 32 psi |
| Elongation Parallel | 219% |
| Elongation Perpendicular | 243% |

The device 3000 may include markers 3023 (see FIGS. 85B and 87D; for clarity only some of the markers 3023 are labelled in the figures) to facilitate visualization during delivery. The markers 3023 may be radiopaque marker bands sewn into the distal free end 3020 of the body 3002. The markers 3023 may be for visualization using fluoroscopy imaging of the distal end 3006 of the device 3000 during delivery. There may be a series of the markers 3023 located circumferentially along the distal surface 3022 of the body 3002 (for clarity, only some of the markers 3023 are labelled in FIG. 85B). In some embodiments, the markers 3023 may additionally or alternatively be located in other areas of the body 3002 and/or on other parts of the device, such as the cover 3100 or frame 3040.

In some embodiments, four platinum iridium (PtIr) radiopaque (RO) tubular markers 3023 are sewn onto the distal end 3006 of the foam body 3002 to enable visualization of the distal edge of the device 3000 under fluoroscopy. In some embodiments, a PtIr marker 3023 is attached to the foam body 3002 at the location of the proximal shoulder 3030 to use as a marker during recapture of the device 3000. Visualization of the proximal and/or distal markers 3023 may facilitate with identifying the amount of recapture. If the device 3000 is recaptured up to but not including the anchors proximal 3090 inside the access sheath, the device 3000 can be redeployed and reused. If the proximal anchors 3090 are recaptured into the access sheath, the device 3000 may be removed and discarded due to permanent deformation of the anchors 3090. In some embodiments, other materials may be used for the markers 3023, such as gold or other suitable materials.

Figure 87A:
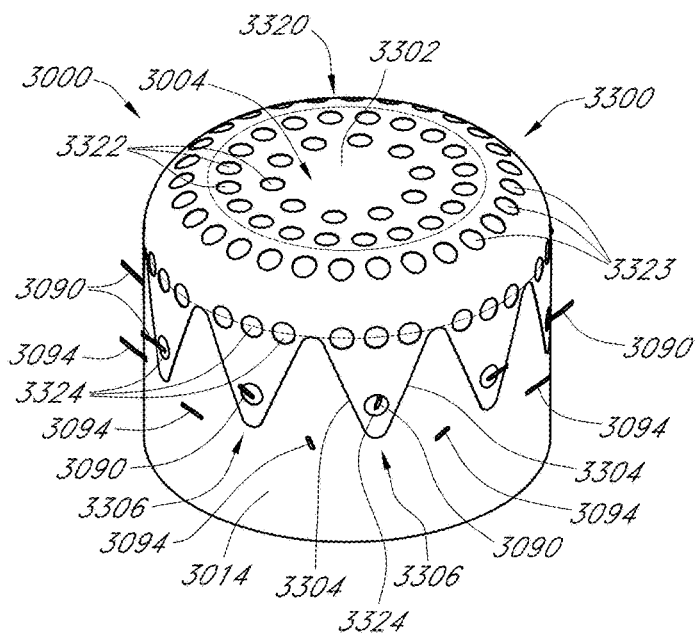
FIGS. 87A-87C are top perspective, side, and cross-section views of another embodiment of an LAA occlusion device.
Figure 87B:
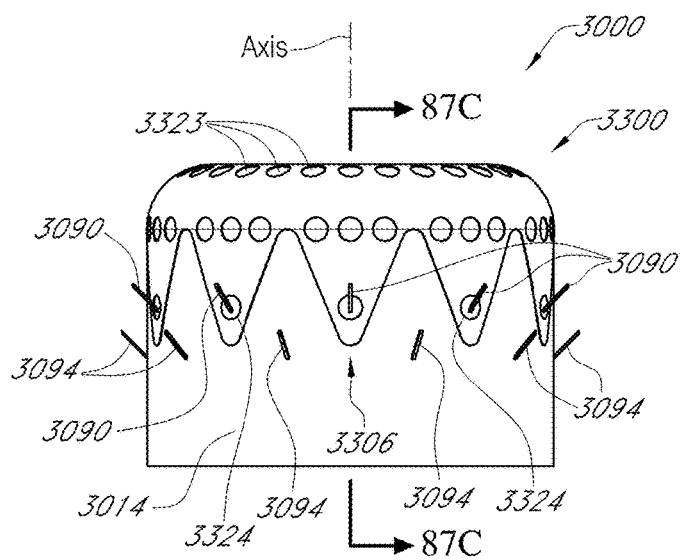
Figure 87C:
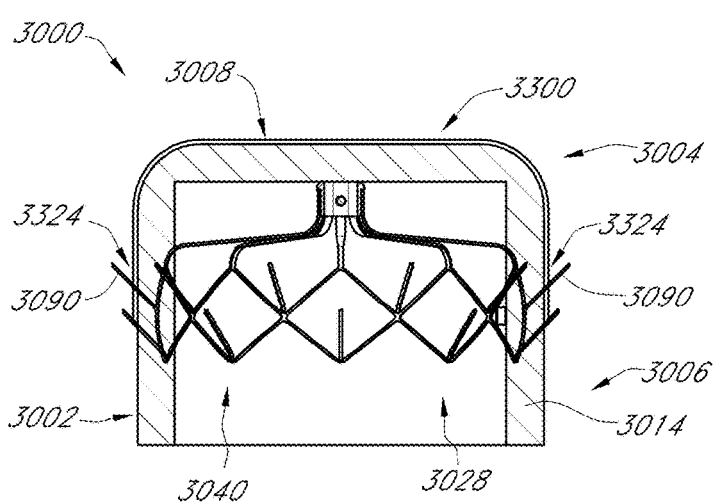
Figure 87D:
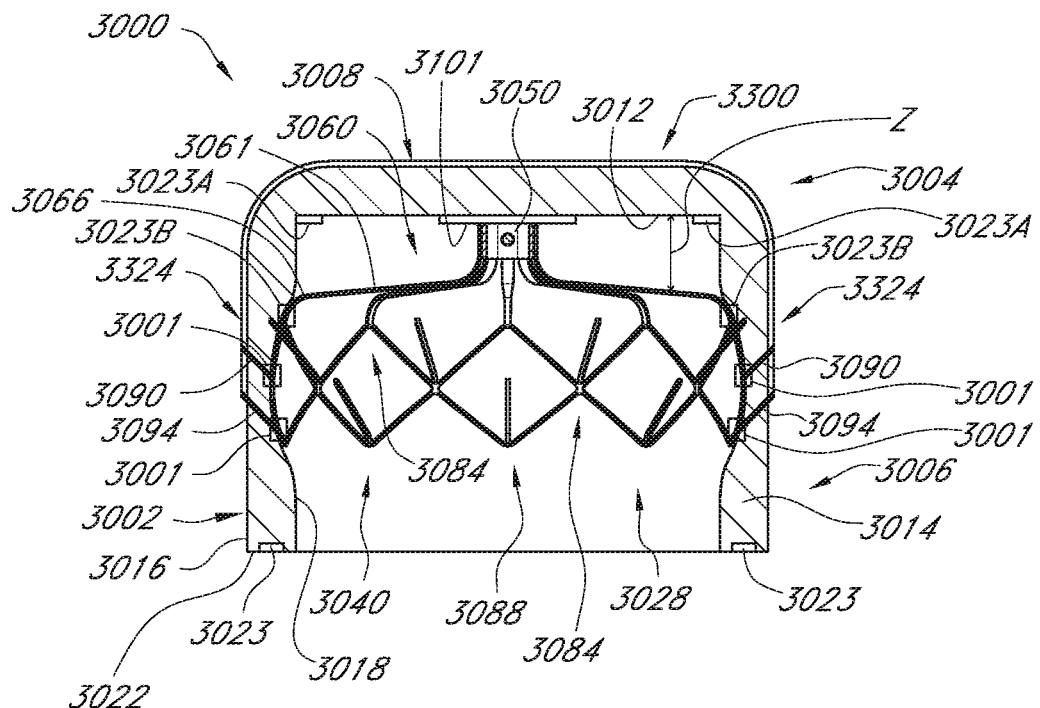
FIGS. 87D-87E are side cross-section views of various embodiments of the LAA occlusion device of FIG. 85D.

As shown in FIGS. 85D and 87D, the device 3000 may include one or more markers 3023A. As one example only, there are three markers 3023A shown. In some embodiments, there may be one marker 3023A. There may be two, four, five or more markers 3023A. In some embodiments, there is one proximal marker 3023A and ten of the distal markers 3023. The markers 3023A may have the same or similar features and/or functionalities as other markers described herein, for example the marker 3023, and vice versa, except as otherwise noted. The markers 3023A may be located at or near the proximal end of the device 3000. As shown, the markers 3023A are located on an inner surface 3012 of the proximal end 3004 of the foam body 3002. The markers 3023A may be located at or near an inner surface of a shoulder 3030 (see FIG. 86B) of the foam body 3002. The markers 3023A may be distributed circumferentially, for example equidistant or equiangular, relative to each other, or they may be at different relative distances from each other. They may be radially located at the same or different location relative to each other. In some embodiments, there is only one marker 3023A. There may be one proximal marker 3023A and four of the distal markers 3023. The one or more markers 3023A may be on the inside, outside, or within the foam body 3002, or combinations thereof. The one or more markers 3023A may be located on or at the distal surface 3022 of the foam body 3022. The markers 3023A may be elongated circumferentially as shown. In some embodiments, the markers 3023A may be linear when the device 3000 is viewed from a particular angle, such as a side view. The markers 3023A may be aligned or oriented in the same or similar orientation, or in different orientations. Some, none, or all of the markers 3023A may be oriented circumferentially, laterally, axially (for example along an inner surface 3018 of the sidewall 3014), other orientations, or combinations thereof.

As further shown in FIG. 87D, there may be one or more markers 3023B. The one or more markers 3023B may have the same or similar features and/or functionalities as the other markers described herein, such as the marker 3023 or 3023A and vice versa, except as otherwise noted. The markers 3023B may be located along the sidewall 3014 of the body 3002. There may be one or more markers 3023B located along an inner surface 3018 of the sidewall 3014.

As shown, two markers 3023B are visible on either side of the interior of the foam body 3002. The markers 3023B are attached through the foam and around the frame 3040. The marker 3023B may be attached, for example sutured, around a proximal face 3060 member of the frame 3040, such as one of the struts 3061. The marker 3023B may be attached to the frame 3040 just proximally of one of the proximal apexes 3084 of the frame 3040, for example at an outer curved portion 3066 of the strut 3061. There may be only one marker 3023B, or two, three, four or more markers 3023B. There may be one of the markers 3023B for each strut 3061. The markers 3023B may be used additionally to connect the frame 3040 with the foam body 3002. The markers 3023B may be sutures as described herein.

The one or more markers 3023A and/or 3023B at or near the proximal end of the device 3000 provide various desirable features. For instance, the marker 3023A at the shoulder 3030 facilitates visualization of the device 3000 during and after implantation. The typically non-circular shape of the opening of the LAA (ostium) may compress the proximal end 3004 of the device and cause the proximal end 3004 to protrude slightly in the proximal direction. However, the shoulder 3030 may provide a location for the marker 3023A where linear bulging of the foam body 3002 in the proximal direction is reduced or prevented. Thus, the marker 3023A in that location can provide a more useful visualization of the positioning of the device 3000 and reduce complexity. For example, in some embodiments, the marker 3023A at the shoulder 3030 (e.g. on an inner surface as shown) may be particularly useful during delivery, allowing for delivery using fluoroscopy imaging only without the need for echo or other ultrasound imaging. The one or more markers 3023B may provide similar benefits.

As further shown in FIGS. 85D and 87D, the device 3000 may include an inner cover 3101. The inner cover 3101 may have the same or similar features and/or functionalities as the cover 3100 (described in further detail below, see section "Proximal Cover"), except as otherwise described. The inner cover 3101 may be a cover for the hub 3050 (see, e.g., FIGS. 86C and 89A-90C). The inner cover 3101 may be formed from expanded Polytetrafluoroethylene ("ePTFE"). The inner cover 3101 may be a separate portion of the same material as the proximal cover 3100.

The inner cover 3101 may be located between the foam body 3002 and the frame 3040. As shown, the inner cover 3101 is located between the inner surface 3012 of the foam body 3002 and a proximal end of the hub 3050 of the frame 3040. The inner cover 3101 may be circular or other shapes. The inner cover 3101 may have an area sufficient to provide a barrier in between the hub 3050 and the proximal end 3004 of the foam body 3002. In some embodiments, the inner cover 3101 may extend radially to an outer circumference of the hub 3050, or it may extend radially to the sidewall 3014 such as to an inner surface 3018 of the foam body 3002, or to any radial locations in between. The inner cover 3101 may have a diameter from about 4 mm to about 22 mm, from about 5 mm to about 15 mm, from about 6 mm to about 10 mm, about 8 mm, or 8 mm. The inner cover 3101 may be flat or generally flat. The inner cover 3101 may have a thickness from about 0.0001"-0.0020", from about 0.0002"-0.0010", about 0.0005", or 0.0005" thick. The inner cover 3101 may include one or more openings 3103 such as holes therethrough. The inner cover 3101 may include two holes 3103 to receive therethrough a tether 3240 (see, e.g., FIGS. 93A-93B). The two holes 3103 in the cover 3101 may align the tether 3240, such as a suture, that extends distally into the hub 3050 through one hole 3103 in the inner cover 3101 and exits proximally back out of the hub 3050 through the other hole 3103 of the inner cover 3101.

The inner cover 3101 may prevent the hub 3050 and/or other features of the frame 3040 from directly contacting the foam material. The cover 3101 may protect the integrity of the foam body 3002 from stresses that may be imparted by the hub 3050 on the foam material. This protection may be desirable for example during loading, deployment, retrieval, re-deployment, etc. of the device 3000. The inner cover 3101 may prevent or reduce damage to the foam body 3002 from the hub 3050.

The foam body 3002 may be attached to various features of the device 3000. The body 3002 may be attached to the frame 3040 at numerous points, including for example the center of the proximal end of the frame 3040, as further described herein. Attachment can be done using suture, such as polypropylene monofilament suture, although other methods known in the art such as adhesive bonding could be utilized. The proximal row of proximal anchors 3090 may be individually attached to (e.g. inserted through) the foam body 3002 to prevent relative movement between the foam body 3002 and the frame 3040. In other embodiments, the foam body 3002 could be formed around the endoskeleton so that the metallic frame is within the foam body 3002, eliminating the need for a secondary attachment step. Attachment of the body 3002 to the frame 3040 promotes retrieval without damage to the foam body 3002, among other advantages. The attachment also ensures that a bumper 3026, further described herein, extends beyond the frame 3040 at all times, including during initial exposure of the device 3000 upon proximal retraction of the delivery sheath.

As shown in FIG. 87D, the device 3000 may include on or more attachments 3001. The attachments 3001 may connect the frame 3040 with the foam body 3002. The attachments 3001 may be sutures. Other suitable attachment structures may be used, including staples, ties, wires, components of the frame 3040, other mechanical attachments, adhesives, other suitable means, or combinations thereof. The attachments 3001 may extend around the frame 3040 and through the foam body 3002, for example through the sidewall 3014.

As shown, four attachments 3001 are visible in FIG. 87D. There are two proximal attachments 3001 and two distal attachments 3001 visible. The proximal attachments 3001 are each located at the base of a respective proximal anchor 3090. The distal attachments 3001 are each located at the base of a respective distal anchor 3094. There may be one, two, three, four, five, six, seven, eight, or more attachments 3001. There may be twenty attachments 3001. There may be one of the attachments 3001 for each anchor 3090, 3094 of the device 3000. The attachments 3001 may each be located at a proximal apex 3084 or at a distal apex 3088 of the frame 3040, as further described herein, for example with respect to FIG. 89A. For example, the attachments 3001 may be wrapped around one or more of the struts 3082, 3086, as further described herein. The attachments 3001 may locally compress the foam body 3002 at and/or around the location of attachment, as further described herein, for example with respect to FIG. 95C. The attachment 3001, such as a suture, may extend from within the cavity 3028, through the foam body 3002, exit the foam body 3002 and extend along the outer surface 3016 of the foam body 3002, extend back into and through the foam body 3002 into the cavity 3028, and be tied or otherwise connected together around the frame 3040. In some embodiments a similar routing of the attachments 3001 may be used with the attachment 3001 tied or otherwise connected together around and outside the foam body 3002. In some embodiments the attachments 3001 may also extend through the cover 3300, or other covers as described herein. The attachments 3001 may extend through the material of the cover 3300. The attachments 3001 may extend through openings in the cover 3300, such as the side openings 3324, or windows 3177 (see, e.g., FIGS. 88B-88E). As shown, the proximal attachments 3001 may extend through the foam body 3002 and through openings in the cover 3300, and the distal attachments 3001 may not extend through the cover 3300 but only through the foam body 3002.

The foam body 3002 may include a coating. In some embodiments, there may not be a coating. In embodiments with a coating, the coating is applied to the interconnected reticulations of the foam material. The body 3002 may be coated with pure polytetrafluoroethylene (PTFE). The PTFE coating minimizes the thrombogenicity of the LA surface, while also reducing the friction of the foam body 3002 against the delivery system to facilitate ease of deployment and retrieval. The body 3002 may be coated with conformable, vacuum deposited, pure PTFE. In addition or alternatively, the body 3002 may be coated with a coating other than PTFE. The coating, whether PTFE or otherwise, may be about 0.5 μm thick, and covers at least a portion of the surface of the interconnected reticulations of the foam without occluding the pores. The coating may be applied to some or all of the foam body 3002. The coating may be applied to some or all of the outer surfaces of the foam body 3002.

In some embodiments, the thickness of the coating is from about 0.1 μm to about 1 μm, from about 0.2 μm to about 0.9 μm, from about 0.3 μm to about 0.8 μm, from about 0.4 μm to about 0.7 μm, about 0.4 μm to about 0.6 μm, or about 0.5 μm thick. In some embodiments, greater or smaller thicknesses of the coating may be applied. The coating has a uniform or substantially uniform thickness. In some embodiments, the coating may have a non-uniform thickness. For example, the portion of the body 3002 facing the LA when implanted, such as the proximal face 3008 and/or shoulder 3030, may have a thicker coating relative to a coating along the sidewall 3014 of the body 3002. In some embodiments, the outer surface 3010 of the proximal face 3008 has a PTFE coating and the proximal face 3008 also has a ePTFE cover 3100.

The coating is applied using a vapor deposition process. In some embodiments, the coating is applied through coating, vapor deposition, plasma deposition, grafting, other suitable processes, or combinations thereof. The coating is applied to the outer surfaces 3010, 3032 and 3016 of, respectively, the proximal face 3008, the shoulder 3030 and the sidewall 3014. In some embodiments the coating is applied to the outer surfaces 3010, 3032 and only partially on the outer surface 3016. In some embodiments the coating is applied to outer and inner surfaces of the body 3002.

In some embodiments, other biocompatible, thromboresistant and/or lubricious materials could be applied to the surface(s) of the foam body 3002 and/or the cover 3100. These materials may encourage tissue ingrowth. Such materials may include, for example, heparin, albumin, collage, polyethylene oxide (PEO), hydrogels, hyaluronic acid, materials that release nitric oxide, oxygen, nitrogen, amines, bioabsorbable polymers, and other biomaterials, pharmacologic agents, and surface modification materials. Additionally, the surface(s) of the body 3002 could be roughened, textured, or otherwise modified or coated to promote healing or to make it more echogenic.

2. Proximal Cover

The device 3000 may include a cover 3100, which may be an ePTFE cover as further described. Other embodiments for this outer cover 3100 are described herein, for example the cover 3101, 3300, 3150, 3151, etc. The various embodiments of the cover may have the same or similar features and/or functionalities as each other, except as otherwise noted. The cover 3100 may have a series of openings. In some embodiments, the cover 3100 may be solid and not have any openings. In some embodiments, the cover 3100 may only have openings to receive anchors and/or a tether therethrough, as further described herein. In some embodiments, the device 3000 may include an inner cover such as an inner cover 3101, as shown and described with respect to FIG. 85D.

The outer cover 3100 is a generally flat material applied over and covering at least a portion of the body 3002. The cover 3100 is on the proximal end 3004 of the device 3000. The cover 3100 covers the proximal face 3008 of the body 3002 and at least part of the sidewall 3014. The cover 3100 covers a proximal portion of the sidewall 3014. The cover 3100 has a proximal surface 3102 that at least partially faces the LA when implanted. The cover 3100 has an outer edge 3104 forming outer vertices 3106 (for clarity, only some of the outer edges 3104 and outer vertices 3106 are labelled in the figures). In some embodiments, the cover 3100 may cover only the proximal face 3008 or portions thereof. In some embodiments, the cover 3100 may extend over more of the sidewall 3014, such as the middle or distal portion thereof, or the entire sidewall 3014.

The cover 3100 may have a thickness measured perpendicularly from the proximal surface 3102 to an opposite distal surface of the cover 3100 that faces the body 3002. The cover 3100 may have a thickness of 0.001" (inches). In some embodiments, the cover 3100 may have a thickness from about 0.00025" to about 0.005", from about 0.0003" to about 0.004", from about 0.0004" to about 0.003", from about 0.0006" to about 0.002", from about 0.0008" to about 0.0015", or about 0.001". In some embodiments, the cover 3100 may have a thickness of 0.0005". In some embodiments, the cover 3100 may have a thickness from about 0.0002" to about 0.0008", from about 0.0003" to about 0.0007", from about 0.0004" to about 0.0006", or about 0.0005".

The cover 3100 may be attached to the frame 3040 through the foam body 3002. The cover 3100 may in addition or alternatively be attached to the body 3002. The cover 3100 may be attached at least two or four or six or more of the outer vertices 3106. The cover 3100 may be attached to the frame 3040 and/or body 3002 at various locations, including at the outer vertices 3106, through the proximal surface 3100, at the proximal face 3008 of the body 3002, other locations, or combinations thereof. The cover 3100 is attached using mechanical attachments, such as sutures. In some embodiments, polypropylene 6-0 sutures are used throughout the device to attach the foam body 3002, proximal cover 3100, and RO markers 3023 to the foam body 3002 and/or frame 3040. In some embodiments, the cover 3100 is attached to the frame 3040 via standard braided or monofilament suture material, such as polypropylene, ePTFE, or polyester. In some embodiments, a polypropylene monofilament is utilized. Proximal anchors 3090 of the frame 3040 (further described herein) may extend through the outer vertices 3106 of the cover 3100. Such penetrating anchors 3090 may further secure the cover 3100 in place relative to the body 3002. In some embodiments, the cover 3100 may be attached to the various parts of the device 3000 with mechanical attachments, fasteners, adhesives, chemical bonds, other suitable techniques, or combinations thereof.

As shown, the cover 3100 is formed from expanded Polytetrafluoroethylene ("ePTFE"). An ePTFE cover 3100 provides many advantages. For example, the ePTFE cover 3100 may enhance the ability to recapture the device 3000 in vivo by distributing the proximal retraction forces applied by the catheter. The cover 3100 may be an ePTFE material approximately 0.001" thick, with the appropriate porosity to encourage healing and minimize thrombus formation, similar to the underlying PTFE coated foam.

An ePTFE cover 3100 may assist in recapture of the implant into the access sheath while providing a smooth, thromboresistant surface which encourages tissue coverage and integration. The ePTFE may cover the entire proximal face and partially covers the sides, as shown in FIG. 85C. The ePTFE cover 3100 is fabricated from a previously laminated sheet comprised of two or more sheets of oriented material, offset to form a biaxially orientated material. Alternatively, one could use a tube, preferably biaxially oriented, that is then cut to form a sheet. The thickness of the final construct can be from 0.0005"-0.005" but is preferably about 0.001".

Figure 88A:
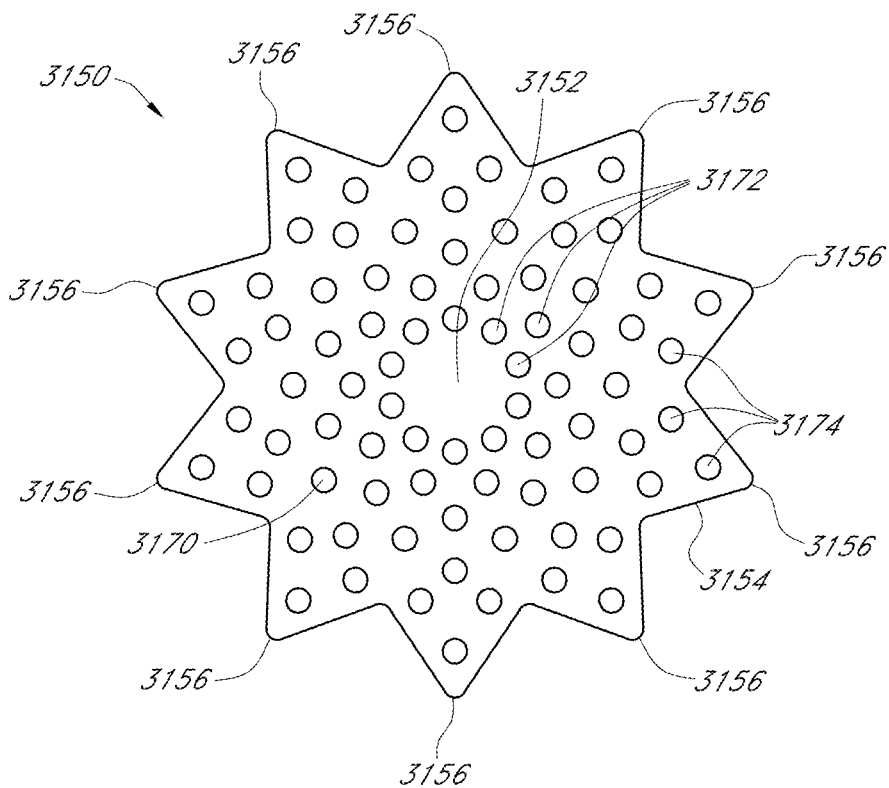
FIG. 88A is a top view of an embodiment of a proximal cover shown in a flat configuration that may be used with the various LAA occlusion devices described herein.
Figure 88B:
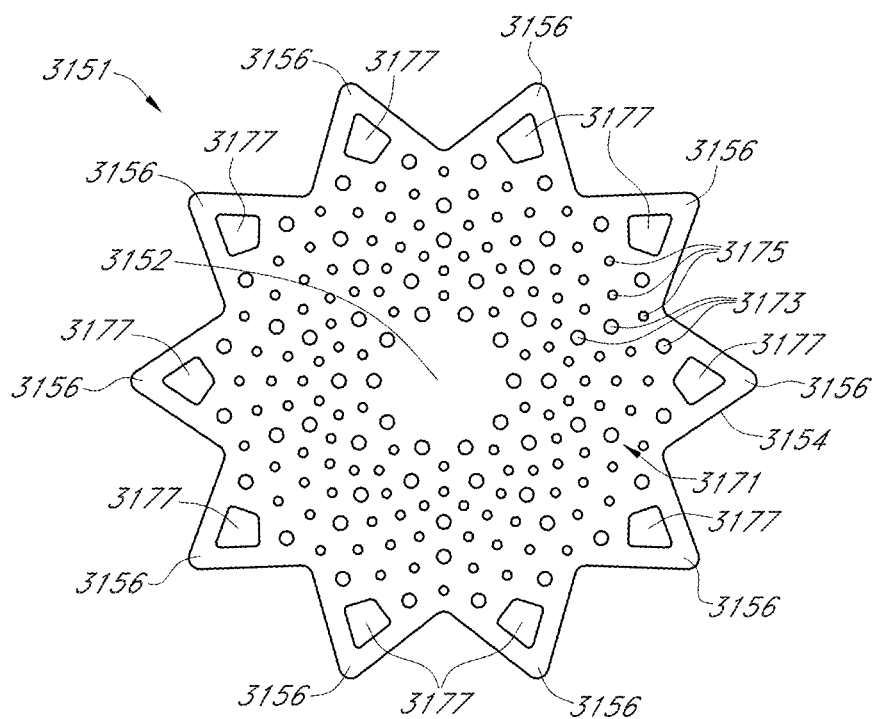
FIGS. 88B-88C are top views of another embodiment of a proximal cover shown, respectively, in a flat configuration and assembled with an LAA occlusion device.

In some embodiments, the cover 3100 is fabricated from other thromboresistant, high strength, biocompatible materials, such as knitted or woven polyester fabrics, polypropylene, polyethylene, non-woven vascular scaffolds, porous films, or bioabsorbable scaffolds such as polylactic acid, polyglycolic acid, and co-polymers. The shape of the cover prior to attachment with the device 3000, such as shown in FIGS. 88A and 88B, minimizes wrinkling and provides a smooth surface following attachment to the implant. This shape may be a star shape, an outer pointed shape, or other shapes.

The cover 3100 may be perforated with a series of openings 3120 (for clarity, only some of the openings 3120 are labelled in the figures). The openings 3120 are perforations or holes formed in the cover 3100 via laser or mechanical cutting. The openings 3120 include proximal openings 3122 and side openings 3124 (for clarity, only some of the proximal openings 3122 and side openings 3124 are labelled in the figures). When the cover 3100 is assembled with the body 3002, the proximal openings 3122 are located over the proximal face 3008 and/or shoulder 3030, and the side openings 3124 are located over the sidewall 3014. In some embodiments, the cover 3100 includes forty proximal openings 3122. In some embodiments, the cover 3100 includes forty side openings 3124. The number of openings 3120 located over the proximal face 3008 and/or shoulder 3030 when assembled with the body 3002 may range from ten to eighty, from twenty to seventy, from thirty to sixty, from thirty five to fifty, or forty openings 3120. The number of openings 3120 located over the sidewall 3014 may range from ten to eighty, from twenty to seventy, from thirty to sixty, from thirty five to fifty, or forty openings 3120.

The openings 3120 may have a variety of sizes. The openings 3120 are 0.070" in width, e.g. minor axis, or diameter for circular openings. The openings 3120 may have a width from about 0.010" to about 0.200", from about 0.020" to about 0.150", from about 0.030" to about 0.110", from about 0.040" to about 0.100", from about 0.050" to about 0.090", from about 0.060" to about 0.080", or about 0.070". In some embodiments, the width may be less than 0.010" or greater than 0.200", such as 0.25", 0.5" or greater. These widths may apply to circular as well as non-circular shaped openings 3120.

In some embodiments, the openings 3120 may be various shapes. The openings 3120 may be elongated slots. The openings 3120 may extend radially along the cover 3100 from or near a center portion of the proximal surface 3102 toward and/or to the outer edge 3104. The openings 3120 may be annular openings extending circumferentially along the cover 3100 and having varying radial positions. The openings 3120 may be of uniform size and shape. Some of the openings 3120 may have varied sizes and/or shapes with respect to other of the openings 3120. The openings 3120 may have various distributions or concentrations about the cover 3100. For example, the openings 3120 may be more densely located in various areas, such as along the proximal surface 3102 that faces the LA, along the shoulder 3030, etc.

The openings 3120 enable blood to flow through the device 3000. The openings 3120 may allow blood to adequately flow through the device 3000 and thereby mitigate the risk of occlusion in the bloodstream should the device 3000 embolize within the vasculature system. In some embodiments, should the device 3000 embolize, it may act as a stationary filter at low pressures but may pass through the bloodstream at higher pressures. In some embodiments, the device 3000 allows for about two to about fourteen liters, from about four to about twelve liters, from about six to about ten liters, or from about eight liters per minute of blood to pass at <30 mmHg pressure drop to prevent shock in the event of a device embolization. In some embodiments, there are forty circular openings 3120 each having a diameter of 0.070", and allowing for approximately eight liters per minute of blood to pass at <30 mmHg pressure drop. In some embodiments, the proximal end of the device 3000 may be a foam layer such as the foam proximal face 3008 or a membrane such as the cover 3100 or both, enclosing the cavity 3028 defined within the tubular side wall 3014 of the body 3002.

In one implementation, having both the foam proximal face 3008 and the cover 3100, the foam body 3002 has the open cell structure further discussed herein that can permit the passage of blood but block escape of embolic debris. The cover 3100 may be occlusive to blood flow, and is present to provide structural integrity and reduced friction for retracting the expanded body 3002 back into the deployment catheter. In one implementation, the cover 3100 is ePTFE in a form that is substantially occlusive to blood flow, as described. In this embodiment, the cover 3100 is therefore provided with a plurality of perfusion windows or openings 3120, so that blood can pass through the open cell foam and cover 3100 but the device 3000 still benefits from the other properties of the cover 3100.

In some embodiments, the device 3000 may allow for a particular flow rate of water at specified conditions, to test the perfusion performance of the device 3000. The device 3000 may have the foam body 3002 and cover 3100 configured to allow for a flow rate of water axially through the device 3000 of at least four liters per minute. The water may be at sixty-eight degrees Fahrenheit (F) or about sixty-eight degrees F. and an upstream pressure of twenty-five millimeters of Mercury (mmHg) or about twenty-five mmHg. In some embodiments, the device 3000 may be configured to allow for flow rates under such conditions from about one liter to about seven liters, from about two liters to about six liters, from about three liters to about five liters, more than two liters, more than three liters, or more than four liters of water per minute. The particular flow rate may depend on the porosity of the foam body 3002 and the open area of the cover 3100. The particular flow rate may depend on the inner cover 3101 features as well. The cover 3100 may have particular percentages of the cover area open with the series of openings, as further described herein, to attain a particular desired flow rate. The flow rate of water at the specified conditions may be used to extrapolate or otherwise calculate the corresponding expected flow rate of blood in the body through the device 3000 should it embolize, as described herein. The device 3000 may allow for a cardiac index from about 1.6-2.4, from about 1.7-2.3, from about 1.8-2.2, from about 1.9-2.1, about 2.0, or 2.0, liters per minute per square meter. The device 3000 may have these and other flow rate capabilities either aligned or approximately aligned with the direction of flow of the fluid, or off-axis where the device 3000 is angled with respect to the direction of flow of the fluid (a flow axis), as further discussed herein for example in the section "Off-Axis Delivery and Deployment."

FIGS. 87A-87C depict an embodiment of the LAA occlusion device 3000 having another embodiment of a cover 3300. The device 3000 includes the foam body 3002 and the frame 3040, and features thereof, as described herein, and additionally includes the cover 3300. The cover 3300 may have the same or similar features and/or functionalities as the cover 3100, and vice versa. The cover 3300 is on the proximal end 3004 of the device 3000. The cover 3300 covers the proximal face 3008 of the body 3002 and a proximal part of the sidewall 3014. The cover 3300 has a proximal surface 3302. The cover 3300 has an outer edge 3304 forming a plurality of at least two or four or six or eight or ten or more outer vertices 3306 (for clarity, only some of the outer vertices 3306 are labelled in the figures). The cover 3300 is attached to the body 3002 at the outer vertices 3306. The proximal anchors 3090 extend through side openings 3324 in the outer vertices 3106 of the cover 3100.

The cover 3300 includes a series of openings 3320. The openings 3320 include proximal openings 3322, shoulder openings 3323, and the side openings 3324. The proximal openings 3322 are located over the proximal end 3004 of the body 3002. The shoulder openings 3323 are located over the shoulder 3030, e.g. a bevel, of the body 3002. The side openings 3324 are located over a proximal portion of the sidewall 3014 of the body 3002. The proximal anchors 3090 may extend through the side openings 3324 that are located in the outer vertices 3106. The openings 3320 may have the same or similar features and/or functionalities as the openings 3120, and vice versa. In some embodiments, the proximal anchors 3090 may extend through the cover 3300 material at or near the outer vertices 3106.

FIG. 88A shows another embodiment of a cover 3150 that may be used with the device 3000. The cover 3150 may have the same or similar features and/or functionalities as the cover 3100 and/or cover 3300, and vice versa. The cover 3150 may be used to cover the proximal face 3008 of the body 3002 and part of the sidewall 3014. The cover 3150 has a proximal surface 3152. The cover 3150 has an outer edge 3154 forming outer vertices 3156. The cover 3150 may be attached to the body 3002 at the outer vertices 3156. The proximal anchors 3090 may extend through the outer vertices 3156 of the cover 3100. The cover 3150 includes a series of openings 3170. The openings 3170 include proximal openings 3172 and side openings 3174 (for clarity, only some of the openings 3170, 3172, 3174 are labelled in the figures). When the cover 3150 is assembled with the body 3002, the proximal openings 3172 are located over the proximal end 3004 and the side openings 3174 are located over the sidewall 3014. As shown, the openings 3174 may be substantially uniformly located along the cover 3150 except for a center region of the proximal surface 3152.

Figure 88C:
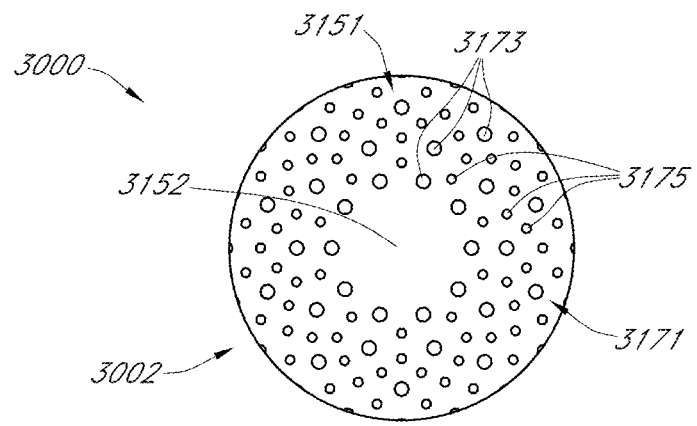

FIG. 88B is a top view of another embodiment of a proximal cover 3151 that may be used with the various LAA occlusion devices described herein. FIG. 88C is a top view showing the cover 3151 assembled with the device 3000. The cover 3151 may have the same or similar features and/or functionalities as other covers described herein, such as the cover 3100 and/or cover 3300, and vice versa, except as otherwise noted. For example, the cover 3151 may include the proximal surface 3152 and outer edge 3154 forming outer vertices 3156.

The cover 3151 further includes another embodiment of a series of openings 3171. The openings 3171 include smaller openings 3175 and larger openings 3173. The openings 3175, 3173 may have the same or similar features and/or functionalities as other cover openings described herein, such as the openings 3120, 3122, 3124, 3320, 3322, 3324, 3170, 3172 and/or 3174, and vice versa. The smaller openings 3175 may be relatively smaller, in width and/or area, than the larger openings 3173. There may be openings with widths or areas smaller than that of the smaller openings 3175, larger than that of the larger openings 3173, or anywhere in between. As shown, the openings 3173, 3175 may be generally uniformly distributed about the proximal surface 3152 of the cover 3151. The openings 3173, 3175 may be circumferentially evenly spaced or approximately evenly spaced about the cover 3151.

There may be a variety of different quantities of each of the openings 3173, 3175. There may be a total of ten, twenty, thirty, forty, fifty, sixty, seventy, eighty, ninety, one hundred, one hundred fifty, two hundred, three hundred, four hundred, or more openings of the series of openings 3171, or any lesser, greater or in between number of openings. The series of openings 3171 may be holes as shown. They may have circular shapes. They may have other shapes, including non-circular, segmented, other shapes, or combinations thereof. The openings 3171 may all have the same general shape or different shapes. In some embodiments, there may not be any holes in the cover 3151.

When the cover 3151 is assembled with the foam body 3002, the large and small openings 3173, 3175 may be located over the proximal end 3004 and/or the sidewall 3014 of the foam body 3002. When assembled with the foam body 3002, on the proximal-facing portion of the cover 3151, there may be a collective total of one hundred forty or about one hundred forty openings 3173, 3175. On this proximal-facing portion of the cover 3151, there may be a collective total from about ten to about three-hundred, from about fifty to about two hundred fifteen, from about one hundred ten to about one hundred seventy, from about one hundred twenty to about one hundred sixty, from about one hundred thirty to about one hundred fifty, or from about one hundred thirty-five to about one hundred forty-five openings 3173, 3175. On this proximal-facing portion of the cover 3151, there may be from about thirty to about fifty, from about thirty-five to about forty-five, about forty, or forty of the larger openings 3173. On this proximal-facing portion of the cover 3151, there may be from about sixty to about one hundred forty, from about eighty to about one hundred twenty, from about ninety to about one hundred ten, about one hundred, or one hundred of the smaller openings 3175.

When assembled with the foam body 3002, on the portion of the cover 3151 located over and/or near the shoulder 3030, such as over the outer surface 3032 of the foam body 3002 (see, e.g., FIG. 86B), there may be from about five to about eighty, from about ten to about forty, from about fifteen to about thirty, about twenty, or twenty of the smaller openings 3175. In some embodiments, at this same portion of the cover 3151, there may be from about five to about eighty, from about ten to about forty, from about fifteen to about thirty, about twenty, or twenty of the larger openings 3173.

When assembled with the foam body 3002, on the portion of the cover 3151 located over and/or near the sidewall 3014, such as over the outer surface 3016 of the foam body 3002 (see, e.g., FIG. 86B), there may be from about five to about eighty, from about ten to about forty, from about fifteen to about thirty, about twenty, or twenty of the larger openings 3173. In some embodiments, at this same portion of the cover 3151, there may be from about five to about eighty, from about ten to about forty, from about fifteen to about thirty, about twenty, or twenty of the smaller openings 3175.

The larger and smaller openings 3173, 3175 may have a variety of different sizes, for example as described herein with respect to the openings 3122. In some embodiments, the openings 3173, 3175 may have diameters ranging from about 0.025 inches to about 0.040 inches. In some embodiments, the larger openings 3173 may be 0.040 inches or about 0.040 inches in diameter. The larger openings 3173 may be from about 0.030 inches to about 0.050 inches, or from about 0.035 inches to about 0.045 inches, in diameter. These values may also refer to the widths, for example maximum widths, of non-circular larger openings 3173. In some embodiments, the smaller openings 3175 may be 0.025 inches or about 0.025 inches, in diameter. The smaller openings 3175 be from about 0.015 inches to about 0.035 inches, or from about 0.020 inches to about 0.030 inches, in diameter. These values may also refer to the widths, for example maximum widths, of non-circular smaller openings 3175.

The series of openings 3171 may be configured to provide a desired amount of open area through the cover 3151. This open area refers to the total area of certain openings in the cover 3151. The cover 3151 may be covering a proximal face 3008 at the proximal end 3004 of the foam body 3002. The open area may refer to openings through the portion of the cover that is over the proximal face 3008 of the foam body 3002 when assembled with the foam body 3002. The series of openings in the various covers described herein may collectively provide the open area. For example, the series of openings 3171 in the cover 3151 over the proximal face of the foam may collectively provide an open area. This is the sum of the area of the openings in the cover 3151 over the proximal face. As further example, the open area may be the sum of the proximal openings 3122 of the cover 3100. As further example, the open area may be the sum of the proximal openings 3322 of the cover 3300.

The open area may be at least five percent of the area of the proximal face 3008 of the foam body 3002. The open area may be at least six, at least seven, at least eight, at least nine, at least ten, at least eleven, at least twelve, at least thirteen, at least fourteen percent, at least fifteen, at least sixteen, at least seventeen, at least eighteen, at least nineteen, at least twenty, at least twenty-five, at least thirty, at least forty, or at least fifty percent, of the area of the proximal face 3008. The open area may be from about one to about fifty percent, from about five to about twenty percent, from about eight to about fifteen percent, from about ten to about twelve percent, or about eleven percent, of the area of the proximal face 3008. The "area" of the proximal face 3008 is understood here to refer to an area equal to $Pi \times R^2$, where R is the radius of the proximal face 3008 and extends perpendicularly from the longitudinal axis of the device 3000. Further, "R" may be measured to the inner boundary of the shoulder 3030, to the outer boundary of the shoulder 3030, or to the outer surface 3016 of the sidewall 3014. Further, as mentioned, some embodiments may not include a cover at all.

The cover 3151 may include one or more windows 3177. As shown, there may be ten windows 3177. There may be one window 3177 for each proximal anchor 3090. There may be four, six, eight, twelve, fourteen or more windows 3177, or any lesser or in between number. The windows 3177 may be openings in the cover 3151. The windows 3177 may be located at or near the outer edge 3154 of the cover 3151. The windows 3177 may be located along portions of the outer edge 3154, for example at or near the outer vertices 3156. The windows 3177 may have a shape conforming to the shape of the cover 3151 at the respective portions of the outer edge 3154. As shown, the window 3177 may be diamond or generally diamond shaped. The window 3177 may be square, rectangular, triangular, rounded, circular, segmented, flattened diamond, other polygonal shapes, other shapes, or combinations thereof. The cover 3150 may be attached to the body 3002 at the outer vertices windows 3177. The windows 3177 may have the same or similar feature and/or functionalities as the side openings 3324, described and shown in FIG. 87B. The proximal anchors 3090 may extend through the windows 3177 of the cover 3151 to retain the cover 3151 on the device 3000.

Figure 88D:
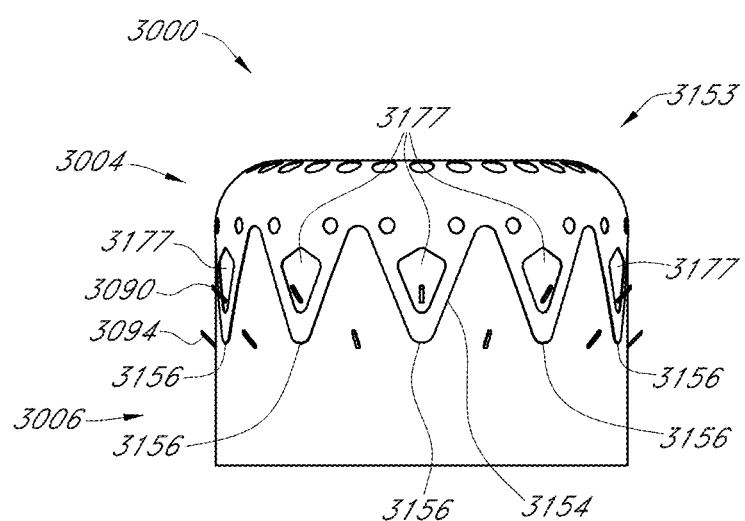
FIG. 88D-88E are side and perspective views, respectively, of another embodiment of a proximal cover shown assembled with an LAA occlusion device.
Figure 88E:
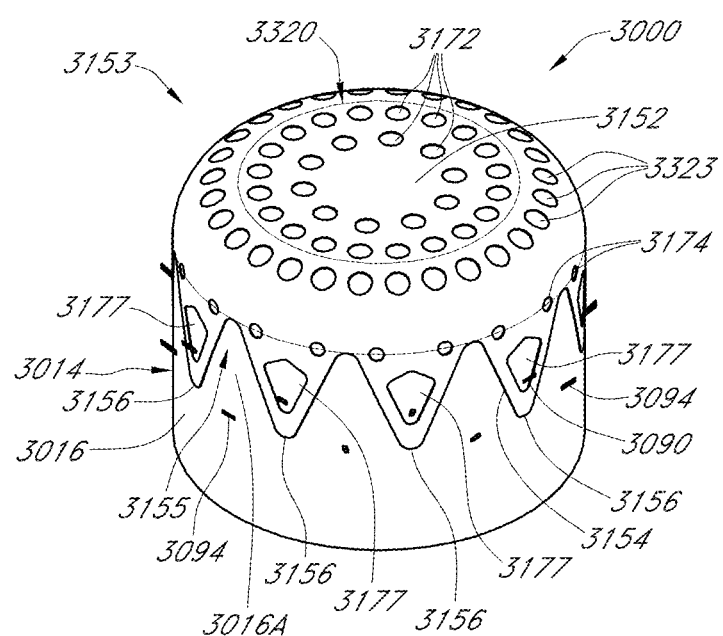

FIG. 88D-88E are side and perspective views, respectively, of another embodiment of a proximal cover 3153 shown assembled with the device, that may be used with the various LAA occlusion devices described herein. The cover 3153 may have the same or similar features and/or functionalities as other covers described herein, such as the cover 3100, 3151, and/or cover 3300, and vice versa, except as otherwise noted. For example, the cover 3151 may include the proximal surface 3152, outer edge 3154 forming outer vertices 3156, and windows 3177.

The device 3000 with cover 3151 may have proximal anchors 3090 extending through the windows 3177. The proximal anchor 3090 may extend through the opening of the respective window 3177. The proximal anchor 3090 may extend through a distal portion of the window 3177, for example to contribute to securing the cover 3153 on the device 3000. The proximal anchors 3090 may extend through the window 3177 at a distal edge or distal vertex of the window 3177. In some embodiments, the proximal anchor 3090 may extend through the cover 3151 material, for example through material adjacent (such as distal) to the window 3177. In some embodiments, the proximal anchor 3090 may extend through various other locations within, adjacent or near the window 3177. Some of the proximal anchors 3090 may extend through first locations and other of the proximal anchors 3090 may extend through second locations of the cover 3153 different from the first locations. For instance, one or more anchors 3090 may extend through a first region of the window 3177, one or more other anchors 3090 may extend through a second region of the window 3177, still one or more other anchors 3090 may extend through other regions, such as through the cover 3153 material, etc.

The cover 3153 may include proximal vertices 3155. The proximal vertices 3155 may be formed by the outer edge 3154. The proximal vertices 3155 may be indentations along the outer edge 3154 of the cover 3153, for example angled as shown or other shapes, configurations, etc. The proximal vertices 3155 may define a region 3016A of the outer surface 3016 of the sidewall 3014. The region 3016A may be partially enveloped by the outer edge 3154 of the cover 3153. The region 3016A may receive one or more of the distal anchors 3094 therethrough. The distal anchor 3094 may extend through a distal portion of the region 3016A, or in other locations within, adjacent, or near the region 3016A. In some embodiments, the distal anchor 3094 may not extend through or near the region 3016. There may be multiple such regions 3016A of the foam body 3002 defined circumferentially about the device 3000 by the cover 3153.

The cover 3153 may include the series of openings 3320, for example as described with respect to FIG. 87A. The series of openings 3320 may include the proximal openings 3172, the shoulder openings 3323, and/or the side openings 3174. The cover 3153 may include different patterns, sizes, distributions, etc. of the openings 3320, for example as shown and described with respect to FIGS. 88B-88C.

3. Compliant Frame

Figure 89A:
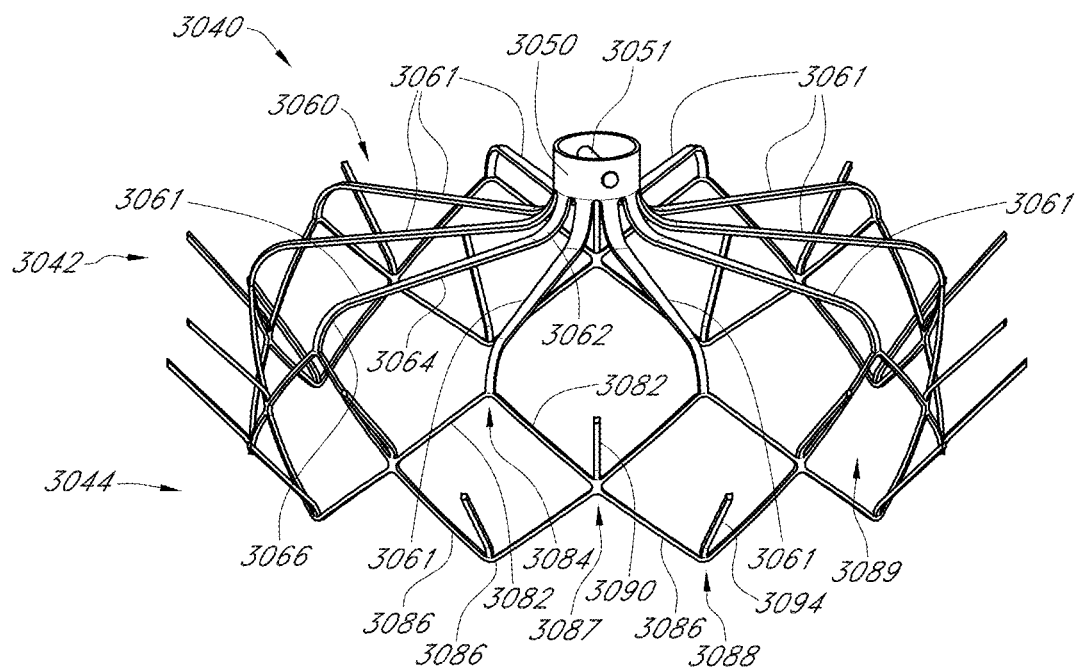
FIGS. 89A and 89B are side perspective and proximal perspective views, respectively, of the frame of FIGS. 85B and 86C shown in a deployed configuration.
Figure 89B:
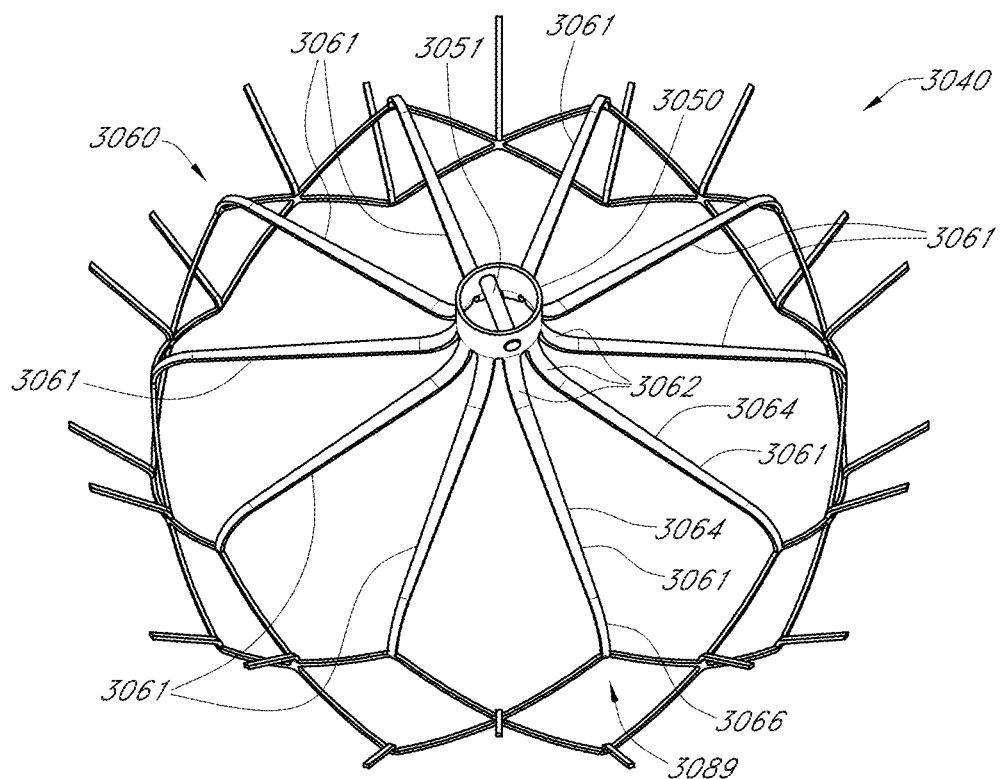

The expandable and compliant support or frame 3040 is shown, for example, in FIGS. 85B, 85D, 86C and 87C-E. FIGS. 89A and 89B are side and proximal perspective views, respectively, of the frame 3040 shown in a deployed configuration and in isolation from the rest of the device 3000. The frame 3040 provides a compliant structure with anchors to facilitate delivery, anchoring, retrieval and to enable the foam body 3002 to compress against the LAA tissue to facilitate sealing, among other things, as further described. The frame 3040 is located inside the cavity 3028 formed by the foam body 3002. In some embodiments, the frame 3040 may be located partially or entirely inside one or more portions of the body 3002, e.g. within the proximal face 3008 and/or the sidewall 3014, as further described. For example, the frame 3040 may be partially located within the sidewall 3014 as shown in FIG. 87C.

The frame 3040 has a proximal end 3042 and an opposite distal end 3004. The frame 3040 may be tubular, e.g. cylindrical, in a free, unconstrained state. Thus the width of the proximal end 3042 may be the same or similar to the width of the distal end 3004 in the free, unconstrained state. In some embodiments, the frame 3040 or portions thereof may be conical or frustoconical, e.g. where in the free, unconstrained state the width of the proximal end 3042 is greater than the width of the distal end 3004 or vice versa.

At the proximal end 3042, the frame 3040 has a proximal hub 3050, shown as a cylindrical nipple. The hub 3050 is a rounded, structural end piece. The hub 3050 may be tubular, e.g. circular and having the cylindrical shape as shown, or may be rounded, non-circular, segmented, other shapes, or combinations thereof. The hub 3050 extends axially and may have a central lumen. The hub 3050 may be wider than it is long, or vice versa. The hub 3050 is hollow and has a sidewall defining a space therethrough, such as a longitudinal opening. In some embodiments, the hub 3050 may be partially hollow, solid, or other configurations. The hub 3050 facilitates delivery and retrieval of the device 3000, as further described. The hub 3050 may provide a central structural attachment, as further described herein. The hub 3050 may be located within the cavity 3028 at a proximal end thereof. In some embodiments, the hub 3050 may be located partially or entirely within the foam body 3002, e.g. within the proximal face 3008.

A pin 3051 is located within the hub 3050 (shown in FIGS. 89A and 89B). The pin 3051 is an elongated, rounded structural element extending laterally across the central lumen. "Lateral" here refers to a direction perpendicular or generally perpendicular to the longitudinal axis. The pin 3051 has a cylindrical shape. The pin 3051 provides a rounded outer surface configured to provide a smooth engagement surface with a tether, as further described. The pin 3051 provides a high strength connection with the frame 3040 to allow for pulling on the device 3000 with sufficient force to re-sheath the device 3000. The pin 3051 may be formed from Nitinol. The pin 3051 is secured across the width, e.g. diameter, of the proximal hub 3050. The pin 3050 may be secured at its two opposite ends with the sidewall of the hub The pin 3051 is configured to be engaged by a tether 3240, which is wrapped around the pin 3051 in sliding engagement for temporary attachment to a delivery catheter, as further described. In some embodiments, the pin 3051 is assembled with a cap 3180, as further described herein, for example with respect to FIGS. 90A-90C.

The frame 3040 at the proximal end 3042 includes a proximal face 3060. The proximal face 3060 may be located within the cavity 3028 at a proximal end thereof. In some embodiments, the proximal face 3060 may be located partially or entirely within the foam body 3002, e.g. within the proximal face 3008 and/or sidewall 3014. The proximal face 3060 includes a series of recapture or reentry struts 3061. The struts 3061 are located at a proximal end of the cavity 3028. In some embodiments, the struts 3061 or portions thereof may be located partially or entirely within the foam body 3002, e.g. within the proximal face 3008 and/or sidewall 3014.

The struts 3061 are elongated structural members. The struts 3061 may have rectangular, circular or other shaped cross-sections. In some embodiments, the struts 3061 have a cross-section, e.g. rectangular, with a width that is greater than a thickness such that the struts 3061 are stiffer in one direction compared to another direction. This width may be in the lateral direction or a direction generally perpendicular to the longitudinal axis of the device 3000 when the device 3000 is in the expanded configuration, with the thickness perpendicular to the width. The struts 3061 may be less stiff in the direction of flexing or bending, for example to facilitate contraction and expansion of the device 3000 in the delivery and expanded configurations. The struts 3061 may be elongated pins. The struts 3061 may extend from the hub 3050, for example, and incline radially outwardly in the distal direction from the hub 3050. The struts 3061 may be attached inside, outside, and/or at the end of the sidewall of the hub 3050. The struts 3061 may be separate parts that are then attached to the hub 3050, for example welding, bonding, fastening, other suitable means, or combinations thereof. In some embodiments, some or all of the struts 3061 and the hub 3050 may be a single, continuous structure formed from the same raw material such as a laser cut hypotube. Some or all of the struts 3061 may be attached, e.g. with sutures as described herein, to the body 3002 and/or the cover 3100 at one or more attachment locations.

Each recapture strut 3061 may include an inner curved portion 3062 connected to a distal end of the hub 3050, a middle straight portion 3064, and/or an outer curved portion 3066 (for clarity, only some of the portions 3062, 3064, 3066 are labelled in the figures). In the deployed configuration, the inner curved portion 3062 extends from the hub 3050 primarily in a distal direction and then curves to face more outwardly radially. The middle straight portion 3064 extends from the inner curved portion 3062 primarily radially but also slightly distally. The outer curved portion 3066 extends from the middle straight portion 3064 primarily in the radial direction and then curves toward the distal direction. The portions may have different shapes in the delivery configuration inside a delivery catheter. In the delivery configuration, the portions may extend primarily distally. The portions may then take the deployed configuration as described upon deployment from the delivery catheter. In some embodiments, the struts 3061 may include fewer or more than the portions 3062, 3064, 3066.

The device 3000 may include ten of the proximal recapture struts 3061. Such configuration may accompany a device 3000 having a foam body 3002 with an outer diameter of 27 mm in the free, unconstrained state. Such configuration may accompany a device 3000 having a foam body 3002 with an outer diameter of 35 mm in the free, unconstrained state. In some embodiments, the device 3000 may have from about two to about thirty, from about four to about twenty, from about six to about eighteen, from about eight to about sixteen, from about ten to about fourteen, or other numbers of struts 3061.

In the deployed configuration, each strut 3061 may extend radially outward and distally at an angle to the axis. This angle, measured relative to a portion of the axis that extends distally from the device 3000, may be from about 60° to about 89.9°, from about 65° to about 88.5°, from about 70° to about 85°, from about 72.5° to about 82.5°, from about 75° to about 80°, or other angular amounts. This angle may be much smaller when the device 3000 is in the delivery catheter. The struts 3061 may bend or flex when transitioning between, or when positioned in, the delivery and expanded configurations. The struts 3061 may bend or flex at the inner curved portion 3062, the middle straight portion 3064, and/or the outer curved portion 3066.

The proximal end 3042 of the frame 3040, such as the proximal face 3060, may therefore have a conical shape in the expanded configuration. The conical proximal face 3060 may facilitate with recapture of the device 3000 back into the delivery catheter. For example, the orientation of the struts 3061 inclining distally and radially outward from the hub 3050 in the expanded configuration provides an advantageous conical shape to the proximal face 3008 such that distal advance of the delivery sheath over the device 3000 will bias the struts 3061 inward and cause the device 3000 to stow back toward the delivery configuration and size for retrieval within the catheter.

The proximal face 3060 foreshortens considerably upon expansion of the device 3000 relative to the delivery configuration. "Foreshortening" here refers to the difference in axial length of the proximal face 3060 between the reduced delivery configuration and the expanded configuration (expanded either freely or as implanted). This length may be measured axially from the distal or proximal end of the hub 3050 to the distal ends of the outer curved portions 3066 of the recapture struts 3061. The proximal face 3060 may foreshorten by 50%, 60%, 70%, 80%, 90% or more. The proximal face 3060 has significantly more foreshortening upon expansion than the tubular body 3080, the latter of which may be referred to as the "working length" or "landing zone." The landing zone is further described with respect to the tubular body 3080 herein.

As shown, the struts 3061 are angularly spaced about the axis in even angular increments. That is, looking at the frame 3040 from the distal or proximal end, the angles between the struts may be equal. In some embodiment, the struts 3061 may not be evenly angularly spaced about the axis as described. The struts 3061 may or may not be symmetrically disposed about the axis or about a plane that includes the axis.

Figure 87E:
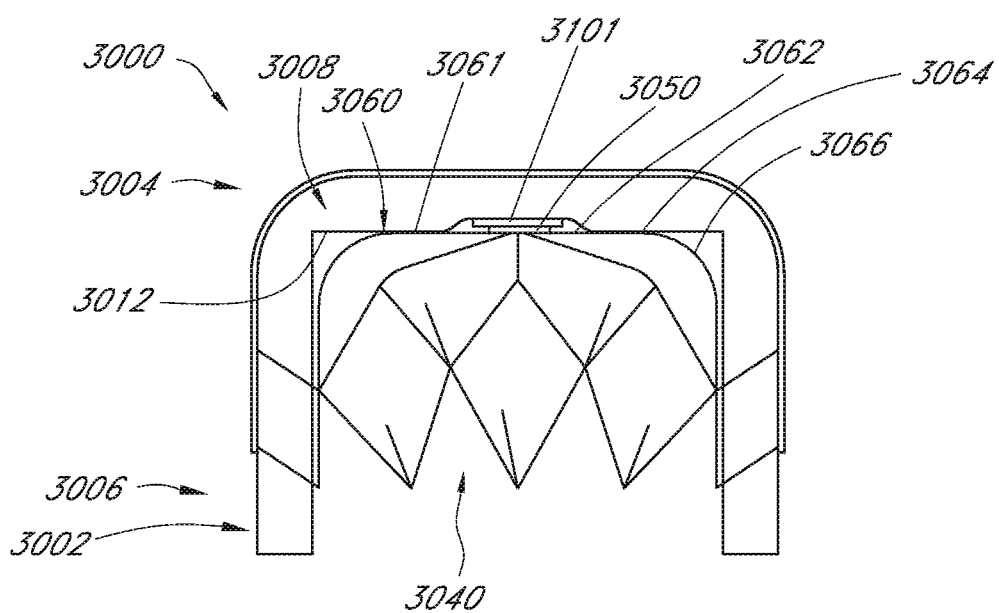

In some embodiments, portions of the frame 3040 may be at various distances from the proximal end of the foam body 3002, such as the proximal end wall having the proximal face 3008. As shown in FIG. 87D, there may be a gap of size Z in the axial direction between the proximal face 3060 of the frame 3040 and the inner surface 3012 of the proximal face 3008. The length of Z may be one, two, three, four, five, six, seven, eight, nine, ten, or more millimeters. The length of Z may vary depending on the radial distance at which it is measured. For instance, the length of Z may decrease, increase, or combinations thereof, as measured along the length of the strut 3061. In some embodiments, the length of Z may be zero at more or points along the length of the strut 3061. As shown in FIG. 87E, the proximal face 3060 or portions thereof may contact the proximal inner surface 3012 of the foam body 3002. The inner curved portion 3062, the straight portion 3064, and/or the outer curved portion 3066 may contact the proximal end wall such as the inner surface 3012 and/or other portions of the foam body 3002. The hub 3050 may compress the proximal face 3008 or proximal end wall of the foam body 3002 slightly in a proximal direction as shown. The proximal face 3008 may therefore have a smaller thickness in this compressed region as compared to other portions of the proximal face 3008, for example portions adjacent to this compressed portion. The hub 3050 may be located based on the axial location of connection of the anchors 3090, 3094 to the sidewall 3014, as described herein. In some embodiments, the hub 300 may not compress the foam body 3002 as shown. In some embodiments, the proximal face 3060 may extend radially outwardly as shown. For instance, the struts 3061, or portions thereof for instance the straight portions 3064, may extend radially outwardly perpendicularly or generally perpendicularly to the longitudinal axis of the device 3000. The proximal face 3060 may extend radially outwardly and incline in a distal direction, as described herein, or it may incline in a proximal direction. The device 3000 may have any of these features in the constrained, unconstrained and/or implanted configurations.

The frame 3040 includes a tubular body 3080. The body 3080 provides a mechanical base structure for the device 3000, as further described. The tubular body 3080 is attached to a distal end of the proximal face 3060 of the frame 3040. The tubular body 3080 extends to the distal end 3044 of the frame 3040. The tubular body 3080 is attached at a proximal end to the outer curved portions 3066 of the recapture struts 3061, as further described. The tubular body 3080 may be attached to other portions of the recapture struts 3061. The tubular body 3080 of the frame 3040 may be attached to the body 3002 and/or the cover 3100, e.g. with sutures as described herein, at one or more attachment locations, as further described. The tubular body 3080 may be located within the cavity 3028. In some embodiments, the tubular body 3080 may be located partially or entirely within the foam body 3002, e.g. within the sidewall 3014.

The tubular body 3080 includes a series of proximal struts 3082 and distal struts 3086 (for clarity, only some of the struts 3082, 3086 are labelled in the figures). The proximal struts 3082 and/or distal struts 3086 may have rectangular, circular or other shaped cross-sections. In some embodiments, the proximal struts 3082 and/or distal struts 3086 have a cross-section, e.g. rectangular, with a width that is greater than a thickness, or vice versa, such that the struts 3061 are stiffer in one direction compared to another direction. The struts 3061 may be less stiff in the direction of flexing or bending, for example to facilitate contraction and expansion of the device 3000 in the delivery and expanded configurations. Proximal ends of pairs of adjacent proximal struts 3082 join at proximal apexes 3084. Each proximal strut 3082 is connected at a respective proximal apex 3084 to a respective outer curved portion 3066 of one of the recapture struts 3061. Each distal end of the proximal struts 3082 connects to a distal end of an adjacent proximal strut 3082 and to proximal ends of two distal struts 3086 at an intermediate vertex 3087. Pairs of adjacent distal struts 3086 extend distally to join at a respective distal apex 3088. A repeating pattern 3089, shown as a diamond shape, may be formed by adjacent pairs of proximal struts 3082 and adjacent pairs of distal struts 3086. Some or all of the proximal struts 3082 and/or distal struts 3086 may be attached, e.g. with sutures as described herein, to the body 3002 and/or the cover 3100 at one or more attachment locations. Some or all of the proximal struts 3082 and/or distal struts 3086 may be located within the cavity 3028. In some embodiments, some or all of the proximal struts 3082 and/or distal struts 3086 may be located partially or entirely within the foam body 3002, e.g. within the sidewall 3014.

There are the same number of proximal apexes 3084 as distal apexes 3088. As shown, there are eleven proximal apexes 3084 and eleven distal apexes 3088. The number of proximal and distal apexes 3084, 3088 may each be at least seven, at least eight, at least nine, at least ten, at least eleven, at least twelve, at least thirteen, at least fourteen, at least fifteen, at least sixteen, or fewer or more apexes. In some embodiments, there may not be the same number of proximal apexes 3084 as distal apexes 3088. In some embodiments, there may be more than one row of the pattern, e.g. diamond pattern, formed by the proximal struts 3082 and distal struts 3086. There may be two, three, four or more rows of the pattern. Some or all of the proximal apexes 3084 and/or distal apexes 3088 may be attached, e.g. with sutures as described herein, to the body 3002 and/or the cover 3100 at one or more attachment locations.

The body 3080 may be tubular, e.g. cylindrical or generally cylindrical, in the expanded configuration. The tubular body 3080 may be cylindrical, rounded, segmented, polygonal, tube-like, other shapes, or combinations thereof, all of which are subsumed non-exhaustively under the category "tubular." The tubular shape is formed by the proximal struts 3082 and distal struts 3086 in the expanded configuration. The tubular shape may also be formed by the outer curve portions 3066 of the recapture struts 3061 in the expanded configuration. The tubular shape may also be formed by the foam body 3002 exerting an outward radial force on the frame 3040. The frame 3040 may therefore have a proximal conical section and a cylindrical working length. In some embodiments, the body 3080 may be conical or frustoconical, for example where the distal end is wider than the proximal end or vice versa.

The tubular body 3080 may be referred to as a "landing zone," as described. This landing zone may refer to the axial length of the body 3080, from a distal-most end to a proximal-most end at the transition to recapture struts 3061, in the expanded configuration. The landing zone may have an axial length as measured from the proximal apex 3084 to the distal apex 3088. The length of the landing zone may be 10 mm or about 10 mm. The landing zone may have a length from about 5 mm to about 15 mm, from about 6 mm to about 14 mm, from about 7 mm to about 13 mm, from about 8 mm to about 12 mm, from about 9 mm to about 11 mm, or other lengths. The tubular body 3080 may foreshorten slightly upon expansion of the device 3000 relative to the delivery configuration. The tubular body 3080 has significantly less foreshortening upon expansion than the length of the proximal face 3060. The tubular body 3080 may foreshorten by no more than about 5%, 10%, 15%, 20% or 30%.

The frame 3040 self-expands upon delivery from the sheath. The proximal face 3060 and the tubular body 3080 will self-expand. Upon expansion, the radially outward portions of the tubular body 3080 will contact and compress the foam body 3002 against tissue of the LAA wall. The tubular body 3080, for example the proximal struts 3082 and distal struts 3086, will contact the inner surface 3018 of the sidewall 3014 and press against the sidewall 3014 so that the outer surface 3016 of the sidewall 3014 contacts and compresses against the LAA wall.

When compressed against the LAA wall, the foam body 3002 provides a larger "footprint" than the skeletal frame 3040 components and forms a complete seal. Thus, the sidewall 3014 acts as a force dissipation layer, spreading radial force out from the struts 3082, 3086 of the frame 3040 over a larger area than just the area of the individual struts 3082, 3086 (e.g. a larger area than just the area of the radially outer surfaces of the struts 3082, 3086). The use of the foam material in the body 3002 and the thickness of that foam, such as 2.5 mm, provide advantages in this regard over devices with thinner and less resilient materials than foam. For example, thin fabrics or similar materials that are pressed against the LAA wall with a skeletal frame will not spread the radial force out, and may even sag or otherwise bend, creating gaps and an unsealed portion of the LAA wall. The foam body 3002 as described herein will take the shape of the LAA wall to create a complete circumferential seal and will also spread out the radial forces from the frame 3040 to create a stronger seal and retention with the foam body 3002.

Further, the device 3000 described herein with the compressible body 3002 allows for a structural frame 3040 that is compliant due to the smaller required radial force from the frame 3040. For example, existing devices with a non-compressible fabric material will have a less effective seal, and so the structural elements of those devices must provide larger radial forces to compensate and ensure an effective seal, resulting in a less compliant device. In contrast, the current device 3000 provides advantages in this regard by having the compressible foam body 3002, allowing for among other things smaller radial forces from, and thus better compliance of, the frame 3040, while still providing an effective seal. This structural configuration has a cascading effect in terms of performance advantages. For instance, the compliance of the device 3000 allows for delivery off-axis while still providing an effective seal, among other advantages as further described herein.

The frame 3040 includes a series of proximal anchors 3090. Each proximal anchor 3090 extends from a respective intermediate vertex 3087. The proximal anchors 3090 may extend from other portions of the tubular body 3080. As shown, in the deployed configuration, the proximal anchors 3090 extend from the tubular body 3080 radially and proximally. The proximal anchors 3090 may extend into an adjacent region of the sidewall 3014. The proximal anchors 3090 may extend through the outer surface 3016 of the sidewall 3014 to penetrate tissue adjacent the device 3000.

The frame 3040 includes a series of distal anchors 3094. Each distal anchor 3094 extends from a respective distal apex 3088. The distal anchors 3094 may extend from other portions of the tubular body 3080. As shown, in the deployed configuration, the distal anchors 3094 extend from the tubular body 3080 radially and proximally. The distal anchors 3094 may extend into an adjacent region of the sidewall 3014. The distal anchors 3094 may extend through the outer surface 3016 of the sidewall 3014 to penetrate tissue adjacent the device 3000. The anchors 3090, 3094 may incline radially outward in a proximal direction to engage the tissue to resist proximal movement of the device 3000.

The anchors 3090, 3094 are elongated structural members. The tips of the anchors 3090, 3094 may be sharpened to facilitate tissue engagement and penetration. The anchors 3090, 3094 may be straight, extending generally along a local axis thereof. The anchors 3090, 3094 may have a curved or other non-straight proximal portion where they attach to the tubular body 3080. In some embodiments, the anchors 3090, 3094 or portions thereof may be non-straight, curved, rounded, segmented, other trajectories, or combinations thereof. In some embodiments, the tissue engaging tips may be curved. In some embodiments, the anchors 3090, 3094 may have engagement features extending radially away from the anchor 3090, 3094, such as barbs, hooks, or other features.

The cross-section of the anchors 3090, 3094 may be rectangular. In some embodiments, the cross-section may be circular, rounded, non-rounded, square, rectangular, polygonal, other shapes, or combinations thereof. The cross-sections may or may not be uniform along the length of the anchor 3090, 3094. The anchors 3090, 3094 may be about 0.006" thick and about 0.008" wide. The anchors 3090, 3094 may range from about 0.003" to about 0.009" in thickness and from about 0.003" to about 0.015" in width. The cross-section of the anchors 3090, 3094 may reduce in size, for example taper, toward the distal tip.

In some embodiments, the anchors 3090, 3094 in the deployed configuration are inclined at an incline angle of about 30° relative to a portion of the central axis that extends proximally from the device 3000. This incline angle may be from about 10 degrees to about 50°, from about 15° to about 45°, from about 20° to about 40°, from about 25° to about 35°, or about 30°. This incline angle of the anchors 3090, 3094 in the delivery configuration may be smaller than in the deployed configuration. The anchors 3090, 3094 may have the angle B, as shown in and described with respect to FIGS. 94A-94C.

The anchors 3090, 3094 may have various lengths. The length of the anchor 3090, 3094 is measured from a proximal end that connects to the tubular body 3080 to a distal tissue engaging tip of the anchor. In some embodiments, the length of the anchors 3090, 3094 may be from about 0.5 mm to about 10 mm, from about 1 mm to about 9 mm, from about 2 mm to about 8 mm, from about 3 mm to about 7 mm, from about 4 mm to about 6 mm, about 5 mm, or other greater or lesser lengths. In some embodiments, the anchors 3090, 3094 are 5 mm long. In some embodiments, the anchors 3090, 3094 are about 5 mm long. In some embodiments, the anchors 3090, 3094 have a length of at least 2.5 mm, at least 3 mm, at least 3.5 mm, at least 4 mm, at least 4.5 mm, at least 5 mm or more. The anchors 3090, 3094 may each be the same or similar length. In some embodiments, the anchors 3090, 3094 may not be the same length. In some embodiments, some or all of the proximal anchors 3090 may have lengths that are less than or greater than some or all of the lengths of the distal anchors 3094. The anchors 3090, 3094 may have the length L, as shown in and described with respect to FIGS. 94A-94C. Further, the outer tips of the anchors 3090, 3094 may extend to an outer radial location that is less than, the same as, or more than a radially outermost surface of the foam body 3002, as shown in and described with respect to FIGS. 94A-94C.

In the expanded configuration, the anchors 3090, 3094 extend for a length outside of the uncompressed sidewall 3014. This length of the anchor 3090, 3094 is measured along a local longitudinal axis of the anchor from the outer surface 3016 of the body 3002 to the distal tip of the anchor. The anchors 3090, 3094 may extend through the sidewall 3014 and/or the cover 3100, and then be trimmed so that the anchors 3090, 3094 extend beyond the sidewall 3014 and/or cover 3100 by the desired length. In a free, unconstrained state, the anchors 3090, 3094 extend about 0.5 mm beyond the outer surface 3016 of the sidewall 3014. In some embodiments, in the free, unconstrained state, the anchors 3090, 3094 extend beyond the outer surface 3016 of the sidewall 3014 for a length of from about 0.1 mm to about 1.5 mm, from about 0.2 mm to about 1.25 mm, from about 0.3 mm to about 1.0 mm, from about 0.4 mm to about 0.8 mm, from about 5 mm to about 0.6 mm, or other greater or lesser lengths. In a compressed state, such as in the delivery configuration or after implantation, the anchors 3090, 3094 extend about 1.0 mm beyond the outer surface 3016 of the sidewall 3014. In some embodiments, in the compressed state, the anchors 3090, 3094 extend beyond the outer surface 3016 of the sidewall 3014 for a length of from about 0.25 mm to about 2.5 mm, from about 0.5 mm to about 2 mm, from about 0.75 mm to about 1.5 mm, from about 0.875 mm to 1.125 mm, or other greater or lesser lengths.

The geometry of the anchors 3090, 3094 provides several advantages. For example, the relatively long length allows for flexibility of the anchors 3090, 3094. This provides for potentially less trauma to the LAA tissue should the device 3000 need to be unanchored and/or retrieved. The anchors 3090, 3094 are less susceptible to loss of strength with off-axis orientation within the LAA. Further, the anchors 3090, 3094 provide high resistance to pull out. For instance, the device 3000 may provide at least about 0.5 lb-force of dislodgment resistance from the LAA. Such pullout tests may be simulated with in vitro or benchtop models, as further described below.

The anchors 3090, 3094 in the illustrated embodiment are located in two circumferential rows. One row is located proximal to the other distal row. Each row has ten anchors each. This configuration may be incorporated, for example, in the device 3000 having a foam body 3002 with a free, unconstrained outer diameter of 27 mm. Each row may have fourteen anchors each. This configuration may be incorporated, for example, in the device 3000 having a foam body 3002 with a free, unconstrained outer diameter of 35 mm. In some embodiments, a single row of anchors 3090, 3094 may have from two to twenty-four, from four to twenty-two, from five to twenty, from six to eighteen, from seven to sixteen, from eight to fifteen, from nine to fourteen, from ten to thirteen anchors, or greater or fewer amounts of anchors 3090 or 3094. In some embodiments, there may only be one row or greater than two rows of anchors. The anchors 3090, 3094 may be spaced circumferentially in a single row.

In embodiments with multiple rows of anchors 3090, 3094, the rows may be circumferentially offset, as shown. That is, as viewed from the proximal or distal end of the device 3000, the anchors 3090, 3094 are angularly spaced apart from each other about the axis. The anchors 3090, 3094 may not be circumferentially offset, e.g. they may be evenly angularly spaced when viewed as described. The anchors 3090, 3094 are located axially at or near a middle portion of the sidewall 3014. The anchors 3090, 3094 may be located such that the tips of the anchors 3090, 3094 extend to adjacent tissue at a middle portion of the sidewall 3014. The offset and middle locations of the anchors 3090, 3094 may ensure engagement with the LAA tissue distal to the ostium. Having the anchors 3090, 3094 located at the largest width, increases the stability of the device 3000. With a cylindrical or generally cylindrical shaped device 3000, the anchors 3090, 3094 effectively sit on the largest diameter of the device 3000. The cylindrical shape provides advantages over typical LAA occluders which taper distally thus decreasing implant stability and locating the anchors on a smaller diameter than the ostial diameter of the occluding surface. In addition to adding stability, the cylindrical shape of the device 3000 along the axial length helps with dislodgement resistance by allowing the anchors 3090, 3094 to be placed on the largest diameter section of the device 3000. In some embodiments, the anchors 3090, 3094 may be located proximal, distal, or centrally along the length of the frame body 3080. In some embodiments, the anchors 3090, 3094 may not be offset and/or may not be angularly evenly spaced.

The anchors 3090, 3094 may provide advantageous flexibility, as demonstrated by pullout tests and in comparison to existing devices. For example, the device 3000 was tested to determine the force required to dislodge the device 3000 from a simulated tissue model by pulling the device 3000 proximally outward from the model. A low durometer silicone tube with a circular inner diameter (ID) was used as the model. For the device 3000 having a foam body 3002 with a 27 mm outer diameter in a free unconstrained state, tubes with ID's of 16.5 mm, 21 mm and 25 mm were tested. The pullout forces for existing devices drop off significantly going up to a 21 mm model, whereas the forces for the device 3000 drop only slightly.

In the largest diameter (25 mm) model, where there is not a lot of interference in the fit, the forces for the existing devices approach zero as the device does not engage the model wall because the anchors are sitting at a smaller diameter on a trailing edge of the device. The device 3000 consistently resists dislodgment with about 0.7 lbs of force. Since there is very little friction resisting pullout, that force is almost entirely resisted by the anchors 3090, 3094. When examining failure modes, all devices eventually begin to slide out of the model. Upon failure, the anchors 3090, 3094 fold backward or sideways before slipping starts. Assuming 0.7 lbs force is required to cause all twenty anchors 3090, 3094 to fold backward, then the force per anchors is estimated to be about 0.035 lbs.

The frame 3040 may be laser cut. The tubular body 3080 may be laser cut from a single tube. The body 3080 may be cut from a tube having a thickness from about 0.002" to about 0.014", or about 0.008". The tube may have an outer diameter (OD) from about 0.05" to about 0.30". The tube may have an outer diameter (OD) of 0.124" for the 27 mm device 3000 (i.e. the embodiment of the device 3000 having a foam body 3002 with an OD of 27 mm in the unconstrained, free state). The tube may have an OD of 0.163" for the 35 mm device 3000 (i.e. the embodiment of the device 3000 having a foam body 3002 with an OD of 35 mm in the unconstrained, free state).

In some embodiments, the body 3080 is laser cut from a superelastic nitinol tube, however, numerous other biocompatible metallic materials can be utilized such as shape memory Nitinol, stainless steel, MP35N, or Elgiloy. The frame 3040 is self-expandable. In some embodiments, a balloon-expandable frame 3040 could be utilized. Additionally, the body 3080 could be fabricated from drawn wire as opposed to being laser cut from a tube.

As shown, an embodiment of the device 3000 includes the frame 3040 having ten proximal recapture struts 3061 and twenty total anchors 3090, 3094, with the foam body 3002 having an outer diameter of 27 mm. In some embodiments, the device 3000 may include the frame 3040 having fourteen proximal recapture struts 3061 and twenty-eight total anchors 3090, 3094, with the foam body 3002 having an outer diameter of 35 mm.

In one embodiment, the frame 3040 includes a proximal hub 3050, tether pin 3051, front face with ten or fourteen recapture struts 3061, a diamond pattern cylindrical body 3080, and twenty or twenty-eight anchors 3090, 3094. The frame proximal face 3060 supports recapture, the frame body 3080 supports the foam cylinder body 3002, and the anchors 3090, 3094 located on the cylinder provide resistance to embolization.

The design of the device 3000 provides numerous advantages, some of which have been described. As further example, the frame 3040 provides many advantages, including but not limited to: 1) implant radial stiffness/compliance—the frame 3040 provides enhanced radial stiffness while still being sufficiently compliant to allow for off-axis implantation, recapture, etc.; 2) dislodgement resistance—the frame 3040 provides for high pullout strength, as described; 3) transcatheter delivery—the frame 3040 can be compressed into a delivery catheter and then fully expand when delivered; 4) recapture—the frame 3040 allows for recapture/retrieval into the delivery catheter after deployment or even after implantation in the LAA; and 5) mechanical integrity—the frame 3040 has acute and long term structural integrity, for example the ability to withstand loading into the delivery catheter, deployment from the catheter, and cyclic loading/fatigue. The frame 3040 also provides a conformable structure to enable the foam body 3002 to compress against the LAA tissue to facilitate sealing and anchoring with minimal compression (oversizing). The resulting compliance of the frame 3040 provides better anchoring than existing solutions, as described.

As further example, the device 3000 seals against irregularly shaped LAA ostia and necks. For instance, a combination of a Nitinol frame 3040 with a foam body 3002 having a coating of PTFE and cover 3100 of ePTFE contribute to ability of the device 3000 to conform to the anatomy and seal against irregular projections and shapes, while providing a smooth thromboresistent LA surface.

As further example, the device 3000 provides for controlled & safe delivery. The design of the combined frame 3040 and foam body 3002 facilitates delivery in a controlled fashion by slowing the speed of expansion. The bumper 3026 acts as an atraumatic leading edge portion when delivering the implant into the LAA mitigating the risk of injury. The user has the ability to recapture and redeploy the device 3000, if necessary. A flexible tether 3240 attachment, as further described, from the delivery catheter to the device 3000 permits the device 3000 to sit tension free immediately following implantation so the user can ensure final appropriate positioning prior to release of the device 3000.

As further example, the device 3000 provides for simplified placement. The foam-covered cylindrical design makes alignment of the device 3000 with the central axis of the LAA during delivery non-critical (by allowing deployment up to, for example, 45 degrees off-axis), which is designed to simplify the implantation procedure, as further described.

As further example, the device 3000 provides for simple sizing. The foam and frame design contributes to the ability to need only two diameters (e.g., 27 mm and 35 mm) to seal the range of expected LAA configurations and diameters (e.g. targeting LAA diameters of 16 to 33 mm). The conformability of the foam and frame allow the 20 mm long implant to fit into LAA's as short as 10 mm deep. The short landing zone requirement (LAA depth) of the device 3000, combined with the need for only two implant diameters, enables treatment of a wide range of LAA anatomies with minimal need for burdensome echo and CT sizing. The conforming nature of the implant is key to facilitating a simple to use product platform that is adaptable to a variety of anatomic structures.

As further example, the device 3000 provides thromboresistant materials and design. The removable tether leaves a smooth, metal-free surface in the LA. Thromboresistant materials (PTFE-coated foam and an ePTFE cover) create a smooth LA face (no metal attachment connection) to reduce anticoagulation needs, enhance thromboresistance, and encourage endothelialization.

As further example, the device 3000 provides thin, low profile anchors 3090, 3094 around the midpoint of the device 3000 to provide secure yet atraumatic anchoring.

4. Distal Bumper

The foam body 3002 has a distal bumper 3026. The bumper 3026 may be a foam distal region of the body 3002, such as a distal portion of the sidewall 3014. The bumper 3026 may be a portion of the foam body 3002 that extends beyond the distal end 3044 of the frame 3040. The bumper 3026 may extend beyond the distal end 3044 of the frame 3040 in the delivery configuration and in the deployed configuration. The body 3002 may be attached to the frame 3040 in various locations such that the body 3002 may stretch in some embodiments, for example in the delivery configuration, to ensure the bumper 3026 extends beyond the frame 3040 upon initially retracting the sheath during delivery.

The device 3000 can conform both in length and diameter due to conformability of both the foam body 3002 and the frame 3040. This allows for the device 3000 to accommodate most patient LAA anatomies with only a couple or few different sizes of the device 3000, such as 27 mm and 35 mm outer diameter body 3002 as described herein, and one length, such as 20 mm. The frame 3040 may thus be shorter than the foam body 3002, resulting in some embodiments in about 5 mm of foam bumper 3026 distal to the distal-most end of the frame 3040. The distal bumper 3026 acts as an atraumatic tip during delivery of the device 3000 and can be compressed following implantation to allow the device 3000 to conform to appendages with a depth (landing zone) as short as 10 mm. This ability to conform both in length and diameter is due to the conformability of both the foam body 3002 and the frame 3040.

The length of the bumper 3026 may be measured axially from the distal-most end of the frame 3040 to the distal surface 3022 of the body 3002. For example, the bumper 3026 may extend from the distal apexes 3088 to the distal surface 3022. The bumper 3026 may have a length of 5 mm or about 5 mm. The bumper 3026 may have a length of about 1 mm, 2 mm, 3 mm, 4 mm, 5 mm, 6 mm, 7 mm, 8 mm, 9 mm or more. The bumper 3026 may have a length from about 2.5 mm to about 7.5 mm, from about 3 mm to about 7 mm, from about 3.5 mm to about 6.5 mm, from about 4 mm to about 6 mm, from about 4.5 mm to about 5.5 mm.

In some embodiments, the bumper 3026 may fold in response to axial and/or radial compression of the device 3000. The bumper 3026 may fold inward, for example radially inward. The folds may be in the axial or approximately in the axial direction. The folds may be circumferential or approximately in the circumferential direction. The folds may be combinations of the radial and circumferential directions, or angled with respect thereto. The folding of the bumper 3026 is further discussed herein, for example in the section "Device Compliance."

5. Cap & Pin

Figure 90A:
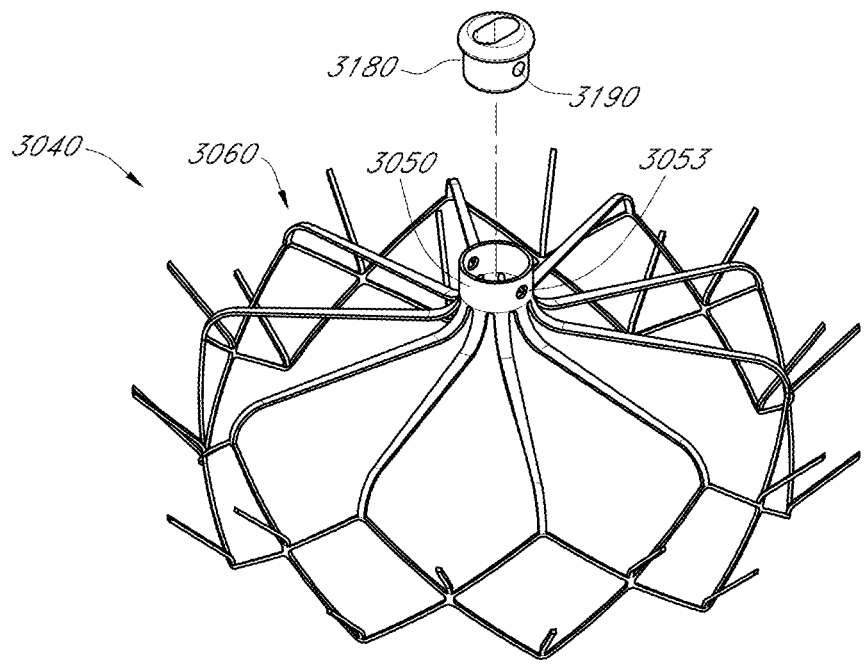
FIGS. 90A-90C are sequential proximal perspective views of an embodiment of a frame showing assembly of a cap and pin with the frame that may be used with the LAA occlusion devices of FIGS. 85A-88E.
Figure 90B:
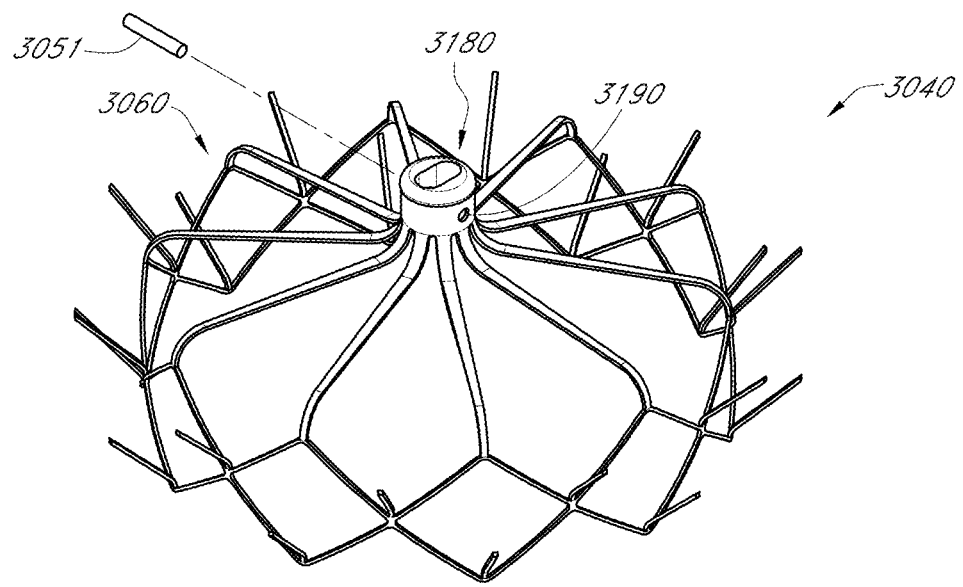
Figure 90C:
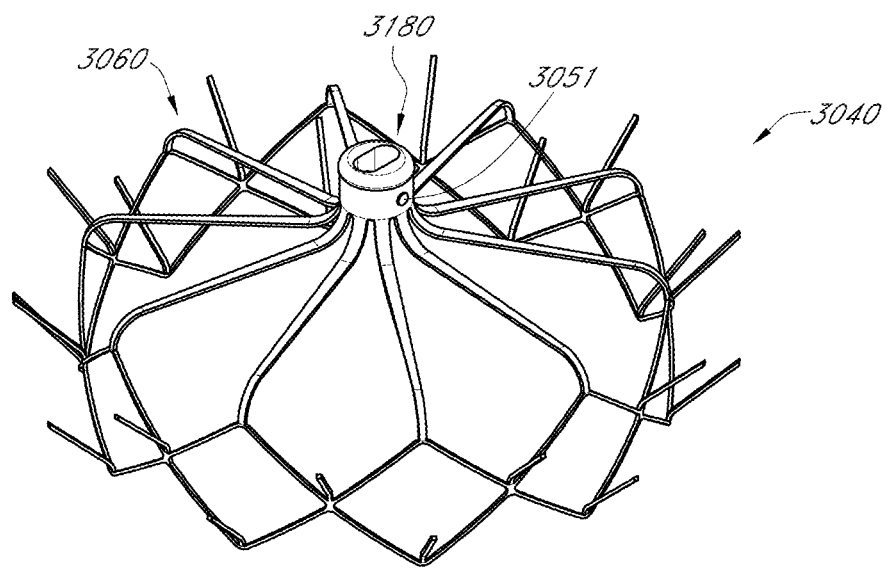
Figure 90D:
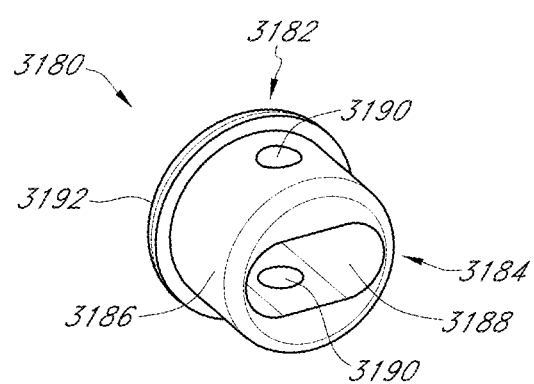
FIG. 90D is a distal perspective view of the cap of FIGS. 90A-90C.

FIGS. 90A-90C are proximal perspective views of the frame 3040 having a cap 3180. FIG. 90D is a distal perspective view of the cap 3180. In some embodiments, the pin 3051 is placed across the proximal hub 3050 diameter and serves to engage the delivery catheter tether 3240 (e.g. a suture), which is wrapped around the pin 3051 for temporary attachment to the delivery catheter 3220, as described further herein for example with respect to FIGS. 89A-89B. As shown, the hub 3050 has a pair of opposite side openings 3053 extending through a sidewall of the hub 3050. The cap 3180 has a corresponding pair of opposite side openings 3190 extending through a sidewall 3184 of the cap 3180. When the cap 3180 is assembled with the hub 3050, the pin 3051 may be inserted through the aligned pairs of openings 3053, 3182. The assembly can be further secured by welding the ends of the pin 3051 to the hub 3050.

As shown in FIG. 90D, the cap 3180 includes a proximal end 3182 and a distal end 3184. The cap 3180 includes a rounded sidewall 3186 extending from the proximal end 3182 to the distal end 3184. The sidewall 3186 defines a longitudinal opening 3188 through the cap 3180. The sidewall 3186 includes a pair of lateral openings 3190 located opposite each other. The cap 3180 includes a flange 3192 at the proximal end 3182 extending radially outward.

The cap 3180 is formed from titanium and the pin 3051 is formed from Nitinol or superelastic Nitinol. In some embodiments, the cap 3180 and/or pin 3051 may be formed from other materials, for example numerous biocompatible metallic or polymeric materials such as shape memory Nitinol, stainless steel, MP35N, Elgiloy, polycarbonate, polysulfone, polyether ether keytone (PEEK), or polymethyl methylacrylate (PMMA) or other materials.

The cap 3180 and pin 3051 facilitate attachment to the tether 3240. The cap 3180 and pin 3051 also mitigate damage to the foam body 3002 during recapture of the device 3000. The cap 3180 also creates an atraumatic surface for the hub 3050 of the frame 3040. For example, the cap 3180 may prevent the hub 3050 from cutting through the foam body 3002 as the device 3000 is collapsed into an access sheath. Without the cap 3180, the sharp edges of the hub 3050 may shear through the foam body 3002 during recapture of the device 3000 into the access sheath.

6. Loading System

Figure 91:
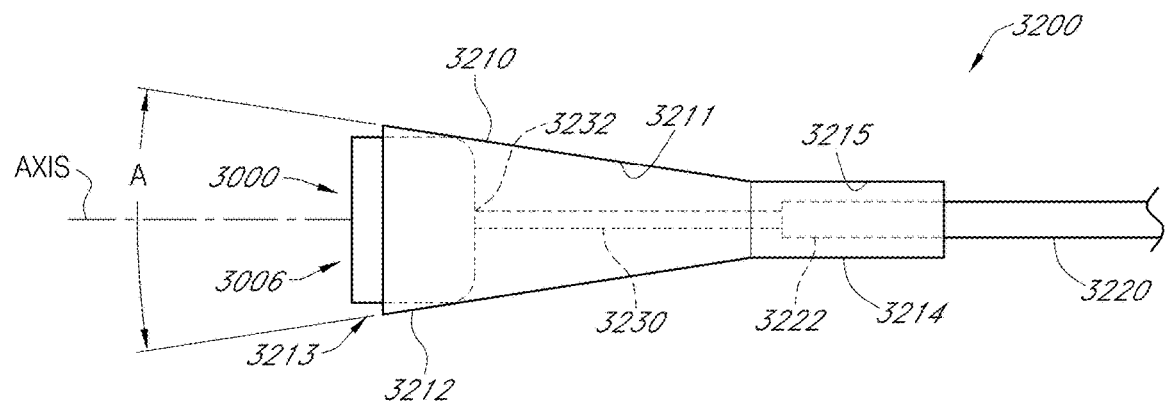
FIG. 91 is a side view of an embodiment of a loading system for loading the device of FIGS. 85A-88E into a delivery catheter.

FIG. 91 is a side view of an embodiment of a loading system 3200 for loading the device 3000 into a delivery catheter 3220. The system 3200 includes a loading tool 3210. The loading tool 3210 has a conical portion 3212, having a distal opening 3213, and a cylindrical portion 3214. The delivery catheter 3220 extends through the cylindrical portion 3214 with a distal end 3222 of the delivery catheter 3220 located within the cylindrical portion 3214. A pusher 3230, such as a pusher catheter, extends through the delivery catheter 3220. A tether 3240 (see FIGS. 92A-92C) is attached to the device 3000 and extends through the loading tool 3210, the delivery catheter 3220 and the pusher 3230. The tether 3240 and pusher 3230 are pulled in the proximal direction while the delivery catheter 3220 and the loading tool 3210 are held stationary. The device 3000 is compressed laterally by the conical portion 3212 as the device 3000 is pulled proximally by the tether 3240 through the loading tool 3210. A distal end 3232 of the pusher 3230 remains adjacent to the proximal end 3004 of the device 3000 as the device 3000 is loaded into the delivery catheter 3220. The removable tether 3240, which may be fabricated from ultra-high molecular weight polyethylene (UHMWPE), is used to attach the implant to the delivery catheter. The material UHMWPE for the tether 3240 may provide high strength and low friction to facilitate delivery of the device 3000.

In some embodiments, the conical portion 3212 of the loading tool 3210 has a chamfered distal edge of approximately 45°-75° (degrees), preferably 60°. In some embodiments, the conical portion 3212 has a distal inner diameter (ID) greater than the outer diameter (OD) of the device 3000 and an angle A of ideally between 15° and 25°, and in one implementation about 20°, to appropriately collapse the anchors 3090, 3094 which may protrude off the foam body 3002 surface at an angle of 30° or about 30°. The distal opening of the conical portion 3210, for example the diameter or greatest width, may be greater than the proximal opening of the conical portion 3210, for example the diameter or greatest width, that couples with the cylindrical portion 3214. The cylindrical portion 3214 may have an opening, for example diameter or greatest width, that is smaller than the distal opening of the conical portion 3210 and/or the same or similar size as the opening at the proximal end of the conical portion 3210.

The decreasing width, for example gradual taper, of the loading tool 3210 ensures, for example, that the frame 3040 folds evenly without crossovers or extra strain. The angled conical portion 3212 may ensure that the anchors 3090, 3094 fold or rotate proximally and not distally. The sidewall of the conical portion 3212 may extend at a "total" angle A as measured between two opposite portions of the sidewall, as shown in FIG. 91. The angle A may be from about 12° to about 35°, from about 15° to about 30°, from about 17° to about 25°, from about 18° to about 22°, about 20°, or 20°. The angle A may be at least 10°, at least 15°, at least 20°, at least 25°, or at least 30°. The angle A may be constant along the axial length of the conical portion 3212. The angle of the conical portion 3212 may also be described with respect to a longitudinal geometric center axis, defined by the conical portion 3212 and/or the cylindrical portion 3214. The sidewall may extend in a direction that is at an angle with respect to such longitudinal axis and which is half of the value of the total angle A. This "half angle" may thus be at least 5°, at least 7.5°, at least 10°, at least 12.5°, or at least 15°, etc. The conical portion 3212 may have a frustoconical shape. The cross-sectional shape of the conical portion 3212 perpendicular to its longitudinal axis may be circular or approximately circular. In some embodiments, this cross section may be rounded, non-circular, segmented, other shapes, or combinations thereof. The cross-sectional shape of the conical portions 3212 may be constant along its axis, or there may be different shapes along the axis. In some embodiments, the angle A may change along the axial length of the conical portion 3212, for example where the inner surface is curved in the axial direction.

The loading tool 3210 may be smooth or generally smooth on its inner surface or surfaces. Inner surfaces 3211, 3215 of the conical portion 3212 and/or cylindrical portion 3214 may be smooth or generally smooth. In some embodiments, these inner surfaces 3211, 3215 or portions thereof may not be smooth. In some embodiments, these inner surfaces 3211, 3215 or portions thereof may be smooth, non-smooth, rough, etched, scored, grooved, have varying degrees of roughness or smoothness, other features, or combinations thereof.

In one example, the tool 3210 may be used by positioning a proximal end of a loading body, such as the tool 3210, adjacent the distal end 3222 of the delivery catheter 3220. The loading body may have a sidewall defining a channel therethrough with the distal opening 3213 at a distal end that is larger than a proximal opening at a proximal end. The left atrial appendage occlusion device 3000 may be advanced proximally through the loading body to thereby radially compress the device 3000. The retracting step may comprise pulling the tether 3240 proximally through the delivery catheter 3220. The device may then be received into the distal end 3222 of the delivery catheter 3220. The device 3000 may be radially compressed within the delivery catheter 3220 having an outer diameter of no more than fifteen French. In some embodiments, the device 3000 may be radially compressed within the delivery catheter 3220 having an outer diameter of no more than ten, eleven, twelve, thirteen, fourteen, fifteen, sixteen, seventeen, eighteen, nineteen, or twenty French. The proximal end of the loading tool 3210 may have an inner diameter configured to provide an interference fit with the distal end 3222 of the delivery catheter 3220. The proximal end of the loading tool, 3210, such as the cylindrical portion 3214, may have an inner diameter slightly larger than the outer diameter of the delivery catheter 3220, for instance slightly larger than 5 mm for a delivery catheter 3220 having an outer diameter of fifteen French. The device 3000 may compress radially to a compressed width in a constrained state that is less than fifty, forty, thirty, twenty, ten, and/or five percent of a radial uncompressed width of the device in an unconstrained state. The radial widths here may be measured perpendicularly to a longitudinal axis of the device 3000, such as defined by the tubular foam body 3002.

The loading tool 3210 may be formed of a material that is biocompatible, strong, transparent and can be molded smooth to minimize friction, such as polycarbonate. In some embodiments, the loading tool 3210 could be formed from hard plastics like Delrin, UHMWPE, Ultem®, polyetherimide, acrylic, metals like stainless steel, aluminum, other materials, or combinations thereof. In some embodiments, the loading tool 3210 may have one or more coatings. Such coating may be applied to reduce friction and therefore loading forces. The coating may be silicone, hydrophilics, various oils, other suitable coatings, or combinations thereof.

7. Delivery System

Figure 92A:
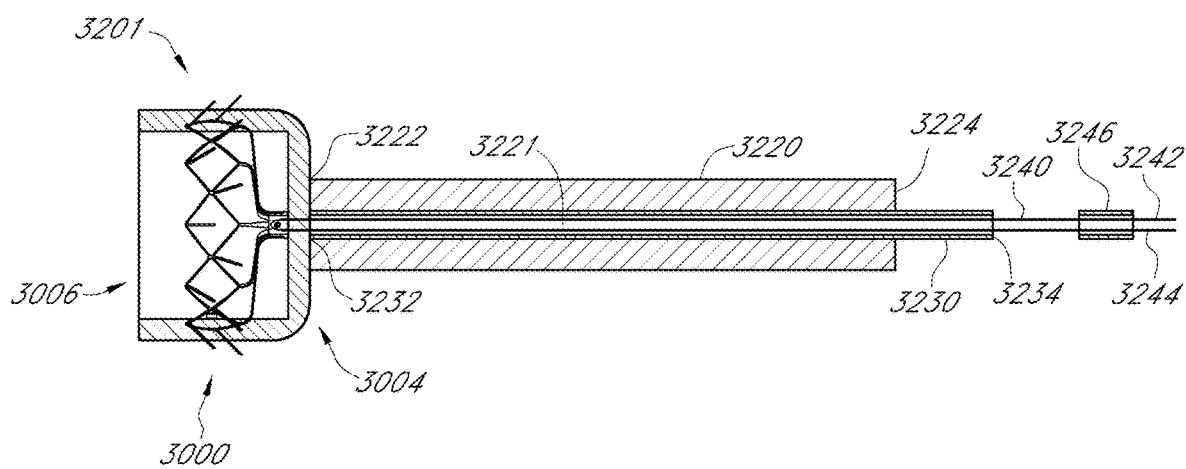
FIG. 92A is a side view of a schematic of a transcatheter delivery system for delivering the device of FIGS. 85A-88E via an artery or vein.
Figure 92B:
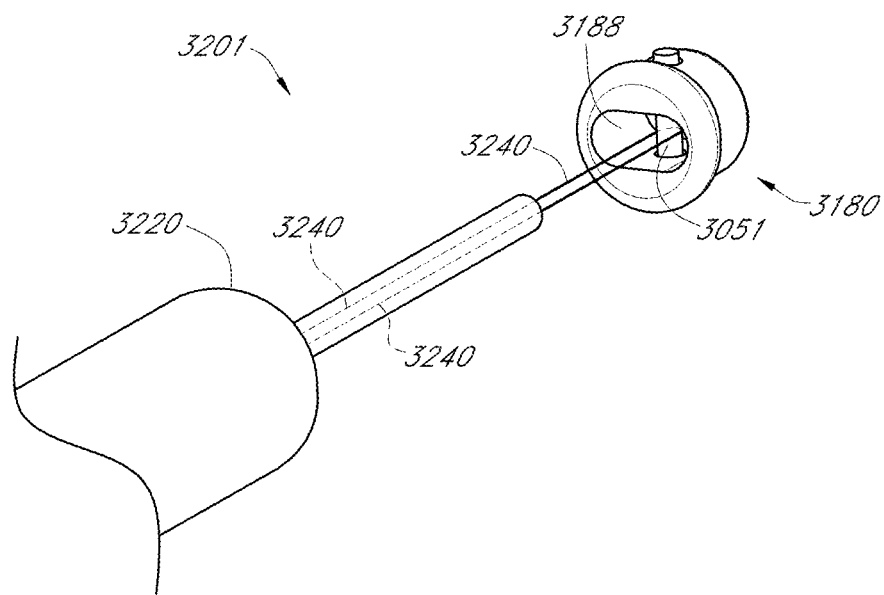
FIGS. 92B-92C are proximal and distal perspective views, respectively, of the delivery system of FIG. 92A, showing an associated tether release mechanism and method.
Figure 92C:
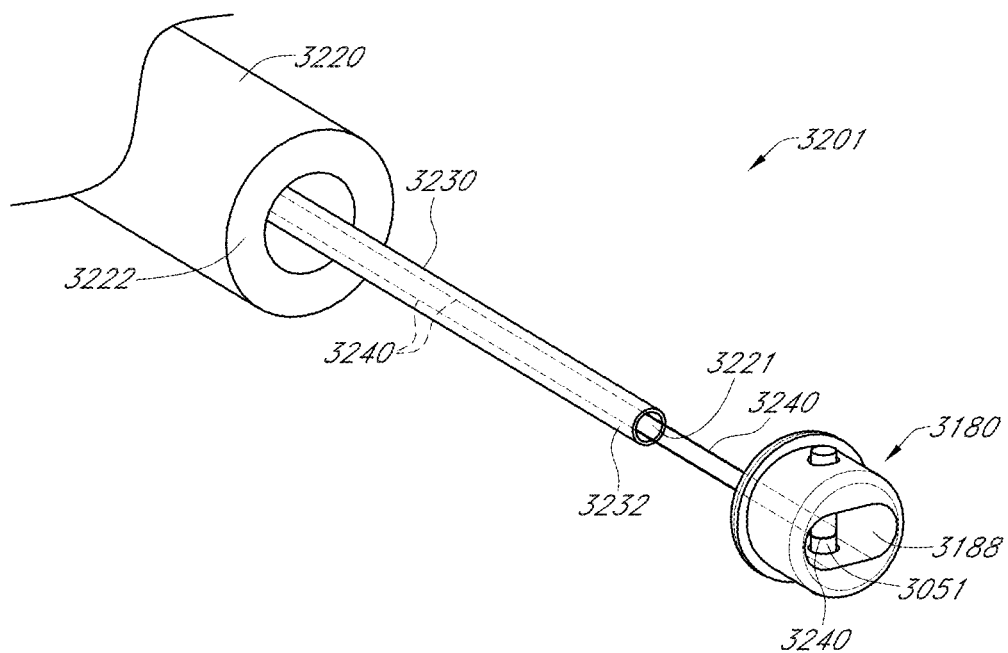

FIG. 92A is a side view of a schematic of a delivery system 3201 for delivering the device 3000. FIGS. 92B-92C are additional views of the system 3201. As shown in FIG. 92A, the delivery system 3201 includes the delivery catheter 3220 having a distal end 3222 and a proximal end 3224. The delivery system 3201 includes the pusher 3230, such as a pusher catheter, having a distal end 3232 and a proximal end 3234. The tether 3240 includes a first end 3242 and a second end 3244. A restraint 3246 secures the first and second ends 3242, 3244.

To deliver the device 3000 to the LAA, an access sheath is placed across the interatrial septum into the LAA through which the delivery catheter 3220, containing the device 3000, is placed. The device 3000 is loaded into the distal end 3222 of the delivery catheter 3220 using the loading tool 3210, either at the point of manufacture or at the treatment site. To load the implant device 3000, the pusher 3230 and tether 3240 are pulled proximally, collapsing the implant device 3000 as it enters the distal tip of the delivery catheter 3220. Once the loaded delivery catheter 3220 is placed through the sheath into the LAA, the pusher 3230, such as a catheter or rod, is held axially steady as the delivery catheter 3220 and access sheath are simultaneously retracted proximally, deploying the implant device 3000.

The tether 3220 passes from the proximal end of the delivery catheter 3220, through an opening 3221 of the catheter pusher 3230, around the implant tether pin 3051, and back through the delivery catheter 3220. When both ends of the tether 3240 (held together by the restraint 3246 at the proximal end of the catheter) are pulled, the device 3000 is pulled into the delivery catheter 3220. Once the device 3000 is properly placed in the anatomy, one end of the ends 3242, 3244 of the tether 3240 is cut and the entire tether 3240 can be removed from the system by pulling proximally on the uncut end and sliding the cut end distally into the system and around the pin 3051, disengaging from the pin 3051. The distal end 3232 of the pusher 3230 and/or the distal end 3222 of the delivery catheter 3220 may contact, for example push against, the proximal end of the device 3000, such as in the relative locations shown in FIG. 92A. For example, the distal end 3232 of the pusher 3230 may contact and prevent proximal movement of the device 3000 during tether 3240 retrieval, as further described herein. Further details of the release of the tether are provided herein, for example with respect to FIGS. 92B-93B.

In some embodiments, the delivery system 3201 may include other features. For example, the delivery catheter 3220 may include an injection lumen. The injection lumen may allow for injecting a radiopaque dye distal to the device 3000 following implantation to check for leaks using fluoroscopy.

8. Tether Release System

FIGS. 92B and 92C are proximal and distal perspective views of the delivery system 3201. An approach to releasing the tether, and other features of the system, are described in this section. For clarity, some features are not shown, such as the cover 3100, foam body 3002, and frame 3040.

The system 3201 as shown in FIGS. 92B and 92C shows the delivery catheter 3220, the pusher 3230 and the hub 3050 in different axial positions relative to each other. In some embodiments, during release, the distal end 3222 of the delivery catheter 3220 may be co-extensive with, or otherwise near or adjacent, the distal end 3232 of the pusher 3230. Further, the distal ends 3222 and/or 3232 may contact or be adjacent the proximal end 3004 of the device 3000, such as contacting or adjacent the cover 3100 and/or foam body 3002. In some embodiments, the distal end 3232 of the pusher may be located distally of the distal end 3222 of the delivery catheter 3220, as shown, during tether 3240 release.

The tether 3240 may extend from a proximal end of the pusher 3230, through the opening 3221 of the pusher 3230, wrap around the pin 3051, and extend proximally back through the opening 3221 of the pusher 3230 and out the proximal end of the pusher 3230, as described with respect to FIG. 92A. The tether 3240 may extend through the cover 3100 and foam body 3002. The tether 3240 may extend distally through first aligned paths in the cover 3100 and foam body 3002, around the pin 3051, and extend proximally back through second aligned paths in the cover 3100 and foam body 3002. The tether 3240 may extend through openings within the inner cover 3101, as described for example with respect to FIGS. 85D and 87D. The tether 3240 may only extend around a distal surface or surfaces of the pin 3051, as shown. The tether 3240 may extend distally and wrap around the pin 3051 and extend distally at 180° or approximately 180° relative to the proximally extending portion. In some embodiments, the tether 3240 may be wrapped one or more times, for example two, three or more times, around the pin 3051. In some embodiments, the tether 3240 may be on a spool about the pin 3051. In some embodiments, the tether 3240 may be wrapped, partially, fully or multiple times, about a bushing that is rotatable coupled about the pin 3051.

The system 3201 may facilitate removal of the tether 3240 while the pusher catheter 3230 is in contact with the device 3000. Such contact may assist, for example, with avoiding or reducing inadvertent dislodgement of the device 3000 from the LAA after implantation and anchoring. For instance, during release of the tether 3240, the pusher 3230 may have the positioning relative to the device 3000 as shown in FIG. 92A. The pusher 3230 may contact the device 3000 on the proximal end 3002 of the device to prevent or reduce any proximal movement of the device 3000 upon tether 3240 removal. For example, there may be friction between the tether 3240 and the pin 3051 as the tether 3240 unwraps about the pin 3051. The distal end of the pusher 3230 may prevent this friction or other forces from dislodging or otherwise moving the device 3000 proximally. In some embodiments, the delivery catheter 3220 may also be contacting, adjacent to, etc. the device 3000. In some embodiments, during tether release and removal, the distal ends of the delivery catheter 3220 and pusher 3230 may be axially co-extensive, adjacent or near each other, etc., as described. Further, the tether 3240 may be proximally pulled completely out of the delivery catheter 3220 and/or pusher 3230 before the delivery catheter 3220 and/or pusher 3230 are removed from the patient. In some embodiments, the tether 3240 may be removed from the patient along with the delivery catheter 3220 and/or pusher 3230, for example while the tether 3240 is still entirely or partially within the pusher 3230.

Figure 93A:
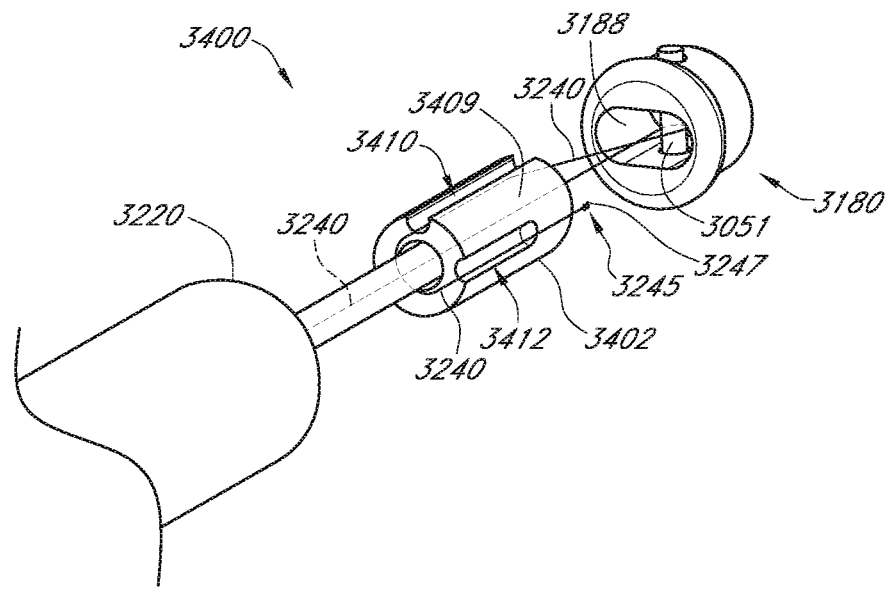
FIGS. 93A and 93B are proximal and distal perspective views respectively of another embodiment of a tether release system that may be used with the device of FIGS. 85A-88E.
Figure 93B:
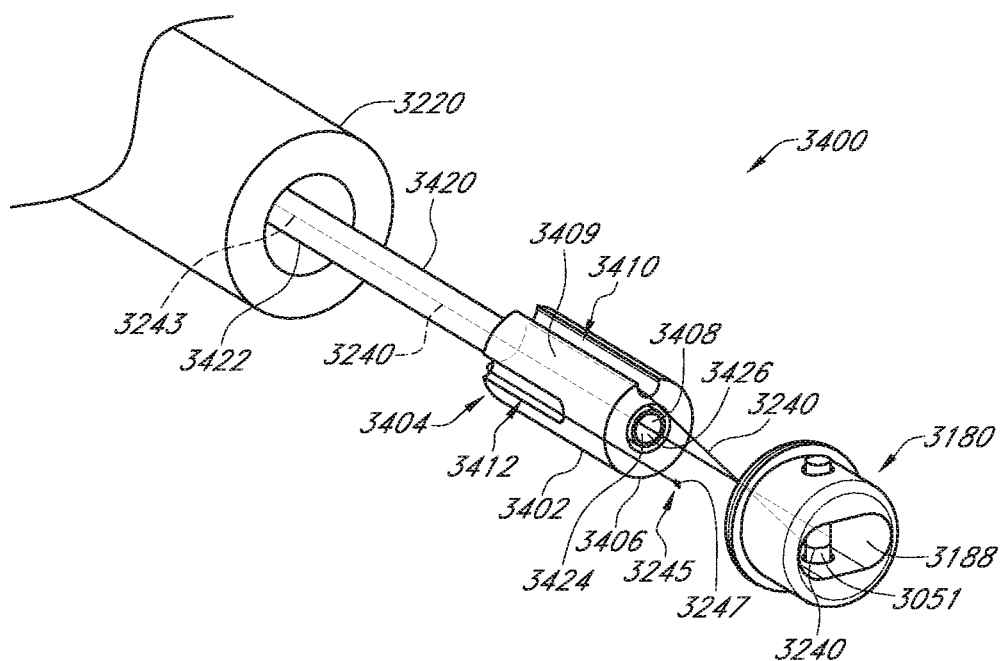

FIGS. 93A and 93B are proximal and distal perspective views respectively of another embodiment of a tether release system 3400. The release system 3400 includes a tube 3420 and a lock 3402. The tube 3420 has a proximal end 3422 and a distal end 3424. An opening 3426 extends through the tube 3420. The system 3400 may be used similarly as described with respect to the system 3201, except as otherwise noted. For example, the pusher 3230 and/or tube 3420 may contact the device 3000 during tether removal, as described.

The lock 3402 includes a proximal end 3404 and a distal end 3406. An opening 3408 defined by a sidewall 3409 extends through the lock 3402 from the proximal end 3404 to the distal end 3406. The tube 3420 extends through the opening 3408 at the proximal end 3404 of the lock 3402 and to the distal end 3406 of the opening 3408. The sidewall 3409 of the lock 3402 has a first groove 3410 extending longitudinally from the proximal end 3404 to the distal end 3406 and extending radially partially through the thickness of the sidewall 3409. The sidewall 3409 of the lock 3402 has a second groove 3412 extending longitudinally from the proximal end 3404 partially along the sidewall 3409 toward the distal end 3406 and radially partially through the thickness of the sidewall 3409.

The tether 3240 includes a first end 3243 and the second end 3245. The tether 3240 extends distally from the first end 3243 within the opening 3426 of the tube 3240 and out through the distal end 3424 of the tube 3420 to the cap 3180. The tether 3240 extends distally into the opening 3188 of the cap 3180 and around the pin 3051 and back in the proximal direction. The tether 3240 then extends proximally into the first groove 3410 of the lock 3402, around the proximal end 3404 of the lock 3402, and then distally into and through the second groove 3412. The tether 3240 terminates at the second end 3245 in a knot 3247.

In use, the knot 3247 may be secured due to the relative location of the lock 3402 and the pusher catheter 3230 inside the delivery catheter 3220. The knot 3247 may be prevented from advancing distally due to the inner diameter of the distal end of the pusher 3230 fitting tightly about the outer diameter of the lock 3402. The grooves 3410 and/or 3412 in the lock 3402 may hold the tether 3240 in an orientation that prevents the tether 3240 from slipping (e.g., if pulled hard enough) when the lock 3402 is engaged in the pusher 3230. The pusher 3230 may be advanced distally to expose the lock 3402, for example the full length f the lock 3402, or portions thereof. When the proximal end of the tether 3240 is pulled proximally, the knot 3247 falls away from the second groove 3412, advances around the proximal end 3404 of the lock 3402, advances distally by falling away from the first groove 3410, into the cap 3180 and around the pin 3051, and then distally through the opening 3408 of the lock 3402 and can be retrieved with the pusher 3230. In some embodiments, the distal end of the lock 3402 may be located axially proximal to the distal end of the tube 3420, for example to contact the device 3000 with the tube 3420 to prevent proximal movement of the device 3000 after implantation, as described above.

9. Off-Axis Delivery and Deployment

The device 3000 may be deployed off-axis within an LAA while still providing a complete, stable, and atraumatic seal. In some embodiments, the device 3000 may be deployed at an angle of at least about 15° or 25° and in some embodiments as much as 35° or 45°, for example, relative to a central longitudinal LAA axis and still provide an effective seal. The LAA axis here is defined as the geometric center of the ostium to the LAA, and tracks the best fit geometric center of the LAA cavity.

This ability of the device 3000 to be deployed off-axis is due in part to the relatively thick, compressible foam body 3002 material, the compliant frame 3040 and the cylindrical shape of the device 3000 with the foam bumper 3026. The device 3000 is stable within the LAA despite having a length that is less than the diameter, or having L/D<1. As described, the length may be 20 mm for the device 3000 having an OD of both 27 mm and 35 mm. Thus not only is flexibility and simplicity allowed with manufacturing processes by having one length, but also stability and effectiveness of the device in use. Further, the axial compressibility of the bumper 3026, combined with the axially compliant frame 3040, allows a 20 mm long device 3000 to be placed within a 10 mm deep LAA, whereas existing LAA closure devices require longer landing zones, or at least landing zones equal to the size of the length of the metallic frame.

In some embodiments, the device 3000 may be configured to allow for sufficient flow of blood in case of accidental embolization, as described herein. Further, the device 3000 may be configured to allow for sufficient flow of blood even if the device 3000 embolizes and is misaligned with the direction of flow of blood. For example, the device 3000 may define a longitudinal axis, and the direction of flow of blood may define a flow axis. The device longitudinal axis may be at an angle with respect to the flow axis and still provide for a sufficient blood flow through the device 3000 should it embolize and lodge within the circulatory system of a patient. Thus, the capabilities of the device 3000 with regard to flow of blood through the device in case of embolization, or tests thereof with water under controlled conditions, as described herein for example with respect to the section "Proximal Cover," may also apply to the device 3000 in such off-axis configurations or orientations with the circulatory system of the body. The device axis may be at an angle of five, ten, twenty, thirty or more degrees with respect to the flow axis and still provide sufficient flow of blood through the device 3000.

10. Anchor/Foam Interface

Figure 94A:
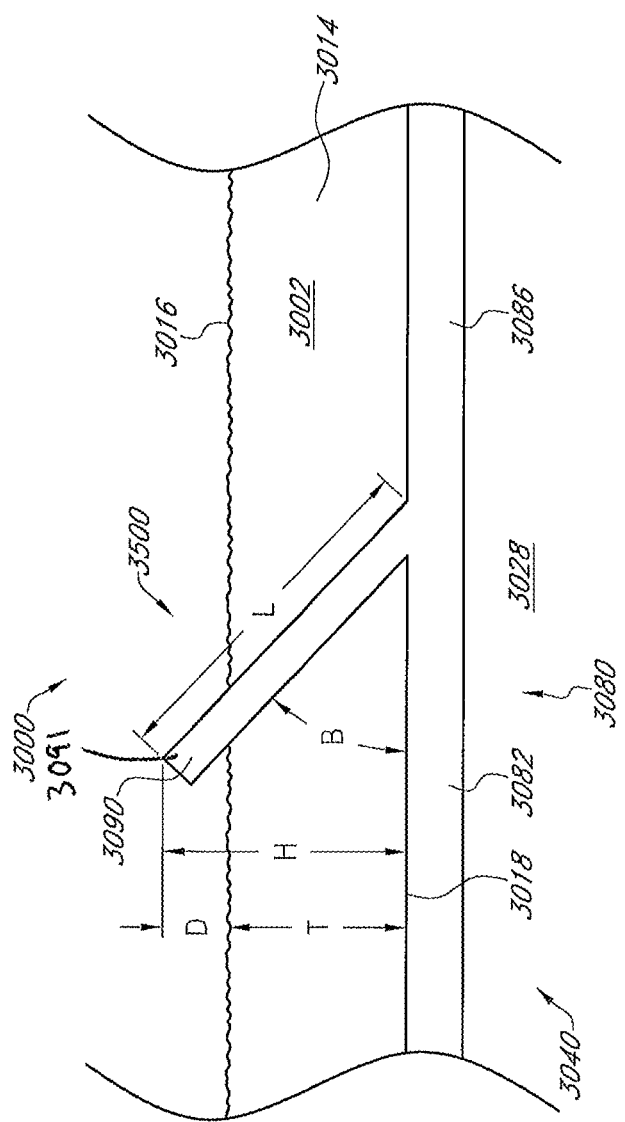
FIGS. 94A-94C depict various embodiments of an anchor/foam interface that may be used with the LAA occlusion devices of FIGS. 85A-88E.
Figure 94B:
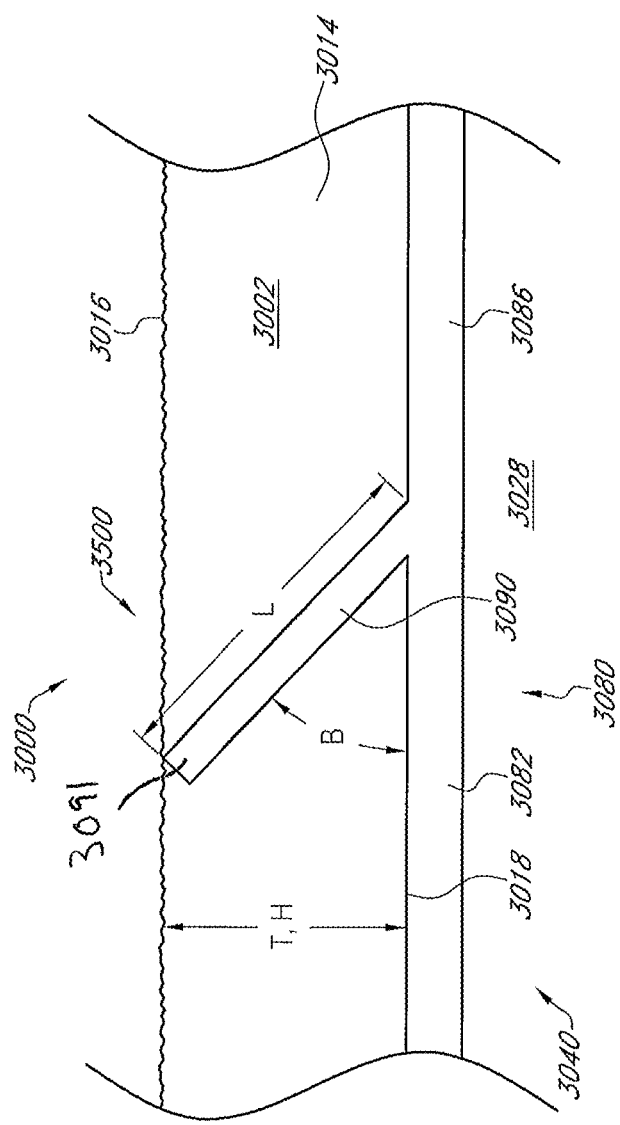
Figure 94C:
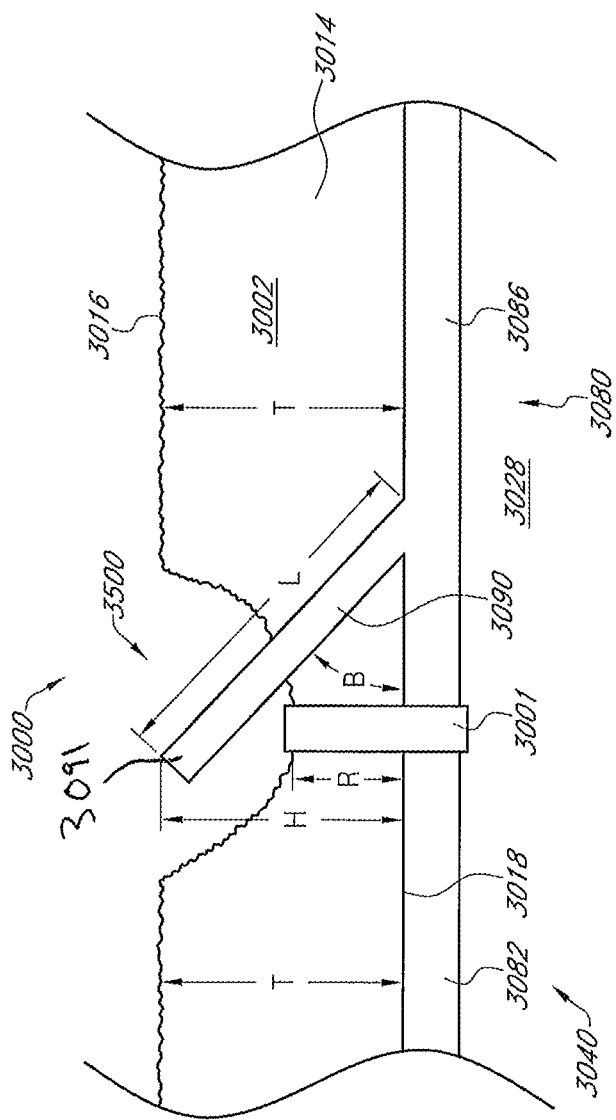

As described, the frame 3040 with anchors 3090, 3094 and foam body 3002 may have a variety of geometries, such as lengths, thicknesses, etc. This section discusses some particular embodiments of the frame 3040, in particular the anchors 3090, 3094, and the foam body 3002. FIGS. 94A-94C depict various embodiments of an anchor/foam interface 3500, using the anchor 3090 as an illustrative example. FIGS. 94A-94C are a side cross-section views of a portion of the device 3000 showing an embodiment of the interface 3500. In some embodiments, the outer tips of the anchors 3090, 3094 may, or may not, extend radially beyond portions of the outer surface 3016 of the foam body 3002, even in an unconstrained configuration, as further described herein.

The interface 3500 includes a portion of the tubular body 3080 of the frame 3040, having the proximal strut 3082 and the distal strut 3086, as described in further detail herein, for example with respect to FIG. 89A. The anchor 3090 extends radially outwardly in a proximal direction from the frame 3040, such as from the tubular body 3080. The same or similar features and/or functionalities as described in this section with respect to the interface 3500 having the anchor 3090 may apply to other anchor/foam interfaces with other anchors, such as anchor/foam interfaces with the distal anchor 3094. For example, the frame 3080 could have a distal end at the base of the anchor 3094, where the distal apes 3088 is located (see, e.g., FIG. 89A).

As shown in FIGS. 94A-94C, the anchor 3090 extends outwardly and proximally from the frame 3040, which may be from the proximal apex 3084 as described herein. The anchor 3090 has an axial length L. The length L extends from the distal base of the anchor 3090 at the frame 3040 to a proximal tip 3091 of the anchor 3090. The length L may include only the straight portion of the anchor 3090, for example if the base of the anchor 3090 is bent. In some embodiments, the length L can include the complete anchor 3090, such that L extends axially along the anchor 3090 from a tip 3091 of the anchor 3090 to the frame 3040. The anchor 3090 is shown with a flat end, but it may be sharpened, angled, etc. The length L may extend proximally to the farthest endpoint axially along the length of the anchor 3090, such as to the tip 3091. In some embodiments, L is 2.5 mm, about 2.5 mm, or from about 2.25 mm to about 2.75 mm. The length L may be a variety of other lengths or within other ranges of lengths, for example as described in further detail herein with respect to the anchors 3090, 3094 in the section "Compliant Frame."

The anchor 3090 extends at an angle B relative to the proximal strut 3082. In some embodiments, the proximal strut 3082 as shown may be considered a projection of the proximal strut 3082 onto a vertical plane that intersects the longitudinal axis of the device 3000 and the anchor 3090. Thus the angle B may be relative to such plane and/or to the strut 3082. For simplicity, the angle B will be described relative to the strut 3082. The angle B may be 30° or about 30°. The angle B may be a variety of other angles or within ranges of angles, for example as described in further detail herein with respect to the anchors 3090, 3094 in the section "Compliant Frame." The anchor further has a radial height H. The radial height H may be the radially outermost extent of the anchor 3090, such as the proximal tip 3091 of the anchor 3090. The length L and angle B may define the radial height H of the anchor 3090. The height H may be in a direction perpendicular to the longitudinal axis of the device 3000 (see, e.g., FIG. 87B).

Further shown is the sidewall 3014 of the foam body 3002. The sidewall 3014 has a thickness T. The thickness T extends radially outward from the inner surface 3018 to the outer surface 3016 of the sidewall 3014. The thickness T may extend radially outward perpendicularly to the longitudinal axis of the device 3000. The thickness T may be equal to a distance from a radially outer portion of the frame 3040 to the outer surface 3016 of the sidewall 3014, for example where the inner surface 3018 of the sidewall 3014 contacts the outside of the frame struts 3082, 3086. The thickness T could be the thickness of the sidewall 3014 in an unconstrained configuration, a compressed configuration while inside the delivery catheter, or a compressed configuration after implantation within the LAA, as further described. The measurement of the thickness T of the sidewall 3014 may be in the same direction as the measurement of the height H of the anchor 3090. The thickness T of the sidewall 3014 may be 2.5 mm or about 2.5 mm. The thickness T of the sidewall 3014 may be other values or ranges of values, for example as described in further detail herein in the section "Compressible Foam Body."

As shown in FIG. 94A, in some embodiments, the height H of the anchor 3090 may be greater than the thickness T of the foam sidewall 3014. The difference may be equal to a delta D. The device 3000 may have this configuration in an unconstrained configuration, for example as resting on a tabletop as described herein. The delta D may be from about 0.05 mm to about 5 mm, from about 0.075 mm to about 4 mm, from about 0.1 mm to about 3 mm, from about 0.2 mm to about 2 mm, from about 0.3 mm to about 1.5 mm, from about 0.4 mm to about 1 mm, about 0.5 mm, or 0.5 mm. In some embodiments, these example values for delta D may be negative, where T is greater than H. In some embodiments, the delta D may be zero, as described with respect to FIG. 94B.

As shown in FIG. 94B, in some embodiments, the height H of the anchor 3090 may be the same as or about the same as the thickness T of the foam sidewall 3014. Thus the delta D may be zero or about zero. The device 3000 may have this configuration in an unconstrained configuration, for example as resting on a tabletop as described herein. The anchors 3090, 3094 may extend through the foam body 3002 to the outer surface 3016 in the unconstrained configuration, and then extend radially outward beyond the outer surface 3016 when loaded for delivery and/or after implantation in the LAA. In other embodiments, the foam body 3002 is locally compressed so the anchor extends beyond the outer surface 3016, as further described.

As shown in FIG. 94C, the device 3000 may include one or more attachments, such as sutures, for example the attachment 3001 described in further detail herein with respect to FIG. 87D. The attachment 3001 may connect the foam body 3002 to the frame 3040. As shown, the attachment 3001 may extend out through the sidewall 3014 and around the outer surface 3016, back in through the sidewall 3014 and around the frame 3040, such as around the proximal strut 3082. The attachment 3001 may locally compress the sidewall 3014 as shown. The sidewall 3014 may have a local radial thickness R. The thickness R may be less than the thickness T. The thickness R may be a local minimum of the thickness of the foam body 3002. The thickness T may be located adjacent or otherwise around the location of the thickness R. The sidewall 3014 may increase in thickness from the location of the thickness R to the surrounding thicknesses T. The increase may be gradual or abrupt.

The local compression of the sidewall 3014 may allow for the anchor 3090 to extend proximally and outwardly beyond the outer surface 3016 of the foam body 3002. As shown, the attachment 3001 may locally compress the thickness of the sidewall 3014 such that the proximal tip 3091 of the anchor 3090 extends at the angle B for the length L beyond the outer surface 3016 of the foam body 3002. The attachment 3001 may be located proximally to the anchor 3090 as shown, or in other location, such as distally to the anchor 3090, adjacent the base of the anchor 3090, farther proximally/distally from the base of the anchor 3090, etc. The attachment 3090 may be located and configured to allow for local compression of the sidewall 3014 to allow the tip 3091 of the anchor 3090 to extend beyond the outer surface 3016 of the foam that is located directly radially inwardly of the tip 3091 of the anchor 3090. In some embodiments the attachment 3001 may be located directly radially inwardly of the tip 3091 of the anchor 3090 (e.g., directly "below" the tip 3091 of the anchor 3090 as oriented in the figure). In some embodiments, there may be multiple attachments 3001 distributed axially along the frame 3040 and all contributing to a single local compression of the foam body 3002 about a particular one of the anchors 3090.

The foam sidewall 3014 may be compressed into the configuration shown in FIG. 94C in an unconstrained configuration. The foam sidewall 3014 may be compressed into the configuration shown in FIG. 94C in a constrained configuration, for example within the delivery catheter or after deployment from the delivery catheter. The foam sidewall 3014 may be compressed into the configuration shown in FIG. 94C from the configurations shown or described with respect to FIG. 94A or 94B. Thus in FIG. 94C, the height H may equal to or approximately equal to the thickness T, or the height H may be greater or less than the thickness T. In some embodiments, in an unconstrained configuration, the length L is 2.5 mm or about 2.5 mm, the angle B is 30° or about 30°, and the thickness T is 2.5 mm or about 2.5 mm.

Design of the anchor length may be based on a balance between longer length to provide flexibility to assist with removal, and shorter length for not penetrating through the LAA wall. The anchors 3090, 3094 may be flexible and capable of bending in the distal direction due to their length. The anchors 3090, 3094 are thus less likely to tear tissue during repositioning and therefore less traumatic. The anchors 3090, 3094 may be longer than other tissue engaging features of existing solutions for LAA occlusion. In some embodiments of the device 3000, the anchors 3090, 3094 are designed to be long enough to effectively anchor into the LAA wall. The foam body 3002 and corresponding thickness of the sidewall 3014 allows the anchors 3090, 3094 to have longer length. An advantage of making the anchors 3090, 3094 longer is to increase their flexibility, making them less damaging to tissue during removal and repositioning. However, anchors 3090, 3094 beyond a certain length may penetrate through the LAA wall, which is not desirable. The foam body 3002 and thickness thereof assists with preserving the advantageous longer length of the anchors 3090, 3094 while mitigating the risk of the anchors 3090, 3094 penetrating through the LAA wall. For example, the foam sidewall 3014 between the struts of the frame 3040 and the tips 3091 of the anchors 3090, 3094 limits how far the anchors 3090, 3094 will penetrate allowing for longer and therefore more flexible anchors 3090, 3094.

For example, with a 2.5 mm foam sidewall 3014 thickness, the anchors 3090, 3094 may be 2.5 mm in axial length and formed at an angle between 30-40 degrees, or 25-45 degrees, off the struts. In some embodiments, as discussed, when the frame 3040 is first placed into the foam body 3002 and anchors 3090, 3094 pierce into the foam sidewall 3014, the tips 3091 of the anchors 3090, 3094 may not extend all the way through the foam as the anchors 3090, 3094 may be radially too short. In some embodiments, the frame 3040 OD is about 24 mm and the foam body 3002, such as foam cup shape, has a sidewall 3014 with an ID of about 22 mm. So there may be an interference fit where the frame 3040 bulges into the foam sidewall 3014. With the anchor 3090, 3094 length and angle, the tips 3091 of the anchors 3090, 3094 are at about 27 mm diameter, which corresponds to just getting to the outer surface 3016 of the sidewall 3014. As discussed, the assembly may be attached by suturing the foam body 3002, and the frame 3040 (and in some locations the cover 3100) together at every anchor-frame interface location. This may cause a dimpling of the foam body 3002 local to the corresponding anchor 3090, 3094, thus exposing a length of the anchor 3090, 3094 at the outer surface 3016. The exposed length of the anchor 3090, 3094 may be a fraction of the total anchor 3090, 3094 length. Further, the anchor 3090, 3094 length and radial height of the foam sidewall 3014 surrounding the anchor 3090, 3094 can be adjusted to expose the desired amount of the anchor 3090, 3094.

In some embodiments, the tip 3091 may be exposed beyond the foam body 3002 when the foam is compressed, but the tip 3091 may be positioned within the foam, below the outer surface 3016, when the foam is uncompressed. Thus, with the foam uncompressed the tip 3091 may not be positioned radially outwardly relative to the outer surface 3016, but with the foam compressed the tip 3091 may be positioned radially outwardly relative to the adjacent portion of the outer surface 3016. Therefore, the tip 3091 may not be exposed with "H" less than "T" in the uncompressed configuration, and the tip 3091 may be exposed with "H" greater than "T" in the compressed configuration.

11. Device Compliance

The device 3000 is capable of conforming to the geometry of the LAA. The device 3000 is designed for compliance such that it can conform to the LAA and reduce or minimize remodeling of the LAA. For example, the device 3000 may be implanted into the LAA and after a period of time the ostium or opening of the LAA may have the same or similar profile as before implantation of the device 3000. Further, the device 3000 may exhibit such properties while conforming to extreme non-circular shapes, both at the opening of the LAA and within the LAA. A single size of the device 3000 may be used for all or a wide range of patients with varying geometries, due to the compliance and other advantages.

Figure 95A:
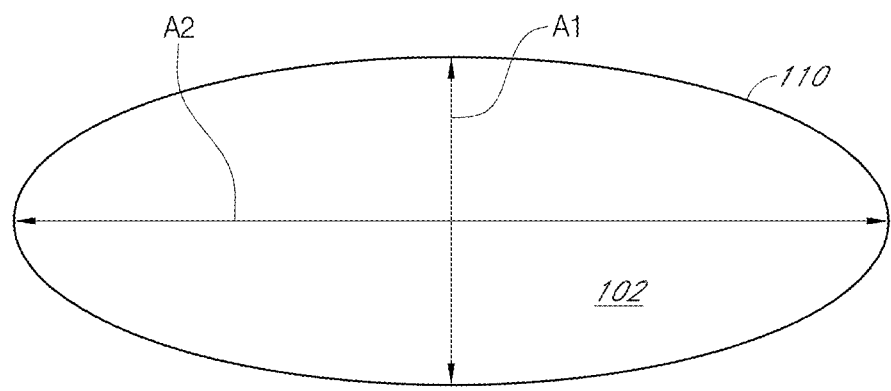
FIG. 95A is a schematic showing an embodiment of a profile of an ostium and an LAA.

FIG. 95A is a schematic showing an embodiment of a profile of the ostium 110. The view shown may be looking into the LAA, for example in a plane that is perpendicular to a geometrically centered axis at the ostium. The geometry of the ostium 110 may vary greatly, as described herein, for example with respect to FIG. 1. As shown in FIG. 95A, the ostium may be approximated as an oval or ellipse having a relatively shorter minor axis A1 and relatively longer major axis A2. The ostium 110 is shown as generally symmetric about the axes A1, A2, but the ostium 110 may have asymmetries, other local grooves, discontinuities, etc. Thus the ostium 110 schematic shown is merely for illustrative purposes to describe the enhanced compliance capabilities of the device 3000. In some embodiments, the minor axis A1 may refer to a maximum width of the ostium 110 in a first direction, and the major axis A2 may refer to a maximum width in a second direction. The first direction may be perpendicular to the second direction.

The lengths of the axes A1, A2 may have a variety of values or ranges of values. The minor axis A1 may be from about 5 mm to about 30 mm, from about 7.5 mm to about 20 mm, from about 10 mm to about 17.5 mm, from about 12 mm to about 15 mm, about 14 mm, or 14 mm. The major axis A2 may be from about 10 mm to about 40 mm, from about 15 mm to about 37 mm, from about 20 mm to about 35 mm, from about 22 mm to about 32 mm, from about 25 mm to about 30 mm, about 27 mm, or 27 mm.

Figure 95B:
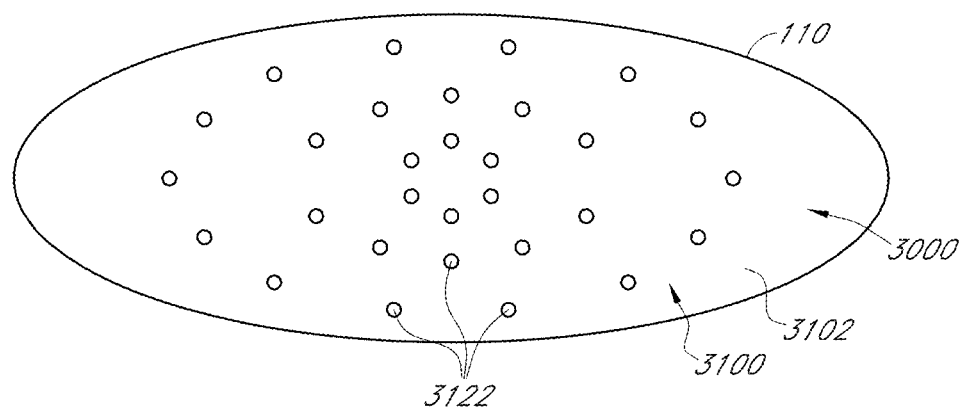
FIG. 95B is a schematic of the LAA occlusion devices of FIGS. 85A-88E as implanted in the ostium and LAA of FIG. 95A, illustrating the conforming capabilities of the devices.

FIG. 95B shows the ostium 110 from the same perspective but with the device 3000 implanted into the LAA. The cover 3100 is visible, showing the proximal surface 3102 with proximal openings 3122. Other covers as described herein may be included, such as the cover 3150, etc. The ostium in 110 with the device 3000 may have the same or similar shape and size as the ostium shown in FIG. 95A without the device 3000. The other portions of the LAA may also have the same shape and sizes before and after implantation of the device 3000. The device 3000 may therefore conform to the shape of the LAA, such as the ostium 110. The device 3000 may conform to the anatomical shape due to the configuration of the foam body 3002 and frame 3040 as described herein. The device 3000 may exhibit sufficient compliance to assume the anatomical shape to provide a sufficient occluding function and without remodeling or otherwise deforming the shape of the LAA, such as the ostium 110.

The LAA may retain the same or similar original size and shape of the LAA immediately after implantation of the device 3000 and for a period of time thereafter. In some embodiments, the anatomical geometry, for example size and shape, of the LAA will still be the same or approximately the same after implantation of the device 3000 after a period of twenty four hours or more, seven days or more, thirty days or more, six months or more, one year or more, five years or more, or longer periods. A test construct having approximately the same geometry, stiffness, etc. may be constructed to confirm the minimal long-term changes in the construct due to the device 3000. A construct having an opening with a minor axis of about 14 mm and a major axis of about 27 mm and with a stiffness generally present in normal LAA ostiums of patients may have the same or similar size and shape after implanting the device 3000 for the aforementioned periods. The device 3000 may allow for the same or similar geometry along the length of the LAA, e.g. distal to the ostium 110, for these periods of time as well, as further described.

In one example use, the device 3000 may be configured to insert into a non-cylindrical opening, having a non-cylindrical profile, of a test body. The test body may be rigid such that the test body does not deform in response to the device 3000 being implanted therein. The test body may be formed of rigid plastics, metals, etc. The opening and profile may have a size and shape substantially similar to that of a native left atrial appendage. The device 3000 may expand radially within the non-cylindrical opening, and conform to the non-cylindrical profile, which may be at least at the opening of the test body. The device 3000 may conform to the opening and have no visible gaps between the device 3000 and the opening. There may be one or more radial gaps that are each no more than five, four, three, two and/or one millimeter across at their widest portion. Such gaps may be measured radially, or perpendicularly to a longitudinal axis extending through the geometric center of the test body opening. The gap may be measured between the outer surface of the device 3000 and the inner surface of the opening of the test body. The gap may be measured at the location of maximum space between the device 3000 and the test body. The device may conform to this shape after a period of at least thirty days, at least sixty days, and/or at least one hundred twenty days after implantation. In another example use, the device 3000 may be configured to insert into a non-cylindrical opening of a test body having a size and radial stiffness substantially similar to that of a native left atrial appendage, expand radially within the non-cylindrical opening, and assume a non-cylindrical profile at least at the opening of the test body after a period of at least thirty days, at least sixty days, and/or at least one hundred twenty days.

Figure 96B:
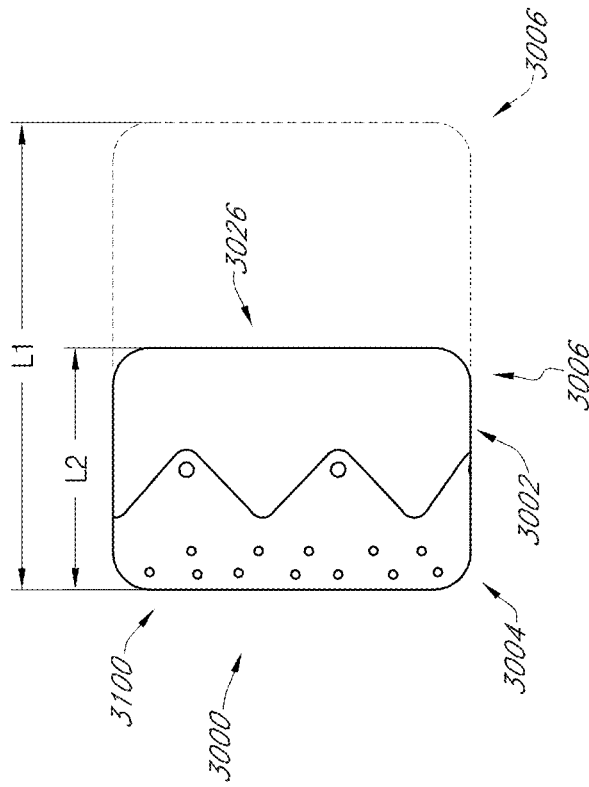
FIG. 96B is a schematic of an LAA occlusion device illustrating the axial compression capabilities of the device of FIGS. 85A-88E.
Figure 96A:
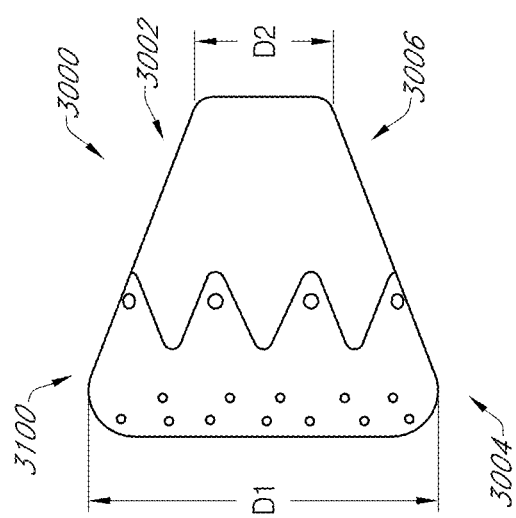
FIG. 96A is a schematic of an LAA occlusion device illustrating the radial compression capabilities of the devices of FIGS. 85A-88E.

FIG. 96A depicts a side view of the device 3000 in a radially constrained configuration. The device 3000 may have the configuration shown after implantation in the LAA, for example after the aforementioned time periods above. The device 3000 is shown with a proximal end 3004 having a width D1 and a distal end having a width D2. The widths D1, D2 may be diameters, or they may be maximum widths of the respective ends of the device 3000. The width D1 is greater than the width D2. In some embodiments, the width D1 may be less than the width D2. In some embodiments, the width D1 may be equal to or approximately equal to the width D2. In some embodiments, the width D2 may be about 15% of the width D1. The width D2 may be 95% or less, 90% or less, 85% or less, 80% or less, 75% or less, 70% or less, 65% or less, 60% or less, 55% or less, 50% or less, 45% or less, 40% or less, 35% or less, 30% or less, 35% or less, 30% or less, 25% or less, 20% or less, 19% or less, 18% or less, 17% or less, 16% or less, 15% or less, 14% or less, 13% or less, 12% or less, 11% or less, or 10% or less of the width D1. In some embodiments, the width D2 may be at other locations along the device 3000 alternatively or in addition to the distal end of the device 3000, for example a portion proximal to and adjacent or near the distal end, a middle portion of the device 3000, etc. In some embodiments, the entire device 3000 or a substantial portion of the device 3000 may have the width D2. For example, the entire device may have the width D2 when constrained within the delivery catheter, as described herein for example in the section "Loading System."

FIG. 96B depicts a side view of the device 3000 in an axially constrained configuration relative to an axially unconstrained configuration. The device 3000 has an axial length L1 in an unconstrained state, and an axial length L2 in the constrained state. The lengths L1, L2 between the proximal end 3004 and the distal end 3006 of the device 3000 in the respective configurations. The device 3000 may have the configuration shown with the length L2 after implantation in the LAA, for example after the aforementioned time periods above. The length L2 is less than the length L1. The length L2 may be 95% or less, 90% or less, 85% or less, 80% or less, 75% or less, 70% or less, 65% or less, 60% or less, 55% or less, 50% or less, 45% or less, or 40% or less of the length L1. In some embodiments, L2 may be equal to or approximately equal to L1.

In some embodiments, the bumper 3026 may allow for extreme shortening of the distal end 3006 of the device. In some embodiments, the bumper 3026 may fold inward to accommodate radial and/or axial constraining of the device 3000. The bumper 3026 may fold radially inward and/or proximally inward. Further, the compliant frame 3040 within the foam body 3002 may allow for further axial shortening beyond the length of the bumper 3026. The frame 3040 may fold radially and/or axially inward.

Further, the cylindrical shape of the device 3000 facilitates with sealing the LAA, even with atypical geometries of the LAA anatomy. The cylindrical shape ensures that the anchors are located at the locations of maximum width of the device 3000. The tubular body 3080 may provide a cylindrical foundation for the anchors 3090, 3094, as described herein, such that the anchors are located at the radially outer most portion of the device 3000. Such cylindrical shape of the device along its longitudinal axis assists with the device 3000 performing the necessary sealing, even in the constrained configurations shown in FIGS. 96A and 96B. In some embodiments, the device 3000 may be constrained both axially and radially, for example with both of the deformations shown in FIGS. 96A and 96B. The compliance of the device 3000 along with the cylindrical shape can ensure superior sealing performance compared to currently available typical LAA occlusion devices.

Figure 97:
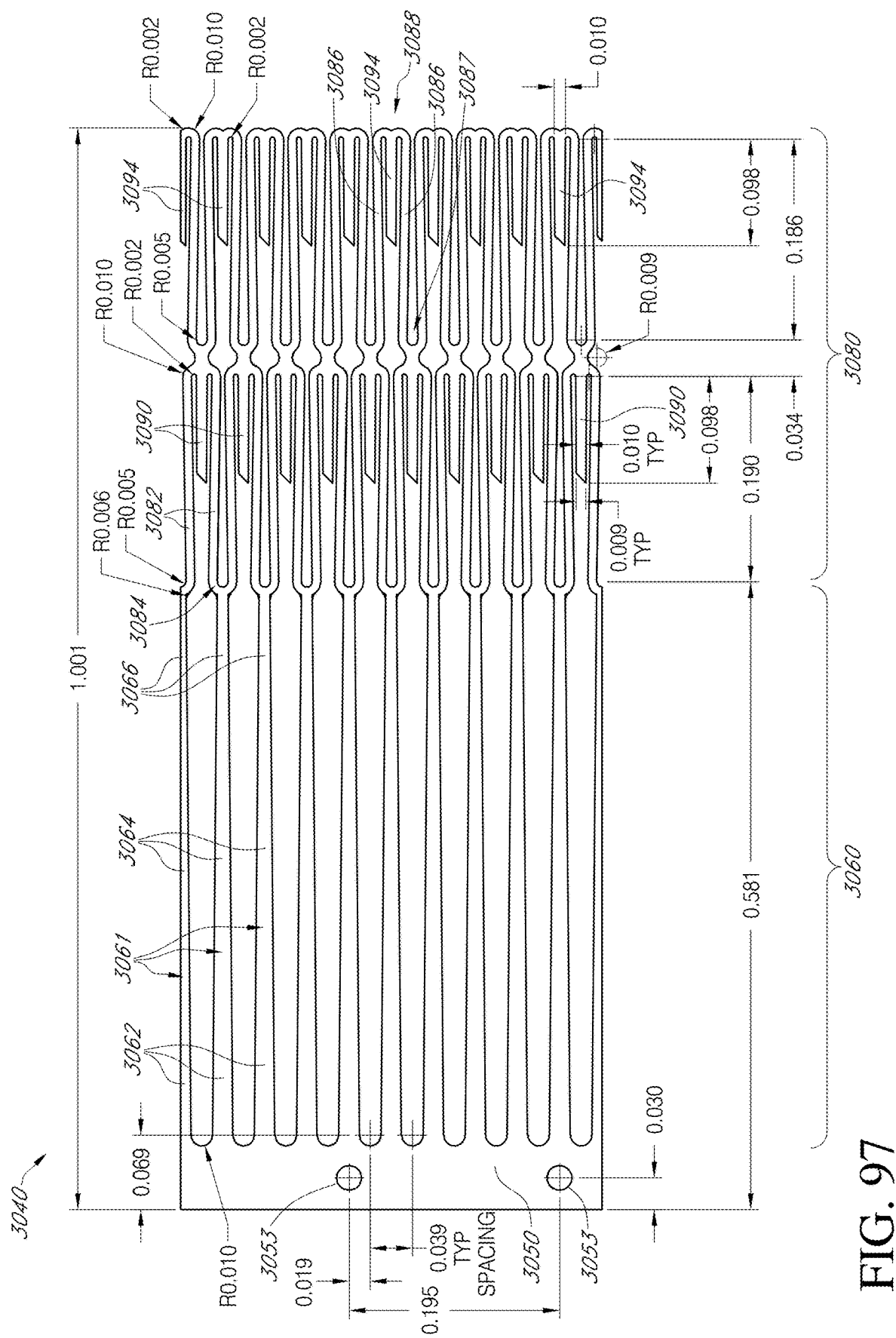
FIG. 97 is a plan view of an embodiment a laser cut tube frame shown in a flat configuration that may be used as the frame for the LAA occlusion devices of FIGS. 85A-88E.

FIG. 97 is a side view of an embodiment a laser cut tube frame 3040 shown in a flat configuration. The frame 3040 may have the various dimensions as shown in inches. The dimensions are just one embodiment and some or all dimensions may be different in other embodiments. The hub 3050 is located at a proximal end having holes 3053. The struts 3061 extend distally from the hub 3050, having curved (when assembled) proximal portions 3062, straight portions 3064, and outer curved (when assembled) portions 3066. The struts 3061 connect at proximal apexes 3084 to the proximal struts 3082. Proximal anchors 3090 extend proximally from intermediate vertices 3087. Distal struts 3086 extend from the vertex 3087 to form the distal apexes 3088, from which the distal anchors 3094 extend proximally. The frame 3040 may have approximately the dimensions shown, or they may vary therefrom. The frame 3040 shown may be used with the device 3000 having a width of 27 mm or about 27 mm.

The device 3000 provides many advantages over existing solutions to LAA occlusion, as described herein. A key advantage is that the device is highly compliant while still providing superior resistance to embolization. This unique feature of being more compliant yet better anchoring is counterintuitive. As compared to existing solutions, the device 3000 is much more conformable and thus able to take the oval shape of the LAA ostium, as described, while also providing superior dislodgement resistance, in some embodiments with a pull out force in bench testing of greater than 0.8 pounds (lbs). [0452]

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A left atrial appendage occlusion device, comprising:
   a foam body having a tubular sidewall and a closed proximal end, the sidewall defining a longitudinal axis and having a radial uncompressed thickness;
   an expandable support coupled with the body; and
   at least one anchor coupled with the support and comprising a free end extending radially outwardly and proximally through the sidewall when the foam of the sidewall is compressed in response to radial expansion of the expandable support within the left atrial appendage, wherein the at least one anchor has a radial height no greater than the radial uncompressed thickness of the sidewall.

2. The left atrial appendage occlusion device of claim 1, wherein the free end extends radially outward in a proximal direction at an angle of at least twenty degrees relative to a portion of the longitudinal axis that extends proximally through the device.

3. The left atrial appendage occlusion device of claim 2, wherein the angle is at least thirty degrees.

4. The left atrial appendage occlusion device of claim 1, wherein the free end extends through a radially-compressed portion of the sidewall having a radial thickness less than the radial uncompressed thickness.

5. The left atrial appendage occlusion device of claim 4, further comprising an attachment that connects the support to the sidewall and radially compresses the sidewall at the radially-compressed portion.

6. The left atrial appendage occlusion device as in claim 1, wherein the radial uncompressed thickness of the sidewall is at least about 0.5 mm.

7. The left atrial appendage occlusion device as in claim 6, wherein the radial uncompressed thickness of the sidewall is at least about 1.5 mm).

8. The left atrial appendage occlusion device as in claim 1, wherein the sidewall extends in a distal direction beyond a distal end of the support by at least about 2 mm in an unconstrained, expanded state.

9. The left atrial appendage occlusion device as in claim 1, wherein the sidewall comprises a foam having a plurality of interconnected reticulations and voids, and further comprising a PTFE coating on at least some of the interconnected reticulations.

10. The left atrial appendage occlusion device as in claim 1, comprising a foam proximal end wall.

11. The left atrial appendage occlusion device as in claim 10, wherein the foam end wall further comprises a cover.

12. The left atrial appendage occlusion device as in claim 11, wherein the cover comprises ePTFE.

13. The left atrial appendage occlusion device as in claim 1, wherein the expandable support is self expandable.

14. The left atrial appendage occlusion device as in claim 1, wherein the expandable support is within a central cavity enclosed by the sidewall.

15. The left atrial appendage occlusion device as in claim 1, wherein the tubular sidewall has a void content of at least about 90%.

16. The left atrial appendage occlusion device as in claim 1, wherein the tubular sidewall has an average pore size of at least about 100 microns.

17. The left atrial appendage occlusion device as in claim 1, wherein the support further comprises at least three recapture struts inclining radially inwardly in a proximal direction to a hub.

18. The left atrial appendage occlusion device as in claim 17, wherein the support comprises a plurality of axially extending side wall struts, with adjacent pairs of side wall struts joined at an apex.

19. The left atrial appendage occlusion device as in claim 17, comprising at least six proximally facing apexes and at least six distally facing apexes.

20. The left atrial appendage occlusion device as in claim 17, wherein each recapture strut is joined to a unique proximally facing apex on the support.

21. The left atrial appendage occlusion device as in claim 20, wherein the recapture struts are integrally formed with the support.

22. The left atrial appendage occlusion device as in claim 1, wherein the tubular sidewall comprises a reticulated, cross linked matrix having at least about 90% void content, an average cell size within the range of from about 250-500 microns, a wall thickness of at least about 2 mm and a compressive strength of at least about 1 psi.

23. The left atrial appendage occlusion device of claim 22, wherein the compressive strength is within a range of from about 1 psi to about 2 psi.

24. A left atrial appendage occlusion device, comprising:
   a foam body having a closed proximal end, a distal end and a tubular sidewall that extends circumferentially about a central axis to form a closed cross-section about a cavity, the sidewall comprising at least one first portion having a first radial thickness and at least one second portion having a second radial thickness that is less than the first radial thickness;
   an expandable support within the cavity and coupled with the body; and
   at least one anchor coupled with the support and comprising a free end extending radially outward and proximally at least partially through the at least one second portion of the sidewall.

25. The left atrial appendage occlusion device of claim 24, wherein the free end is angled relative to the central axis.

26. The left atrial appendage occlusion device of claim 25, wherein the free end extends radially outward in a proximal direction at an angle of at least twenty degrees relative to a portion of the central axis that extends proximally to the device.

27. The left atrial appendage occlusion device of claim 26, wherein the angle is at least thirty degrees.

28. The left atrial appendage occlusion device of claim 25, wherein the free end extends through the at least one second portion of the sidewall such that a portion of the at least one anchor extends outwardly beyond an outer surface of the at least one second portion of the sidewall.

29. The left atrial appendage occlusion device of claim 25, wherein the at least one anchor has an axial length that is equal to the first radial thickness.

30. The left atrial appendage occlusion device of claim 24, wherein the support comprises a tubular frame portion configured to expand radially outward to compress the sidewall against a wall of a left atrial appendage after implantation of the device.

31. The left atrial appendage occlusion device of claim 24, further comprising a proximal cover that covers at least a portion of a proximal face of the foam body.

32. A left atrial appendage occlusion device, comprising:
- a tubular foam body having a closed, proximal circular end;
- an expandable support coupled with the foam body, the support comprising a tubular portion having a plurality of struts with pairs of adjacent struts forming proximal and distal apexes; and
- an anchor extending from the tubular portion of the support and comprising a tip extending radially outwardly and proximally at least partially into the tubular foam body;
- wherein the device is configured to:
  - insert into a non-cylindrical opening of a rigid test body having a non-cylindrical profile,
  - expand radially within the non-cylindrical opening, and conform to the non-cylindrical profile at least at the opening of the test body.

33. The left atrial appendage occlusion device of claim 32, wherein the foam body includes a compressible side wall extending between a proximal end and a distal end and defines a central cavity.

34. The left atrial appendage occlusion device of claim 33, wherein the expandable support is configured to compress the side wall against an inner surface of the test body.

35. The left atrial appendage occlusion device of claim 32, wherein the device after conforming to the non-cylindrical profile leaves no radial gap between the device and the test body having a maximum radial dimension of more than five millimeters.

36. The left atrial appendage occlusion device of claim 35, wherein the device after conforming to the non-cylindrical profile leaves no radial gap between the device and the test body having a maximum radial dimension of more than three millimeters.

37. The left atrial appendage occlusion device of claim 32, wherein the tubular foam body comprises a proximal face at the closed circular end and a rounded sidewall extending distally from the proximal face.

* * * * *